US007202335B2

(12) United States Patent
Goddard et al.

(10) Patent No.: US 7,202,335 B2
(45) Date of Patent: Apr. 10, 2007

(54) PRO300 POLYPEPTIDES

(75) Inventors: Audrey Goddard, San Francisco, CA (US); Paul J. Godowski, Hillsborough, CA (US); J. Christopher Grimaldi, San Francisco, CA (US); Austin L. Gurney, Belmont, CA (US); William I. Wood, Hillsborough, CA (US)

(73) Assignee: Genentech, Inc., South San Francisco, CA (US)

( * ) Notice: Subject to any disclaimer, the term of this patent is extended or adjusted under 35 U.S.C. 154(b) by 370 days.

(21) Appl. No.: 10/063,516

(22) Filed: May 1, 2002

(65) Prior Publication Data

US 2003/0181708 A1 Sep. 25, 2003

Related U.S. Application Data

(63) Continuation of application No. 10/006,867, filed on Dec. 6, 2001, which is a continuation of application No. PCT/US00/23328, filed on Aug. 24, 2000, which is a continuation-in-part of application No. 09/380,138, filed as application No. PCT/US99/05028 on Mar. 8, 1999.

(60) Provisional application No. 60/082,797, filed on Apr. 22, 1998.

(51) Int. Cl.
*C07K 14/00* (2006.01)
*C07K 5/00* (2006.01)
*C12N 15/00* (2006.01)

(52) U.S. Cl. .................. 530/350; 530/300; 530/402; 435/69.7; 435/69.8

(58) Field of Classification Search ................ 530/350, 530/402
See application file for complete search history.

(56) References Cited

U.S. PATENT DOCUMENTS

| 5,536,637 | A | 7/1996 | Jacobs |
| 6,025,156 | A | 2/2000 | Gwynn et al. |
| 6,124,433 | A | 9/2000 | Falb et al. |
| 6,156,500 | A | 12/2000 | Falb |
| 6,162,604 | A | 12/2000 | Jacob |
| 6,228,582 | B1 | 5/2001 | Rodier et al. |
| 6,395,306 | B1 | 5/2002 | Cui et al. |
| 6,414,117 | B1 | 7/2002 | Levinson |
| 6,465,185 | B1 | 10/2002 | Goldfine et al. |
| 6,498,235 | B2 | 12/2002 | Sheppard et al. |
| 6,562,343 | B1 | 5/2003 | Levinson |
| 6,645,499 | B1 | 11/2003 | Lal et al. |
| 6,730,502 | B2 | 5/2004 | Van Hijum et al. |
| 6,737,522 | B2 | 5/2004 | Sundick et al. |

FOREIGN PATENT DOCUMENTS

| WO | WO 97/38085 | 10/1997 |
| WO | WO 01/16318 | * 3/2001 |
| WO | WO 01/29221 A2 | 4/2001 |

OTHER PUBLICATIONS

Gygi et al. Mol. Cell. Biol. 19(3): 1720-1730, 1999.*
Pennica et al. Proc. Natl. Acad. Sci. USA. 95: 14717-14722, 1998.*
Hittelman Ann. NY Acad. Sci. 952: 1-12, 2001.*
Hu et al. J. Proteome Res. 2: 405-412, 2003.*
Fessler et al. A genomic and proteomic analysis of activation of the human neutrophil by lipopolysaccharide and its mediation by p38 mitogen-activated protein kinase. J. Biol. Chem. 277(35): 31291-31302, Aug. 2002.*
Saito-Hisaminato et al. DNA Res. 9:35, 2002.*
Celis et al. FEBS Lett. 480: Feb. 16, 2000.*
Heddwen et al. cDNA array identification of genes regulated in rat medulla in response to vasopressin infusion. Am. J. Physiol. Renal Physiol. 284: F218-F228, 2003.*
Berner et al. Clinicopathological associations of CD44 mRNA and protein expression in primary breast carcinomas. Histopathology 42: 546-554, 2003.*
Toler et al. Loss of communication in ovarian cancer. Am J. of Obs. Gyn. 194: e27-e31, 2006.*
Sugg et al. Cytoplasmic staining of erbB-2 but not mRNA levels correlates with differentiation in human thyroid neoplasia. Clinical Endocrinol. 49: 629-637, 1998.*
Oda et al. Expression of MDR1/p-glycoprotein and multidrug resistance-associated protein in childhood solid tumours. Virchows Arch. 430: 99-105, 1997.*
Klein, et al. Selection for Genes Encoding Secreted Proteins and Receptors. *Proc. Natl. Acad. Sci.*, 93: 7108-7113 (1996).
Alberts, et al. 1994. *Molecular Biology of the Cell*, 3rd Edition, pp. 403-404, 453. New York: Garland Publishing.
Alberts; et al. 2002. *Molecular Biology of the Cell 4th Edition*, pp. 302, 363-364, 379, 435. New York: Garland Publishing.
Grimaldi, et al. 1989. The t(5;14) chromosonal translocation in a case of acute lymphocytic leukemia joins the interleukin-3 gene to the immunoglobulin heavy chain gene. *Blood*, 73(8):2081-2085.
Hanna, et al. Aug. 1999. HER-2/neu breast cancer predictive testing. *Pathology Associates Medical Laboratories*.
Hyman et al. Nov. 2002. Impact of DNA Amplification of Gene Expression Patterns. *Cancer Research*, 62:6240-6245.
Lewin, B. 1994. Oncogenes: Gene Expression and Cancer, Chap. 39, pp. 1196-1201. *Genes V*. New York: Oxford University Press.
Lewin, B. 1997. Regulation of Transcription, Chap. 29, pp. 847-848. *Genes VI*. New York: Oxford University Press.

(Continued)

*Primary Examiner*—Christine J. Saoud
(74) *Attorney, Agent, or Firm*—Elizabeth M. Barnes; Mark T. Kresnak; Knobbe Martens Olson & Bear LLP

(57) ABSTRACT

The present invention is directed to novel polypeptides and to nucleic acid molecules encoding those polypeptides. Also provided herein are vectors and host cells comprising those nucleic acid sequences, chimeric polypeptide molecules comprising the polypeptides of the present invention fused to heterologous polypeptide sequences, antibodies which bind to the polypeptides of the present invention and to methods for producing the polypeptides of the present invention.

8 Claims, 168 Drawing Sheets

OTHER PUBLICATIONS

Meeker, et al. 1990. Activation of the interleukin-3 gene by chromosome translocation in acute lymphocytic leukemia with eosinophilia. *Blood*, 76(2):285-289.

Meric, et al. 2002. Translation initiation in cancer: A novel target for therapy. *Molecular Cancer Therapeutics*, 1:971-979.

Ørntoft, et al. 2002. Genome-wide study of gene copy numbers, transcripts, and protein levels in pairs of non-invasive and invasive human transitional cell carcinomas. *Molecular & Cellular Proteomics*, 1:37-45.

Pollack, et al. 2002. Microarray analysis reveals a major direct role of DNA copy number alteration in the transcriptional program of human breast tumors. *PNAS*, 99(20):12963-12968.

Singleton, et al. 1992. Clinical and pathologic significance of the c-*erb*B-2 (*HER-2/neu*) oncogene. *Pathol. Annu*, 1(27):165-190.

Zhigang, et al. 2004. Prostate stem cell antigen (PSCA) expression in human prostate cancer tissues and its potential role in prostate carcinogenesis and progression of prostate cancer. *World Journal of Surgical Oncology*, 2:13.

Allman, et al. 1996. BCL-6 expression during B-cell activation. *Blood*, 87(12):5257-5268.

Chen, et al. 2002. Discordant Protein and mRNA Expression in Lung Adenocarcinomas. *Molecular & Cellular Proteomics 1.4*, 304-313.

Fu, et al. 1996. Translational regulation of human p53 gene expression. *The EMBO Journal*, vol. 15, No. 16, pp. 4392-4401.

Gökmen-Polar, et al., Feb. 2001, Elevated Protein Kinase C βII Is an Early Promotive Event in Colon Carcinogenesis, *Cancer Research*, vol. 61, pp. 1375-1381.

Hanash, S. 2003. Making sense of microarray data to classify cancer. *The Pharmacogenomics Journal*, 3:308-311.

Hanash, S. Mar. 2005. Integrated global profiling of cancer. *Nature Reviews, Applied Proteomics Collection*, pp. 9-14.

Hancock, W. S. 2004. Do We Have Enough Biomarkers? *Journal of Proteome Research*, 3(4):685.

Haynes, et al., 1998. Proteome analysis: Biological assay or data archive? *Electrophoresis*, vol. 19, pp. 1862-1871.

Jang A. Hill RP, Sep. 1997. An examination of the effects of hypoxia, acidosis, and glucose starvation on the expression of metastasis-associated genes in murine tumor cells. *Clin. Exp. Metastasis* 15(5): pp. 469-483.

Konopka, et al. Jun. 1986. Variable Expression of the Translocated c-abl Oncogene in Philadelphia-Chromosome-Positive B-Lymphoid Cell Lines from Chronic Myelogenous Leukemia Patients, *National Academy of Sciences of the United States of America*, vol. 83, No. 11, pp. 4049-4052.

Ohara, et al. 2001. Directional cDNA library construction assisted by the in vitro recombination reaction. *Nucleic Acids Research*, vol. 29, No. e22, pp. 1-8.

Powell, et al. Oct. 1998. Expression of cytochrome P4502E1 in human liver: assessment by mRNA, genotype and phenotype. *Pharmacogenetics*, vol. 5: pp. 411-421.

Vallejo, et al. Dec. 2000. Evidence of tissue-specific, post-transcriptional regulation of NRF-2 expression. *Biochimie* 82(12): 1129-33.

Wang, et al. 1996. mRNA Differential display: Application in the discovery of novel pharmacological targets. *Trends Pharmacol. Sci.*, 17(8):276-279.

Anderson, et al. 1997. A comparison of selected mRNA and protein abundances in human liver. *Electrophoresis*, 18:533.

Labaer, Joshua. 2003. Letter to the editor: Mining the literature and large datasets. *Nature Biotechnology*, 21(9):976.

Lian, et al. 2001. Genomic and proteomic analysis of the myeloid differentiation program. *Blood*, 98(3):513.

Lichtinghagen, et al. 2002. Different mRNA and protein expression of matrix metalloproteinases 2 and 9 and tissue inhibitor of metalloproteinases 1 in benign and malignant prostate tissue. *European Urology*, 42:398.

Tokunaga, et al. 2000. Application of quantitative RT.

Valle, et al. 2003. New approaches for biomarker discovery in lung cancer. *Expert Rev. Mol. Diagn.* 3(1), 55.

Wang, et al. 2002 Novel candidate tumor marker genes for lung adenocarcinoma. *Oncogene*, 21:7598.

Yousef, et al. 2003. Parallel overexpression of seven kallikrein genes in ovarian cancer. *Cancer Research*, 63:2223.

2002-2003 Catalog & Technical Reference, New England BioLabs, Inc., p. 122.

Abe, et al. "An increased high-mobility group A2 expression level is associated with malignant phenotype in pancreatic exocrine tissue." *Br J Cancer*. Dec. 1, 2003;89(11):2104-9. (Abstract Only).

Ando, et al. "Selective apoptosis of natural killer-cell tumours by I-asparaginase." *Br. J. Haematol*. Sep. 2005;130(6):860-8. (Abstract Only).

Aust, et al. "Human thyroid carcinoma cell lines and normal thyrocytes: expression and regulation of matrix metalloproteinase-1 and tissue matrix metalloproteinases inhibitor-1 messenger-RNA and protein." *Thyroid*. Oct. 1997;7(5):713-24. (Abstract Only).

Barnes, et al. "Expression of embryonic fibronectin isoform EIIIA parallels alpha-smooth muscle actin in maturing and diseased kidney." *J Histochem Cytochem*. Jun. 1999;47(6):787-98. (Abstract Only).

Bea, et al. "BMI-1 gene amplification and overexpression in hematological malignancies occur mainly in mantle cell lymphomas." *Cancer Res*. Mar. 15, 2001;61(6):2409-12. (Abstract Only).

Blaschke, et al. "Rapid quantitation of proinflammatory and chemoattractant cytokine expression in small tissue samples and monocyte-derived dendritic cells: validation of a new real-time RT-PCR technology." *J Immunol Methods*. Dec. 1, 2000;246(1-2):79-90. (Abstract Only).

Buckley, et al. "Butyrate-induced reversal of dexamethasone resistance in autonomous rat Nb2 lymphoma cells." *Apoptosis*. 1997;2(6):518-28. (Abstract Only).

Caberlotto, et al. "Alterations in neuropeptide Y levels and Y1 binding sites in the Flinders Sensitive Line rats, a genetic animal model of depression."*Neurosci Lett*. Apr. 23, 1999;265(3):191-4. (Abstract Only).

Caberlotto, et al. "Neurokinin 1 receptor and relative abundance of the short and long isoforms in the human brain." *Eur J Neurosci*. May 2003;17(9):1736-46. (Abstract Only).

Celis, et al. 2000. Gene expression profiling: monitoring transcription and translation products using DNA microarrays and proteomics. *FEBS Letters*, 480:2-16.

Choi, et al. "Characterization of cyclin D2 expression in human endometrium." 166: *J Soc Gynecol Investig*. Jan.-Feb. 2002;9(1):41-6. (Abstract Only).

Couvelard, et al. "Human chorionic gonadotropin beta expression in malignant Barrett's oesophagus." *Virchows Arch*. Sep. 2004;445(3):279-84. Epub Aug. 10, 2004. (Abstract Only).

Crick, F. 1970. Central dogma of molecular biology. *Nature*, 227:561-563.

Dagenais, et al. "Downregulation of ENaC activity and expression by TNF-alpha in alveolar epithelial cells." *Am J Physiol Lung Cell Mol Physiol*. Feb. 2004;286(2):L301-11. Epub Sep. 26, 2003. (Abstract Only).

de Boer, et al. "Involvement of the CCND1 gene in hairy cell leukemia." *Ann Oncol*. Mar. 1996;7(3):251-6. (Abstract Only).

Debieve, et al. "Inhibin and activin production and subunit expression in human placental cells cultured in vitro." *Mol Hum Reprod*. Aug. 2000;6(8):743-9. (Abstract Only).

Dong, et al. "Expression of membrane-type matrix metalloproteinases 4, 5, and 6 in mouse corneas infected with *P. aeruginosa*." *Invest Ophthalmol Vis Sci*. Dec. 2001;42(13):3223-7. (Abstract Only).

Duchrow, et al. "Assessment of proliferative activity in colorectal carcinomas by quantitative reverse transcriptase-polymerase chain reaction (RT-PCR)." *Cancer Invest*. 2001;19(6):588-96. (Abstract Only).

Dyer, et al. "Molecular characterisation of carbohydrate digestion and absorption in equine small intestine." *Equine Vet J*. Jul. 2002;34(4):349-58. (Abstract Only).

Egwuagu, et al. "Suppressors of cytokine signaling proteins are differentially expressed in Th1 and Th2 cells: implications for Th cell lineage commitment and maintenance." *J Immunol*. Apr. 1, 2002;168(7):3181-7. (Abstract Only).

Eleore, et al. "Modulation of the glutamatergic receptors (AMPA and NMDA) and of glutamate vesicular transporter 2 in the rat facial nucleus after axotomy." *Neuroscience*. 2005;136(1):147-60. Epub Sep. 21, 2005. (Abstract only).

El-Ghrablv, et al. "Intravitreal invading cells contribute to vitreal cytokine milieu in proliferative vitreoretinopathy." *Br J Ophthalmol*. Apr. 2001;85(4):461-70. (Abstract only).

Feroze-Merzoug, et al. 2001. Molecular profiling in prostate cancer. *Cancer and Metastasis Reviews*, 20:165-171.

Forsberg, et al. "Altered levels of scavenging enzymes in embryos subjected to a diabetic environment." *Free Radic Res*. Jun. 1996;24(6):451-9. (Abstract Only).

Frevschuss, et al. "Induction of the estrogen receptor by growth hormone and glucocorticoid substitution in primary cultures of rat hepatocytes." *Endocrinology*. Oct. 1993;133(4):1548-54. (Abstract Only).

Fu, et al. "Cyclin D1-negative mantle cell lymphoma: a clinicopathologic study based on gene expression profiling." *Blood*. Dec. 15, 2005; 106(13):4315-21. Epub Aug. 25, 2005. (Abstract Only).

Fuchs, et al. "Oxytocin receptors in bovine cervix: distribution and gene expression during the estrous cycle." *Biol Reprod*, Mar. 1996;54(3):700-8. (Abstract only).

Furuta, et al. "Silencing of the thrombomodulin gene in human malignant melanoma" *Melanoma Res*. Feb. 2005;15(1):15-20. (Abstract Only).

Futcher, et al. "A sampling of the yeast proteome." *Mol Cell Biol*. Nov. 1999;19(11):7357-7368.

George, et al. "Pre-translational regulation of cytochrome P450 genes is responsible for disease-specific changes of individual P450 enzymes among patients with cirrhosis." *Biochem Pharmacol*. Mar. 30, 1995;49(7):873-81. (Abstract Only).

Giroux, et al. "Cyclooxygenase-2 expression in macrophages: modulation by protein kinase C-alpha." *J Immunol*. Oct. 1, 2000;165(7):3985-91. (Abstract Only).

Gnatenko, et al. "Transcript profiling of human platelets using microarray and serial analysis of gene expression." *Blood*. Mar. 15, 2003;101(6):2285-93. Epub Nov. 14, 2002. (Abstract Only).

Godbout, et al. "Overexpression of a DEAD box protein (DDX1) in neuroblastoma and retinoblastoma cell lines." *J Biol Chem*. Aug. 14, 1998;273(33):21161-8. (Abstract Only).

Goldenberg, et al. "Modulation of gap junction mediated intercellular communication in TM3 Leydig cells." *J Endocrinol*. May 2003;177(2):327-35. (Abstract Only).

Golebiowski, et al. "Expression level of Ubc9 protein in rat tissues." *Acta Biochim Pol*. 2003;50(4):1065-73. (Abstract Only).

Greenbaum, et al. 2003. Comparing protein abundance and mRNA expression levels on a genomic scale. *Genome Biology*, 4(9):117. 1-117.8.

Grem, et al. "Thymidine kinase, thymidylate synthase, and dihydropyrimidine dehydrogenase profiles of cell lines of the National Cancer Institute's Anticancer Drub Screen." *Clin Cancer Res*. Apr. 2001;7(4):999-1009. (Abstract Only).

Grenback, et al. "Galanin in pituitary adenomas." *Regul Pept*. Feb. 15, 2004;117(2):127-39. (Abstract Only).

Gromova, et al. "Protein abundancy and mRNA levels of the adipocyte-type fatty acid binding protein correlate in non-invasive and invasive bladder transitional cell carcinomas." *Int J Oncol*. Aug. 1998;13(2):379-83 (Abstract Only).

Guo, et al. "The pathogenic role of macrophage migration inhibitory factor in acute respiratory distress syndrome" *Zhonghua Jie He He Hu Xi Za Zhi*. Jun. 2002;25(6):337-40. (Abstract Only).

Habu, et al. "Restored expression and activity of organic ion transporters rOAT1, rOAT3 and rOCT2 after hyperuricemia in the rat kidney." *Biochem Pharmacol*. Mar. 15, 2005;69(6):993-9. (Abstract Only).

Hahn, et al. "Regulation of cytochrome P4501A1 in teleosts: sustained induction of CYP1A1 mRNA, protein, and catalytic activity by 2,3,7,8-tetrachlorodibenzofuran in the marine fish *Stenotomus chrysops*." *Toxicol Appl Pharmacol*. Aug. 1994;127(2):187-98. (Abstract Only).

Hahnel, et al. "Expression of the pS2 gene in breast tissues assessed by pS2-mRNA analysis and pS2-protein radioimmunoassay." *Breast Cancer Res Treat*. 1992;24(1):71-4. (Abstract Only).

Hamilton, et al. "The role of the epidermal growth factor receptor in sustaining neutrophil inflammation in severe asthma." *Clin Exp Allergy*. Feb. 2003;33(2):233-40. (Abstract Only).

Hassett, et al. "Human hepatic microsomal epoxide hydrolase: comparative analysis of polymorphic expression." *Arch Biochem Biophys*. Jan. 15, 1997;337(2):275-83. (Abstract Only).

Holten-Andersen, et al. "Localization of tissue inhibitor of metalloproteinases 1 (TIMP-1) in human colorectal adenoma and adenocarcinoma." *Int J Cancer*. Jan. 10, 2005;113(2):198-206. (Abstract Only).

Houghten, et al. 1986. Relative Importance of Position and Individual Amino Acid Residues in Peptide Antigen-Antibody Interactions: Implications in the Mechanism of Antigenic Drift and Antigenic Shift. New Approaches to Immunization, *Vaccines86*, Cold Spring Harbor Laboratory, p. 21-25.

Huang, et al. "Tissue plasminogen activator induced by dengue virus infection of human endothelial cells." *J Med Virol*. Aug. 2003;70(4):610-6. (Abstract Only).

Huettner, et al. "Neu oncogene expression in ovarian tumors: a quantitative study." *Mod Pathol*. May 1992;5(3):250-6. (Abstract Only).

Hui, et al. "Real-time quantitative RT-PCR of cyclin D1 mRNA in mantle cell lymphoma: comparison with FISH and immunohistochemistry." *Leuk Lymphoma*. Aug. 2003;44(8):1385-94. (Abstract Only).

Husain, et al. "Elevation of topoisomerase I messenger RNA, protein, and catalytic activity in human tumors: demonstration of tumor-type specificity and implications for cancer chemotherapy." *Cancer Res*. Jan. 15, 1994;54(2):539-46. (Abstract Only).

Ihmann, et al. "High-level mRNA quantification of proliferation marker pKi-67 is correlated with favorable prognosis in colorectal carcinoma"0 *J Cancer Res Clin Oncol*. Dec. 2004;130(12):749-56. Epub Sep. 21, 2004. (Abstract Only).

Ikegami, et al. "Modulation of glucagon receptor expression and response in transfected human embryonic kidney cells." *Am J Physiol Cell Physiol*. Oct. 2001;281(4):C1396-402. (Abstract Only).

Irving, et al. 2000. Proteins emerge from disarray *Nature Biotechnology* 18:932-933.

Jacquemin, et al. "Developmental regulation of acidic fibroblast growth factor (aFGF) expression in bovine retina." *Int J Dev Biol*. Sep. 1993;37(3):417-23. (Abstract Only).

Jaime, et al. "The p21 (Cip1) protein, a cyclin inhibitor, regulates the levels and the intracellular localization of CDC25A in mice regenerating livers." *Hepatology*. May 2002;35(5):1063-71. (Abstract Only).

Janssens, et al. "Alteration of frizzled expression in renal cell carcinoma." *Tumour Biol*. Jul.-Aug. 2004;25(4):161-71. (Abstract Only).

Jungbluth, et al. "Immunohistochemical analysis of NY-ESO-1 antigen expression in normal and malignant human tissues." *Int J Cancer*. Jun. 15, 2001;92(6):856-60. (Abstract Only).

Kalabis, et al. "Multidrug resistance phosphoglycoprotein (ABCB1) in the mouse placenta: fetal protection" *Biol Reprod*. Oct. 2005;73(4):591-7. Epub May 25, 2005. (Abstract Only).

Kammori, et al. "Expression of human telomerase reverse transcriptase gene and protein, and of estrogen and progesterone receptors, in breast tumors: Preliminary data from neo-adjuvant chemotherapy." *Int J. Oncol*. Nov. 2005;27(5):1257-63. (Abstract Only).

Khal, et al. "Expression of the ubiquitin-proteasome pathway and muscle loss in experimental cancer cachexia." *Br J Cancer*. Oct. 3, 2005; 93(7):774-80. (Abstract Only).

Khal, et al. "Increased expression of proteasome subunits in skeletal muscle of cancer patients with weight loss." *Int J Biochem Cell Biol*. Oct. 2005;37(10):2196-206. Epub Dec. 2004. (Abstract Only).

Kogo, et al. "Cell type-specific occurrence of caveolin-1alpha and -1beta in the lung caused by expression of distinct mRNAs." *J Biol Chem*. Jun. 11, 2004;279(24):25574-81. Epub Apr. 2, 2004. (Abstract Only).

Kommoss, et al. "Oncogene and growth factor expression in ovarian cancer." *Acta Obstet Gynecol Scand Suppl.* 1992;155:19-24. (Abstract Only).

Kumar, et al. "Somatostatin receptors in primary human breast cancer: quantitative analysis of mRNA for subtypes 1-5 and correlation with receptor protein expression and tumor pathology." *Breast Cancer Res Treat.* Jul. 2005;92(2):175-86. (Abstract Only).

Kuo, et al. "Atranscriptomic and proteomic analysis of the effect of CpG-ODN on human THP-1 monocytic leukemia cells." *Proteomics.* Mar. 2005;5(4):894-906. (Abstract Only).

Landmark, et al. "Cellular location and age-dependent changes of the regulatory subunits of cAMP-dependent protein kinase in rat testis." *J Reprod Fertil.* Nov. 1993;99(2):323-34. (Abstract Only).

Lassmann, et al. "Quantification of CK20 gene and protein expression in colorectal cancer by RT-PCR and immunohistochemistry reveals inter- and intratumour heterogeneity." *J Pathol.* Oct. 2002;198(2):198-206. (Abstract Only).

Legrand, et al. "Expression of the multidrug resistance-associated protein (MRP) mRNA and protein in normal peripheral blood and bone marrow haemopoietic cells." *Br J Haematol.* Jul. 1996;94(1):23-33. (Abstract Only).

Lemstrom, et al. "Vascular endothelial growth factor enhances cardiac allograft arteriosclerosis." *Circulation.* May 28, 2002;105(21):2524-30. (Abstract Only).

Li, et al. "Enhanced expressions of arachidonic acid-sensitive tandem-pore domain potassium channels in rat experimental acute cerebral ischemia." *Biochem Biophys Res Commun.* Feb. 25, 2005;327(4):1163-9. (Abstract Only).

Li, et al. "Retinal preconditioning and the induction of heat-shock protein 27." *Invest Ophthalmol Vis Sci.* Mar. 2003;44(3):1299-304. (Abstract Only).

Lindberg, et al. "Increasing expression of tissue plasminogen activator and plasminogen activator inhibitor type 2 in dog gingival tissues with progressive inflammation." *Arch Oral Biol.* Jan. 2001;46(1):23-31. (Abstract Only).

Macabeo-Ong, et al."Effect of duration of fixation on quantitative reverse transcription polymerase chain reaction analyses." *Mod Pathol.* Sep. 2002;15(9):979-87. (Abstract Only).

Madoz-Gurpide, et al. 2003. Molecular analysis of cancer using DNA and protein microarrays. *Adv. Exp. Med. Biol.*, 532:51-58.

Maruyama, et al. "Id-1 and Id-2 are overexpressed in pancreatic cancer and in dysplastic lesions in chronic pancreatitis." *Am J Pathol.* Sep. 1999;155(3):815-22. (Abstract Only).

McGuiness, et al. Mar. 1991, Point mutation in meningococcal *por* A gene associated with increased endemic disease. *The Lancet*, 337:514-517.

McGuiness. et al., Feb. 1993, Class 1 outer membrane protein of *Neisseria meningitides*: epitope analysis of the antigenic diversity between strains, implications for subtype definition and molecular epidemiology. *Mol. Microbiology*, 7:505-514.

Meehan, et al. "Tightly regulated and inducible expression of a yoked hormone-receptor complex in HEK 293 cells." *J Mol Endocrinol.* Feb. 2004;32(1):247-55. (Abstract Only).

Mendoza-Rodriguez, et al. "c-fos and estrogen receptor gene expression pattern in the rat uterine epithelium during the estrous cycle." *Mol Reprod Dev.* Apr. 2003;64(4):379-88. (Abstract Only).

Meoni, et al. "[3H]MK-801 binging and the mRNA for the NMDAR1 subunit of the NMDA receptor are differentially distributed in human and rat forebrain." *Brain Res Mol Brain Res.* Feb. 1998;54(1):13-23. (Abstract Only).

Mezzano, et al. "Overexpression of chemokines, fibrogenic cytokines, and myofibroblasts in human membranous nephropathy." *Kidney Int.* Jan. 2000;57(1):147-58. (Abstract Only).

Mingrone, et al. "Decreased uncoupling protein expression and intramyocytic triglyceride depletion in formerly obese subjects." *Obes Res.* May 2003;11(5):632-40. (Abstract Only).

Miralles, et al. "Differential expression of the short and long forms of the gamma 2 subunit of the GABAA/benzodiazepine receptors." *Brain Res Mol Brain Res.* Jul. 1994;24(1-4):129-39. (Abstract Only).

Mizrachi, et al. "Follicle-stimulating hormone receptor and its messenger ribonucleic acid are present in the bovine cervix and can regulate cervical prostanoid synthesis." *Biol Reprod.* Sep. 1999;61(3):776-84. (Abstract Only).

Monaghan, et al. "The alpha(v)beta6 integrin receptor for Foot-and-mouth disease virus is expressed constitutively on the epithelial cells targeted in cattle." *J Gen Virol.* Oct. 2005;86(Pt 10):2769-80. (Abstract Only).

Montuori, et al. "Urokinase-mediated posttranscriptional regulation of urokinase-receptor expression in non small cell lung carcinoma." *Int J Cancer.* Jun. 20, 2003;105(3):353-60. (Abstract Only).

Munaut, et al. "Vascular endothelial growth factor expression correlates with matrix metalloproteinases MT1-MMP, MMP-2 and MMP-9 in human glioblastomas." *Int J Cancer.* Oct. 10, 2003;106(6):848-55. (Abstract Only).

Nagaraja, et al. "Gene expression signatures and biomarkers of noninvasive and invasive breast cancer cells: comprehensive profiles by representational difference analysis, microarrays and proteomics." *Oncogene.* (2006) 25:2328-2388.

Nie, et al. "DNA hypermethylation is a mechanism for loss of expression of the HLA class I genes in human esophageal squamous cell carcinomas." *Carcinogenesis.* Oct. 2001;22(10):1615-23. (Abstract Only).

Nuciforo, et al. "Molecular and immunohistochemical analysis of HER2/neu oncogene in synovial sarcoma." *Hum Pathol.* Jul. 2003;34(7):639-45. (Abstract Only).

Oberringer, et al. "Differential expression of heat shock protein 70 in well healing and chronic human wound tissue." *Biochem Biophys Res Commun.* Sep. 25, 1995;214(3):1009-14. (Abstract Only).

Pachmann, et al. "Expression of bcr-abl mRNA in individual chronic myelogenous leukaemia cells as determined by in situ amplification." *Br J Haematol.* Mar. 2001;112(3):749-59. (Abstract Only).

Pairon, et al. "Cell localization and regulation of expression of cytochrome P450 1A1 and 2B1 in rat lung after induction with 3-methylcholanthrene using mRNA hybridization and immunohistochemistry." *Am J Respir Cell Mol Biol.* Oct. 1994;11(4):386-96. (Abstract Only).

Papotti, et al. "Correlative immunohistochemical and reverse transcriptase polymerase chain reaction analysis of somatostatin receptor type 2 in neuroendocrine tumors of the lung." *Diagn Mol Pathol.* Mar. 2000;9(1):47-57. (Abstract Only).

Papotti, et al. "Expression of somatostatin receptor types 1-5 in 81 cases of gastrointestinal and pancreatic endocrine tumors. A correlative immunohistochemical and reverse-transcriptase polymerase chain reaction analysis." *Virchows Arch.* May 2002;440(5):461-75. Epub Mar. 23, 2002. (Abstract Only).

Paredes, et al. "P-cadherin overexpression is an indicator of clincial outcome in invasive breast carcinomas and is associated with CDH3 promoter hypomethylation." *Clin Cancer Res* Aug. 15, 2005;11(16):5869-77. (Abstract Only).

Politis, et al. "Mammary-derived growth inhibitor protein and messenger ribonucleic acid concentrations in different physiological states of the gland." *J Dairy Sci.* Jun. 1992;75(6):1423-9. (Abstract Only).

Pressman, et al. "T-cell receptor V beta-family usage in primary cutaneous and primary nodal T-cell non-Hodgkin's lymphomas." *J Invest Dermatol.* Nov. 1992;99(5):587-93. (Abstract Only).

Pullig, et al. "Matrilin-3 in human articular cartilage: increased expression in osteoarthritis." *Osteoarthritis Cartilage.* Apr. 2002;10(4):253-63. (Abstract Only).

Rey, et al. "Up-regulation of mitochondrial peripheral benzodiazepine receptor expression by tumor necrosis factor alpha in testicular leydig cells. Possible involvement in cell survival." *Biochem Pharmacol.* Dec. 1, 2000;60(11):1639-46. (Abstract Only).

Rudlowski, et al. "GLUT1 messenger RNA and protein induction relates to the malignant transformation of cervical cancer." *Am J Clin Pathol.* Nov. 2003;120(5):691-8. (Abstract Only).

Sagynaliev, et al. "Web-based data warehouse on gene expression in human colorectal cancer." *Proteomics* 2005, 5:3066-3078.

Saito-Hisaminato et al., Feb. 2002 (Genome-Wide Profiling of Gene Expression in 29 Normal Human Tissues with a cDNA Microarray. *DNA Research 9*, 35-45.

Sasaki, et al. "Expression and distribution of laminin alpha1 and alpha2 chains in embryonic and adult mouse tissues: an immunochemical approach." *Exp Cell Res.* May 1, 2002;275(2):185-99. (Abstract Only).

Sedelies, et al. "Discordant regulation of granzyme H and granzyme B expression in human lymphocytes." *J Biol Chem.* Jun. 18, 2004;279(25):26581-7. Epub Apr. 6, 2004. (Abstract Only).

Shen, et al. "BCL2 protein expression parallels its mRNA level in normal and malignant B cells.": *Blood.* Nov. 1, 2004;104(9):2936-9. Epub Jul. 8, 2004. (Abstract Only).

Shinohara, et al. "Quantitative determinations of the steady state transcript levels of hexokinase isozymes and glucose transporter isoforms in normal rat tissues and the malignant tumor cell line AH130." *Biochim Biophys Acta.* Jan. 5, 1998;1368(1):129-36. (Abstract Only).

Silvers, et al. "UVA irradiation-induced activation of activator protein-1 is correlated with induced expression of AP-1 family members in the human keratinocyte cell line HaCaT." *Photochem Photobiol.* Mar. 2002;75(3):302-10. (Abstract Only).

Song, et al. "Rat kidney glutamyl aminopeptidase (aminopeptidase A): molecular identity and cellular localization." *Am J Physiol.* Oct. 1994;267(4 Pt2):F546-57. (Abstract Only).

Spaziani, et al. "Tumor necrosis factor-alpha upregulates the prostagladin E2 EP1 receptor subtype and the cyclooxygenase-2 isoform in cultured amnion WISH cells." *J Interferon Cytokine Res.* Dec. 1998;18(12):1039-44. (Abstract Only).

Spika, et al. "Transcriptional activity of potent glucocorticoids: relevance of glucocorticoid receptor isoforms and drug metabolites." *Skin Pharmacol Appl Skin Physiol.* May-Jun. 2003;16(3):143-50. (Abstract Only).

Splinter, et al. "Specific inhibition of AQP1 water channels in isolated rat intrahepatic bile duct units by small interfering RNAs." *J Biol Chem.* Feb. 21, 2003;278(8):6268-74. Epub Dec. 4, 2002. (Abstract Only).

Stearns, et al. "Type IV collagenase (M(r) 72,000) expression in human prostate:benign and malignant tissue." *Cancer Res.* Feb. 15, 1993;53(4):878-83. (Abstract Only).

Stein, et al. "The decompensated detrusor III: impact of bladder outlet obstruction on sarcoplasmic endoplasmic reticulum protein and gene expression." *J Urol.* Sep. 2000;164(3 Pt 2):1026-30. (Abstract Only).

Strickland, et al. "TNF-alpha and IL-8 are upregulated in the epidermis of normal human skin after UVB exposure: correlation with neutrophil accumulation and E-selectin expression." *J Invest Dermatol.* May 1997;108(5):763-8. (Abstract Only).

Strutz, et al. "Basic fibroblast growth factor expression is increased in human renal fibrogenesis and may mediate autocrine fibroblast proliferation." *Kidney Int.* Apr. 2000;57(4):1521-38. (Abstract Only).

Takahashi, et al. "Adiposity elevates plasma MCP-1 levels leading to the increased CD1 1b-positive monocytes in mice." : *J Biol Chem.* Nov. 21, 2003;278(47):46654-60. Epub Sep. 16, 2003. (Abstract Only).

Takimoto, et al. "Augmented expression of neuronal nitric oxide synthase in the atria parasympathetically decreases heart rate during acute myocardial infarction in rats." *Circulation.* Jan. 29, 2002;105(4):490-6. (Abstract Only).

Telek, et al. "Differential upregulation of cellular adhesion molecules at the sites of oxidative stress in experimental acute pancreatitis." *J Surg Res.* Mar. 2001;96(1):56-67. (Abstract Only).

Timchenko, et al. "Myotonic dystrophy: an unstable CTG repeat in a protein kinase gene." *Semin Cell Biol.* Feb. 1995;6(1):13-9. (Abstract Only).

Torronen, et al. "Induction of class 3 aldehyde dehydrogenase in the mouse hepatoma cell line Hepa-1 by various chemicals." *Chem Biol Interact.* Aug. 14, 1992;83(2):107-19. (Abstract Only).

Ullmannova, et al. "Relationship between cyclin D1 and p21 (Waf1/Cip1) during differentiation of human myeloid leukemia cell lines." *Leuk Res.* Dec. 2003;27(12):1115-23. (Abstract Only).

Van Beers, et al. "Intestinal carbamoyl phosphate synthase I in human and rat. Expression during development shows species differences and mosaic expression in duodenum of both species." *J Histochem Cytochem.* Feb. 1998;46(2):231-40. (Abstract Only).

van der Wilt, et al. "Expression of deoxycytidine kinase in leukaemic cells compared with solid tumour cell lines, liver metastases and normal liver." *Eur J Cancer.* Mar. 2003;39(5):691-7. (Abstract Only).

Waldherr, et al. "Expression of cytokines and growth factors in human glomerulonephritides." *Pediatr Nephrol.* Aug. 1993;7(4):471-8. (Abstract Only).

Waghray, et al. "Identification of androgen-refulated genes in the prostate cancer cell line LNCaP by serial analysis of gene expression and proteomic analysis." *Proteomics* 2001, 1:1327-1338.

Walmer, et al. "Malignant transformation of the human endometrium is associated with overexpression of lactoferrin messenger RNA and protein." *Cancer Res.* Mar. 1, 1995;55(5):1168-75. (Abstract Only).

Wang, et al. "Cell proliferation in human soft tissue tumors correlates with platelet-derived growth factor B chain expression: an immunohistochemical and in situ hybridization study." *Cancer Res.* Jan. 15, 1994;54(2):560-4. (Abstract Only).

Wang, et al. "Down-regulation of prostate-specific antigen expression by finasteride through inhibition of complex formation between androgen receptor and steroid receptor-binding consensus in the promoter of the PSA gene in LNCaP cells." *Cancer Res.* Feb. 15, 1997;57(4):714-9. (Abstract Only).

Wang, et al. "Expression of cadherins and catenins in paired tumor and non-neoplastic primary prostate cultures and corresponding prostatectomy specimens." *Urol Res.* Oct. 2000;28(5):308-15. (Abstract Only).

Weterman, et al. "Expression of calcyclin in human melanocytic lesions." *Cancer Res.* Dec. 15, 1993;53(24):6061-6. (Abstract Only).

Williams, et al. "Estrogen regulation of the cytochrome P450 3A subfamily in humans." *J Pharmacol Exp Ther.* Nov. 2004;311(2):728-35. Epub Jul. 2004. (Abstract Only).

Winstead E.R., 2000. The Evolving Art of Arrays, www.genomenewsnetwork.org, pp. 1-4.

Wojtaszek, et al. "Severely decreased MARCKS expression correlates with ras reversion but not with mitogenic responsiveness." *Oncogene.* Mar. 1993;8(3):755-60. (Abstract Only).

Xi, et al. "Expression of human telomerase reverse transcriptase in cervix cancer and its significance" *Zhonghua Fu Chan Ke Za Zhi.* Jun. 2005;40(6):407-10. (Abstract Only).

Zhong, et al. "Expression of superoxide dismutases, catalase, and glutathione peroxidase in glioma cells." *Free Radic Biol Med.* Dec. 1999;27(11-12):1334-45. (Abstract Only).

\* cited by examiner

FIGURE 1

GGGGCTTCGGCGCCAGCGGCCAGCGCTAGTCGGTCTGGTAAGGATTTACAAAAGGTGCAGGTATG
AGCAGGTCTGAAGACTAACATTTTGTGAAGTTGTAAAACAGAAAACCTGTTAGAAATGGGTGGT
TTCAGCAAGGCCTCAGTTTCCTTCCTTCAGCCCTTGTAATTTGGACATCTGCTGCTTTCATATTT
TCATACATTACTGCAGTAACACTCCACCATATAGACCCGGCTTTACCTTATATCAGTGACACTGG
TACAGTAGCTCCAGAAAAATGCTTATTTGGGGCAATGCTAAATATTGCGGCAGTTTTATGCATTG
CTACCATTTATGTTCGTTATAAGCAAGTTCATGCTCTGAGTCCTGAAGAGAACGTTATCATCAAA
TTAAACAAGGCTGGCCTTGTACTTGGAATACTGAGTTGTTTAGGACTTTCTATTGTGGCAAACTT
CCAGAAAACAACCCTTTTGCTGCACATGTAAGTGGAGCTGTGCTTACCTTTGGTATGGGCTCAT
TATATATGTTTGTTCAGACCATCCTTTCCTACCAAATGCAGCCCAAAATCCATGGCAAACAAGTC
TTCTGGATCAGACTGTTGTTGGTTATCTGGTGTGGAGTAAGTGCACTTAGCATGCTGACTTGCTC
ATCAGTTTTGCACAGTGGCAATTTTGGGACTGATTTAGAACAGAAACTCCATTGGAACCCCGAGG
ACAAAGGTTATGTGCTTCACATGATCACTACTGCAGCAGAATGGTCTATGTCATTTTCCTTCTTT
GGTTTTTTCCTGACTTACATTCGTGATTTTCAGAAAATTTCTTTACGGGTGGAAGCCAATTTACA
TGGATTAACCCTCTATGACACTGCACCTTGCCCTATTAACAATGAACGAACACGGCTACTTTCCA
GAGATATTTGATGAAAGGATAAAATATTTCTGTAATGATTATGATTCTCAGGGATTGGGGAAAGG
TTCACAGAAGTTGCTTATTCTTCTGAAATTTTCAACCACTTAATCAAGGCTGACAGTAACACT
GATGAATGCTGATAATCAGGAACATGAAAGAAGCCATTTGATAGATTATTCTAAAGGATATCAT
CAAGAAGACTATTAAAAACACCTATGCCTATACTTTTTATCTCAGAAAATAAAGTCAAAAGACT
ATG

FIGURE 2

<subunit 1 of 1, 266 aa, 1 stop
<MW: 29766, pI: 8.39, NX(S/T): 0

MWWFQQGLSFLPSALVIWTSAAFIFSYITAVTLHHIDPALPYISDTGTVAPEKCLFGAMLNIAAV
LCIATIYVRYKQVHALSPEENVIIKLNKAGLVLGILSCLGLSIVANFQKTTLFAAHVSGAVLTFG
MGSLYMFVQTILSYQMQPKIHGKQVFWIRLLLVIWCGVSALSMLTCSSVLHSGNFGTDLEQKLHW
NPEDKGYVLHMITTAAEWSMSFSFFGFFLTYIRDFQKISLRVEANLHGLTLYDTAPCPINNERTR
LLSRDI

Important features:

Type II transmembrane domain:

amino acids 13-33

Other Transmembrane domains:

amino acids 54-73, 94-113, 160-180, 122-141

N-myristoylation sites.

amino acids 57-63, 95-101, 99-105, 124-130, 183-189

FIGURE 3

CGGACGCGTGGGCGGACGCGTGGGGGAGAGCCGCAGTCCCGGCTGCAGCACCTGGGAGAAGGCAGACC
GTGTGAGGGGGCCTGTGGCCCCAGCGTGCTGTGGCCTCGGGGAGTGGGAAGTGGAGGCAGGAGCCTTC
CTTACACTTCGCC<u>ATG</u>AGTTTCCTCATCGACTCCAGCATCATGATTACCTCCCAGATACTATTTTTG
GATTTGGGTGGCTTTTCTTCATGCGCCAATTGTTTAAAGACTATGAGATACGTCAGTATGTTGTACAG
GTGATCTTCTCCGTGACGTTTGCATTTTCTTGCACCATGTTTGAGCTCATCATCTTTGAAATCTTAGG
AGTATTGAATAGCAGCTCCCGTTATTTTCACTGGAAAATGAACCTGTGTGTAATTCTGCTGATCCTGG
TTTTCATGGTGCCTTTTTACATTGGCTATTTTATTGTGAGCAATATCCGACTACTGCATAAACAACGA
CTGCTTTTTTCCTGTCTCTTATGGCTGACCTTTATGTATTTCTTCTGGAAACTAGGAGATCCCTTTCC
CATTCTCAGCCCAAAACATGGGATCTTATCCATAGAACAGCTCATCAGCCGGGTTGGTGTGATTGGAG
TGACTCTCATGGCTCTTCTTTCTGGATTTGGTGCTGTCAACTGCCCATACACTTACATGTCTTACTTC
CTCAGGAATGTGACTGACACGGATATTCTAGCCCTGGAACGGCGACTGCTGCAAACCATGGATATGAT
CATAAGCAAAAGAAAAGGATGGCAATGGCACGGAGAACAATGTTCCAGAAGGGGGAAGTGCATAACA
AACCATCAGGTTTCTGGGGAATGATAAAAAGTGTTACCACTTCAGCATCAGGAAGTGAAAATCTTACT
CTTATTCAACAGGAAGTGGATGCTTTGGAAGAATTAAGCAGGCAGCTTTTTCTGGAAACAGCTGATCT
ATATGCTACCAAGGAGAGAATAGAATACTCCAAAACCTTCAAGGGGAAATATTTTAATTTTCTTGGTT
ACTTTTTCTCTATTTACTGTGTTTGGAAAATTTTCATGGCTACCATCAATATTGTTTTTGATCGAGTT
GGGAAAACGGATCCTGTCACAAGAGGCATTGAGATCACTGTGAATTATCTGGGAATCCAATTTGATGT
GAAGTTTTGGTCCCAACACATTTCCTTCATTCTTGTTGGAATAATCATCGTCACATCCATCAGAGGAT
TGCTGATCACTCTTACCAAGTTCTTTTATGCCATCTCTAGCAGTAAGTCCTCCAATGTCATTGTCCTG
CTATTAGCACAGATAATGGGCATGTACTTTGTCTCCTCTGTGCTGCTGATCCGAATGAGTATGCCTTT
AGAATACCGCACCATAATCACTGAAGTCCTTGGAGAACTGCAGTTCAACTTCTATCACCGTTGGTTTG
ATGTGATCTTCCTGGTCAGCGCTCTCTCTAGCATACTCTTCCTCTATTTGGCTCACAAACAGGCACCA
GAGAAGCAAATGGCACCT<u>TGA</u>ACTTAAGCCTACTACAGACTGTTAGAGGCCAGTGGTTTCAAAATTTA
GATATAAGAGGGGGGAAAAATGGAACCAGGGCCTGACATTTTATAAACAAACAAAATGCTATGGTAGC
ATTTTTCACCTTCATAGCATACTCCTTCCCCGTCAGGTGATACTATGACCATGAGTAGCATCAGCCAG
AACATGAGAGGGAGAACTAACTCAAGACAATACTCAGCAGAGAGCATCCCGTGTGGATATGAGGCTGG
TGTAGAGGCGGAGAGGAGCCAAGAAACTAAAGGTGAAAATACACTGGAACTCTGGGGCAAGACATGT
CTATGGTAGCTGAGCCAAACACGTAGGATTTCCGTTTTAAGGTTCACATGGAAAGGTTATAGCTTTG
CCTTGAGATTGACTCATTAAAATCAGAGACTGTAACAAAAAAAAAAAAAAAAAAAAAGGGCGGCCGCG
ACTCTAGAGTCGACCTGCAGAAGCTTGGCCGCCATGGCCCAACTTGTTTATTGCAGCTTATAATG

FIGURE 4

MSFLIDSSIMITSQILFFGFGWLFFMRQLFKDYEIRQYVVQVIFSVTFAFSCTMFELIIFEILGV
LNSSSRYFHWKMNLCVILLILVFMVPFYIGYFIVSNIRLLHKQRLLFSCLLWLTFMYFFWKLGDP
FPILSPKHGILSIEQLISRVGVIGVTLMALLSGFGAVNCPYTYMSYFLRNVTDTDILALERRLLQ
TMDMIISKKKRMAMARRTMFQKGEVHNKPSGFWGMIKSVTTSASGSENLTLIQQEVDALEELSRQ
LFLETADLYATKERIEYSKTFKGKYFNFLGYFFSIYCVWKIFMATINIVFDRVGKTDPVTRGIEI
TVNYLGIQFDVKFWSQHISFILVGIIIVTSIRGLLITLTKFFYAISSSKSSNVIVLLLAQIMGMY
FVSSVLLIRMSMPLEYRTIITEVLGELQFNFYHRWFDVIFLVSALSSILFLYLAHKQAPEKQMAP

Important features:

Signal peptide:

amino acids 1-23

Potential transmembrane domains:

amino acids 37-55, 81-102, 150-168, 288-311, 338-356, 375-398, 425-444

N-glycosylation sites.

amino acids 67-70, 180-183 and 243-246

Eukaryotic cobalamin-binding proteins amino acids 151-160

FIGURE 5

AGCAGGGAAATCCGGATGTCTCGGTTATGAAGTGGAGCAGTGAGTGTGAGCCTCAACATAGTTCC
AGAACTCTCCATCCGGACTAGTTATTGAGCATCTGCCTCTCATATCACCAGTGGCCATCTGAGGT
GTTTCCCTGGCTCTGAAGGGGTAGGCACATGGCCAGGTGCTTCAGCCTGGTGTTGCTTCTCACT
TCCATCTGGACCACGAGGCTCCTGGTCCAAGGCTCTTTGCGTGCAGAAGAGCTTTCCATCCAGGT
GTCATGCAGAATTATGGGGATCACCCTTGTGAGCAAAAAGGCGAACCAGCAGCTGAATTTCACAG
AAGCTAAGGAGGCCTGTAGGCTGCTGGGACTAAGTTTGGCCGGCAAGGACCAAGTTGAAACAGCC
TTGAAAGCTAGCTTTGAAACTTGCAGCTATGGCTGGGTTGGAGATGGATTCGTGGTCATCTCTAG
GATTAGCCCAAACCCCAAGTGTGGGAAAAATGGGGTGGGTGTCCTGATTTGGAAGGTTCCAGTGA
GCCGACAGTTTGCAGCCTATTGTTACAACTCATCTGATACTTGGACTAACTCGTGCATTCCAGAA
ATTATCACCACCAAAGATCCCATATTCAACACTCAAACTGCAACACAAACAACAGAATTTATTGT
CAGTGACAGTACCTACTCGGTGGCATCCCCTTACTCTACAATACCTGCCCCTACTACTACTCCTC
CTGCTCCAGCTTCCACTTCTATTCCACGGAGAAAAAAATTGATTTGTGTCACAGAAGTTTTTATG
GAAACTAGCACCATGTCTACAGAAACTGAACCATTTGTTGAAAATAAAGCAGCATTCAAGAATGA
AGCTGCTGGGTTTGGAGGTGTCCCCACGGCTCTGCTAGTGCTTGCTCTCCTCTTCTTTGGTGCTG
CAGCTGGTCTTGGATTTTGCTATGTCAAAAGGTATGTGAAGGCCTTCCCTTTTACAAACAAGAAT
CAGCAGAAGGAAATGATCGAAACCAAAGTAGTAAAGGAGGAGAAGGCCAATGATAGCAACCCTAA
TGAGGAATCAAAGAAAACTGATAAAAACCCAGAAGAGTCCAAGAGTCCAAGCAAAACTACCGTGC
GATGCCTGGAAGCTGAAGTTTAGATGAGACAGAAATGAGGAGACACACCTGAGGCTGGTTTCTTT
CATGCTCCTTACCCTGCCCCAGCTGGGGAAATCAAAAGGGCCAAAGAACCAAAGAAGAAAGTCCA
CCCTTGGTTCCTAACTGGAATCAGCTCAGGACTGCCATTGGACTATGGAGTGCACCAAAGAGAAT
GCCCTTCTCCTTATTGTAACCCTGTCTGGATCCTATCCTCCTACCTCCAAAGCTTCCCACGGCCT
TTCTAGCCTGGCTATGTCCTAATAATATCCCACTGGGAGAAAGGAGTTTTGCAAAGTGCAAGGAC
CTAAAACATCTCATCAGTATCCAGTGGTAAAAGGCCTCCTGGCTGTCTGAGGCTAGGTGGGTTG
AAAGCCAAGGAGTCACTGAGACCAAGGCTTTCTCTACTGATTCCGCAGCTCAGACCCTTTCTTCA
GCTCTGAAAGAGAAACACGTATCCCACCTGACATGTCCTTCTGAGCCCGGTAAGAGCAAAAGAAT
GGCAGAAAAGTTTAGCCCCTGAAAGCCATGGAGATTCTCATAACTTGAGACCTAATCTCTGTAAA
GCTAAAATAAAGAAATAGAACAAGGCTGAGGATACGACAGTACACTGTCAGCAGGGACTGTAAAC
ACAGACAGGGTCAAAGTGTTTCTCTGAACACATTGAGTTGGAATCACTGTTTAGAACACACACA
CTTACTTTTTCTGGTCTCTACCACTGCTGATATTTTCTCTAGGAAATATACTTTTACAAGTAACA
AAAATAAAAACTCTTATAAATTTCTATTTTTATCTGAGTTACAGAAATGATTACTAAGGAAGATT
ACTCAGTAATTTGTTTAAAAAGTAATAAAATTCAACAAACATTTGCTGAATAGCTACTATATGTC
AAGTGCTGTGCAAGGTATTACACTCTGTAATTGAATATTATTCCTCAAAAAATTGCACATAGTAG
AACGCTATCTGGGAAGCTATTTTTTTCAGTTTTGATATTTCTAGCTTATCTACTTCCAAACTAAT
TTTTATTTTTGCTGAGACTAATCTTATTCATTTCTCTAATATGGCAACCATTATAACCTTAATT
TATTATTAACATACCTAAGAAGTACATTGTTACCTCTATATACCAAAGCACATTTTAAAAGTGCC
ATTAACAAATGTATCACTAGCCCTCCTTTTCCAACAAGAAGGGACTGAGAGATGCAGAAATATT
TGTGACAAAAAATTAAAGCATTTAGAAAACTT

FIGURE 6

MARCFSLVLLLTSIWTTRLLVQGSLRAEELSIQVSCRIMGITLVSKKANQQLNFTEAKEACRLLG
LSLAGKDQVETALKASFETCSYGWVGDGFVVISRISPNPKCGKNGVGVLIWKVPVSRQFAAYCYN
SSDTWTNSCIPEIITTKDPIFNTQTATQTTEFIVSDSTYSVASPYSTIPAPTTTPPAPASTSIPR
RKKLICVTEVFMETSTMSTETEPFVENKAAFKNEAAGFGGVPTALLVLALLFFGAAAGLGFCYVK
RYVKAFPFTNKNQQKEMIETKVVKEEKANDSNPNEESKKTDKNPEESKSPSKTTVRCLEAEV

Signal sequence:
amino acids 1-16

Transmembrane domain:
amino acids 235-254

N-glycosylation site.
amino acids 53-57, 130-134, 289-293

Casein kinase II phosphorylation site.
amino acids 145-149, 214-218

Tyrosine kinase phosphorylation site.
amino acids 79-88

N-myristoylation site.
amino acids 23-29, 65-71, 234-240, 235-239, 249-255, 253-259

FIGURE 7

```
CGCCGCGCTCCCGCACCCGCGGCCCGCCCACCGCGCCGCTCCCGCATCTGCACCCGCAGCCCGGC
GGCCTCCCGGCGGGAGCGAGCAGATCCAGTCCGGCCCGCAGCGCAACTCGGTCCAGTCGGGGCGG
CGGCTGCGGGCGCAGAGCGGAGATGCAGCGGCTTGGGGCCACCCTGCTGTGCCTGCTGCTGGCGG
CGGCGGTCCCCACGGCCCCCGCGCCCGCTCCGACGGCGACCTCGGCTCCAGTCAAGCCCGGCCCG
GCTCTCAGCTACCCGCAGGAGGAGGCCACCCTCAATGAGATGTTCCGCGAGGTTGAGGAACTGAT
GGAGGACACGCAGCACAAATTGCGCAGCGCGGTGGAAGAGATGGAGGCAGAAGAAGCTGCTGCTA
AAGCATCATCAGAAGTGAACCTGGCAAACTTACCTCCCAGCTATCACAATGAGACCAACACAGAC
ACGAAGGTTGGAAATAATACCATCCATGTGCACCGAGAAATTCACAAGATAACCAACAACCAGAC
TGGACAAATGGTCTTTTCAGAGACAGTTATCACATCTGTGGGAGACGAAGAAGGCAGAAGGAGCC
ACGAGTGCATCATCGACGAGGACTGTGGGCCCAGCATGTACTGCCAGTTTGCCAGCTTCCAGTAC
ACCTGCCAGCCATGCCGGGGCCAGAGGATGCTCTGCACCCGGGACAGTGAGTGCTGTGGAGACCA
GCTGTGTGTCTGGGGTCACTGCACCAAAATGGCCACCAGGGGCAGCAATGGGACCATCTGTGACA
ACCAGAGGGACTGCCAGCCGGGGCTGTGCTGTGCCTTCCAGAGAGGCCTGCTGTTCCCTGTGTGC
ACACCCCTGCCCGTGGAGGGCGAGCTTTGCCATGACCCCGCCAGCCGGCTTCTGGACCTCATCAC
CTGGGAGCTAGAGCCTGATGGAGCCTTGGACCGATGCCCTTGTGCCAGTGGCCTCCTCTGCCAGC
CCCACAGCCACAGCCTGGTGTATGTGTGCAAGCCGACCTTCGTGGGGAGCCGTGACCAAGATGGG
GAGATCCTGCTGCCCAGAGAGGTCCCCGATGAGTATGAAGTTGGCAGCTTCATGGAGGAGGTGCG
CCAGGAGCTGGAGGACCTGGAGAGGAGCCTGACTGAAGAGATGGCGCTGGGGGAGCCTGCGGCTG
CCGCCGCTGCACTGCTGGGAGGGGAAGAGATTTAGATCTGGACCAGGCTGTGGGTAGATGTGCAA
TAGAAATAGCTAATTTATTTCCCCAGGTGTGTGCTTTAGGCGTGGGCTGACCAGGCTTCTTCCTA
CATCTTCTTCCCAGTAAGTTTCCCCTCTGGCTTGACAGCATGAGGTGTTGTGCATTTGTTCAGCT
CCCCCAGGCTGTTCTCCAGGCTTCACAGTCTGGTGCTTGGGAGAGTCAGGCAGGGTTAAACTGCA
GGAGCAGTTTGCCACCCCTGTCCAGATTATTGGCTGCTTTGCCTCTACCAGTTGGCAGACAGCCG
TTTGTTCTACATGGCTTTGATAATTGTTTGAGGGGAGGAGATGGAAACAATGTGGAGTCTCCCTC
TGATTGGTTTTGGGGAAATGTGGAGAAGAGTGCCCTGCTTTGCAAACATCAACCTGGCAAAAATG
CAACAAATGAATTTTCCACGCAGTTCTTTCCATGGGCATAGGTAAGCTGTGCCTTCAGCTGTTGC
AGATGAAATGTTCTGTTCACCCTGCATTACATGTGTTTATTCATCCAGCAGTGTTGCTCAGCTCC
TACCTCTGTGCCAGGGCAGCATTTTCATATCCAAGATCAATTCCCTCTCTCAGCACAGCCTGGGG
AGGGGGTCATTGTTCTCCTCGTCCATCAGGGATCTCAGAGGCTCAGAGACTGCAAGCTGCTTGCC
CAAGTCACACAGCTAGTGAAGACCAGAGCAGTTTCATCTGGTTGTGACTCTAAGCTCAGTGCTCT
CTCCACTACCCCACACCAGCCTTGGTGCCACCAAAAGTGCTCCCCAAAAGGAAGGAGAATGGGAT
TTTTCTTGAGGCATGCACATCTGGAATTAAGGTCAAACTAATTCTCACATCCCTCTAAAAGTAAA
CTACTGTTAGGAACAGCAGTGTTCTCACAGTGTGGGGCAGCCGTCCTTCTAATGAAGACAATGAT
ATTGACACTGTCCCTCTTTGGCAGTTGCATTAGTAACTTTGAAAGGTATATGACTGAGCGTAGCA
TACAGGTTAACCTGCAGAAACAGTACTTAGGTAATTGTAGGGCGAGGATTATAAATGAAATTTGC
AAAATCACTTAGCAGCAACTGAAGACAATTATCAACCACGTGGAGAAAATCAAACCGAGCAGGGC
TGTGTGAAACATGGTTGTAATATGCGACTGCGAACACTGAACTCTACGCCACTCCACAAATGATG
TTTTCAGGTGTCATGGACTGTTGCCACCATGTATTCATCCAGAGTTCTTAAAGTTTAAAGTTGCA
CATGATTGTATAAGCATGCTTTCTTTGAGTTTTAAATTATGTATAAACATAAGTTGCATTTAGAA
ATCAAGCATAAATCACTTCAACTGCAAAAAAAAAAAAAAAAAAAAAAAAAA
```

FIGURE 8

MQRLGATLLCLLLAAAVPTAPAPAPTATSAPVKPGPALSYPQEEATLNEMFREVEELMEDTQHKL
RSAVEEMEAEEAAAKASSEVNLANLPPSYHNETNTDTKVGNNTIHVHREIHKITNNQTGQMVFSE
TVITSVGDEEGRRSHECIIDEDCGPSMYCQFASFQYTCQPCRGQRMLCTRDSECCGDQLCVWGHC
TKMATRGSNGTICDNQRDCQPGLCCAFQRGLLFPVCTPLPVEGELCHDPASRLLDLITWELEPDG
ALDRCPCASGLLCQPHSHSLVYVCKPTFVGSRDQDGEILLPREVPDEYEVGSFMEEVRQELEDLE
RSLTEEMALGEPAAAAAALLGGEEI

Signal sequence:

amino acids 1-19

N-glycosylation site.

amino acids 96-100, 106-110, 121-125, 204-208

Casein kinase II phosphorylation site.

amino acids 46-50, 67-71, 98-102, 135-139, 206-210, 312-316, 327-331

N-myristoylation site.

amino acids 202-208, 217-223

Amidation site.

amino acids 140-144

FIGURE 9

<u>CGG</u>ACGCGTGGGCGGACGCGTGGGGGCTGTGAGAAAGTGCCAATAAATACATCATGCAACCCCAC
GGCCCACCTTGTGAACTCCTCGTGCCCAGGGCTGATGTGCGTCTTCCAGGGCTACTCATCCAAAG
GCCTAATCCAACGTTCTGTCTTCAATCTGCAAATCTATGGGGTCCTGGGGCTCTTCTGGACCCTT
AACTGGGTACTGGCCCTGGGCCAATGCGTCCTCGCTGGAGCCTTTGCCTCCTTCTACTGGGCCTT
CCACAAGCCCCAGGACATCCCTACCTTCCCCTTAATCTCTGCCTTCATCCGCACACTCCGTTACC
ACACTGGGTCATTGGCATTTGGAGCCCTCATCCTGACCCTTGTGCAGATAGCCCGGGTCATCTTG
GAGTATATTGACCACAAGCTCAGAGGAGTGCAGAACCCTGTAGCCCGCTGCATCATGTGCTGTTT
CAAGTGCTGCCTCTGGTGTCTGGAAAAATTTATCAAGTTCCTAAACCGCAATGCATACATCATGA
TCGCCATCTACGGGAAGAATTTCTGTGTCTCAGCCAAAAATGCGTTCATGCTACTCATGCGAAAC
ATTGTCAGGGTGGTCGTCCTGGACAAAGTCACAGACCTGCTGCTGTTCTTTGGGAAGCTGCTGGT
GGTCGGAGGCGTGGGGGTCCTGTCCTTCTTTTTTTCTCCGGTCGCATCCCGGGGCTGGGTAAAG
ACTTTAAGAGCCCCCACCTCAACTATTACTGGCTGCCCATCATGACCTCCATCCTGGGGGCCTAT
GTCATCGCCAGCGGCTTCTTCAGCGTTTTCGGCATGTGTGTGGACACGCTCTTCCTCTGCTTCCT
GGAAGACCTGGAGCGGAACAACGGCTCCCTGGACCGGCCCTACTACATGTCCAAGAGCCTTCTAA
AGATTCTGGGCAAGAAGAACGAGGCGCCCCGGACAACAAGAAGAGGAAGAAG<b><u>TGA</u></b>CAGCTCCGG
CCCTGATCCAGGACTGCACCCCACCCCCACCGTCCAGCCATCCAACCTCACTTCGCCTTACAGGT
CTCCATTTTGTGGTAAAAAAGGTTTTAGGCCAGGCGCCGTGGCTCACGCCTGTAATCCAACACT
TTGAGAGGCTGAGGCGGGCGGATCACCTGAGTCAGGAGTTCGAGACCAGCCTGGCCAACATGGTG
AAACCTCCGTCTCTATTAAAAATACAAAAATTAGCCGAGAGTGGTGGCATGCACCTGTCATCCCA
GCTACTCGGGAGGCTGAGGCAGGAGAATCGCTTGAACCCGGGAGGCAGAGGTTGCAGTGAGCCGA
GATCGCGCCACTGCACTCCAACCTGGGTGACAGACTCTGTCTCCAAAACAAAACAAACAAACAAA
AAGATTTTATTAAAGATATTTTGTTAACTC

FIGURE 10

RTRGRTRGGCEKVPINTSCNPTAHLVNSSCPGLMCVFQGYSSKGLIQRSVFNLQIYGVLGLFWTL
NWVLALGQCVLAGAFASFYWAFHKPQDIPTFPLISAFIRTLRYHTGSLAFGALILTLVQIARVIL
EYIDHKLRGVQNPVARCIMCCFKCCLWCLEKFIKFLNRNAYIMIAIYGKNFCVSAKNAFMLLMRN
IVRVVVLDKVTDLLLFFGKLLVVGGVGVLSFFFFSGRIPGLGKDFKSPHLNYYWLPIMTSILGAY
VIASGFFSVFGMCVDTLFLCFLEDLERNNGSLDRPYYMSKSLLKILGKKNEAPPDNKKRKK

Important features:

Transmembrane domains:

amino acids 57-80 (type II), 110-126, 215-231, 254-274

N-glycosylation sites.

amino acids 16-20, 27-31, 289-293

Hypothetical YBR002c family proteins.

amino acids 276-288

Ammonium transporters proteins.

amino acids 204-231

N-myristoylation sites.

amino acids 60-66, 78-84

Amidation site.

amino acids 306-310

FIGURE 11

GCCCCGCGCCCGGCGCCGGGCGCCCGAAGCCGGGAGCCACCGCCATGGGGGCCTGCCTGGGAGCCTGC
TCCCTGCTCAGCTGCGCGTCCTGCCTCTGCGGCTCTGCCCCCTGCATCCTGTGCAGCTGCTGCCCCGC
CAGCCGCAACTCCACCGTGAGCCGCCTCATCTTCACGTTCTTCCTCTTCCTGGGGGTGCTGGTGTCCA
TCATTATGCTGAGCCCGGGCGTGGAGAGTCAGCTCTACAAGCTGCCCTGGGTGTGTGAGGAGGGGGCC
GGGATCCCCACCGTCCTGCAGGGCCACATCGACTGTGGCTCCCTGCTTGGCTACCGCGCTGTCTACCG
CATGTGCTTCGCCACGGCGGCCTTCTTCTTCTTCTTTTTCACCCTGCTCATGCTCTGCGTGAGCAGCA
GCCGGGACCCCGGGCTGCCATCCAGAATGGGTTTTGGTTCTTTAAGTTCCTGATCCTGGTGGGCCTC
ACCGTGGGTGCCTTCTACATCCCTGACGGCTCCTTCACCAACATCTGGTTCTACTTCGGCGTCGTGGG
CTCCTTCCTCTTCATCCTCATCCAGCTGGTGCTGCTCATCGACTTTGCGCACTCCTGGAACCAGCGGT
GGCTGGGCAAGGCCGAGGAGTGCGATTCCCGTGCCTGGTACGCAGGCCTCTTCTTCTTCACTCTCCTC
TTCTACTTGCTGTCGATCGCGGCCGTGGCGCTGATGTTCATGTACTACACTGAGCCCAGCGGCTGCCA
CGAGGGCAAGGTCTTCATCAGCCTCAACCTCACCTTCTGTGTCTGCGTGTCCATCGCTGCTGTCCTGC
CCAAGGTCCAGGACGCCCAGCCCAACTCGGGTCTGCTGCAGGCCTCGGTCATCACCCTCTACACCATG
TTTGTCACCTGGTCAGCCCTATCCAGTATCCCTGAACAGAAATGCAACCCCCATTTGCCAACCCAGCT
GGGCAACGAGACAGTTGTGGCAGGCCCCGAGGGCTATGAGACCCAGTGGTGGGATGCCCCGAGCATTG
TGGGCCTCATCATCTTCCTCCTGTGCACCCTCTTCATCAGTCTGCGCTCCTCAGACCACCGGCAGGTG
AACAGCCTGATGCAGACCGAGGAGTGCCCACCTATGCTAGACGCCACACAGCAGCAGCAGCAGCAGGT
GGCAGCCTGTGAGGGCCGGGCCTTTGACAACGAGCAGGACGGCGTCACCTACAGCTACTCCTTCTTCC
ACTTCTGCCTGGTGCTGGCCTCACTGCACGTCATGATGACGCTCACCAACTGGTACAAGCCCGGTGAG
ACCCGGAAGATGATCAGCACGTGGACCGCCGTGTGGGTGAAGATCTGTGCCAGCTGGGCAGGGCTGCT
CCTCTACCTGTGGACCCTGGTAGCCCCACTCCTCCTGCGCAACCGCGACTTCAGCTGAGGCAGCCTCA
CAGCCTGCCATCTGGTGCCTCCTGCCACCTGGTGCCTCTCGGCTCGGTGACAGCCAACCTGCCCCCTC
CCCACACCAATCAGCCAGGCTGAGCCCCACCCCTGCCCCAGCTCCAGGACCTGCCCCTGAGCCGGGC
CTTCTAGTCGTAGTGCCTTCAGGGTCCGAGGAGCATCAGGCTCCTGCAGAGCCCCATCCCCCGCCAC
ACCCACACGGTGGAGCTGCCTCTTCCTTCCCCTCCTCCCTGTTGCCCATACTCAGCATCTCGGATGAA
AGGGCTCCCTTGTCCTCAGGCTCCACGGGAGCGGGGCTGCTGGAGAGAGCGGGGAACTCCCACCACAG
TGGGCATCCGGCACTGAAGCCCTGGTGTTCCTGGTCACGTCCCCAGGGGACCCTGCCCCCTTCCTG
GACTTCGTGCCTTACTGAGTCTCTAAGACTTTTTCTAATAAACAAGCCAGTGCGTGTAAAAAAAA

FIGURE 12

MGACLGACSLLSCASCLCGSAPCILCSCCPASRNSTVSRLIFTFFLFLGVLVSIIMLSPGVESQL
YKLPWVCEEGAGIPTVLQGHIDCGSLLGYRAVYRMCFATAAFFFFFFTLLMLCVSSSRDPRAAIQ
NGFWFFKFLILVGLTVGAFYIPDGSFTNIWFYFGVVGSFLFILIQLVLLIDFAHSWNQRWLGKAE
ECDSRAWYAGLFFFTLLFYLLSIAAVALMFMYYTEPSGCHEGKVFISLNLTFCVCVSIAAVLPKV
QDAQPNSGLLQASVITLYTMFVTWSALSSIPEQKCNPHLPTQLGNETVVAGPEGYETQWWDAPSI
VGLIIFLLCTLFISLRSSDHRQVNSLMQTEECPPMLDATQQQQQQVAACEGRAFDNEQDGVTYSY
SFFHFCLVLASLHVMMTLTNWYKPGETRKMISTWTAVWVKICASWAGLLLYLWTLVAPLLLRNRD
FS

Signal sequence:

amino acids 1-20

Transmembrane domains:

amino acids 40-58, 101-116, 134-150, 162-178, 206-223, 240-257, 272-283, 324-340, 391-406, 428-444

FIGURE 13

CGGGCCAGCCTGGGGCGGCCGGCCAGGAACCACCCGTTAAGGTGTCTTCTCTTTAGGGATGGTGA
GGTTGGAAAAAGACTCCTGTAACCCTCCTCCAGG<u>ATG</u>AACCACCTGCCAGAAGACATGGAGAACG
CTCTCACCGGGAGCCAGAGCTCCCATGCTTCTCTGCGCAATATCCATTCCATCAACCCCACACAA
CTCATGGCCAGGATTGAGTCCTATGAAGGAAGGGAAAAGAAAGGCATATCTGATGTCAGGAGGAC
TTTCTGTTTGTTTGTCACCTTTGACCTCTTATTCGTAACATTACTGTGGATAATAGAGTTAAATG
TGAATGGAGGCATTGAGAACACATTAGAGAAGGAGGTGATGCAGTATGACTACTATTCTTCATAT
TTTGATATATTTCTTCTGGCAGTTTTTCGATTTAAAGTGTTAATACTTGCATATGCTGTGTGCAG
ACTGCGCCATTGGTGGGCAATAGCGTTGACAACGGCAGTGACCAGTGCCTTTTTACTAGCAAAAG
TGATCCTTTCGAAGCTTTTCTCTCAAGGGGCTTTTGGCTATGTGCTGCCCATCATTTCATTCATC
CTTGCCTGGATTGAGACGTGGTTCCTGGATTTCAAAGTGTTACCTCAAGAAGCAGAAGAAGAAAA
CAGACTCCTGATAGTTCAGGATGCTTCAGAGAGGGCAGCACTTATACCTGGTGGTCTTTCTGATG
GTCAGTTTTATTCCCCTCCTGAATCCGAAGCAGGATCTGAAGAAGCTGAAGAAAACAGGACAGT
GAGAAACCACTTTTAGAACTA<u>TGA</u>GTACTACTTTTGTTAAATGTGAAAAACCCTCACAGAAAGTC
ATCGAGGCAAAAGAGGCAGGCAGTGGAGTCTCCCTGTCGACAGTAAAGTTGAAATGGTGACGTC
CACTGCTGGCTTTATTGAACAGCTAATAAAGATTTATTTATTGTAATACCTCACAAACGTTGTAC
CATATCCATGCACATTTAGTTGCCTGCCTGTGGCTGGTAAGGTAATGTCATGATTCATCCTCTCT
TCAGTGAGACTGAGCCTGATGTGTTAACAAATAGGTGAAGAAAGTCTTGTGCTGTATTCCTAATC
AAAAGACTTAATATATTGAAGTAACACTTTTTAGTAAGCAAGATACCTTTTTATTTCAATTCAC
AGAATGGAATTTTTTTGTTTCATGTCTCAGATTTATTTTGTATTTCTTTTTTAACACTCTACATT
TCCCTTGTTTTTTAACTCATGCACATGTGCTCTTTGTACAGTTTTAAAAGTGTAATAAAATCTG
ACATGTCAATGTGGCTAGTTTTATTTTTCTTGTTTTGCATTATGTGTATGGCCTGAAGTGTTGGA
CTTGCAAAAGGGGAAGAAAGGAATTGCGAATACATGTAAAATGTCACCAGACATTTGTATTATTT
TTATCATGAAATCATGTTTTTCTCTGATTGTTCTGAAATGTTCTAAATACTCTTATTTTGAATGC
ACAAAATGACTTAAACCATTCATATCATGTTTCCTTTGCGTTCAGCCAATTTCAATTAAAATGAA
CTAAATTAAAAA

FIGURE 14

MNHLPEDMENALTGSQSSHASLRNIHSINPTQLMARIESYEGREKKGISDVRRTFCLFVTFDLLF
VTLLWIIELNVNGGIENTLEKEVMQYDYYSSYFDIFLLAVFRFKVLILAYAVCRLRHWWAIALTT
AVTSAFLLAKVILSKLFSQGAFGYVLPIISFILAWIETWFLDFKVLPQEAEEENRLLIVQDASER
AALIPGGLSDGQFYSPPESEAGSEEAEEKQDSEKPLLEL

Important features of the protein:

Signal peptide:

amino acids 1-20

Transmembrane domains:

amino acids 54-72, 100-118, 130-144, 146-166

N-myristoylation sites.

amino acids 14-20, 78-84, 79-85, 202-208, 217-223

FIGURE 15

ACTCGAACGCAGTTGCTTCGGGACCCAGGACCCCCTCGGGCCCGACCCGCCAGGAAAGACTGAGG
CCGCGGCCTGCCCCGCCCGGCTCCCTGCGCCGCCGCCGCCTCCCGGGACAGAAG<u>ATG</u>TGCTCCAG
GGTCCCTCTGCTGCTGCCGCTGCTCCTGCTACTGGCCCTGGGGCCTGGGGTGCAGGGCTGCCCAT
CCGGCTGCCAGTGCAGCCAGCCACAGACAGTCTTCTGCACTGCCCGCCAGGGGACCACGGTGCCC
CGAGACGTGCCACCCGACACGGTGGGGCTGTACGTCTTTGAGAACGGCATCACCATGCTCGACGC
AGGCAGCTTTGCCGGCCTGCCGGGCCTGCAGCTCCTGGACCTGTCACAGAACCAGATCGCCAGCC
TGCCCAGCGGGGTCTTCCAGCCACTCGCCAACCTCAGCAACCTGGACCTGACGGCCAACAGGCTG
CATGAAATCACCAATGAGACCTTCCGTGGCCTGCGGCGCCTCGAGCGCCTCTACCTGGGCAAGAA
CCGCATCCGCCACATCCAGCCTGGTGCCTTCGACACGCTCGACCGCCTCCTGGAGCTCAAGCTGC
AGGACAACGAGCTGCGGCACTGCCCCGCTGCGCCTGCCCCGCCTGCTGCTGCTGGACCTCAGC
CACAACAGCCTCCTGGCCCTGGAGCCCGGCATCCTGGACACTGCCAACGTGGAGGCGCTGCGGCT
GGCTGGTCTGGGGCTGCAGCAGCTGGACGAGGGGCTCTTCAGCCGCTTGCGCAACCTCCACGACC
TGGATGTGTCCGACAACCAGCTGGAGCGAGTGCCACCTGTGATCCGAGGCCTCCGGGGCCTGACG
CGCCTGCGGCTGGCCGGCAACACCCGCATTGCCCAGCTGCGGCCCGAGGACCTGGCCGGCCTGGC
TGCCCTGCAGGAGCTGGATGTGAGCAACCTAAGCCTGCAGGCCCTGCCTGGCGACCTCTCGGGCC
TCTTCCCCCGCCTGCGGCTGCTGGCAGCTGCCCGCAACCCCTTCAACTGCGTGTGCCCCCTGAGC
TGGTTTGGCCCCTGGGTGCGCGAGAGCCACGTCACACTGGCCAGCCCTGAGGAGACGCGCTGCCA
CTTCCCGCCCAAGAACGCTGGCCGGCTGCTCCTGGAGCTTGACTACGCCGACTTTGGCTGCCCAG
CCACCACCACCACAGCCACAGTGCCCACCACGAGGCCCGTGGTGCGGGAGCCCACAGCCTTGTCT
TCTAGCTTGGCTCCTACCTGGCTTAGCCCCACAGCGCCGGCCACTGAGGCCCCAGCCCGCCCTC
CACTGCCCCACCGACTGTAGGGCCTGTCCCCAGCCCCAGGACTGCCCACCGTCCACCTGCCTCA
ATGGGGGCACATGCCACCTGGGGACACGGCACCACCTGGCGTGCTTGTGCCCCGAAGGCTTCACG
GGCCTGTACTGTGAGAGCCAGATGGGGCAGGGGACACGGCCCAGCCCTACACCAGTCACGCCGAG
GCCACCACGGTCCCTGACCCTGGGCATCGAGCCGGTGAGCCCCACCTCCCTGCGCGTGGGGCTGC
AGCGCTACCTCCAGGGGAGCTCCGTGCAGCTCAGGAGCCTCCGTCTCACCTATCGCAACCTATCG
GGCCCTGATAAGCGGCTGGTGACGCTGCGACTGCCTGCCTCGCTCGCTGAGTACACGGTCACCCA
GCTGCGGCCCAACGCCACTTACTCCGTCTGTGTCATGCCTTTGGGGCCCGGGCGGGTGCCGGAGG
GCGAGGAGGCCTGCGGGGAGCCCATACACCCCAGCCGTCCACTCCAACCACGCCCCAGTCACC
CAGGCCCGCGAGGGCAACCTGCCGCTCCTCATTGCGCCCGCCCTGGCCGCGGTGCTCCTGGCCGC
GCTGGCTGCGGTGGGGGCAGCCTACTGTGTGCGGCGGGGCGGGCCATGGCAGCAGCGGCTCAGG
ACAAAGGGCAGGTGGGGCCAGGGGCTGGGCCCCTGGAACTGGAGGGAGTGAAGGTCCCCTTGGAG
CCAGGCCCGAAGGCAACAGAGGGCGGTGGAGAGGCCCTGCCCAGCGGGTCTGAGTGTGAGGTGCC
ACTCATGGGCTTCCCAGGGCCTGGCCTCCAGTCACCCCTCCACGCAAAGCCCTACATC<u>TAA</u>GCCA
GAGAGAGACAGGGCAGCTGGGGCCGGGCTCTCAGCCAGTGAGATGGCCAGCCCCCTCCTGCTGCC
ACACCACGTAAGTTCTCAGTCCCAACCTCGGGGATGTGTGCAGACAGGGCTGTGTGACCACAGCT
GGGCCCTGTTCCCTCTGGACCTCGGTCTCCTCATCTGTGAGATGCTGTGGCCCAGCTGACGAGCC
CTAACGTCCCCAGAACCGAGTGCCTATGAGGACAGTGTCCGCCCTGCCCTCCGCAACGTGCAGTC
CCTGGGCACGGCGGGCCCTGCCATGTGCTGGTAACGCATGCCTGGGTCCTGCTGGGCTCTCCCAC
TCCAGGCGGACCCTGGGGGCCAGTGAAGGAAGCTCCCGGAAAGAGCAGAGGGAGAGCGGGTAGGC
GGCTGTGTGACTCTAGTCTTGGCCCCAGGAAGCGAAGGAACAAAAGAAACTGGAAAGGAAGATGC
TTTAGGAACATGTTTGCTTTTTTAAAATATATATATTTATAAGAGATCCTTTCCCATTTATTCT
GGGAAGATGTTTTTCAAACTCAGAGACAAGGACTTTGGTTTTTGTAAGACAAACGATGATATGAA
GGCCTTTTGTAAGAAAAAATAAAAGATGAAGTGTGAAA

FIGURE 16

```
MCSRVPLLLPLLLLLALGPGVQGCPSGCQCSQPQTVFCTARQGTTVPRDVPPDTVGLYVFENGIT
MLDAGSFAGLPGLQLLDLSQNQIASLPSGVFQPLANLSNLDLTANRLHEITNETFRGLRRLERLY
LGKNRIRHIQPGAFDTLDRLLELKLQDNELRALPPLRLPRLLLLDLSHNSLLALEPGILDTANVE
ALRLAGLGLQQLDEGLFSRLRNLHDLDVSDNQLERVPPVIRGLRGLTRLRLAGNTRIAQLRPEDL
AGLAALQELDVSNLSLQALPGDLSGLFPRLRLLAAARNPFNCVCPLSWFGPWVRESHVTLASPEE
TRCHFPPKNAGRLLLELDYADFGCPATTTTATVPTTRPVVREPTALSSSLAPTWLSPTAPATEAP
SPPSTAPPTVGPVPQPQDCPPSTCLNGGTCHLGTRHHLACLCPEGFTGLYCESQMGQGTRPSPTP
VTPRPPRSLTLGIEPVSPTSLRVGLQRYLQGSSVQLRSLRLTYRNLSGPDKRLVTLRLPASLAEY
TVTQLRPNATYSVCVMPLGPGRVPEGEEACGEAHTPPAVHSNHAPVTQAREGNLPLLIAPALAAV
LLAALAAVGAAYCVRRGRAMAAAAQDKGQVGPGAGPLELEGVKVPLEPGPKATEGGGEALPSGSE
CEVPLMGFPGPGLQSPLHAKPYI
```

Important features:

Signal peptide:

amino acids 1-23

Transmembrane domain:

amino acids 579-599

EGF-like domain cysteine pattern signature.

amino acids 430-442

Leucine zipper pattern.

amino acids 197-219, 269-291

N-glycosylation sites.

amino acids 101-105, 117-121, 273-277, 500-504, 528-532

Tyrosine kinase phosphorylation sites.

amino acids 124-131, 337-345

N-myristoylation sites.

amino acids 23-29, 27-33, 70-76, 142-148, 187-193, 348-354, 594-600, 640-646

FIGURE 17

```
GCAGCGGCGAGGCGGCGGTGGTGGCTGAGTCCGTGGTGGCAGAGGCGAAGGCGACAGCTATGCG
GGTCCGGATAGGGCTGACGCTGCTGCTGTGTGCGGTGCTGCTGAGCTTGGCCTCGGCGTCCTCGG
ATGAAGAAGGCAGCCAGGATGAATCCTTAGATTCCAAGACTACTTTGACATCAGATGAGTCAGTA
AAGGACCATACTACTGCAGGCAGAGTAGTTGCTGGTCAAATATTTCTTGATTCAGAAGAATCTGA
ATTAGAATCCTCTATTCAAGAAGAGGAAGACAGCCTCAAGAGCCAAGAGGGGGAAAGTGTCACAG
AAGATATCAGCTTTCTAGAGTCTCCAAATCCAGAAAACAAGGACTATGAAGAGCCAAAGAAAGTA
CGGAAACCAGCTTTGACCGCCATTGAAGGCACAGCACATGGGGAGCCCTGCCACTTCCCTTTTCT
TTTCCTAGATAAGGAGTATGATGAATGTACATCAGATGGGAGGGAAGATGGCAGACTGTGGTGTG
CTACAACCTATGACTACAAAGCAGATGAAAAGTGGGGCTTTTGTGAAACTGAAGAAGAGGCTGCT
AAGAGACGGCAGATGCAGGAAGCAGAAATGATGTATCAAACTGGAATGAAAATCCTTAATGGAAG
CAATAAGAAAGCCAAAAAGAGAAGCATATCGGTATCTCCAAAAGGCAGCAAGCATGAACCATA
CCAAAGCCCTGGAGAGAGTGTCATATGCTCTTTTATTTGGTGATTACTTGCCACAGAATATCCAG
GCAGCGAGAGAGATGTTTGAGAAGCTGACTGAGGAAGGCTCTCCCAAGGGACAGACTGCTCTTGG
CTTTCTGTATGCCTCTGGACTTGGTGTTAATTCAAGTCAGGCAAAGGCTCTTGTATATTATACAT
TTGGAGCTCTTGGGGGCAATCTAATAGCCCACATGGTTTTGGTAAGTAGACTTTAGTGGAAGGCT
AATAATATTAACATCAGAAGAATTTGTGGTTTATAGCGGCCACAACTTTTTCAGCTTTCATGATC
CAGATTTGCTTGTATTAAGACCAAATATTCAGTTGAACTTCCTTCAAATTCTTGTTAATGGATAT
AACACATGGAATCTACATGTAAATGAAAGTTGGTGGAGTCCACAATTTTTCTTTAAAATGATTAG
TTTGGCTGATTGCCCCTAAAAAGAGAGATCTGATAAATGGCTCTTTTAAATTTTCTCTGAGTTG
GAATTGTCAGAATCATTTTTTACATTAGATTATCATAATTTTAAAAATTTTTCTTTAGTTTTTCA
AAATTTTGTAAATGGTGGCTATAGAAAAACAACATGAAATATTATACAATATTTTGCAACAATGC
CCTAAGAATTGTTAAAATTCATGGAGTTATTTGTGCAGAATGACTCCAGAGAGCTCTACTTTCTG
TTTTTTACTTTTCATGATTGGCTGTCTTCCCATTTATTCTGGTCATTTATTGCTAGTGACACTGT
GCCTGCTTCCAGTAGTCTCATTTTCCCTATTTGCTAATTTGTTACTTTTTCTTTGCTAATTTGG
AAGATTAACTCATTTTTAATAAAATTATGTCTAAGATTAAAAAAAAAAAAAAAAAAAAAAAAAAA
AAAAAAAAAAAAAAAAAAAAAAAAAAAAAAAAAAAAAAAAAAA
```

FIGURE 18

MRVRIGLTLLLCAVLLSLASASSDEEGSQDESLDSKTTLTSDESVKDHTTAGRVVAGQIFLDSEESEL
ESSIQEEEDSLKSQEGESVTEDISFLESPNPENKDYEEPKKVRKPALTAIEGTAHGEPCHFPFLFLDK
EYDECTSDGREDGRLWCATTYDYKADEKWGFCETEEEAAKRRQMQEAEMMYQTGMKILNGSNKKSQKR
EAYRYLQKAASMNHTKALERVSYALLFGDYLPQNIQAAREMFEKLTEEGSPKGQTALGFLYASGLGVN
SSQAKALVYYTFGALGGNLIAHMVLVSRL

Important features:

Signal peptide:

amino acids 1-21

N-glycosylation sites.

amino acids 195-199, 217-221, 272-276

Tyrosine kinase phosphorylation site.

amino acids 220-228

N-myristoylation sites.

amino acids 120-126, 253-259, 268-274, 270-274, 285-291, 289-295

Glycosaminoglycan attachment site.

amino acids 267-271

Microbodies C-terminal targeting signal.

amino acids 299-303

Type II fibronectin collagen-binding domain protein.

amino acids 127-169

Fructose-bisphosphate aldolase class-II protein.

amino acids 101-119

FIGURE 19

AATTCAGATTTTAAGCCCATTCTGCAGTGGAATTTCATGAACTAGCAAGAGGACACCATCTTCTT
GTATTATACAAGAAAGGAGTGTACCTATCACACACAGGGGGAAAA<u>ATG</u>CTCTTTTGGGTGCTAGG
CCTCCTAATCCTCTGTGGTTTTCTGTGGACTCGTAAAGGAAAACTAAAGATTGAAGACATCACTG
ATAAGTACATTTTTATCACTGGATGTGACTCGGGCTTTGGAAACTTGGCAGCCAGAACTTTTGAT
AAAAAGGGATTTCATGTAATCGCTGCCTGTCTGACTGAATCAGGATCAACAGCTTTAAAGGCAGA
AACCTCAGAGAGACTTCGTACTGTGCTTCTGGATGTGACCGACCCAGAGAATGTCAAGAGGACTG
CCCAGTGGGTGAAGAACCAAGTTGGGGAGAAAGGTCTCTGGGGTCTGATCAATAATGCTGGTGTT
CCCGGCGTGCTGGCTCCCACTGACTGGCTGACACTAGAGGACTACAGAGAACCTATTGAAGTGAA
CCTGTTTGGACTCATCAGTGTGACACTAAATATGCTTCCTTTGGTCAAGAAAGCTCAAGGGAGAG
TTATTAATGTCTCCAGTGTTGGAGGTCGCCTTGCAATCGTTGGAGGGGCTATACTCCATCCAAA
TATGCAGTGGAAGGTTTCAATGACAGCTTAAGACGGGACATGAAAGCTTTTGGTGTGCACGTCTC
ATGCATTGAACCAGGATTGTTCAAAACAAACTTGGCAGATCCAGTAAAGGTAATTGAAAAAAAAC
TCGCCATTTGGGAGCAGCTGTCTCCAGACATCAAACAACAATATGGAGAAGGTTACATTGAAAAA
AGTCTAGACAAACTGAAAGGCAATAAATCCTATGTGAACATGGACCTCTCTCCGGTGGTAGAGTG
CATGGACCACGCTCTAACAAGTCTCTTCCCTAAGACTCATTATGCCGCTGGAAAAGATGCCAAAA
TTTTCTGGATACCTCTGTCTCACATGCCAGCAGCTTTGCAAGACTTTTTATTGTTGAAACAGAAA
GCAGAGCTGGCTAATCCCAAGGCAGTG<u>TGA</u>CTCAGCTAACCACAAATGTCTCCTCCAGGCTATGA
AATTGGCCGATTTCAAGAACACATCTCCTTTTCAACCCCATTCCTTATCTGCTCCAACCTGGACT
CATTTAGATCGTGCTTATTTGGATTGCAAAAGGGAGTCCCACCATCGCTGGTGGTATCCCAGGGT
CCCTGCTCAAGTTTTCTTTGAAAAGGAGGGCTGGAATGGTACATCACATAGGCAAGTCCTGCCCT
GTATTTAGGCTTTGCCTGCTTGGTGTGATGTAAGGGAAATTGAAAGACTTGCCCATTCAAAATGA
TCTTTACCGTGGCCTGCCCCATGCTTATGGTCCCCAGCATTTACAGTAACTTGTGAATGTTAAGT
ATCATCTCTTATCTAAATATTAAAAGATAAGTCAACCCAAAAAAAAAAAAAAAAAAAAAAAAAAA
AAAAAAAAAAAA

FIGURE 20

MLFWVLGLLILCGFLWTRKGKLKIEDITDKYIFITGCDSGFGNLAARTFDKKGFHVIAACLTESG
STALKAETSERLRTVLLDVTDPENVKRTAQWVKNQVGEKGLWGLINNAGVPGVLAPTDWLTLEDY
REPIEVNLFGLISVTLNMLPLVKKAQGRVINVSSVGGRLAIVGGGYTPSKYAVEGFNDSLRRDMK
AFGVHVSCIEPGLFKTNLADPVKVIEKKLAIWEQLSPDIKQQYGEGYIEKSLDKLKGNKSYVNMD
LSPVVECMDHALTSLFPKTHYAAGKDAKIFWIPLSHMPAALQDFLLLKQKAELANPKAV

Important features of the protein:

Signal peptide:

amino acids 1-17

Transmembrane domain:

amino acids 136-152

N-glycosylation sites.

amino acids 161-163, 187-190 and 253-256

Glycosaminoglycan attachment site.

amino acids 39-42

N-myristoylation sites.

amino acids 36-41, 42-47, 108-113, 166-171, 198-203 and 207-212

FIGURE 21

CTGAGGCGGCGGTAGC<u>ATG</u>GAGGGGGAGAGTACGTCGGCGGTGCTCTCGGGCTTTGTGCTCGGCG
CACTCGCTTTCCAGCACCTCAACACGGACTCGGACACGGAAGGTTTTCTTCTTGGGGAAGTAAAA
GGTGAAGCCAAGAACAGCATTACTGATTCCCAAATGGATGATGTTGAAGTTGTTTATACAATTGA
CATTCAGAAATATATTCCATGCTATCAGCTTTTAGCTTTTATAATTCTTCAGGCGAAGTAAATG
AGCAAGCACTGAAGAAATATTATCAAATGTCAAAAGAATGTGGTAGGTTGGTACAAATTCCGT
CGTCATTCAGATCAGATCATGACGTTTAGAGAGAGGCTGCTTCACAAAAACTTGCAGGAGCATTT
TTCAAACCAAGACCTTGTTTTCTGCTATTAACACCAAGTATAATAACAGAAAGCTGCTCTACTC
ATCGACTGGAACATTCCTTATATAAACCTCAAAAAGGACTTTTTCACAGGGTACCTTTAGTGGTT
GCCAATCTGGGCATGTCTGAACAACTGGGTTATAAAACTGTATCAGGTTCCTGTATGTCCACTGG
TTTTAGCCGAGCAGTACAAACACACAGCTCTAAATTTTTTGAAGAAGATGGATCCTTAAAGGAGG
TACATAAGATAAATGAAATGTATGCTTCATTACAAGAGGAATTAAAGAGTATATGCAAAAAGTG
GAAGACAGTGAACAAGCAGTAGATAAACTAGTAAAGGATGTAAACAGATTAAAACGAGAAATTGA
GAAAAGGAGAGGAGCACAGATTCAGGCAGCAAGAGAGAAGAACATCCAAAAAGACCCTCAGGAGA
ACATTTTCTTTGTCAGGCATTACGGACCTTTTTCCAAATTCTGAATTTCTTCATTCATGTGTT
ATGTCTTTAAAAAATAGACATGTTTCTAAAAGTAGCTGTAACTACAACCACCATCTCGATGTAGT
AGACAATCTGACCTTAATGGTAGAACACACTGACATTCCTGAAGCTAGTCCAGCTAGTACACCAC
AAATCATTAAGCATAAAGCCTTAGACTTAGATGACAGATGGCAATTCAAGAGATCTCGGTTGTTA
GATACACAAGACAAACGATCTAAAGCAAATACTGGTAGTAGTAACCAAGATAAAGCATCCAAAAT
GAGCAGCCCAGAAACAGATGAAGAAATTGAAAGATGAAGGGTTTTGGTGAATATTCACGGTCTC
CTACATTT<u>TGA</u>TCCTTTTAACCTTACAAGGAGATTTTTTATTTGGCTGATGGGTAAAGCCAAAC
ATTTCTATTGTTTTACTATGTTGAGCTACTTGCAGTAAGTTCATTTGTTTTACTATGTTCACC
TGTTTGCAGTAATACACAGATAACTCTTAGTGCATTTACTTCACAAAGTACTTTTTCAAACATCA
GATGCTTTTATTTCCAAACCTTTTTTTCACCTTTCACTAAGTTGTTGAGGGGAAGGCTTACACAG
ACACATTCTTTAGAATTGGAAAAGTGAGACCAGGCACAGTGGCTCACACCTGTAATCCCAGCACT
TAGGGAAGACAAGTCAGGAGGATTGATTGAAGCTAGGAGTTAGAGACCAGCCTGGGCAACGTATT
GAGACCATGTCTATTAAAAAATAAAATGGAAAAGCAAGAATAGCCTTATTTTCAAAATATGGAAA
GAAATTTATATGAAAATTTATCTGAGTCATTAAAATTCTCCTTAAGTGATACTTTTTAGAAGTA
CATTATGGCTAGAGTTGCCAGATAAAATGCTGGATATCATGCAATAAATTTGCAAAACATCATCT
AAAATTTAAAAAAAAAAAAAAAAAAAAAA

FIGURE 22

MEGESTSAVLSGFVLGALAFQHLNTDSDTEGFLLGEVKGEAKNSITDSQMDDVEVVYTIDIQKYI
PCYQLFSFYNSSGEVNEQALKKILSNVKKNVVGWYKFRRHSDQIMTFRERLLHKNLQEHFSNQDL
VFLLLTPSIITESCSTHRLEHSLYKPQKGLFHRVPLVVANLGMSEQLGYKTVSGSCMSTGFSRAV
QTHSSKFFEEDGSLKEVHKINEMYASLQEELKSICKKVEDSEQAVDKLVKDVNRLKREIEKRRGA
QIQAAREKNIQKDPQENIFLCQALRTFFPNSEFLHSCVMSLKNRHVSKSSCNYNHHLDVVDNLTL
MVEHTDIPEASPASTPQIIKHKALDLDDRWQFKRSRLLDTQDKRSKANTGSSNQDKASKMSSPET
DEEIEKMKGFGEYSRSPTF

Important features:

Signal peptide:

amino acids 1-19

N-glycosylation sites.

amino acids 75-79, 322-326

N-myristoylation site.

amino acids 184-154

Growth factor and cytokines receptors family.

amino acids 134-150

FIGURE 23

GGCACAGCCGCGCGGCGGAGGGCAGAGTCAGCCGAGCCGAGTCCAGCCGGACGAGCGGACCAGCGCAGGGCAGCCCAA
GCAGCGCGCAGCGAACGCCCGCCGCCGCCCACACCCTCTGCGGTCCCCGCGGCGCCTGCCACCCTTCCCTCCTTCCCC
GCGTCCCCGCCTCGCCGGCCAGTCAGCTTGCCGGGTTCGCTGCCCCGCGAAACCCCGAGGTCACCAGCCCGCGCCTCT
GCTTCCCTGGGCCGCGCGCCGCCTCCACGCCCTCCTTCTCCCCTGGCCCGGCGCCTGGCACCGGGGACCGTTGCCTGA
CGCGAGGCCCAGCTCTACTTTTCGCCCCGCGTCTCCTCCGCCTGCTCGCCTCTTCCACCAACTCCAACTCCTTCTCCC
TCCAGCTCCACTCGCTAGTCCCCGACTCCGCCAGCCCTCGGCCCGCTGCCGTAGCGCCGCTTCCCGTCCGGTCCCAAA
GGTGGGAACGCGTCCGCCCCGGCCCGCACCATGGCACGGTTCGGCTTGCCCGCGCTTCTCTGCACCCTGGCAGTGCTC
AGCGCCGCGCTGCTGGCTGCCGAGCTCAAGTCGAAAAGTTGCTCGGAAGTGCGACGTCTTTACGTGTCCAAAGGCTTC
AACAAGAACGATGCCCCCCTCCACGAGATCAACGGTGATCATTTGAAGATCTGTCCCCAGGGTTCTACCTGCTGCTCT
CAAGAGATGGAGGAGAAGTACAGCCTGCAAAGTAAAGATGATTTCAAAAGTGTGGTCAGCGAACAGTGCAATCATTTG
CAAGCTGTCTTTGCTTCACGTTACAAGAAGTTTGATGAATTCTTCAAAGAACTACTTGAAAATGCAGAGAAATCCCTG
AATGATATGTTTGTGAAGACATATGGCCATTTATACATGCAAAATTCTGAGCTATTTAAAGATCTCTTCGTAGAGTTG
AAACGTTACTACGTGGTGGGAAATGTGAACCTGGAAGAAATGCTAAATGACTTCTGGGCTCGCCTCCTGGAGCGGATG
TTCCGCCTGGTGAACTCCCAGTACCACTTTACAGATGAGTATCTGGAATGTGTGAGCAAGTATACGGAGCAGCTGAAG
CCCTTCGGAGATGTCCCTCGCAAATTGAAGCTCCAGGTTACTCGTGCTTTTGTAGCAGCCCGTACTTTCGCTCAAGGC
TTAGCGGTTGCGGGAGATGTCGTGAGCAAGGTCTCCGTGGTAAACCCCACAGCCCAGTGTACCCATGCCCTGTTGAAG
ATGATCTACTGCTCCCACTGCCGGGGTCTCGTGACTGTGAAGCCATGTTACAACTACTGCTCAAACATCATGAGAGGC
TGTTTGGCCAACCAAGGGGATCTCGATTTTGAATGGAACAATTTCATAGATGCTATGCTGATGGTGGCAGAGAGGCTA
GAGGGTCCTTTCAACATTGAATCGGTCATGGATCCCATCGATGTGAAGATTTCTGATGCTATTATGAACATGCAGGAT
AATAGTGTTCAAGTGTCTCAGAAGGTTTTCCAGGGATGTGGACCCCCCAAGCCCCTCCCAGCTGGACGAATTTCTCGT
TCCATCTCTGAAAGTGCCTTCAGTGCTCGCTTCAGACCACATCACCCCGAGGAACGCCCAACCACAGCAGCTGGCACT
AGTTTGGACCGACTGGTTACTGATGTCAAGGAGAAACTGAAACAGGCCAAGAAATTCTGGTCCTCCCTTCCGAGCAAC
GTTTGCAACGATGAGAGGATGGCTGCAGGAAACGGCAATGAGGATGACTGTTGGAATGGGAAAGGCAAAAGCAGGTAC
CTGTTTGCAGTGACAGGAAATGGATTAGCCAACCAGGGCAACAACCCAGAGGTCCAGGTTGACACCAGCAAACCAGAC
ATACTGATCCTTCGTCAAATCATGGCTCTTCGAGTGATGACCAGCAAGATGAAGAATGCATACAATGGGAACGACGTG
GACTTCTTTGATATCAGTGATGAAAGTAGTGGAGAAGGAAGTGGAAGTGGCTGTGAGTATCAGCAGTGCCCTTCAGAG
TTTGACTACAATGCCACTGACCATGCTGGGAAGAGTGCCAATGAGAAAGCCGACAGTGCTGGTGTCCGTCCTGGGGCA
CAGGCCTACCTCCTCACTGTCTTCTGCATCTTGTTCCTGGTTATGCAGAGAGAGTGGAGATAATTCTCAAACTCTGAG
AAAAAGTGTTCATCAAAAAGTTAAAAGGCACCAGTTATCACTTTTCTACCATCCTAGTGACTTTGCTTTTTAAATGAA
TGGACAACAATGTACAGTTTTTACTATGTGGCCACTGGTTTAAGAAGTGCTGACTTTGTTTTCTCATTCAGTTTTGGG
AGGAAAAGGGACTGTGCATTGAGTTGGTTCCTGCTCCCCAAACCATGTTAAACGTGGCTAACAGTGTAGGTACAGAA
CTATAGTTAGTTGTGCATTTGTGATTTTATCACTCTATTATTTGTTTGTATGTTTTTTTCTCATTTCGTTTGTGGGTT
TTTTTTTCCAACTGTGATCTCGCCTTGTTTCTTACAAGCAAACCAGGGTCCCTTCTTGGCACGTAACATGTACGTATT
TCTGAAATATTAAATAGCTGTACAGAAGCAGGTTTTATTTATCATGTTATCTTATTAAAAGAAAAAGCCCAAAAAGC

FIGURE 24

MARFGLPALLCTLAVLSAALLAAELKSKSCSEVRRLYVSKGFNKNDAPLHEINGDHLKICPQGST
CCSQEMEEKYSLQSKDDFKSVVSEQCNHLQAVFASRYKKFDEFFKELLENAEKSLNDMFVKTYGH
LYMQNSELFKDLFVELKRYYVVGNVNLEEMLNDFWARLLERMFRLVNSQYHFTDEYLECVSKYTE
QLKPFGDVPRKLKLQVTRAFVAARTFAQGLAVAGDVVSKVSVVNPTAQCTHALLKMIYCSHCRGL
VTVKPCYNYCSNIMRGCLANQGDLDFEWNNFIDAMLMVAERLEGPFNIESVMDPIDVKISDAIMN
MQDNSVQVSQKVFQGCGPPKPLPAGRISRSISESAFSARFRPHHPEERPTTAAGTSLDRLVTDVK
EKLKQAKKFWSSLPSNVCNDERMAAGNGNEDDCWNGKGKSRYLFAVTGNGLANQGNNPEVQVDTS
KPDILILRQIMALRVMTSKMKNAYNGNDVDFFDISDESSGEGSGSGCEYQQCPSEFDYNATDHAG
KSANEKADSAGVRPGAQAYLLTVFCILFLVMQREWR

Important features:

Signal peptide:

amino acids 1-22

ATP/GTP-binding site motif A (P-loop).

amino acids 515-524

N-glycosylation site.

amino acids 514-518

Glycosaminoglycan attachment sites.

amino acids 494-498, 498-502

N-myristoylation sites.

amino acids 63-69, 224-230, 276-282, 438-444, 497-503, 531-537

Glypicans proteins.

amino acids 54-75, 105-157, 238-280, 309-346, 423-460, 468-506

FIGURE 25

CTCGCCCTCAAATGGGAACGCTGGCCTGGGACTAAAGCATAGACCACCAGGCTGAGTATCCTGAC
CTGAGTCATCCCCAGGGATCAGGAGCCTCCAGCAGGGAACCTTCCATTATATTCTTCAAGCAACT
TACAGCTGCACCGACAGTTGCGATGAAAGTTCTAATCTCTTCCCTCCTCCTGTTGCTGCCACTAA
TGCTGATGTCCATGGTCTCTAGCAGCCTGAATCCAGGGGTCGCCAGAGGCCACAGGGACCGAGGC
CAGGCTTCTAGGAGATGGCTCCAGGAAGGCGGCCAAGAATGTGAGTGCAAAGATTGGTTCCTGAG
AGCCCCGAGAAGAAAATTCATGACAGTGTCTGGGCTGCCAAAGAAGCAGTGCCCCTGTGATCATT
TCAAGGGCAATGTGAAGAAAACAAGACACCAAAGGCACCACAGAAAGCCAAACAAGCATTCCAGA
GCCTGCCAGCAATTTCTCAAACAATGTCAGCTAAGAAGCTTTGCTCTGCCTTTGTAGGAGCTCTG
AGCGCCACTCTTCCAATTAAACATTCTCAGCCAAGAAGACAGTGAGCACACCTACCAGACACTC
TTCTTCTCCCACCTCACTCTCCCACTGTACCCACCCCTAAATCATTCCAGTGCTCTCAAAAAGCA
TGTTTTTCAAGATCATTTGTTTGTTGCTCTCTCTAGTGTCTTCTTCTCGTCAGTCTTAGCCT
GTGCCCTCCCCTTACCCAGGCTTAGGCTTAATTACCTGAAAGATTCCAGGAAACTGTAGCTTCCT
AGCTAGTGTCATTTAACCTTAAATGCAATCAGGAAAGTAGCAAACAGAAGTCAATAAATATTTTT
AAATGTCAAAAAAAAAAAAAAAAA

FIGURE 26

MKVLISSLLLLLPLMLMSMVSSSLNPGVARGHRDRGQASRRWLQEGGQECECKDWFLRAPRRKFM
TVSGLPKKQCPCDHFKGNVKKTRHQRHHRKPNKHSRACQQFLKQCQLRSFALPL

Important features:

Signal peptide:

amino acids 1-22

N-myristoylation sites.

amino acids 27-33, 46-52

FIGURE 27

GGACGCCAGCGCCTGCAGAGGCTGAGCAGGGAAAAAGCCAGTGCCCCAGCGGAAGCACAGCTCAG
AGCTGGTCTGCC<u>ATG</u>GACATCCTGGTCCCACTCCTGCAGCTGCTGGTGCTGCTTCTTACCCTGCC
CCTGCACCTCATGGCTCTGCTGGGCTGCTGGCAGCCCCTGTGCAAAAGCTACTTCCCCTACCTGA
TGGCCGTGCTGACTCCCAAGAGCAACCGCAAGATGGAGAGCAAGAAACGGGAGCTCTTCAGCCAG
ATAAAGGGGCTTACAGGAGCCTCCGGGAAAGTGGCCCTACTGGAGCTGGGCTGCGGAACCGGAGC
CAACTTTCAGTTCTACCCACCGGGCTGCAGGGTCACCTGCCTAGACCCAAATCCCCACTTTGAGA
AGTTCCTGACAAAGAGCATGGCTGAGAACAGGCACCTCCAATATGAGCGGTTTGTGGTGGCTCCT
GGAGAGGACATGAGACAGCTGGCTGATGGCTCCATGGATGTGGTGGTCTGCACTCTGGTGCTGTG
CTCTGTGCAGAGCCCAAGGAAGGTCCTGCAGGAGGTCCGGAGAGTACTGAGACCGGGAGGTGTGC
TCTTTTTCTGGGAGCATGTGGCAGAACCATATGGAAGCTGGGCCTTCATGTGGCAGCAAGTTTTC
GAGCCCACCTGGAAACACATTGGGGATGGCTGCTGCCTCACCAGAGAGACCTGGAAGGATCTTGA
GAACGCCCAGTTCTCCGAAATCCAAATGGAACGACAGCCCCCTCCCTTGAAGTGGCTACCTGTTG
GGCCCCACATCATGGGAAAGGCTGTCAAACAATCTTTCCCAAGCTCCAAGGCACTCATTTGCTCC
TTCCCCAGCCTCCAATTAGAACAAGCCACCCACCAGCCTATCTATCTTCCACTGAGAGGGACC<u>TA</u>
<u>G</u>CAGAATGAGAGAAGACATTCATGTACCACCTACTAGTCCCTCTCTCCCCAACCTCTGCCAGGGC
AATCTCTAACTTCAATCCCGCCTTCGACAGTGAAAAAGCTCTACTTCTACGCTGACCCAGGGAGG
AAACACTAGGACCCTGTTGTATCCTCAACTGCAAGTTTCTGGACTAGTCTCCCAACGTTTGCCTC
CCAATGTTGTCCCTTTCCTTCGTTCCCATGGTAAAGCTCCTCTCGCTTTCCTCCTGAGGCTACAC
CCATGCGTCTCTAGGAACTGGTCACAAAAGTCATGGTGCCTGCATCCCTGCCAAGCCCCCCTGAC
CCTCTCTCCCACTACCACCTTCTTCCTGAGCTGGGGGCACCAGGGAGAATCAGAGATGCTGGGG
ATGCCAGAGCAAGACTCAAAGAGGCAGAGGTTTTGTTCTCAAATATTTTTAATAAATAGACGAA
ACCACG

FIGURE 28

MDILVPLLQLLVLLLTLPLHLMALLGCWQPLCKSYFPYLMAVLTPKSNRKMESKKRELFSQIKGL
TGASGKVALLELGCGTGANFQFYPPGCRVTCLDPNPHFEKFLTKSMAENRHLQYERFVVAPGEDM
RQLADGSMDVVVCTLVLCSVQSPRKVLQEVRRVLRPGGVLFFWEHVAEPYGSWAFMWQQVFEPTW
KHIGDGCCLTRETWKDLENAQFSEIQMERQPPPLKWLPVGPHIMGKAVKQSFPSSKALICSFPSL
QLEQATHQPIYLPLRGT

Important features:
Signal peptide:
amino acids 1-23

Leucine zipper pattern.
amino acids 10-32

N-myristoylation sites.
amino acids 64-70, 78-84, 80-86, 91-97, 201-207

FIGURE 29

CAATGTTTGCCTATCCACCTCCCCCAAGCCCCTTTACCT<u>ATG</u>CTGCTGCTAACGCTGCTGCTGCT
GCTGCTGCTGCTTAAAGGCTCATGCTTGGAGTGGGGACTGGTCGGTGCCCAGAAAGTCTCTTCTG
CCACTGACGCCCCCATCAGGGATTGGGCCTTCTTTCCCCCTTCCTTTCTGTGTCTCCTGCCTCAT
CGGCCTGCCATGACCTGCAGCCAAGCCCAGCCCCGTGGGGAAGGGGAGAAAGTGGGGGATGGC<u>TA</u>
<u>A</u>GAAAGCTGGGAGATAGGGAACAGAAGAGGGTAGTGGGTGGGCTAGGGGGGCTGCCTTATTTAAA
GTGGTTGTTTATGATTCTTATACTAATTTATACAAAGATATTAAGGCCCTGTTCATTAAGAAATT
GTTCCCTTCCCCTGTGTTCAATGTTTGTAAAGATTGTTCTGTGTAAATATGTCTTTATAATAAAC
AGTTAAAAGCTGAAAAAAAAAAAAAAAAAAAAAAAAAAA

FIGURE 30

MLLLTLLLLLLLLKGSCLEWGLVGAQKVSSATDAPIRDWAFFPPSFLCLLPHRPAMTCSQAQPRG
EGEKVGDG

Important features:

Signal peptide:

amino acids 1-15

Growth factor and cytokines receptors family:

amino acids 3-18

FIGURE 31

```
GTTTGAATTCCTTCAACTATACCCACAGTCCAAAAGCAGACTCACTGTGTCCCAGGCTACCAGTT
CCTCCAAGCAAGTCATTTCCCTTATTTAACCGATGTGTCCCTCAAACACCTGAGTGCTACTCCCT
ATTTGCATCTGTTTTGATAAATGATGTTGACACCCTCCACCGAATTCTAAGTGGAATCATGTCGG
GAAGAGATACAATCCTTGGCCTGTGTATCCTCGCATTAGCCTTGTCTTTGGCCATGATGTTTACC
TTCAGATTCATCACCACCCTTCTGGTTCACATTTTCATTTCATTGGTTATTTTGGGATTGTTGTT
TGTCTGCGGTGTTTATGGTGGCTGTATTATGACTATACCAACGACCTCAGCATAGAATTGGACA
CAGAAAGGGAAAATATGAAGTGCGTGCTGGGGTTTGCTATCGTATCCACAGGCATCACGGCAGTG
CTGCTCGTCTTGATTTTGTTCTCAGAAGAGAATAAAATTGACAGTTGAGCTTTTCCAAATCAC
AAATAAAGCCATCAGCAGTGCTCCCTTCCTGCTGTTCCAGCCACTGTGGACATTTGCCATCCTCA
TTTTCTTCTGGGTCCTCTGGGTGGCTGTGCTGCTGAGCCTGGGAACTGCAGGAGCTGCCCAGGTT
ATGGAAGGCGGCCAAGTGGAATATAAGCCCCTTTCGGGCATTCGGTACATGTGGTCGTACCATTT
AATTGGCCTCATCTGGACTAGTGAATTCATCCTTGCGTGCCAGCAAATGACTATAGCTGGGGCAG
TGGTTACTTGTTATTTCAACAGAAGTAAAAATGATCCTCCTGATCATCCCATCCTTTCGTCTCTC
TCCATTCTCTTCTTCTACCATCAAGGAACCGTTGTGAAAGGGTCATTTTAATCTCTGTGGTGAG
GATTCCGAGAATCATTGTCATGTACATGCAAAACGCACTGAAAGAACAGCAGCATGGTGCATTGT
CCAGGTACCTGTTCCGATGCTGCTACTGCTGTTTCTGGTGTCTTGACAAATACCTGCTCCATCTC
AACCAGAATGCATATACTACAACTGCTATTAATGGGACAGATTTCTGTACATCAGCAAAGATGC
ATTCAAAATCTTGTCCAAGAACTCAAGTCACTTTACATCTATTAACTGCTTTGGAGACTTCATAA
TTTTTCTAGGAAAGGTGTTAGTGGTGTGTTTCACTGTTTTTGGAGGACTCATGGCTTTTAACTAC
AATCGGGCATTCCAGGTGTGGGCAGTCCCTCTGTTATTGGTAGCTTTTTTTGCCTACTTAGTAGC
CCATAGTTTTTTATCTGTGTTTGAAACTGTGCTGGATGCACTTTTCCTGTGTTTTGCTGTTGATC
TGGAAACAAATGATGGATCGTCAGAAAAGCCCTACTTTATGGATCAAGAATTTCTGAGTTTCGTA
AAAAGGAGCAACAAATTAAACAATGCAAGGGCACAGCAGGACAAGCACTCATTAAGGAATGAGGA
GGGAACAGAACTCCAGGCCATTGTGAGATAGATACCCATTTAGGTATCTGTACCTGGAAAACATT
TCCTTCTAAGAGCCATTTACAGAATAGAAGATGAGACCACTAGAGAAAGTTAGTGAATTTTTTT
TTAAAAGACCTAATAAACCCTATTCTTCCTCAAAA
```

FIGURE 32

MSGRDTILGLCILALALSLAMMFTFRFITTLLVHIFISLVILGLLFVCGVLWWLYYDYTNDLSIE
LDTERENMKCVLGFAIVSTGITAVLLVLIFVLRKRIKLTVELFQITNKAISSAPFLLFQPLWTFA
ILIFFWVLWVAVLLSLGTAGAAQVMEGGQVEYKPLSGIRYMWSYHLIGLIWTSEFILACQQMTIA
GAVVTCYFNRSKNDPPDHPILSSLSILFFYHQGTVVKGSFLISVVRIPRIIVMYMQNALKEQQHG
ALSRYLFRCCYCCFWCLDKYLLHLNQNAYTTTAINGTDFCTSAKDAFKILSKNSSHFTSINCFGD
FIIFLGKVLVVCFTVFGGLMAFNYNRAFQVWAVPLLLVAFFAYLVAHSFLSVFETVLDALFLCFA
VDLETNDGSSEKPYFMDQEFLSFVKRSNKLNNARAQQDKHSLRNEEGTELQAIVR

Important features:

Signal peptide:

amino acids 1-20

Putative transmembrane domains:

amino acids 35-54, 75-97, 126-146, 185-204, 333-350, 352-371

N-glycosylation sites.

amino acids 204-208, 295-299, 313-317

N-myristoylation sites.

amino acids 147-153, 178-184, 196-202, 296-275, 342-348

FIGURE 33

```
GTTCGATTAGCTCCTCTGAGAAGAAGAGAAAAGGTTCTTGGACCTCTCCCTGTTTCTTCCTTAGA
ATAATTTGTATGGGATTTGTGATGCAGGAAAGCCTAAGGGAAAAAGAATATTCATTCTGTGTGGT
GAAAATTTTTGAAAAAAAAATTGCCTTCTTCAAACAAGGGTGTCATTCTGATATTATGAGGAC
TGTTGTTCTCACTATGAAGGCATCTGTTATTGAAATGTTCCTTGTTTTGCTGGTGACTGGAGTAC
ATTCAAACAAAGAAACGGCAAAGAAGATTAAAAGGCCCAAGTTCACTGTGCCTCAGATCAACTGC
GATGTCAAAGCCGGAAAGATCATCGATCCTGAGTTCATTGTGAAATGTCCAGCAGGATGCCAAGA
CCCCAAATACCATGTTTATGGCACTGACGTGTATGCATCCTACTCCAGTGTGTGTGGCGCTGCCG
TACACAGTGGTGTGCTTGATAATTCAGGAGGGAAAATACTTGTTCGGAAGGTTGCTGGACAGTCT
GGTTACAAAGGGAGTTATTCCAACGGTGTCCAATCGTTATCCCTACCACGATGGAGAGAATCCTT
TATCGTCTTAGAAAGTAAACCCAAAAAGGGTGTAACCTACCCATCAGCTCTTACATACTCATCAT
CGAAAAGTCCAGCTGCCCAAGCAGGTGAGACCACAAAAGCCTATCAGAGGCCACCTATTCCAGGG
ACAACTGCACAGCCGGTCACTCTGATGCAGCTTCTGGCTGTCACTGTAGCTGTGGCCACCCCCAC
CACCTTGCCAAGGCCATCCCCTTCTGCTGCTTCTACCACCAGCATCCCCAGACCACAATCAGTGG
GCCACAGGAGCCAGGAGATGGATCTCTGGTCCACTGCCACCTACACAAGCAGCCAAAACAGGCCC
AGAGCTGATCCAGGTATCCAAAGGCAAGATCCTTCAGGAGCTGCCTTCCAGAAACCTGTTGGAGC
GGATGTCAGCCTGGGACTTGTTCCAAAAGAAGAATTGAGCACACAGTCTTTGGAGCCAGTATCCC
TGGGAGATCCAAACTGCAAAATTGACTTGTCGTTTTAATTGATGGGAGCACCAGCATTGGCAAA
CGGCGATTCCGAATCCAGAAGCAGCTCCTGGCTGATGTTGCCCAAGCTCTTGACATTGGCCCTGC
CGGTCCACTGATGGGTGTTGTCCAGTATGGAGACAACCCTGCTACTCACTTTAACCTCAAGACAC
ACACGAATTCTCGAGATCTGAAGACAGCCATAGAGAAAATTACTCAGAGAGGAGGACTTTCTAAT
GTAGGTCGGGCCATCTCCTTTGTGACCAAGAACTTCTTTTCCAAAGCCAATGGAAACAGAAGCGG
GGCTCCCAATGTGGTGGTGGTGATGGTGGATGGCTGGCCCACGGACAAAGTGGAGGAGGCTTCAA
GACTTGCGAGAGAGTCAGGAATCAACATTTTCTTCATCACCATTGAAGGTGCTGCTGAAAATGAG
AAGCAGTATGTGGTGGAGCCCAACTTTGCAAACAAGGCCGTGTGCAGAACAAACGGCTTCTACTC
GCTCCACGTGCAGAGCTGGTTTGGCCTCCACAAGACCCTGCAGCCTCTGGTGAAGCGGGTCTGCG
ACACTGACCGCCTGGCCTGCAGCAAGACCTGCTTGAACTCGGCTGACATTGGCTTCGTCATCGAC
GGCTCCAGCAGTGTGGGGACGGGCAACTTCCGCACCGTCCTCCAGTTTGTGACCAACCTCACCAA
AGAGTTTGAGATTTCCGACACGGACACGCGCATCGGGGCCGTGCAGTACACCTACGAACAGCGGC
TGGAGTTTGGGTTCGACAAGTACAGCAGCAAGCCTGACATCCTCAACGCCATCAAGAGGGTGGGC
TACTGGAGTGGTGGCACCAGCACGGGGGCTGCCATCAACTTCGCCCTGGAGCAGCTCTTCAAGAA
GTCCAAGCCCAACAAGAGGAAGTTAATGATCCTCATCACCGACGGGAGGTCCTACGACGACGTCC
GGATCCCAGCCATGGCTGCCCATCTGAAGGGAGTGATCACCTATGCGATAGGCGTTGCCTGGGCT
GCCCAAGAGGAGCTAGAAGTCATTGCCACTCACCCCGCCAGAGACCACTCCTTCTTTGTGGACGA
GTTTGACAACCTCCATCAGTATGTCCCCAGGATCATCCAGAACATTTGTACAGAGTTCAACTCAC
AGCCTCGGAACTGAATTCAGAGCAGGCAGAGCACCAGCAAGTGCTGCTTTACTAACTGACGTGTT
GGACCACCCCACCGCTTAATGGGCACGCACGGTGCATCAAGTCTTGGGCAGGGCATGGAGAAAC
AAATGTCTTGTTATTATTCTTTGCCATCATGCTTTTCATATTCCAAAACTTGGAGTTACAAAGA
TGATCACAAACGTATAGAATGAGCCAAAAGGCTACATCATGTTGAGGGTGCTGGAGATTTTACAT
TTTGACAATTGTTTTCAAAATAAATGTTCGGAATACAGTGCAGCCCTTACGACAGGCTTACGTAG
AGCTTTTGTGAGATTTTAAGTTGTTATTTCTGATTTGAACTCTGTAACCCTCAGCAAGTTTCAT
TTTTGTCATGACAATGTAGGAATTGCTGAATTAAATGTTTAGAAGGATGAAAAATAAAAAAAAAA
AAAAAAAAAAAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAG
```

FIGURE 34

MRTVVLTMKASVIEMFLVLLVTGVHSNKETAKKIKRPKFTVPQINCDVKAGKIIDPEFIVKCPAG
CQDPKYHVYGTDVYASYSSVCGAAVHSGVLDNSGGKILVRKVAGQSGYKGSYSNGVQSLSLPRWR
ESFIVLESKPKKGVTYPSALTYSSSKSPAAQAGETTKAYQRPPIPGTTAQPVTLMQLLAVTVAVA
TPTTLPRPSPSAASTTSIPRPQSVGHRSQEMDLWSTATYTSSQNRPRADPGIQRQDPSGAAFQKP
VGADVSLGLVPKEELSTQSLEPVSLGDPNCKIDLSFLIDGSTSIGKRRFRIQKQLLADVAQALDI
GPAGPLMGVVQYGDNPATHFNLKTHTNSRDLKTAIEKITQRGGLSNVGRAISFVTKNFFSKANGN
RSGAPNVVVVMVDGWPTDKVEEASRLARESGINIFFITIEGAAENEKQYVVEPNFANKAVCRTNG
FYSLHVQSWFGLHKTLQPLVKRVCDTDRLACSKTCLNSADIGFVIDGSSSVGTGNFRTVLQFVTN
LTKEFEISDTDTRIGAVQYTYEQRLEFGFDKYSSKPDILNAIKRVGYWSGGTSTGAAINFALEQL
FKKSKPNKRKLMILITDGRSYDDVRIPAMAAHLKGVITYAIGVAWAAQEELEVIATHPARDHSFF
VDEFDNLHQYVPRIIQNICTEFNSQPRN

Important features:
Signal peptide:
amino acids 1-26

Transmembrane domain:
amino acids 181-200

N-glycosylation sites.
amino acids 390-394, 520-524

N-myristoylation sites.
amino acids 23-29, 93-99, 115-121, 262-268, 367-373, 389-395, 431-437, 466-472, 509-515, 570-576, 571-577, 575-581, 627-633

Amidation site.
amino acids 304-308

FIGURE 35

CCGAGCACAGGAGATTGCCTGCGTTTAGGAGGTGGCTGCGTTGTGGGAAAAGCTATCAAGGAAGAAATTGC
CAAACCATGTCTTTTTTTCTGTTTTCAGAGTAGTTCACAACAGATCTGAGTGTTTTAATTAAGCATGGAAT
ACAGAAAACAACAAAAAACTTAAGCTTTAATTTCATCTGGAATTCCACAGTTTTCTTAGCTCCCTGGACCC
GGTTGACCTGTTGGCTCTTCCCGCTGGCTGCTCTATCACGTGGTGCTCTCCGACTACTCACCCCGAGTGTA
AAGAACCTTCGGCTCGCGTGCTTCTGAGCTGCTGTGGATGGCCTCGGCTCTCTGGACTGTCCTTCCGAGTA
GGATGTCACTGAGATCCCTCAAATGGAGCCTCCTGCTGCTGTCACTCCTGAGTTTCTTTGTGATGTGGTAC
CTCAGCCTTCCCCACTACAATGTGATAGAACGCGTGAACTGGATGTACTTCTATGAGTATGAGCCGATTTA
CAGACAAGACTTTCACTTCACACTTCGAGAGCATTCAAACTGCTCTCATCAAAATCCATTTCTGGTCATTC
TGGTGACCTCCCACCCTTCAGATGTGAAAGCCAGGCAGGCCATTAGAGTTACTTGGGGTGAAAAAAGTCT
TGGTGGGGATATGAGGTTCTTACATTTTTCTTATTAGGCCAAGAGGCTGAAAAGGAAGACAAAATGTTGGC
ATTGTCCTTAGAGGATGAACACCTTCTTTATGGTGACATAATCCGACAAGATTTTTAGACACATATAATA
ACCTGACCTTGAAAACCATTATGGCATTCAGGTGGGTAACTGAGTTTTGCCCCAATGCCAAGTACGTAATG
AAGACAGACACTGATGTTTTCATCAATACTGGCAATTTAGTGAAGTATCTTTTAAACCTAAACCACTCAGA
GAAGTTTTTCACAGGTTATCCTCTAATTGATAATTATTCCTATAGAGGATTTTACCAAAAAACCCATATTT
CTTACCAGGAGTATCCTTTCAAGGTGTTCCCTCCATACTGCAGTGGGTTGGGTTATATAATGTCCAGAGAT
TTGGTGCCAAGGATCTATGAAATGATGGGTCACGTAAAACCCATCAAGTTTGAAGATGTTTATGTCGGGAT
CTGTTTGAATTTATTAAAAGTGAACATTCATATTCCAGAAGACACAAATCTTTTCTTTCTATATAGAATCC
ATTTGGATGTCTGTCAACTGAGACGTGTGATTGCAGCCCATGGCTTTTCTTCCAAGGAGATCATCACTTTT
TGGCAGGTCATGCTAAGGAACACCACATGCCATTATTAACTTCACATTCTACAAAAAGCCTAGAAGGACAG
GATACCTTGTGGAAAGTGTTAAATAAAGTAGGTACTGTGGAAAATTCATGGGGAGGTCAGTGTGCTGGCTT
ACACTGAACTGAAACTCATGAAAAACCCAGACTGGAGACTGGAGGGTTACACTTGTGATTTATTAGTCAGG
CCCTTCAAAGATGATATGTGGAGGAATTAAATATAAAGGAATTGGAGGTTTTTGCTAAAGAAATTAATAGG
ACCAAACAATTTGGACATGTCATTCTGTAGACTAGAATTTCTTAAAAGGGTGTTACTGAGTTATAAGCTCA
CTAGGCTGTAAAAACAAAACAATGTAGAGTTTTATTTATTGAACAATGTAGTCACTTGAAGGTTTTGTGTA
TATCTTATGTGGATTACCAATTTAAAAATATATGTAGTTCTGTGTCAAAAAACTTCTTCACTGAAGTTATA
CTGAACAAAATTTTACCTGTTTTGGTCATTTATAAAGTACTTCAAGATGTTGCAGTATTTCACAGTTATT
ATTATTTAAAATTACTTCAACTTTGTGTTTTTAAATGTTTTGACGATTTCAATACAAGATAAAAAGGATAG
TGAATCATTCTTTACATGCAAACATTTTCCAGTTACTTAACTGATCAGTTTATTATTGATACATCACTCCA
TTAATGTAAAGTCATAGGTCATTATTGCATATCAGTAATCTCTTGGACTTTGTTAAATATTTTACTGTGGT
AATATAGAGAAGAATTAAAGCAAGAAAATCTGAAAA

FIGURE 36

MASALWTVLPSRMSLRSLKWSLLLLSLLSFFVMWYLSLPHYNVIERVNWMYFYEYEPIYRQDFHF
TLREHSNCSHQNPFLVILVTSHPSDVKARQAIRVTWGEKKSWWGYEVLTFFLLGQEAEKEDKMLA
LSLEDEHLLYGDIIRQDFLDTYNNLTLKTIMAFRWVTEFCPNAKYVMKTDTDVFINTGNLVKYLL
NLNHSEKFFTGYPLIDNYSYRGFYQKTHISYQEYPFKVFPPYCSGLGYIMSRDLVPRIYEMMGHV
KPIKFEDVYVGICLNLLKVNIHIPEDTNLFFLYRIHLDVCQLRRVIAAHGFSSKEIITFWQVMLR
NTTCHY

Important features:

Type II transmembrane domain:

amino acids 20-39

N-glycosylation sites.

amino acids 72-76, 154-158, 198-202, 212-216, 326-330

Glycosaminoglycan attachment site.

amino acids 239-243

Ly-6 / u-PAR domain proteins.

amino acids 23-37

N-myristoylation site.

amino acids 271-277

FIGURE 37

CGCTCGGGCACCAGCCGCGGCAAGGATGGAGCTGGGTTGCTGGACGCAGTTGGGGCTCACTTTTCTTCAGCTCCTTCTCATC
TCGTCCTTGCCAAGAGAGTACACAGTCATTAATGAAGCCTGCCCTGGAGCAGAGTGGAATATCATGTGTCGGGAGTGCTGTG
AATATGATCAGATTGAGTGCGTCTGCCCCGGAAAGAGGGAAGTCGTGGGTTATACCATCCCTTGCTGCAGGAATGAGGAGAA
TGAGTGTGACTCCTGCCTGATCCACCCAGGTTGTACCATCTTTGAAAACTGCAAGAGCTGCCGAAATGGCTCATGGGGGGT
ACCTTGGATGACTTCTATGTGAAGGGGTTCTACTGTGCAGAGTGCCGAGCAGGCTGGTACGGAGGAGACTGCATGCGATGTG
GCCAGGTTCTGCGAGCCCCAAAGGGTCAGATTTTGTTGGAAAGCTATCCCCTAAATGCTCACTGTGAATGGACCATTCATGC
TAAACCTGGGTTTGTCATCCAACTAAGATTTGTCATGTTGAGTCTGGAGTTTGACTACATGTGCCAGTATGACTATGTTGAG
GTTCGTGATGGAGACAACCGCGATGGCCAGATCATCAAGCGTGTCTGTGGCAACGAGCGGCCAGCTCCTATCCAGAGCATAG
GATCCTCACTCCACGTCCTCTTCCACTCCGATGGCTCCAAGAATTTTGACGGTTTCCATGCCATTTATGAGGAGATCACAGC
ATGCTCCTCATCCCCTTGTTTCCATGACGGCACGTGCGTCCTTGACAAGGCTGGATCTTACAAGTGTGCCTGCTTGGCAGGC
TATACTGGGCAGCGCTGTGAAAATCTCCTTGAAGAAAGAAACTGCTCAGACCCTGGGGCCCAGTCAATGGGTACCAGAAAA
TAACAGGGGGCCCTGGGCTTATCAACGGACGCCATGCTAAAATTGGCACCGTGGTGTCTTTCTTTTGTAACAACTCCTATGT
TCTTAGTGGCAATGAGAAAAGAACTTGCCAGCAGAATGGAGAGTGGTCAGGGAAACAGCCCATCTGCATAAAAGCCTGCCGA
GAACCAAAGATTTCAGACCTGGTGAGAAGGAGAGTTCTTCCGATGCAGGTTCAGTCAAGGGAGACACCATTACACCAGCTAT
ACTCAGCGGCCTTCAGCAAGCAGAAACTGCAGAGTGCCCCTACCAAGAAGCCAGCCCTTCCCTTTGGAGATCTGCCCATGGG
ATACCAACATCTGCATACCCAGCTCCAGTATGAGTGCATCTCACCCTTCTACCGCCGCCTGGGCAGCAGCAGGAGGACATGT
CTGAGGACTGGGAAGTGGAGTGGGCGGGCACCATCCTGCATCCCTATCTGCGGGAAAATTGAGAACATCACTGCTCCAAAGA
CCCAAGGGTTGCGCTGGCCGTGGCAGGCAGCCATCTACAGGAGGACCAGCGGGGTGCATGACGGCAGCCTACACAAGGGAGC
GTGGTTCCTAGTCTGCAGCGGTGCCCTGGTGAATGAGCGCACTGTGGTGGTGGCTGCCCACTGTGTTACTGACCTGGGGAAG
GTCACCATGATCAAGACAGCAGACCTGAAAGTTGTTTTGGGGAAATTCTACCGGGATGATGACCGGGATGAGAAGACCATCC
AGAGCCTACAGATTTCTGCTATCATTCTGCATCCCAACTATGACCCCATCCTGCTTGATGCTGACATCGCCATCCTGAAGCT
CCTAGACAAGGCCCGTATCAGCACCCGAGTCCAGCCCATCTGCCTCGCTGCCAGTCGGGATCTCAGCACTTCCTTCCAGGAG
TCCCACATCACTGTGGCTGGCTGGAATGTCCTGGCAGACGTGAGGAGCCCTGGCTTCAAGAACGACACACTGCGCTCTGGGG
TGGTCAGTGTGGTGGACTCGCTGCTGTGTGAGGAGCAGCATGAGGACCATGGCATCCCAGTGAGTGTCACTGATAACATGTT
CTGTGCCAGCTGGGAACCCACTGCCCCTTCTGATATCTGCACTGCAGAGACAGGAGGCATCGCGGCTGTGTCCTTCCCGGGA
CGAGCATCTCCTGAGCCACGCTGGCATCTGATGGGACTGGTCAGCTGGAGCTATGATAAAACATGCAGCCACAGGCTCTCCA
CTGCCTTCACCAAGGTGCTGCCTTTTAAAGACTGGATTGAAAGAAATATGAAATGACCATGCTCATGCACTCCTTGAGAAG
TGTTTCTGTATATCCGTCTGTACGTGTGTCATTGCGTGAAGCAGTGTGGGCCTGAAGTGTGATTTGGCCTGTGAACTTGGCT
GTGCCAGGGCTTCTGACTTCAGGGACAAAACTCAGTGAAGGGTGAGTAGACCTCCATTGCTGGTAGGCTGATGCCGCGTCCA
CTACTAGGACAGCCAATTGGAAGATGCCAGGGCTTGCAAGAAGTAAGTTTCTTCAAAGAAGACCATATACAAAACCTCTCCA
CTCCACTGACCTGGTGGTCTTCCCCAACTTTCAGTTATACGAATGCCATCAGCTTGACCAGGGAAGATCTGGGCTTCATGAG
GCCCCTTTTGAGGCTCTCAAGTTCTAGAGAGCTGCCTGTGGGACAGCCCAGGGCAGCAGAGCTGGGATGTGGTGCATGCCTT
TGTGTACATGGCCACAGTACAGTCTGGTCCTTTTCCTTCCCCATCTCTTGTACACATTTTAATAAAATAAGGGTTGGCTTCT
GAACTACAAAAAAAAAAAAAAAAAAAAAAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAAAA

FIGURE 38

MELGCWTQLGLTFLQLLLISSLPREYTVINEACPGAEWNIMCRECCEYDQIECVCPGKREVVGYT
IPCCRNEENECDSCLIHPGCTIFENCKSCRNGSWGGTLDDFYVKGFYCAECRAGWYGGDCMRCGQ
VLRAPKGQILLESYPLNAHCEWTIHAKPGFVIQLRFVMLSLEFDYMCQYDYVEVRDGDNRDGQII
KRVCGNERPAPIQSIGSSLHVLFHSDGSKNFDGFHAIYEEITACSSSPCFHDGTCVLDKAGSYKC
ACLAGYTGQRCENLLEERNCSDPGGPVNGYQKITGGPGLINGRHAKIGTVVSFFCNNSYVLSGNE
KRTCQQNGEWSGKQPICIKACREPKISDLVRRRVLPMQVQSRETPLHQLYSAAFSKQKLQSAPTK
KPALPFGDLPMGYQHLHTQLQYECISPFYRRLGSSRRTCLRTGKWSGRAPSCIPICGKIENITAP
KTQGLRWPWQAAIYRRTSGVHDGSLHKGAWFLVCSGALVNERTVVVAAHCVTDLGKVTMIKTADL
KVVLGKFYRDDDRDEKTIQSLQISAIILHPNYDPILLDADIAILKLLDKARISTRVQPICLAASR
DLSTSFQESHITVAGWNVLADVRSPGFKNDTLRSGVVSVVDSLLCEEQHEDHGIPVSVTDNMFCA
SWEPTAPSDICTAETGGIAAVSFPGRASPEPRWHLMGLVSWSYDKTCSHRLSTAFTKVLPFKDWI
ERNMK

Important features of the protein:
Signal peptide:
amino acids 1-23
EGF-like domain cysteine pattern signature.
amino acids 260-272
N-glycosylation sites.
amino acids 96-100, 279-283, 316-320, 451-455, 614-618
N-myristoylation sites.
amino acids 35-41, 97-103, 256-262, 284-290, 298-304, 308-314, 474-480, 491-497, 638-644, 666-672
Amidation site.
amino acids 56-60
Serine proteases, trypsin family.
amino acids 489-506
CUB domain proteins profile.
amino acids 150-167

FIGURE 39

```
GGTTCCTACATCCTCTCATCTGAGAATCAGAGAGCATAATCTTCTTACGGGCCCGTGATTTATTAACGTGGCTTAATC
TGAAGGTTCTCAGTCAAATTCTTTGTGATCTACTGATTGTGGGGCATGGCAAGGTTTGCTTAAAGGAGCTTGGCTGG
TTTGGGCCCTTGTAGCTGACAGAAGGTGGCCAGGGAGAATGCAGCACACTGCTCGGAGAATGAAGGCGCTTCTGTTGC
TGGTCTTGCCTTGGCTCAGTCCTGCTAACTACATTGACAATGTGGGCAACCTGCACTTCCTGTATTCAGAACTCTGTA
AAGGTGCCTCCCACTACGGCCTGACCAAAGATAGGAAGAGGCGCTCACAAGATGGCTGTCCAGACGGCTGTGCGAGCC
TCACAGCCACGGCTCCCTCCCCAGAGGTTTCTGCAGCTGCCACCATCTCCTTAATGACAGACGAGCCTGGCCTAGACA
ACCCTGCCTACGTGTCCTCGGCAGAGGACGGGCAGCCAGCAATCAGCCCAGTGGACTCTGGCCGGAGCAACCGAACTA
GGGCACGGCCCTTTGAGAGATCCACTATTAGAAGCAGATCATTTAAAAAAATAAATCGAGCTTTGAGTGTTCTTCGAA
GGACAAAGAGCGGGAGTGCAGTTGCCAACCATGCCGACCAGGGCAGGGAAAATTCTGAAAACACCACTGCCCCTGAAG
TCTTTCCAAGGTTGTACCACCTGATTCCAGATGGTGAAATTACCAGCATCAAGATCAATCGAGTAGATCCCAGTGAAA
GCCTCTCTATTAGGCTGGTGGGAGGTAGCGAAACCCCACTGGTCCATATCATTATCCAACACATTTATCGTGATGGGG
TGATCGCCAGAGACGGCCGGCTACTGCCAGGAGACATCATTCTAAAGGTCAACGGGATGGACATCAGCAATGTCCCTC
ACAACTACGCTGTGCGTCTCCTGCGGCAGCCCTGCCAGGTGCTGTGGCTGACTGTGATGCGTGAACAGAAGTTCCGCA
GCAGGAACAATGGACAGGCCCCGGATGCCTACAGACCCCGAGATGACAGCTTTCATGTGATTCTCAACAAAAGTAGCC
CCGAGGAGCAGCTTGGAATAAAACTGGTGCGCAAGGTGGATGAGCCTGGGGTTTTCATCTTCAATGTGCTGGATGGCG
GTGTGGCATATCGACATGGTCAGCTTGAGGAGAATGACCGTGTGTTAGCCATCAATGGACATGATCTTCGATATGGCA
GCCCAGAAAGTGCGGCTCATCTGATTCAGGCCAGTGAAAGACGTGTTCACCTCGTCGTGTCCCGCCAGGTTCGGCAGC
GGAGCCCTGACATCTTTCAGGAAGCCGGCTGGAACAGCAATGGCAGCTGGTCCCCAGGGCCAGGGGAGAGGAGCAACA
CTCCCAAGCCCCTCCATCCTACAATTACTTGTCATGAGAAGGTGGTAAATATCCAAAAAGACCCCGGTGAATCTCTCG
GCATGACCGTCGCAGGGGGAGCATCACATAGAGAATGGGATTTGCCTATCTATGTCATCAGTGTTGAGCCCGGAGGAG
TCATAAGCAGAGATGGAAGAATAAAAACAGGTGACATTTTGTTGAATGTGGATGGGGTCGAACTGACAGAGGTCAGCC
GGAGTGAGGCAGTGGCATTATTGAAAAGAACATCATCCTCGATAGTACTCAAAGCTTTGGAAGTCAAAGAGTATGAGC
CCCAGGAAGACTGCAGCAGCCCAGCAGCCCTGGACTCCAACCACAACATGGCCCCACCCAGTGACTGGTCCCCATCCT
GGGTCATGTGGCTGGAATTACCACGGTGCTTGTATAACTGTAAAGATATTGTATTACGAAGAAACACAGCTGGAAGTC
TGGGCTTCTGCATTGTAGGAGGTTATGAAGAATACAATGGAAACAAACCTTTTTTCATCAAATCCATTGTTGAAGGAA
CACCAGCATACAATGATGGAAGAATTAGATGTGGTGATATTCTTCTTGCTGTCAATGGTAGAAGTACATCAGGAATGA
TACATGCTTGCTTGGCAAGACTGCTGAAAGAACTTAAAGGAAGAATTACTCTAACTATTGTTTCTTGGCCTGGCACTT
TTTTATAGAATCAATGATGGGTCAGAGGAAAACAGAAAAATCACAAATAGGCTAAGAAGTTGAAACACTATATTTATC
TTGTCAGTTTTTATATTTAAAGAAAGAATACATTGTAAAAATGTCAGGAAAAGTATGATCATCTAATGAAAGCCAGTT
ACACCTCAGAAAATATGATTCCAAAAAAATTAAAACTACTAGTTTTTTTTCAGTGTGGAGGATTTCTCATTACTCTAC
AACATTGTTTATATTTTTTCTATTCAATAAAAAGCCCTAAAACAACTAAAATGATTGATTTGTATACCCCACTGAATT
CAAGCTGATTTAAATTTAAAATTTGGTATATGCTGAAGTCTGCCAAGGGTACATTATGGCCATTTTTAATTTACAGCT
AAAATATTTTTTAAAATGCATTGCTGAGAAACGTTGCTTTCATCAAACAAGAATAAATATTTTTCAGAAGTTAAA
```

FIGURE 40

MKALLLLVLPWLSPANYIDNVGNLHFLYSELCKGASHYGLTKDRKRRSQDGCPDGCASLTATAPS
PEVSAAATISLMTDEPGLDNPAYVSSAEDGQPAISPVDSGRSNRTRARPFERSTIRSRSFKKINR
ALSVLRRTKSGSAVANHADQGRENSENTTAPEVFPRLYHLIPDGEITSIKINRVDPSESLSIRLV
GGSETPLVHIIIQHIYRDGVIARDGRLLPGDIILKVNGMDISNVPHNYAVRLLRQPCQVLWLTVM
REQKFRSRNNGQAPDAYRPRDDSFHVILNKSSPEEQLGIKLVRKVDEPGVFIFNVLDGGVAYRHG
QLEENDRVLAINGHDLRYGSPESAAHLIQASERRVHLVVSRQVRQRSPDIFQEAGWNSNGSWSPG
PGERSNTPKPLHPTITCHEKVVNIQKDPGESLGMTVAGGASHREWDLPIYVISVEPGGVISRDGR
IKTGDILLNVDGVELTEVSRSEAVALLKRTSSSIVLKALEVKEYEPQEDCSSPAALDSNHNMAPP
SDWSPSWVMWLELPRCLYNCKDIVLRRNTAGSLGFCIVGGYEEYNGNKPFFIKSIVEGTPAYNDG
RIRCGDILLAVNGRSTSGMIHACLARLLKELKGRITLTIVSWPGTFL

Important features:

Signal peptide:

amino acids 1-15

N-glycosylation sites.

amino acids 108-112, 157-161, 289-293, 384-388

Tyrosine kinase phosphorylation sites.

amino acids 433-441, 492-500

N-myristoylation sites.

amino acids 51-57, 141-147, 233-239, 344-350, 423-429, 447-453, 467-473, 603-609

FIGURE 41

ACCAGGCATTGTATCTTCAGTTGTCATCAAGTTCGCAATCAGATTGGAAAAGCTCAACTTGAAGCTTT
CTTGCCTGCAGTGAAGCAGAGAGATAGATATTATTCACGTAATAAAAAAC<u>ATG</u>GGCTTCAACCTGACT
TTCCACCTTTCCTACAAATTCCGATTACTGTTGCTGTTGACTTTGTGCCTGACAGTGGTTGGGTGGGC
CACCAGTAACTACTTCGTGGGTGCCATTCAAGAGATTCCTAAAGCAAAGGAGTTCATGGCTAATTTCC
ATAAGACCCTCATTTTGGGGAAGGGAAAAACTCTGACTAATGAAGCATCCACGAAGAAGGTAGAACTT
GACAACTGTCCTTCTGTGTCTCCTTACCTCAGAGGCCAGAGCAAGCTCATTTTCAAACCAGATCTCAC
TTTGGAAGAGGTACAGGCAGAAAATCCCAAAGTGTCCAGAGGCCGGTATCGCCCTCAGGAATGTAAAG
CTTTACAGAGGGTCGCCATCCTCGTTCCCCACCGGAACAGAGAGAAACACCTGATGTACCTGCTGGAA
CATCTGCATCCCTTCCTGCAGAGGCAGCAGCTGGATTATGGCATCTACGTCATCCACCAGGCTGAAGG
TAAAAAGTTTAATCGAGCCAAACTCTTGAATGTGGGCTATCTAGAAGCCCTCAAGGAAGAAAATTGGG
ACTGCTTTATATTCCACGATGTGGACCTGGTACCCGAGAATGACTTTAACCTTTACAAGTGTGAGGAG
CATCCCAAGCATCTGGTGGTTGGCAGGAACAGCACTGGGTACAGGTTACGTTACAGTGGATATTTTGG
GGGTGTTACTGCCCTAAGCAGAGAGCAGTTTTTCAAGGTGAATGGATTCTCTAACAACTACTGGGGAT
GGGGAGGCGAAGACGATGACCTCAGACTCAGGGTTGAGCTCCAAAGAATGAAAATTTCCCGGCCCCTG
CCTGAAGTGGGTAAATATACAATGGTCTTCCACACTAGAGACAAAGGCAATGAGGTGAACGCAGAACG
GATGAAGCTCTTACACCAAGTGTCACGAGTCTGGAGAACAGATGGGTTGAGTAGTTGTTCTTATAAAT
TAGTATCTGTGGAACACAATCCTTTATATATCAACATCACAGTGGATTTCTGGTTTGGTGCA<u>TGA</u>CCC
TGGATCTTTTGGTGATGTTTGGAAGAACTGATTCTTTGTTTGCAATAATTTTGGCCTAGAGACTTCAA
ATAGTAGCACACATTAAGAACCTGTTACAGCTCATTGTTGAGCTGAATTTTTCCTTTTTGTATTTTCT
TAGCAGAGCTCCTGGTGATGTAGAGTATAAAACAGTTGTAACAAGACAGCTTTCTTAGTCATTTTGAT
CATGAGGGTTAAATATTGTAATATGGATACTTGAAGGACTTTATATAAAAGGATGACTCAAAGGATAA
AATGAACGCTATTTGAGGACTCTGGTTGAAGGAGATTTATTTAAATTTGAAGTAATATATTATGGGAT
AAAAGGCCACAGGAAATAAGACTGCTGAATGTCTGAGAGAACCAGAGTTGTTCTCGTCCAAGGTAGAA
AGGTACGAAGATACAATACTGTTATTCATTTATCCTGTACAATCATCTGTGAAGTGGTGGTGTCAGGT
GAGAAGGCGTCCACAAAAGAGGGGAGAAAAGGCGACGAATCAGGACACAGTGAACTTGGGAATGAAGA
GGTAGCAGGAGGGTGGAGTGTCGGCTGCAAAGGCAGCAGTAGCTGAGCTGGTTGCAGGTGCTGATAGC
CTTCAGGGGAGGACCTGCCCAGGTATGCCTTCCAGTGATGCCCACCAGAGAATACATTCTCTATTAGT
TTTTAAAGAGTTTTTGTAAAATGATTTTGTACAAGTAGGATATGAATTAGCAGTTTACAAGTTTACAT
ATTAACTAATAATAAATATGTCTATCAAATACCTCTGTAGTAAAATGTGAAAAAGCAAAA

FIGURE 42

MGFNLTFHLSYKFRLLLLLTLCLTVVGWATSNYFVGAIQEIPKAKEFMANFHKTLILGKGKTLTN
EASTKKVELDNCPSVSPYLRGQSKLIFKPDLTLEEVQAENPKVSRGRYRPQECKALQRVAILVPH
RNREKHLMYLLEHLHPFLQRQQLDYGIYVIHQAEGKKFNRAKLLNVGYLEALKEENWDCFIFHDV
DLVPENDFNLYKCEEHPKHLVVGRNSTGYRLRYSGYFGGVTALSREQFFKVNGFSNNYWGWGGED
DDLRLRVELQRMKISRPLPEVGKYTMVFHTRDKGNEVNAERMKLLHQVSRVWRTDGLSSCSYKLV
SVEHNPLYINITVDFWFGA

Important features:
Signal peptide:
amino acids 1-27

N-glycosylation sites.
amino acids 4-8, 220-224, 335-339

Xylose isomerase proteins.
amino acids 191-202

FIGURE 43

```
GCTCAAGACCCAGCAGTGGGACAGCCAGACAGACGGCACGATGGCACTGAGCTCCCAGATCTGGG
CCGCTTGCCTCCTGCTCCTCCTCCTCCTCGCCAGCCTGACCAGTGGCTCTGTTTTCCCACAACAG
ACGGGACAACTTGCAGAGCTGCAACCCCAGGACAGAGCTGGAGCCAGGGCCAGCTGGATGCCCAT
GTTCCAGAGGCGAAGGAGGCGAGACACCCACTTCCCCATCTGCATTTTCTGCTGCGGCTGCTGTC
ATCGATCAAAGTGTGGGATGTGCTGCAAGACGTAGAACCTACCTGCCCTGCCCCCGTCCCTCCC
TTCCTTATTTATTCCTGCTGCCCCAGAACATAGGTCTTGGAATAAAATGGCTGGTTCTTTTGTTT
TCCAAAAAAAAAAAAAAAAAAAAAAAAAAAAAAAAAAAAAAAAAAAAAAAAAAAAAAAAAAAAAA
AAAAAAAAAAAAAAAAAAAAAAAAAAAA
```

FIGURE 44

MALSSQIWAACLLLLLLLASLTSGSVFPQQTGQLAELQPQDRAGARASWMPMFQRRRRRDTHFPI
CIFCCGCCHRSKCGMCCKT

Important features:

Signal peptide:

amino acids 1-24 cAMP- and cGMP-dependent protein kinase phosphorylation site.

amino acids 58-59

N-myristoylation site.

amino acids 44-50

Prokaryotic membrane lipoprotein lipid attachment site.

amino acids 1-12

FIGURE 45

GTGGCTTCATTTCAGTGGCTGACTTCCAGAGAGCAATATGGCTGGTTCCCCAACATGCCTCACCC
TCATCTATATCCTTTGGCAGCTCACAGGGTCAGCAGCCTCTGGACCCGTGAAAGAGCTGGTCGGT
TCCGTTGGTGGGGCCGTGACTTTCCCCCTGAAGTCCAAAGTAAAGCAAGTTGACTCTATTGTCTG
GACCTTCAACACAACCCCTCTTGTCACCATACAGCCAGAAGGGGGCACTATCATAGTGACCCAAA
ATCGTAATAGGGAGAGAGTAGACTTCCCAGATGGAGGCTACTCCCTGAAGCTCAGCAAACTGAAG
AAGAATGACTCAGGGATCTACTATGTGGGGATATACAGCTCATCACTCCAGCAGCCCTCCACCCA
GGAGTACGTGCTGCATGTCTACGAGCACCTGTCAAAGCCTAAAGTCACCATGGGTCTGCAGAGCA
ATAAGAATGGCACCTGTGTGACCAATCTGACATGCTGCATGGAACATGGGGAAGAGGATGTGATT
TATACCTGGAAGGCCCTGGGGCAAGCAGCCAATGAGTCCCATAATGGGTCCATCCTCCCCATCTC
CTGGAGATGGGGAGAAAGTGATATGACCTTCATCTGCGTTGCCAGGAACCCTGTCAGCAGAAACT
TCTCAAGCCCCATCCTTGCCAGGAAGCTCTGTGAAGGTGCTGCTGATGACCCAGATTCCTCCATG
GTCCTCCTGTGTCTCCTGTTGGTGCCCCTCCTGCTCAGTCTCTTTGTACTGGGGCTATTTCTTTG
GTTTCTGAAGAGAGAGAGACAAGAAGAGTACATTGAAGAGAAGAAGAGAGTGGACATTTGTCGGG
AAACTCCTAACATATGCCCCCATTCTGGAGAGAACACAGAGTACGACACAATCCCTCACACTAAT
AGAACAATCCTAAAGGAAGATCCAGCAAATACGGTTTACTCCACTGTGGAAATACCGAAAAAGAT
GGAAAATCCCCACTCACTGCTCACGATGCCAGACACACCAAGGCTATTTGCCTATGAGAATGTTA
TCTAGACAGCAGTGCACTCCCCTAAGTCTCTGCTCA

FIGURE 46

MAGSPTCLTLIYILWQLTGSAASGPVKELVGSVGGAVTFPLKSKVKQVDSIVWTFNTTPLVTIQP
EGGTIIVTQNRNRERVDFPDGGYSLKLSKLKKNDSGIYYVGIYSSSLQQPSTQEYVLHVYEHLSK
PKVTMGLQSNKNGTCVTNLTCCMEHGEEDVIYTWKALGQAANESHNGSILPISWRWGESDMTFIC
VARNPVSRNFSSPILARKLCEGAADDPDSSMVLLCLLLVPLLLSLFVLGLFLWFLKRERQEEYIE
EKKRVDICRETPNICPHSGENTEYDTIPHTNRTILKEDPANTVYSTVEIPKKMENPHSLLTMPDT
PRLFAYENVI

Important features:

Signal peptide:

amino acids 1-22

Transmembrane domain:

amino acids 224-250

Leucine zipper pattern.

amino acids 229-251

N-glycosylation sites.

amino acids 98-102, 142-146, 148-152, 172-176, 176-180, 204-208, 291-295

FIGURE 47

GGCTCGAGCGTTTCTGAGCCAGGGGTGACC<u>ATG</u>ACCTGCTGCGAAGGATGGACATCCTGCAATGG
ATTCAGCCTGCTGGTTCTACTGCTGTTAGGAGTAGTTCTCAATGCGATACCTCTAATTGTCAGCT
TAGTTGAGGAAGACCAATTTTCTCAAAACCCCATCTCTTGCTTTGAGTGGTGGTTCCCAGGAATT
ATAGGAGCAGGTCTGATGGCCATTCCAGCAACAACAATGTCCTTGACAGCAAGAAAAAGAGCGTG
CTGCAACAACAGAACTGGAATGTTTCTTTCATCATTTTTCAGTGTGATCACAGTCATTGGTGCTC
TGTATTGCATGCTGATATCCATCCAGGCTCTCTTAAAAGGTCCTCTCATGTGTAATTCTCCAAGC
AACAGTAATGCCAATTGTGAATTTTCATTGAAAAACATCAGTGACATTCATCCAGAATCCTTCAA
CTTGCAGTGGTTTTTCAATGACTCTTGTGCACCTCCTACTGGTTTCAATAAACCCACCAGTAACG
ACACCATGGCGAGTGGCTGGAGAGCATCTAGTTTCCACTTCGATTCTGAAGAAAACAAACATAGG
CTTATCCACTTCTCAGTATTTTTAGGTCTATTGCTTGTTGGAATTCTGGAGGTCCTGTTTGGGCT
CAGTCAGATAGTCATCGGTTTCCTTGGCTGTCTGTGTGGAGTCTCTAAGCGAAGAAGTCAAATTG
TG<u>TAG</u>TTTAATGGGAATAAAATGTAAGTATCAGTAGTTTGAAAAAAAAAAA

FIGURE 48

MTCCEGWTSCNGFSLLVLLLLGVVLNAIPLIVSLVEEDQFSQNPISCFEWWFPGIIGAGLMAIPA
TTMSLTARKRACCNNRTGMFLSSFFSVITVIGALYCMLISIQALLKGPLMCNSPSNSNANCEFSL
KNISDIHPESFNLQWFFNDSCAPPTGFNKPTSNDTMASGWRASSFHFDSEENKHRLIHFSVFLGL
LLVGILEVLFGLSQIVIGFLGCLCGVSKRRSQIV

Important features:

Transmembrane domains:

amino acids 10-31 (type II), 50-72, 87-110, 191-213

N-glycosylation sites.

amino acids 80-84, 132-136, 148-152, 163-167 cAMP- and cGMP-dependent protein kinase phosphorylation site.

amino acids 223-227

N-myristoylation sites.

amino acids 22-28, 54-60, 83-89, 97-103, 216-222

Prokaryotic membrane lipoprotein lipid attachment site.

amino acids 207-218

TNFR/NGFR family cysteine-rich region protein.

amino acids 4-12

FIGURE 49

ATCCGTTCTCTGCGCTGCCAGCTCAGGTGAGCCCTCGCCAAGGTGACCTCGCAGGACACTGGTGA
AGGAGCAGTGAGGAACCTGCAGAGTCACACAGTTGCTGACCAATTGAGCTGTGAGCCTGGAGCAG
ATCCGTGGGCTGCAGACCCCCGCCCCAGTGCCTCTCCCCTGCAGCCCTGCCCCTCGAACTGTGA
CATGGAGAGAGTGACCCTGGCCCTTCTCCTACTGGCAGGCCTGACTGCCTTGGAAGCCAATGACC
CATTTGCCAATAAAGACGATCCCTTCTACTATGACTGGAAAAACCTGCAGCTGAGCGGACTGATC
TGCGGAGGGCTCCTGGCCATTGCTGGGATCGCGGCAGTTCTGAGTGGCAAATGCAAATACAAGAG
CAGCCAGAAGCAGCACAGTCCTGTACCTGAGAAGGCCATCCCACTCATCACTCCAGGCTCTGCCA
CTACTTGCTGAGCACAGGACTGGCCTCCAGGGATGGCCTGAAGCCTAACACTGGCCCCAGCACC
TCCTCCCCTGGGAGGCCTTATCCTCAAGGAAGGACTTCTCTCCAAGGGCAGGCTGTTAGGCCCCT
TTCTGATCAGGAGGCTTCTTTATGAATTAAACTCGCCCCACCACCCCTCA

FIGURE 50

MERVTLALLLLAGLTALEANDPFANKDDPFYYDWKNLQLSGLICGGLLAIAGIAAVLSGKCKYKS
SQKQHSPVPEKAIPLITPGSATTC

Important features:

Signal peptide:

amino acids 1-16

Transmembrane domain:

amino acids 36-59

N-myristoylation sites.

amino acids 41-47, 45-51, 84-90

Extracellular proteins SCP/Tpx-1/Ag5/PR-1/Sc7.

amino acids 54-67

FIGURE 51

GTGGACTCTGAGAAGCCCAGGCAGTTGAGGACAGGAGAGAGAAGGCTGCAGACCCAGAGGGAGGG
AGGACAGGGAGTCGGAAGGAGGAGGACAGAGGAGGGCACAGAGACGCAGAGCAAGGGCGGCAAGG
AGGAGACCCTGGTGGGAGGAAGACACTCTGGAGAGAGAGGGGGCTGGGCAGAGATGAAGTTCCAG
GGGCCCCTGGCCTGCCTCCTGCTGGCCCTCTGCCTGGGCAGTGGGGAGGCTGGCCCCCTGCAGAG
CGGAGAGGAAAGCACTGGGACAAATATTGGGGAGGCCCTTGGACATGGCCTGGGAGACGCCCTGA
GCGAAGGGGTGGGAAAGGCCATTGGCAAAGAGGCCGGAGGGGCAGCTGGCTCTAAAGTCAGTGAG
GCCCTTGGCCAAGGGACCAGAGAAGCAGTTGGCACTGGAGTCAGGCAGGTTCCAGGCTTTGGCGC
AGCAGATGCTTTGGGCAACAGGGTCGGGGAAGCAGCCCATGCTCTGGGAAACACTGGGCACGAGA
TTGGCAGACAGGCAGAAGATGTCATTCGACACGGAGCAGATGCTGTCCGCGGCTCCTGGCAGGGG
GTGCCTGGCCACAGTGGTGCTTGGGAAACTTCTGGAGGCCATGGCATCTTTGGCTCTCAAGGTGG
CCTTGGAGGCCAGGGCCAGGGCAATCCTGGAGGTCTGGGGACTCCGTGGGTCCACGGATACCCCG
GAAACTCAGCAGGCAGCTTTGGAATGAATCCTCAGGGAGCTCCCTGGGGTCAAGGAGGCAATGGA
GGGCCACCAAACTTTGGGACCAACACTCAGGGAGCTGTGGCCCAGCCTGGCTATGGTTCAGTGAG
AGCCAGCAACCAGAATGAAGGGTGCACGAATCCCCCACCATCTGGCTCAGGTGGAGGCTCCAGCA
ACTCTGGGGGAGGCAGCGGCTCACAGTCGGGCAGCAGTGGCAGTGGCAGCAATGGTGACAACAAC
AATGGCAGCAGCAGTGGTGGCAGCAGCAGTGGCAGCAGCAGTGGCAGCAGCAGTGGCGGCAGCAG
TGGCGGCAGCAGTGGTGGCAGCAGTGGCAACAGTGGTGGCAGCAGAGGTGACAGCGGCAGTGAGT
CCTCCTGGGGATCCAGCACCGGCTCCTCCTCCGGCAACCACGGTGGGAGCGGCGGAGGAAATGGA
CATAAACCCGGGTGTGAAAAGCCAGGGAATGAAGCCCGCGGGAGCGGGGAATCTGGGATTCAGGG
CTTCAGAGGACAGGGAGTTTCCAGCAACATGAGGGAAATAAGCAAAGAGGGCAATCGCCTCCTTG
GAGGCTCTGGAGACAATTATCGGGGCAAGGGTCGAGCTGGGGCAGTGGAGGAGGTGACGCTGTT
GGTGGAGTCAATACTGTGAACTCTGAGACGTCTCCTGGGATGTTTAACTTTGACACTTTCTGGAA
GAATTTTAAATCCAAGCTGGGTTTCATCAACTGGGATGCCATAAACAAGGACCAGAGAAGCTCTC
GCATCCCGTGACCTCCAGACAAGGAGCCACCAGATTGGATGGGAGCCCCCACACTCCCTCCTTAA
AACACCACCCTCTCATCACTAATCTCAGCCCTTGCCCTTGAAATAAACCTTAGCTGCCCCACAAA
AAAAAAAAAAAAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAA

FIGURE 52

MKFQGPLACLLLALCLGSGEAGPLQSGEESTGTNIGEALGHGLGDALSEGVGKAIGKEAGGAAGSKVS
EALGQGTREAVGTGVRQVPGFGAADALGNRVGEAAHALGNTGHEIGRQAEDVIRHGADAVRGSWQGVP
GHSGAWETSGGHGIFGSQGGLGGQGQGNPGGLGTPWVHGYPGNSAGSFGMNPQGAPWGQGGNGGPPNF
GTNTQGAVAQPGYGSVRASNQNEGCTNPPPSGSGGGSSNSGGGSGSQSGSSGSGSNGDNNNGSSSGGS
SSGSSSGSSSGGSSGGSSGGSSGNSGGSRGDSGSESSWGSSTGSSSGNHGGSGGGNGHKPGCEKPGNE
ARGSGESGIQGFRGQGVSSNMREISKEGNRLLGGSGDNYRGQGSSWGSGGGDAVGGVNTVNSETSPGM
FNFDTFWKNFKSKLGFINWDAINKDQRSSRIP

Signal peptide:

amino acids 1-21

N-glycosylation site.

amino acids 265-269

Glycosaminoglycan attachment site.

amino acids 235-239, 237-241, 244-248, 255-259, 324-328, 388-392

Casein kinase II phosphorylation site.

amino acids 26-30, 109-113, 259-263, 300-304, 304-308

N-myristoylation site.

amino acids 17-23, 32-38, 42-48, 50-56, 60-66, 61-67, 64-70, 74-80,
90-96, 96-102, 130-136, 140-146, 149-155, 152-158, 155-161,
159-165, 163-169, 178-184, 190-196, 194-200, 199-205, 218-224,
236-242, 238-244, 239-245, 240-246, 245-251, 246-252, 249-252,
253-259, 256-262, 266-272, 270-276, 271-277, 275-281, 279-285,
283-289, 284-290, 287-293, 288-294, 291-297, 292-298, 295-301,
298-304, 305-311, 311-317, 315-321, 319-325, 322-328, 323-329,
325-331, 343-349, 354-360, 356-362, 374-380, 381-387, 383-389,
387-393, 389-395, 395-401

Cell attachment sequence.

amino acids 301-304

FIGURE 53

GGAGAAGAGGTTGTGTGGGACAAGCTGCTCCCGACAGAAG<u>ATG</u>TCGCTGCTGAGCCTGCCCTGG
CTGGGCCTCAGACCGGTGGCAATGTCCCCATGGCTACTCCTGCTGCTGGTTGTGGGCTCCTGGCT
ACTCGCCCGCATCCTGGCTTGGACCTATGCCTTCTATAACAACTGCCGCCGGCTCCAGTGTTTCC
CACAGCCCCCAAAACGGAACTGGTTTTGGGGTCACCTGGGCCTGATCACTCCTACAGAGGAGGGC
TTGAAGGACTCGACCCAGATGTCGGCCACCTATTCCCAGGGCTTTACGGTATGGCTGGGTCCCAT
CATCCCCTTCATCGTTTTATGCCACCCTGACACCATCCGGTCTATCACCAATGCCTCAGCTGCCA
TTGCACCCAAGGATAATCTCTTCATCAGGTTCCTGAAGCCCTGGCTGGGAGAAGGGATACTGCTG
AGTGGCGGTGACAAGTGGAGCCGCCACCGTCGGATGCTGACGCCCGCCTTCCATTTCAACATCCT
GAAGTCCTATATAACGATCTTCAACAAGAGTGCAAACATCATGCTTGACAAGTGGCAGCACCTGG
CCTCAGAGGGCAGCAGTCGTCTGGACATGTTTGAGCACATCAGCCTCATGACCTTGGACAGTCTA
CAGAAATGCATCTTCAGCTTTGACAGCCATTGTCAGGAGAGGCCCAGTGAATATATTGCCACCAT
CTTGGAGCTCAGTGCCCTTGTAGAGAAAAGAAGCCAGCATATCCTCCAGCACATGGACTTTCTGT
ATTACCTCTCCCATGACGGGCGGCGCTTCCACAGGGCCTGCCGCCTGGTGCATGACTTCACAGAC
GCTGTCATCCGGGAGCGGCGTCGCACCCTCCCCACTCAGGGTATTGATGATTTTTCAAAGACAA
AGCCAAGTCCAAGACTTTGGATTTCATTGATGTGCTTCTGCTGAGCAAGGATGAAGATGGGAAGG
CATTGTCAGATGAGGATATAAGAGCAGAGGCTGACACCTTCATGTTTGGAGGCCATGACACCACG
GCCAGTGGCCTCTCCTGGGTCCTGTACAACCTTGCGAGGCACCCAGAATACCAGGAGCGCTGCCG
ACAGGAGGTGCAAGAGCTTCTGAAGGACCGCGATCCTAAAGAGATTGAATGGGACGACCTGGCCC
AGCTGCCCTTCCTGACCATGTGCGTGAAGGAGAGCCTGAGGTTACATCCCCAGCTCCCTTCATC
TCCCGATGCTGCACCCAGGACATTGTTCTCCCAGATGGCCGAGTCATCCCCAAAGGCATTACCTG
CCTCATCGATATTATAGGGGTCCATCACAACCCAACTGTGTGGCCGGATCCTGAGGTCTACGACC
CCTTCCGCTTTGACCCAGAGAACAGCAAGGGGAGGTCACCTCTGGCTTTTATTCCTTTCTCCGCA
GGGCCCAGGAACTGCATCGGGCAGGCGTTCGCCATGGCGGAGATGAAAGTGGTCCTGGCGTTGAT
GCTGCTGCACTTCCGGTTCCTGCCAGACCACACTGAGCCCCGCAGGAAGCTGGAATTGATCATGC
GCGCCGAGGGCGGGCTTTGGCTGCGGGTGGAGCCCCTGAATGTAGGCTTGCAG<u>TGA</u>CTTTCTGAC
CCATCCACCTGTTTTTTTGCAGATTGTCATGAATAAAACGGTGCTGTCAAA

FIGURE 54

MSLLSLPWLGLRPVAMSPWLLLLLVVGSWLLARILAWTYAFYNNCRRLQCFPQPPKRNWFWGHLG
LITPTEEGLKDSTQMSATYSQGFTVWLGPIIPFIVLCHPDTIRSITNASAAIAPKDNLFIRFLKP
WLGEGILLSGGDKWSRHRRMLTPAFHFNILKSYITIFNKSANIMLDKWQHLASEGSSRLDMFEHI
SLMTLDSLQKCIFSFDSHCQERPSEYIATILELSALVEKRSQHILQHMDFLYYLSHDGRRFHRAC
RLVHDFTDAVIRERRRTLPTQGIDDFFKDKAKSKTLDFIDVLLLSKDEDGKALSDEDIRAEADTF
MFGGHDTTASGLSWVLYNLARHPEYQERCRQEVQELLKDRDPKEIEWDDLAQLPFLTMCVKESLR
LHPPAPFISRCCTQDIVLPDGRVIPKGITCLIDIIGVHHNPTVWPDPEVYDPFRFDPENSKGRSP
LAFIPFSAGPRNCIGQAFAMAEMKVVLALMLLHFRFLPDHTEPRRKLELIMRAEGGLWLRVEPLN
VGLQ

Important features:

Transmembrane domains:

amino acids 13-32 (type II), 77-102

Cytochrome P450 cysteine heme-iron ligand signature.

amino acids 461-471

N-glycosylation sites.

amino acids 112-116, 168-172

FIGURE 55

ATCGCATCAATTGGGAGTACCATCTTCCTC<u>ATG</u>GGACCAGTGAAACAGCTGAAGCGAATGTTTGA
GCCTACTCGTTTGATTGCAACTATCATGGTGCTGTTGTGTTTTGCACTTACCCTGTGTTCTGCCT
TTTGGTGGCATAACAAGGGACTTGCACTTATCTTCTGCATTTTGCAGTCTTTGGCATTGACGTGG
TACAGCCTTTCCTTCATACCATTTGCAAGGGATGCTGTGAAGAAGTGTTTTGCCGTGTGTCTTGC
A<u>TAA</u>TTCATGGCCAGTTTTATGAAGCTTTGGAAGGCACTATGGACAGAAGCTGGTGGACAGTTTT
GTAACTATCTTCGAAACCTCTGTCTTACAGACATGTGCCTTTTATCTTGCAGCAATGTGTTGCTT
GTGATTCGAACATTTGAGGGTTACTTTTGGAAGCAACAATACATTCTCGAACCTGAATGTCAGTA
GCACAGGATGAGAAGTGGGTTCTGTATCTTGTGGAGTGGAATCTTCCTCATGTACCTGTTTCCTC
TCTGGATGTTGTCCCACTGAATTCCCATGAATACAAACCTATTCAGCAACAGCAAAAAAAAAAA
AAAAAAAAAAAAAAAAAAAAAAAAAAAAAAAAAAAAAAAAAAAAAAAAAAAAAA

FIGURE 56

MGPVKQLKRMFEPTRLIATIMVLLCFALTLCSAFWWHNKGLALIFCILQSLALTWYSLSFIPFAR
DAVKKCFAVCLA

Important features:

Signal peptide:

amino acids 1-33

Type II fibronectin collagen-binding domain protein.
amino acids 30-72

FIGURE 57

CGGCTCGAGCTCGAGCCGAATCGGCTCGAGGGGCAGTGGAGCACCCAGCAGGCCGCCAACATGCTCTGTCTGTGCCTG
TACGTGCCGGTCATCGGGGAAGCCCAGACCGAGTTCCAGTACTTTGAGTCGAAGGGGCTCCCTGCCGAGCTGAAGTCC
ATTTTCAAGCTCAGTGTCTTCATCCCCTCCCAGGAATTCTCCACCTACCGCCAGTGGAAGCAGAAAATTGTACAAGCT
GGAGATAAGGACCTTGATGGGCAGCTAGACTTTGAAGAATTTGTCCATTATCTCCAAGATCATGAGAAGAAGCTGAGG
CTGGTGTTTAAGATTTTGGACAAAAAGAATGATGGACGCATTGACGCGCAGGAGATCATGCAGTCCCTGCGGGACTTG
GGAGTCAAGATATCTGAACAGCAGGCAGAAAAAATTCTCAAGAGCATGGATAAAAACGGCACGATGACCATCGACTGG
AACGAGTGGAGAGACTACCACCTCCTCCACCCCGTGGAAAACATCCCCGAGATCATCCTCTACTGGAAGCATTCCACG
ATCTTTGATGTGGGTGAGAATCTAACGGTCCCGGATGAGTTCACAGTGGAGGAGAGGCAGACGGGGATGTGGTGGAGA
CACCTGGTGGCAGGAGGTGGGGCAGGGGCCGTATCCAGAACCTGCACGGCCCCCTGGACAGGCTCAAGGTGCTCATG
CAGGTCCATGCCTCCCGCAGCAACAACATGGGCATCGTTGGTGGCTTCACTCAGATGATTCGAGAAGGAGGGGCCAGG
TCACTCTGGCGGGGCAATGGCATCAACGTCCTCAAAATTGCCCCCGAATCAGCCATCAAATTCATGGCCTATGAGCAG
ATCAAGCGCCTTGTTGGTAGTGACCAGGAGACTCTGAGGATTCACGAGAGGCTTGTGGCAGGGTCCTTGGCAGGGGCC
ATCGCCCAGAGCAGCATCTACCCAATGGAGGTCCTGAAGACCCGGATGGCGCTGCGGAAGACAGGCCAGTACTCAGGA
ATGCTGGACTGCGCCAGGAGGATCCTGGCCAGAGAGGGGGTGGCCGCCTTCTACAAAGGCTATGTCCCCAACATGCTG
GGCATCATCCCCTATGCCGGCATCGACCTTGCAGTCTACGAGACGCTCAAGAATGCCTGGCTGCAGCACTATGCAGTG
AACAGCGCGGACCCCGGCGTGTTTGTGCTCCTGGCCTGTGGCACCATGTCCAGTACCTGTGGCCAGCTGGCCAGCTAC
CCCCTGGCCCTAGTCAGGACCCGGATGCAGGCGCAAGCCTCTATTGAGGCGCGCTCCGGAGGTGACCATGAGCAGCCTC
TTCAAACATATCCTGCGGACCGAGGGGGCCTTCGGGCTGTACAGGGGGCTGGCCCCCAACTTCATGAAGGTCATCCCA
GCTGTGAGCATCAGCTACGTGGTCTACGAGAACCTGAAGATCACCCTGGGCGTGCAGTCGCGGTGACGGGGGGAGGGC
CGCCCCGGCAGTGGACTCGCTGATCCTGGGCCGCAGCCTGGGGTGTGCAGCCATCTCATTCTGTGAATGTGCCAACACT
AAGCTGTCTCGAGCCAAGCTGTGAAAACCCTAGACGCACCCGCAGGGAGGGTGGGGAGAGCTGGCAGGCCCAGGCTT
GTCCTGCTGACCCCAGCAGACCCTCCTGTTGGTTCCAGCGAAGACCACAGGCATTCCTTAGGGTCCAGGGTCAGCAGG
CTCCGGGCTCACATGTGTAAGGACAGGACATTTTCTGCAGTGCCTGCCAATAGTGAGCTTGGAGCCTGGAGGCCGGCT
TAGTTCTTCCATTTCACCCTTGCAGCCAGCTGTTGGCCACGGCCCCTGCCCTCTGGTCTGCCGTGCATCTCCCTGTGC
CCTCTTGCTGCCTGCCTGTCTGCTGAGGTAAGGTGGGAGGAGGGCTACAGCCCACATCCCACCCCCTCGTCCAATCCC
ATAATCCATGATGAAAGGTGAGGTCACGTGGCCTCCCAGGCCTGACTTCCCAACCTACAGCATTGACGCCAACTTGGC
TGTGAAGGAAGAGGAAAGGATCTGGCCTTGTGGTCACTGGCATCTGAGCCCTGCTGATGGCTGGGGCTCTCGGGCATG
CTTGGGAGTGCAGGGGGCTCGGGCTGCCTGGCCTGGCTGCACAGAAGGCAAGTGCTGGGGCTCATGGTGCTCTGAGCT
GGCCTGGACCCTGTCAGGATGGGCCCCACCTCAGAACCAAACTCACTGTCCCCACTGTGGCATGAGGGCAGTGGAGCA
CCATGTTTGAGGGCGAAGGGCAGAGCGTTTGTGTGTTCTGGGGAGGGAAGGAAAAGGTGTTGGAGGCCTTAATTATGG
ACTGTTGGGAAAAGGGTTTTGTCCAGAAGGACAAGCCGGACAAATGAGCGACTTCTGTGCTTCCAGAGGAAGACGAGG
GAGCAGGAGCTTGGCTGACTGCTCAGAGTCTGTTCTGACGCCCTGGGGGTTCCTGTCCAACCCCAGCAGGGGCGCAGC
GGGACCAGCCCCACATTCCACTTGTGTCACTGCTTGGAACCTATTTATTTTGTATTTATTTGAACAGAGTTATGTCCT
AACTATTTTTATAGATTTGTTTAATTAATAGCTTGTCATTTCAAGTTCATTTTTTATTCATATTTATGTTCATGGTT
GATTGTACCTTCCCAAGCCCGCCCAGTGĠGATGGGAGGAGGAGGAGAAGGGGGCCTTGGGCCGCTGCAGTCACATCT
GTCCAGAGAAATTCCTTTTGGGACTGGAGGCAGAAAAGCGGCCAGAAGGCAGCAGCCCTGGCTCCTTTCCTTTGGCAG
GTTGGGGAAGGGCTTGCCCCCAGCCTTAGGATTTCAGGGTTTGACTGGGGGCGTGGAGAGAGAGGGAGGAACCTCAAT
AACCTTGAAGGTGGAATCCAGTTATTTCCTGCGCTGCGAGGGTTTCTTTATTTCACTCTTTTCTGAATGTCAAGGCAG
TGAGGTGCCTCTCACTGTGAATTTGTGGTGGGCGGGGCTGGAGGAGAGGGTGGGGGGCTGGCTCCGTCCCTCCCAGC
CTTCTGCTGCCCTTGCTTAACAATGCCGGCCAACTGGCGACCTCACGGTTGCACTTCCATTCCACCAGAATGACCTGA
TGAGGAAATCTTCAATAGGATGCAAAGATCAATGCAAAAATTGTTATATATGAACATATAACTGGAGTCGTCAAAAAG
CAAATTAAGAAAGAATTGGACGTTAGAAGTTGTCATTTAAAGCAGCCTTCTAATAAAGTTGTTTCAAAGCTGAAAAAA
AAAAAAAAAAAAAAAAAAAAAAAAAAAAAAAAAAAAAAAAAAAAAAAAAAAAAAAA

FIGURE 58

MLCLCLYVPVIGEAQTEFQYFESKGLPAELKSIFKLSVFIPSQEFSTYRQWKQKIVQAGDKDLDG
QLDFEEFVHYLQDHEKKLRLVFKILDKKNDGRIDAQEIMQSLRDLGVKISEQQAEKILKSMDKNG
TMTIDWNEWRDYHLLHPVENIPEIILYWKHSTIFDVGENLTVPDEFTVEERQTGMWWRHLVAGGG
AGAVSRTCTAPLDRLKVLMQVHASRSNNMGIVGGFTQMIREGGARSLWRGNGINVLKIAPESAIK
FMAYEQIKRLVGSDQETLRIHERLVAGSLAGAIAQSSIYPMEVLKTRMALRKTGQYSGMLDCARR
ILAREGVAAFYKGYVPNMLGIIPYAGIDLAVYETLKNAWLQHYAVNSADPGVFVLLACGTMSSTC
GQLASYPLALVRTRMQAQASIEGAPEVTMSSLFKHILRTEGAFGLYRGLAPNFMKVIPAVSISYV
VYENLKITLGVQSR

Important features:

Signal peptide:

amino acids 1-16

Putative transmembrane domains:

amino acids 284-304, 339-360, 376-394

Mitochondrial energy transfer proteins signature.

amino acids 206-215, 300-309

N-glycosylation sites.

amino acids 129-133, 169-173

Elongation Factor-hand calcium-binding protein.

amino acids 54-73, 85-104, 121-140

FIGURE 59

GGAAGGCAGCGGCAGCTCCACTCAGCCAGTACCCAGATACGCTGGGAACCTTCCCCAGCCATGGC
TTCCCTGGGGCAGATCCTCTTCTGGAGCATAATTAGCATCATCATTATTCTGGCTGGAGCAATTG
CACTCATCATTGGCTTTGGTATTTCAGGGAGACACTCCATCACAGTCACTACTGTCGCCTCAGCT
GGGAACATTGGGGAGGATGGAATCCTGAGCTGCACTTTTGAACCTGACATCAAACTTTCTGATAT
CGTGATACAATGGCTGAAGGAAGGTGTTTTAGGCTTGGTCCATGAGTTCAAAGAAGGCAAAGATG
AGCTGTCGGAGCAGGATGAAATGTTCAGAGGCCGGACAGCAGTGTTTGCTGATCAAGTGATAGTT
GGCAATGCCTCTTTGCGGCTGAAAAACGTGCAACTCACAGATGCTGGCACCTACAAATGTTATAT
CATCACTTCTAAAGGCAAGGGGAATGCTAACCTTGAGTATAAAACTGGAGCCTTCAGCATGCCGG
AAGTGAATGTGGACTATAATGCCAGCTCAGAGACCTTGCGGTGTGAGGCTCCCCGATGGTTCCCC
CAGCCCACAGTGGTCTGGGCATCCCAAGTTGACCAGGGAGCCAACTTCTCGGAAGTCTCCAATAC
CAGCTTTGAGCTGAACTCTGAGAATGTGACCATGAAGGTTGTGTCTGTGCTCTACAATGTTACGA
TCAACAACACATACTCCTGTATGATTGAAAATGACATTGCCAAAGCAACAGGGGATATCAAAGTG
ACAGAATCGGAGATCAAAAGGCGGAGTCACCTACAGCTGCTAAACTCAAAGGCTTCTCTGTGTGT
CTCTTCTTTCTTTGCCATCAGCTGGGCACTTCTGCCTCTCAGCCCTTACCTGATGCTAAAATAAT
GTGCCTTGGCCACAAAAAAGCATGCAAAGTCATTGTTACAACAGGGATCTACAGAACTATTTCAC
CACCAGATATGACCTAGTTTTATATTTCTGGGAGGAAATGAATTCATATCTAGAAGTCTGGAGTG
AGCAAACAAGAGCAAGAAACAAAAAGAAGCCAAAAGCAGAAGGCTCCAATATGAACAAGATAAAT
CTATCTTCAAAGACATATTAGAAGTTGGGAAAATAATTCATGTGAACTAGACAAGTGTGTTAAGA
GTGATAAGTAAAATGCACGTGGAGACAAGTGCATCCCCAGATCTCAGGGACCTCCCCCTGCCTGT
CACCTGGGGAGTGAGAGGACAGGATAGTGCATGTTCTTTGTCTCTGAATTTTTAGTTATATGTGC
TGTAATGTTGCTCTGAGGAAGCCCCTGGAAAGTCTATCCCAACATATCCACATCTTATATTCCAC
AAATTAAGCTGTAGTATGTACCCTAAGACGCTGCTAATTGACTGCCACTTCGCAACTCAGGGGCG
GCTGCATTTTAGTAATGGGTCAAATGATTCACTTTTTATGATGCTTCCAAAGGTGCCTTGGCTTC
TCTTCCCAACTGACAAATGCCAAAGTTGAGAAAAATGATCATAATTTTAGCATAAACAGAGCAGT
CGGGGACACCGATTTTATAAATAAACTGAGCACCTTCTTTTTAAACAAAAAAAAAAAAAAAAAAA
AAAAAAAAAAAAAAAAAAAAAAAAAAAAAAAAAA

FIGURE 6o

MASLGQILFWSIISIIIILAGAIALIIGFGISGRHSITVTTVASAGNIGEDGILSCTFEPDIKLS
DIVIQWLKEGVLGLVHEFKEGKDELSEQDEMFRGRTAVFADQVIVGNASLRLKNVQLTDAGTYKC
YIITSKGKGNANLEYKTGAFSMPEVNVDYNASSETLRCEAPRWFPQPTVVWASQVDQGANFSEVS
NTSFELNSENVTMKVVSVLYNVTINNTYSCMIENDIAKATGDIKVTESEIKRRSHLQLLNSKASL
CVSSFFAISWALLPLSPYLMLK

Important features:

Signal peptide:

amino acids 1-28

Transmembrane domain:

amino acids 258-281

N-glycosylation sites.

amino acids 112-116, 160-164, 190-194, 196-200, 205-209, 216-220, 220-224

N-myristoylation sites.

amino acids 52-58, 126-132, 188-194

FIGURE 61

TGACGTCAGAATCACCATGGCCAGCTATCCTTACCGGCAGGGCTGCCCAGGAGCTGCAGGACAAG
CACCAGGAGCCCCTCCGGGTAGCTACTACCCTGGACCCCCCAATAGTGGAGGGCAGTATGGTAGT
GGGCTACCCCCTGGTGGTGGTTATGGGGGTCCTGCCCCTGGAGGGCCTTATGGACCACCAGCTGG
TGGAGGGCCCTATGGACACCCCAATCCTGGGATGTTCCCCTCTGGAACTCCAGGAGGACCATATG
GCGGTGCAGCTCCCGGGGGCCCCTATGGTCAGCCACCTCCAAGTTCCTACGGTGCCCAGCAGCCT
GGGCTTTATGGACAGGGTGGCGCCCCTCCCAATGTGGATCCTGAGGCCTACTCCTGGTTCCAGTC
GGTGGACTCAGATCACAGTGGCTATATCTCCATGAAGGAGCTAAAGCAGGCCCTGGTCAACTGCA
ATTGGTCTTCATTCAATGATGAGACCTGCCTCATGATGATAAACATGTTTGACAAGACCAAGTCA
GGCCGCATCGATGTCTACGGCTTCTCAGCCCTGTGGAAATTCATCCAGCAGTGGAAGAACCTCTT
CCAGCAGTATGACCGGGACCGCTCGGGCTCCATTAGCTACACAGAGCTGCAGCAAGCTCTGTCCC
AAATGGGCTACAACCTGAGCCCCCAGTTCACCCAGCTTCTGGTCTCCCGCTACTGCCCACGCTCT
GCCAATCCTGCCATGCAGCTTGACCGCTTCATCCAGGTGTGCACCCAGCTGCAGGTGCTGACAGA
GGCCTTCCGGGAGAAGGACACAGCTGTACAAGGCAACATCCGGCTCAGCTTCGAGGACTTCGTCA
CCATGACAGCTTCTCGGATGCTATGACCCAACCATCTGTGGAGAGTGGAGTGCACCAGGGACCTT
TCCTGGCTTCTTAGAGTGAGAGAAGTATGTGGACATCTCTTCTTTTCCTGTCCCTCTAGAAGAAC
ATTCTCCCTTGCTTGATGCAACACTGTTCCAAAAGAGGGTGGAGAGTCCTGCATCATAGCCACCA
AATAGTGAGGACCGGGGCTGAGGCCACACAGATAGGGGCCTGATGGAGGAGAGGATAGAAGTTGA
ATGTCCTGATGGCCATGAGCAGTTGAGTGGCACAGCCTGGCACCAGGAGCAGGTCCTTGTAATGG
AGTTAGTGTCCAGTCAGCTGAGCTCCACCCTGATGCCAGTGGTGAGTGTTCATCGGCCTGTTACC
GTTAGTACCTGTGTTCCCTCACCAGGCCATCCTGTCAAACGAGCCCATTTTCTCCAAAGTGGAAT
CTGACCAAGCATGAGAGAGATCTGTCTATGGGACCAGTGGCTTGGATTCTGCCACACCCATAAAT
CCTTGTGTGTTAACTTCTAGCTGCCTGGGGCTGGCCCTGCTCAGACAAATCTGCTCCCTGGGCAT
CTTTGGCCAGGCTTCTGCCCCTGCAGCTGGGACCCCTCACTTGCCTGCCATGCTCTGCTCGGCT
TCAGTCTCCAGGAGACAGTGGTCACCTCTCCCTGCCAATACTTTTTTTAATTTGCATTTTTTTTC
ATTTGGGGCCAAAAGTCCAGTGAAATTGTAAGCTTCAATAAAAGGATGAAACTCTGA

FIGURE 62

MASYPYRQGCPGAAGQAPGAPPGSYYPGPPNSGGQYGSGLPPGGGYGGPAPGGPYGPPAGGGPYG
HPNPGMFPSGTPGGPYGGAAPGGPYGQPPPSSYGAQQPGLYGQGGAPPNVDPEAYSWFQSVDSDH
SGYISMKELKQALVNCNWSSFNDETCLMMINMFDKTKSGRIDVYGFSALWKFIQQWKNLFQQYDR
DRSGSISYTELQQALSQMGYNLSPQFTQLLVSRYCPRSANPAMQLDRFIQVCTQLQVLTEAFREK
DTAVQGNIRLSFEDFVTMTASRML

Important features of the protein:

Signal peptide:

amino acids 1-19

N-glycosylation site.

amino acids 147-150

Casein kinase II phosphorylation sites.

amino acids 135-138, 150-153, 202-205, 271-274

N-myristoylation sites.

amino acids 9-14, 15-20, 19-24, 33-38, 34-39, 39-44, 43-48, 61-66, 70-75, 78-83, 83-88, 87-92, 110-115

FIGURE 63

CAGG<u>ATG</u>CAGGGCCGCGTGGCAGGGAGCTGCGCTCCTCTGGGCCTGCTCCTGGTCTGTCTTCATC
TCCCAGGCCTCTTTGCCCGGAGCATCGGTGTTGTGGAGGAGAAAGTTTCCCAAAACTTCGGGACC
AACTTGCCTCAGCTCGGACAACCTTCCTCCACTGGCCCCTCTAACTCTGAACATCCGCAGCCCGC
TCTGGACCCTAGGTCTAATGACTTGGCAAGGGTTCCTCTGAAGCTCAGCGTGCCTCCATCAGATG
GCTTCCCACCTGCAGGAGGTTCTGCAGTGCAGAGGTGGCCTCCATCGTGGGGCTGCCTGCCATG
GATTCCTGGCCCCCTGAGGATCCTTGGCAGATGATGGCTGCTGCGGCTGAGGACCGCCTGGGGGA
AGCGCTGCCTGAAGAACTCTCTTACCTCTCCAGTGCTGCGGCCCTCGCTCCGGGCAGTGGCCCTT
TGCCTGGGGAGTCTTCTCCCGATGCCACAGGCCTCTCACCTGAGGCTTCACTCCTCCACCAGGAC
TCGGAGTCCAGACGACTGCCCCGTTCTAATTCACTGGGAGCCGGGGAAAAATCCTTTCCCAACG
CCCTCCCTGGTCTCTCATCCACAGGGTTCTGCCTGATCACCCCTGGGGTACCCTGAATCCCAGTG
TGTCCTGGGGAGGTGGAGGCCCTGGGACTGGTTGGGGAACGAGGCCCATGCCACACCCTGAGGGA
ATCTGGGGTATCAATAATCAACCCCCAGGTACCAGCTGGGGAAATATTAATCGGTATCCAGGAGG
CAGCTGGGGAAATATTAATCGGTATCCAGGAGGCAGCTGGGGGAATATTAATCGGTATCCAGGAG
GCAGCTGGGGGAATATTCATCTATACCCAGGTATCAATAACCCATTTCCTCCTGGAGTTCTCCGC
CCTCCTGGCTCTTCTTGGAACATCCCAGCTGGCTTCCCTAATCCTCCAAGCCCTAGGTTGCAGTG
GGGC<u>TAG</u>AGCACGATAGAGGGAAACCCAACATTGGGAGTTAGAGTCCTGCTCCCGCCCCTTGCTG
TGTGGGCTCAATCCAGGCCCTGTTAACATGTTTCCAGCACTATCCCCACTTTTCAGTGCCTCCCC
TGCTCATCTCCAATAAAATAAAAGCACTTATGAAAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAAAAA

FIGURE 64

MQGRVAGSCAPLGLLLVCLHLPGLFARSIGVVEEKVSQNFGTNLPQLGQPSSTGPSNSEHPQPAL
DPRSNDLARVPLKLSVPPSDGFPPAGGSAVQRWPPSWGLPAMDSWPPEDPWQMMAAAAEDRLGEA
LPEELSYLSSAAALAPGSGPLPGESSPDATGLSPEASLLHQDSESRRLPRSNSLGAGGKILSQRP
PWSLIHRVLPDHPWGTLNPSVSWGGGGPGTGWGTRPMPHPEGIWGINNQPPGTSWGNINRYPGGS
WGNINRYPGGSWGNINRYPGGSWGNIHLYPGINNPFPPGVLRPPGSSWNIPAGFPNPPSPRLQWG

Important features of the protein:
Signal peptide:
amino acids 1-26

Casein kinase II phosphorylation sites.
amino acids 56-59, 155-158

N-myristoylation sites.
amino acids 48-53, 220-225, 221-226, 224-229, 247-252, 258-263, 259-264, 269-274, 270-275, 280-285, 281-286, 305-310

FIGURE 65

AAGGAGAGGCCACCGGGACTTCAGTGTCTCCTCCATCCCAGGAGCGCAGTGGCCACTATGGGGTC
TGGGCTGCCCCTTGTCCTCCTCTTGACCCTCCTTGGCAGCTCACATGGAACAGGGCCGGGTATGA
CTTTGCAACTGAAGCTGAAGGAGTCTTTTCTGACAAATTCCTCCTATGAGTCCAGCTTCCTGGAA
TTGCTTGAAAAGCTCTGCCTCCTCCTCCATCTCCCTTCAGGGACCAGCGTCACCCTCCACCATGC
AAGATCTCAACACCATGTTGTCTGCAACACATGACAGCCATTGAAGCCTGTGTCCTTCTTGGCCC
GGGCTTTTGGGCCGGGGATGCAGGAGGCAGGCCCCGACCCTGTCTTTCAGCAGGCCCCCACCCTC
CTGAGTGGCAATAAATAAAATTCGGTATGCTG

FIGURE 66

MGSGLPLVLLLTLLGSSHGTGPGMTLQLKLKESFLTNSSYESSFLELLEKLCLLLHLPSGTSVTL
HHARSQHHVVCNT

Important features:

Signal peptide:

amino acids 1-19

N-glycosylation site.

amino acids 37-41

N-myristoylation sites.

amino acids 15-21, 19-25, 60-66

FIGURE 67

ACGGACCGAGGGTTCGAGGGAGGGACACGGACCAGGAACCTGAGCTAGGTCAAAGACGCCCGGGC
CAGGTGCCCCGTCGCAGGTGCCCCTGGCCGGAGATGCGGTAGGAGGGGCGAGCGCGAGAAGCCCC
TTCCTCGGCGCTGCCAACCCGCCACCCAGCCCATGGCGAACCCCGGGCTGGGGCTGCTTCTGGCG
CTGGGCCTGCCGTTCCTGCTGGCCCGCTGGGGCCGAGCCTGGGGGCAAATACAGACCACTTCTGC
AAATGAGAATAGCACTGTTTTGCCTTCATCCACCAGCTCCAGCTCCGATGGCAACCTGCGTCCGG
AAGCCATCACTGCTATCATCGTGGTCTTCTCCCTCTTGGCTGCCTTGCTCCTGGCTGTGGGGCTG
GCACTGTTGGTGCGGAAGCTTCGGGAGAAGCGGCAGACGGAGGGCACCTACCGGCCCAGTAGCGA
GGAGCAGTTCTCCCATGCAGCCGAGGCCCGGGCCCCTCAGGACTCCAAGGAGACGGTGCAGGGCT
GCCTGCCCATCTAGGTCCCCTCTCCTGCATCTGTCTCCCTTCATTGCTGTGTGACCTTGGGGAAA
GGCAGTGCCCTCTCTGGGCAGTCAGATCCACCCAGTGCTTAATAGCAGGGAAGAAGGTACTTCAA
AGACTCTGCCCCTGAGGTCAAGAGAGGATGGGGCTATTCACTTTTATATATTTATATAAAATTAG
TAGTGAGATGTAAAAAAAAAAAAAAAAAA

FIGURE 68

MANPGLGLLLALGLPFLLARWGRAWGQIQTTSANENSTVLPSSTSSSSDGNLRPEAITAIIVVFS
LLAALLLAVGLALLVRKLREKRQTEGTYRPSSEEQFSHAAEARAPQDSKETVQGCLPI

Important features:

Signal peptide:

amino acids 1-19

Transmembrane domain:

amino acids 56-80

N-glycosylation site.

amino acids 36-40 cAMP- and cGMP-dependent protein kinase phosphorylation site.

amino acids 86-90

Tyrosine kinase phosphorylation site.

amino acids 86-94

N-myristoylation sites.

amino acids 7-13, 26-32

FIGURE 69

```
GCCAGGAATAACTAGAGAGGAACAATGGGGTTATTCAGAGGTTTTGTTTTCCTCTTAGTTCTGTGCCTGCTGCACCAG
TCAAATACTTCCTTCATTAAGCTGAATAATAATGGCTTTGAAGATATTGTCATTGTTATAGATCCTAGTGTGCCAGAA
GATGAAAAATAATTGAACAAATAGAGGATATGGTGACTACAGCTTCTACGTACCTGTTTGAAGCCACAGAAAAAAGA
TTTTTTTTCAAAAATGTATCTATATTAATTCCTGAGAATTGGAAGGAAAATCCTCAGTACAAAAGGCCAAAACATGAA
AACCATAAACATGCTGATGTTATAGTTGCACCACCTACACTCCAGGTAGAGATGAACCATACACCAAGCAGTTCACA
GAATGTGGAGAGAAAGGCGAATACATTCACTTCACCCCTGACCTTCTACTTGGAAAAAAACAAAATGAATATGGACCA
CCAGGCAAACTGTTTGTCCATGAGTGGGCTCACCTCCGGTGGGGAGTGTTTGATGAGTACAATGAAGATCAGCCTTTC
TACCGTGCTAAGTCAAAAAAAATCGAAGCAACAAGGTGTTCCGCAGGTATCTCTGGTAGAAATAGAGTTTATAAGTGT
CAAGGAGGCAGCTGTCTTAGTAGAGCATGCAGAATTGATTCTACAACAAAACTGTATGGAAAAGATTGTCAATTCTTT
CCTGATAAAGTACAAACAGAAAAAGCATCCATAATGTTTATGCAAAGTATTGATTCTGTTGTTGAATTTTGTAACGAA
AAAACCCATAATCAAGAAGCTCCAAGCCTACAAAACATAAAGTGCAATTTTAGAAGTACATGGGAGGTGATTAGCAAT
TCTGAGGATTTTAAAAACACCATACCCATGGTGACACCACCTCCTCCACCTGTCTTCTCATTGCTGAAGATCAGTCAA
AGAATTGTGTGCTTAGTTCTTGATAAGTCTGGAAGCATGGGGGGTAAGGACCGCCTAAATCGAATGAATCAAGCAGCA
AAACATTTCCTGCTGCAGACTGTTGAAAATGGATCCTGGGTGGGGATGGTTCACTTTGATAGTACTGCCACTATTGTA
AATAAGCTAATCCAAATAAAAAGCAGTGATGAAAGAAACACACTCATGGCAGGATTACCTACATATCCTCTGGGAGGA
ACTTCCATCTGCTCTGGAATTAAATATGCATTTCAGGTGATTGGAGAGCTACATTCCCAACTCGATGGATCCGAAGTA
CTGCTGCTGACTGATGGGGAGGATAACACTGCAAGTTCTTGTATTGATGAAGTGAAACAAAGTGGGGCATTGTTCAT
TTTATTGCTTTGGGAAGAGCTGCTGATGAAGCAGTAATAGAGATGAGCAAGATAACAGGAGGAAGTCATTTTTATGTT
TCAGATGAAGCTCAGAACAATGGCCTCATTGATGCTTTTGGGGCTCTTACATCAGGAAATACTGATCTCTCCCAGAAG
TCCCTTCAGCTCGAAAGTAAGGGATTAACACTGAATAGTAATGCCTGGATGAACGACACTGTCATAATTGATAGTACA
GTGGGAAAGGACACGTTCTTTCTCATCACATGGAACAGTCTGCCTCCAGTATTTCTCTCTGGGATCCCAGTGGAACA
ATAATGGAAAATTTCACAGTGGATGCAACTTCCAAAATGGCCTATCTCAGTATTCCAGGAACTGCAAAGGTGGGCACT
TGGGCATACAATCTTCAAGCCAAAGCGAACCCAGAAACATTAACTATTACAGTAACTTCTCGAGCAGCAAATTCTTCT
GTGCCTCCAATCACAGTGAATGCTAAAATGAATAAGGACGTAAACAGTTTCCCCAGCCCAATGATTGTTTACGCAGAA
ATTCTACAAGGATATGTACCTGTTCTTGGAGCCAATGTGACTGCTTTCATTGAATCACAGAATGGACATACAGAAGTT
TTGGAACTTTTGGATAATGGTGCAGGCGCTGATTCTTTCAAGAATGATGGAGTCTACTCCAGGTATTTTACAGCATAT
ACAGAAAATGGCAGATATAGCTTAAAAGTTCGGGCTCATGGAGGAGCAAACACTGCCAGGCTAAAATTACGGCCTCCA
CTGAATAGAGCCGCGTACATACCAGGCTGGGTAGTGAACGGGGAAATTGAAGCAAACCCGCCAAGACCTGAAATTGAT
GAGGATACTCAGACCACCTTGGAGGATTTCAGCCGAACAGCATCCGGAGGTGCATTTGTGGTATCACAAGTCCCAAGC
CTTCCCTTGCCTGACCAATACCCACCAAGTCAAATCACAGACCTTGATGCCACAGTTCATGAGGATAAGATTATTCTT
ACATGGACAGCACCAGGAGATAATTTTGATGTTGGAAAAGTTCAACGTTATATCATAAGAATAAGTGCAAGTATTCTT
GATCTAAGAGACAGTTTTGATGATGCTCTTCAAGTAAATACTACTGATCTGTCACCAAAGGAGGCCAACTCCAAGGAA
AGCTTTGCATTTAAACCAGAAAATATCTCAGAAGAAATGCAACCCACATATTTATTGCCATTAAAAGTATAGATAAA
AGCAATTTGACATCAAAAGTATCCAACATTGCACAAGTAACTTTGTTTATCCCTCAAGCAAATCCTGATGACATTGAT
CCTACACCTACTCCTACTCCTACTCCTACTCCTGATAAAAGTCATAATTCTGGAGTTAATATTTCTACGCTGGTATTG
TCTGTGATTGGGTCTGTTGTAATTGTTAACTTTATTTTAAGTACCACCATTTGAACCTTAACGAAGAAAAAATCTTC
AAGTAGACCTAGAAGAGAGTTTTAAAAAACAAAACAATGTAAGTAAAGGATATTTCTGAATCTTAAAATTCATCCCAT
GTGTGATCATAAACTCATAAAAATAATTTTAAGATGTCGGAAAAGGATACTTTGATTAAATAAAAACACTCATGGATA
TGTAAAAACTGTCAAGATTAAAATTTAATAGTTTCATTTATTTGTTATTTTATTTGTAAGAAATAGTGATGAACAAAG
ATCCTTTTTCATACTGATACCTGGTTGTATATTATTTGATGCAACAGTTTTCTGAAATGATATTTCAAATTGCATCAA
GAAATTAAAATCATCTATCTGAGTAGTCAAAATACAAGTAAAGGAGAGCAAATAAACAACATTTGGAAAAAAAAAAA
AAAAAAAAAAAAAAAAAAAAAAAAAAAAAAAAAAAAAAAAAAAAAAAAAAAAAAAAAAAAAAAA
```

FIGURE 70

MGLFRGFVFLLVLCLLHQSNTSFIKLNNNGFEDIVIVIDPSVPEDEKIIEQIEDMVTTASTYLFE
ATEKRFFFKNVSILIPENWKENPQYKRPKHENHKHADVIVAPPTLPGRDEPYTKQFTECGEKGEY
IHFTPDLLLGKKQNEYGPPGKLFVHEWAHLRWGVFDEYNEDQPFYRAKSKKIEATRCSAGISGRN
RVYKCQGGSCLSRACRIDSTTKLYGKDCQFFPDKVQTEKASIMFMQSIDSVVEFCNEKTHNQEAP
SLQNIKCNFRSTWEVISNSEDFKNTIPMVTPPPPPVFSLLKISQRIVCLVLDKSGSMGGKDRLNR
MNQAAKHFLLQTVENGSWVGMVHFDSTATIVNKLIQIKSSDERNTLMAGLPTYPLGGTSICSGIK
YAFQVIGELHSQLDGSEVLLLTDGEDNTASSCIDEVKQSGAIVHFIALGRAADEAVIEMSKITGG
SHFYVSDEAQNNGLIDAFGALTSGNTDLSQKSLQLESKGLTLNSNAWMNDTVIIDSTVGKDTFFL
ITWNSLPPSISLWDPSGTIMENFTVDATSKMAYLSIPGTAKVGTWAYNLQAKANPETLTITVTSR
AANSSVPPITVNAKMNKDVNSFPSPMIVYAEILQGYVPVLGANVTAFIESQNGHTEVLELLDNGA
GADSFKNDGVYSRYFTAYTENGRYSLKVRAHGGANTARLKLRPPLNRAAYIPGWVVNGEIEANPP
RPEIDEDTQTTLEDFSRTASGGAFVVSQVPSLPLPDQYPPSQITDLDATVHEDKIILTWTAPGDN
FDVGKVQRYIIRISASILDLRDSFDDALQVNTTDLSPKEANSKESFAFKPENISEENATHIFIAI
KSIDKSNLTSKVSNIAQVTLFIPQANPDDIDPTPTPTPTPDKSHNSGVNISTLVLSVIGSVVI
VNFILSTTI

Signal peptide:

amino acids 1-21

Putative transmembrane domains:

amino acids 284-300, 617-633

Leucine zipper pattern.

amino acids 469-491, 476-498

N-glycosylation site.

amino acids 20-24, 75-79, 340-344, 504-508, 542-546, 588-592, 628-632, 811-815, 832-836, 837-841, 852-856, 896-900

FIGURE 71

```
CTCCTTAGGTGGAAACCCTGGGAGTAGAGTACTGACAGCAAAGACCGGGAAAGACCATACGTCCCCGGGCAGGGGTGA
CAACAGGTGTCATCTTTTTGATCTCGTGTGTGGCTGCCTTCCTATTTCAAGGAAAGACGCCAAGGTAATTTTGACCCA
GAGGAGCAATGATGTAGCCACCTCCTAACCTTCCCTTCTTGAACCCCCAGTTATGCCAGGATTTACTAGAGAGTGTCA
ACTCAACCAGCAAGCGGCTCCTCGGCTTAACTTGTGGTTGGAGGAGAGAACCTTTGTGGGGCTGCGTTCTCTTAGCA
GTGCTCAGAAGTGACTTGCCTGAGGGTGGACCAGAAGAAAGGAAAGGTCCCCTCTTGCTGTTGGCTGCACATCAGGAA
GGCTGTGATGGGAATGAAGGTGAAAACTTGGAGATTTCACTTCAGTCATTGCTTCTGCCTGCAAGATCATCCTTTAAA
AGTAGAGAAGCTGCTCTGTGTGGTGGTTAACTCCAAGAGGCAGAACTCGTTCTAGAAGGAAATGGATGCAAGCAGCTC
CGGGGGCCCCAAACGCATGCTTCCTGTGGTCTAGCCCAGGGAAGCCCTTCCGTGGGGCCCCGGCTTTGAGGGATGCC
ACCGGTTCTGGACGCATGGCTGATTCCTGAATGATGATGGTTCGCCGGGGGCTGCTTGCGTGGATTTCCCGGGTGGTG
GTTTTGCTGGTGCTCCTCTGCTGTGCTATCTCTGTCCTGTACATGTTGGCCTGCACCCCAAAAGGTGACGAGGAGCAG
CTGGCACTGCCCAGGGCCAACAGCCCCACGGGGAAGGAGGGGTACCAGGCCGTCCTTCAGGAGTGGGAGGAGCAGCAC
CGCAACTACGTGAGCAGCCTGAAGCGGCAGATCGCACAGTCAAGGAGGAGCTGCAGGAGAGGAGTGAGCAGCTCAGG
AATGGGCAGTACCAAGCCAGCGATGCTGCTGGCCTGGGTCTGGACAGGAGCCCCCCAGAGAAAACCCAGGCCGACCTC
CTGGCCTTCCTGCACTCGCAGGTGGACAAGGCAGAGGTGAATGCTGGCGTCAAGCTGGCCACAGAGTATGCAGCAGTG
CCTTTCGATAGCTTTACTCTACAGAAGGTGTACCAGCTGGAGACTGGCCTTACCCGCCACCCCGAGGAGAAGCCTGTG
AGGAAGGACAAGCGGGATGAGTTGGTGGAAGCCATTGAATCAGCCTTGGAGACCCTGAACAATCCTGCAGAGAACAGC
CCCAATCACCGTCCTTACACGGCCTCTGATTTCATAGAAGGGATCTACCGAACAGAAAGGGACAAAGGGACATTGTAT
GAGCTCACCTTCAAAGGGGACCACAAACACGAATTCAAACGGCTCATCTTATTTCGACCATTCAGCCCCATCATGAAA
GTGAAAAATGAAAAGCTCAACATGGCCAACACGCTTATCAATGTTATCGTGCCTCTAGCAAAAAGGGTGGACAAGTTC
CGGCAGTTCATGCAGAATTTCAGGGAGATGTGCATTGAGCAGGATGGGAGAGTCCATCTCACTGTTGTTTACTTTGGG
AAAGAAGAAATAAATGAAGTCAAAGGAATACTTGAAAACACTTCCAAAGCTGCCAACTTCAGGAACTTTACCTTCATC
CAGCTGAATGGAGAATTTTCTCGGGGAAAGGGACTTGATGTTGGAGCCCGCTTCTGGAAGGGAAGCAACGTCCTTCTC
TTTTTCTGTGATGTGGACATCTACTTCACATCTGAATTCCTCAATACGTGTAGGCTGAATACACAGCCAGGGAAGAAG
GTATTTTATCCAGTTCTTTTCAGTCAGTACAATCCTGGCATAATATACGGCCACCATGATGCAGTCCCTCCCTTGGAA
CAGCAGCTGGTCATAAAGAAGGAAACTGGATTTTGGAGAGACTTTGGATTTGGGATGACGTGTCAGTATCGGTCAGAC
TTCATCAATATAGGTGGGTTTGATCTGGACATCAAAGGCTGGGGCGGAGAGGATGTGCACCTTTATCGCAAGTATCTC
CACAGCAACCTCATAGTGGTACGGACGCCTGTGCGAGGACTCTTCCACCTCTGGCATGAGAAGCGCTGCATGGACGAG
CTGACCCCCGAGCAGTACAAGATGTGCATGCAGTCCAAGGCCATGAACGAGGCATCCCACGGCCAGCTGGGCATGCTG
GTGTTCAGGCACGAGATAGAGGCTCACCTTCGCAAACAGAAACAGAAGACAAGTAGCAAAAAAACATGAACTCCCAGA
GAAGGATTGTGGGAGACACTTTTTCTTTCCTTTTGCAATTACTGAAAGTGGCTGCAACAGAGAAAGACTTCCATAAA
GGACGACAAAAGAATTGGACTGATGGGTCAGAGATGAGAAAGCCTCCGATTTCTCTCTGTTGGGCTTTTTACAACAGA
AATCAAAATCTCCGCTTTGCCTGCAAAAGTAACCCAGTTGCACCCTGTGAAGTGTCTGACAAAGGCAGAATGCTTGTG
AGATTATAAGCCTAATGGTGTGGAGGTTTTGATGGTGTTTACAATACACTGAGACCTGTTGTTTTGTGTGCTCATTGA
AATATTCATGATTTAAGAGCAGTTTTGTAAAAAATTCATTAGCATGAAAGGCAAGCATATTTCTCCTCATATGAATGA
GCCTATCAGCAGGGCTCTAGTTTCTAGGAATGCTAAAATATCAGAAGGCAGGAGAGGAGATAGGCTTATTATGATACT
AGTGAGTACATTAAGTAAAATAAAATGGACCAGAAAAGAAAAGAAACCATAAATATCGTGTCATATTTTCCCCAAGAT
TAACCAAAAATAATCTGCTTATCTTTTGGTTGTCCTTTTAACTGTCTCCGTTTTTTCTTTTATTTAAAAATGCACT
TTTTTTCCCTTGTGAGTTATAGTCTGCTTATTTAATTACCACTTTGCAAGCCTTACAAGAGAGCACAAGTTGGCCTAC
ATTTTTATATTTTTTAAGAAGATACTTTGAGATGCATTATGAGAACTTTCAGTTCAAAGCATCAAATTGATGCCATAT
CCAAGGACATGCCAAATGCTGATTCTGTCAGGCACTGAATGTCAGGCATTGAGACATAGGGAAGGAATGGTTTGTACT
AATACAGACGTACAGATACTTTCTCTGAAGAGTATTTTCGAAGAGGAGCAACTGAACACTGGAGGAAAAGAAAATGAC
ACTTTCTGCTTTACAGAAAAGGAAACTCATTCAGACTGGTGATATCGTGATGTACCTAAAAGTCAGAAACCACATTTT
CTCCTCAGAAGTAGGGACCGCTTTCTTACCTGTTTAAATAAACCAAAGTATACCGTGTGAACCAAACAATCTCTTTTC
AAAACAGGGTGCTCCTCCTGGCTTCTGGCTTCCATAAGAAGAAATGGAGAAAAATATATATATATATATATATATTGT
GAAAGATCAATCCATCTGCCAGAATCTAGTGGGATGGAAGTTTTTGCTACATGTTATCCACCCCAGGCCAGGTGGAAG
TAACTGAATTATTTTTTAAATTAAGCAGTTCTACTCAATCACCAAGATGCTTCTGAAAATTGCATTTTATTACCATTT
CAAACTATTTTTTAAAAATAAATACAGTTAACATAGAGTGGTTTCTTCATTCATGTGAAAATTATTAGCCAGCACCAG
ATGCATGAGCTAATTATCTCTTTGAGTCCTTGCTTCTGTTTGCTCACAGTAAACTCATTGTTTAAAAGCTTCAAGAAC
ATTCAAGCTGTTGGTGTGTTAAAAAATGCATTGTATTGATTTGTACTGGTAGTTTATGAAATTTAATTAAAACACAGG
CCATGAATGGAAGGTGGTATTGCACAGCTAATAAAATATGATTTGTGGATATGAA
```

FIGURE 72

MMMVRRGLLAWISRVVVLLVLLCCAISVLYMLACTPKGDEEQLALPRANSPTGKEGYQAVLQEWE
EQHRNYVSSLKRQIAQLKEELQERSEQLRNGQYQASDAAGLGLDRSPPEKTQADLLAFLHSQVDK
AEVNAGVKLATEYAAVPFDSFTLQKVYQLETGLTRHPEEKPVRKDKRDELVEAIESALETLNNPA
ENSPNHRPYTASDFIEGIYRTERDKGTLYELTFKGDHKHEFKRLILFRPFSPIMKVKNEKLNMAN
TLINVIVPLAKRVDKFRQFMQNFREMCIEQDGRVHLTVVYFGKEEINEVKGILENTSKAANFRNF
TFIQLNGEFSRGKGLDVGARFWKGSNVLLFFCDVDIYFTSEFLNTCRLNTQPGKKVFYPVLFSQY
NPGIIYGHHDAVPPLEQQLVIKKETGFWRDFGFGMTCQYRSDFINIGGFDLDIKGWGGEDVHLYR
KYLHSNLIVVRTPVRGLFHLWHEKRCMDELTPEQYKMCMQSKAMNEASHGQLGMLVFRHEIEAHL
RKQKQKTSSKKT

Important features:
Signal peptide:
amino acids 1-27

N-glycosylation sites.
amino acids 315-319, 324-328

N-myristoylation sites.
amino acids 96-102, 136-142, 212-218, 311-317, 339-345, 393-399

Amidation site.
amino acids 377-381

FIGURE 73

```
GAGACTGCAGAGGGAGATAAAGAGAGAGGGCAAAGAGGCAGCAAGAGATTTGTCCTGGGGATCCA
GAAACCCATGATACCCTACTGAACACCGAATCCCCTGGAAGCCCACAGAGACAGAGACAGCAAGA
GAAGCAGAGATAAATACACTCACGCCAGGAGCTCGCTCGCTCTCTCTCTCTCTCTCTCACTCCTC
CCTCCCTCTCTCTGCCTGTCCTAGTCCTCTAGTCCTCAAATTCCCAGTCCCCTGCACCCCTTC
CTGGGACACTATGTTGTTCTCCGCCCTCCTGCTGGAGGTGATTTGGATCCTGGCTGCAGATGGGG
GTCAACACTGGACGTATGAGGGCCCACATGGTCAGGACCATTGGCCAGCCTCTTACCCTGAGTGT
GGAAACAATGCCCAGTCGCCCATCGATATTCAGACAGACAGTGTGACATTTGACCCTGATTTGCC
TGCTCTGCAGCCCCACGGATATGACCAGCCTGGCACCGAGCCTTTGGACCTGCACAACAATGGCC
ACACAGTGCAACTCTCTCTGCCCTCTACCCTGTATCTGGGTGGACTTCCCCGAAAATATGTAGCT
GCCCAGCTCCACCTGCACTGGGGTCAGAAAGGATCCCCAGGGGGGTCAGAACACCAGATCAACAG
TGAAGCCACATTTGCAGAGCTCCACATTGTACATTATGACTCTGATTCCTATGACAGCTTGAGTG
AGGCTGCTGAGAGGCCTCAGGGCCTGGCTGTCCTGGGCATCCTAATTGAGGTGGGTGAGACTAAG
AATATAGCTTATGAACACATTCTGAGTCACTTGCATGAAGTCAGGCATAAAGATCAGAAGACCTC
AGTGCCTCCCTTCAACCTAAGAGAGCTGCTCCCCAAACAGCTGGGGCAGTACTTCCGCTACAATG
GCTCGCTCACAACTCCCCCTTGCTACCAGAGTGTGCTCTGGACAGTTTTTATAGAAGGTCCCAG
ATTTCAATGGAACAGCTGGAAAAGCTTCAGGGGACATTGTTCTCCACAGAAGAGGAGCCCTCTAA
GCTTCTGGTACAGAACTACCGAGCCCTTCAGCCTCTCAATCAGCGCATGGTCTTTGCTTCTTTCA
TCCAAGCAGGATCCTCGTATACCACAGGTGAAATGCTGAGTCTAGGTGTAGGAATCTTGGTTGGC
TGTCTCTGCCTTCTCCTGGCTGTTTATTTCATTGCTAGAAAGATTCGGAAGAAGAGGCTGGAAAA
CCGAAAGAGTGTGGTCTTCACCTCAGCACAAGCCACGACTGAGGCATAAATTCCTTCTCAGATAC
CATGGATGTGGATGACTTCCCTTCATGCCTATCAGGAAGCCTCTAAAATGGGGTGTAGGATCTGG
CCAGAAACACTGTAGGAGTAGTAAGCAGATGTCCTCCTTCCCCTGGACATCTCTTAGAGAGGAAT
GGACCCAGGCTGTCATTCCAGGAAGAACTGCAGAGCCTTCAGCCTCTCCAAACATGTAGGAGGAA
ATGAGGAAATCGCTGTGTTGTTAATGCAGAGANCAAACTCTGTTTAGTTGCAGGGGAAGTTTGGG
ATATACCCCAAAGTCCTCTACCCCCTCACTTTTATGGCCCTTTCCCTAGATATACTGCGGGATCT
CTCCTTAGGATAAAGAGTTGCTGTTGAAGTTGTATATTTTTGATCAATATATTTGGAAATTAAAG
TTTCTGACTTT
```

FIGURE 74

MLFSALLLEVIWILAADGGQHWTYEGPHGQDHWPASYPECGNNAQSPIDIQTDSVTFDPDLPALQ
PHGYDQPGTEPLDLHNNGHTVQLSLPSTLYLGGLPRKYVAAQLHLHWGQKGSPGGSEHQINSEAT
FAELHIVHYDSDSYDSLSEAAERPQGLAVLGILIEVGETKNIAYEHILSHLHEVRHKDQKTSVPP
FNLRELLPKQLGQYFRYNGSLTTPPCYQSVLWTVFYRRSQISMEQLEKLQGTLFSTEEEPSKLLV
QNYRALQPLNQRMVFASFIQAGSSYTTGEMLSLGVGILVGCLCLLLAVYFIARKIRKKRLENRKS
VVFTSAQATTEA

Important features of the protein:
Signal peptide:
amino acids 1-15

Transmembrane domain:
amino acids 291-310

N-glycosylation site.
amino acids 213-216

Eukaryotic-type carbonic anhydrases proteins
amino acids 197-245, 104-140, 22-69

FIGURE 75

TGCCGCTGCCGCCGCTGCTGCTGTTGCTCCTGGCGGCGCCTTGGGGACGGGCAGTTCCCTGTGTC
TCTGGTGGTTTGCCTAAACCTGCAAACATCACCTTCTTATCCATCAACATGAAG<u>AATG</u>TCCTACA
ATGGACTCCACCAGAGGGTCTTCAAGGAGTTAAAGTTACTTACACTGTGCAGTATTTCATCACAA
ATTGGCCCACCAGAGGTGGCACTGACTACAGATGAGAAGTCCATTTCTGTTGTCCTGACAGCTCC
AGAGAAGTGGAAGAGAAATCCAGAAGACCTTCCTGTTTCCATGCAACAAATATACTCCAATCTGA
AGTATAACGTGTCTGTGTTAATACTAAATCAAACAGAACGTGGTCCCAGTGTGTGACCAACCAC
ACGCTGGTGCTCACCTGGCTGGAGCCGAACACTCTTTACTGCGTACACGTGGAGTCCTTCGTCCC
AGGGCCCCCTCGCCGTGCTCAGCCTTCTGAGAAGCAGTGTGCCAGGACTTTGAAAGATCAATCAT
CAGAGTTCAAGGCTAAAATCATCTTCTGGTATGTTTGCCCATATCTATTACCGTGTTTCTTTTT
TCTGTGATGGGCTATTCCATCTACCGATATATCCACGTTGGCAAAGAGAAACACCCAGCAAATTT
GATTTGATTTATGGAAATGAATTTGACAAAGATTCTTTGTGCCTGCTGAAAAAATCGTGATTA
ACTTTATCACCCTCAATATCTCGGATGATTCTAAAATTTCTCATCAGGATATGAGTTTACTGGGA
AAAAGCAGTGATGTATCCAGCCTTAATGATCCTCAGCCCAGCGGGAACCTGAGGCCCCCTCAGGA
GGAAGAGGAGGTGAAACATTTAGGGTATGCTTCGCATTTGATGGAAATTTTTTGTGACTCTGAAG
AAAACACGGAAGGTACTTCTCTCACCCAGCAAGAGTCCCTCAGCAGAACAATACCCCCGGATAAA
ACAGTCATTGAATATGAATATGATGTCAGAACCACTGACATTTGTGCGGGGCCTGAAGAGCAGGA
GCTCAGTTTGCAGGAGGAGGTGTCCACACAAGGAACATTATTGGAGTCGCAGGCAGCGTTGGCAG
TCTTGGGCCCGCAAACGTTACAGTACTCATACACCCCTCAGCTCCAAGACTTAGACCCCCTGGCG
CAGGAGCACACAGACTCGGAGGAGGGGCCGGAGGAAGAGCCATCGACGACCCTGGTCGACTGGGA
TCCCCAAACTGGCAGGCTGTGTATTCCTTCGCTGTCCAGCTTCGACCAGGATTCAGAGGGCTGCG
AGCCTTCTGAGGGGATGGGCTCGGAGAGGAGGTCTTCTATCTAGACTCTATGAGGAGCCGGCT
CCAGACAGGCCACCAGGAGAAAATGAAACCTATCTCATGCAATTCATGGAGGAATGGGGGTTATA
TGTGCAGATGGAAAAC<u>TGA</u>TGCCAACACTTCCTTTTGCCTTTTGTTTCCTGTGCAAACAAGTGAG
TCACCCCTTTGATCCCAGCCATAAAGTACCTGGGATGAAAGAAGTTTTTTCCAGTTTGTCAGTGT
CTGTGAGAATTACTTATTTCTTTTCTCTATTCTCATAGCACGTGTGTGATTGGTTCATGCATGTA
GGTCTCTTAACAATGATGGTGGGCCTCTGGAGTCCAGGGGCTGGCCGGTTGTTCTATGCAGAGAA
AGCAGTCAATAAATGTTTGCCAGACTGGGTGCAGAATTTATTCAGGTGGGTGT

FIGURE 76

MSYNGLHQRVFKELKLLTLCSISSQIGPPEVALTTDEKSISVVLTAPEKWKRNPEDLPVSMQQIY
SNLKYNVSVLNTKSNRTWSQCVTNHTLVLTWLEPNTLYCVHVESFVPGPPRRAQPSEKQCARTLK
DQSSEFKAKIIFWYVLPISITVFLFSVMGYSIYRYIHVGKEKHPANLILIYGNEFDKRFFVPAEK
IVINFITLNISDDSKISHQDMSLLGKSSDVSSLNDPQPSGNLRPPQEEEEVKHLGYASHLMEIFC
DSEENTEGTSLTQQESLSRTIPPDKTVIEYEYDVRTTDICAGPEEQELSLQEEVSTQGTLLESQA
ALAVLGPQTLQYSYTPQLQDLDPLAQEHTDSEEGPEEEPSTTLVDWDPQTGRLCIPSLSSFDQDS
EGCEPSEGDGLGEEGLLSRLYEEPAPDRPPGENETYLMQFMEEWGLYVQMEN

Important features:

Signal peptide:

amino acids 1-28

Transmembrane domain:

amino acids 140-163

N-glycosylation sites.

amino acids 71-74, 80-83, 89-92, 204-207, 423-426

FIGURE 77

```
GAGGAGCGGGCCGAGGACTCCAGCGTGCCCAGGTCTGGCATCCTGCACTTGCTGCCCTCTGACAC
CTGGGAAGATGGCCGGCCCGTGGACCTTCACCCTTCTCTGTGGTTTGCTGGCAGCCACCTTGATC
CAAGCCACCCTCAGTCCCACTGCAGTTCTCATCCTCGGCCCAAAAGTCATCAAAGAAAAGCTGAC
ACAGGAGCTGAAGGACCACAACGCCACCAGCATCCTGCAGCAGCTGCCGCTGCTCAGTGCCATGC
GGGAAAAGCCAGCCGGAGGCATCCCTGTGCTGGGCAGCCTGGTGAACACCGTCCTGAAGCACATC
ATCTGGCTGAAGGTCATCACAGCTAACATCCTCCAGCTGCAGGTGAAGCCCTCGGCCAATGACCA
GGAGCTGCTAGTCAAGATCCCCCTGGACATGGTGGCTGGATTCAACACGCCCCTGGTCAAGACCA
TCGTGGAGTTCCACATGACGACTGAGGCCCAAGCCACCATCCGCATGGACACCAGTGCAAGTGGC
CCCACCCGCCTGGTCCTCAGTGACTGTGCCACCAGCCATGGGAGCCTGCGCATCCAACTGCTGTA
TAAGCTCTCCTTCCTGGTGAACGCCTTAGCTAAGCAGGTCATGAACCTCCTAGTGCCATCCCTGC
CCAATCTAGTGAAAAACCAGCTGTGTCCCGTGATCGAGGCTTCCTTCAATGGCATGTATGCAGAC
CTCCTGCAGCTGGTGAAGGTGCCCATTTCCCTCAGCATTGACCGTCTGGAGTTTGACCTTCTGTA
TCCTGCCATCAAGGGTGACACCATTCAGCTCTACCTGGGGGCCAAGTTGTTGGACTCACAGGGAA
AGGTGACCAAGTGGTTCAATAACTCTGCAGCTTCCCTGACAATGCCCACCCTGGACAACATCCCG
TTCAGCCTCATCGTGAGTCAGGACGTGGTGAAAGCTGCAGTGGCTGCTGTGCTCTCTCCAGAAGA
ATTCATGGTCCTGTTGGACTCTGTGCTTCCTGAGAGTGCCCATCGGCTGAAGTCAAGCATCGGGC
TGATCAATGAAAAGGCTGCAGATAAGCTGGGATCTACCCAGATCGTGAAGATCCTAACTCAGGAC
ACTCCCGAGTTTTTTATAGACCAAGGCCATGCCAAGGTGGCCCAACTGATCGTGCTGGAAGTGTT
TCCCTCCAGTGAAGCCCTCCGCCCTTTGTTCACCCTGGGCATCGAAGCCAGCTCGGAAGCTCAGT
TTTACACCAAAGGTGACCAACTTATACTCAACTTGAATAACATCAGCTCTGATCGGATCCAGCTG
ATGAACTCTGGGATTGGCTGGTTCCAACCTGATGTTCTGAAAAACATCATCACTGAGATCATCCA
CTCCATCCTGCTGCCGAACCAGAATGGCAAATTAAGATCTGGGGTCCCAGTGTCATTGGTGAAGG
CCTTGGGATTCGAGGCAGCTGAGTCCTCACTGACCAAGGATGCCCTTGTGCTTACTCCAGCCTCC
TTGTGGAAACCCAGCTCTCCTGTCTCCCAGTGAAGACTTGGATGGCAGCCATCAGGGAAGGCTGG
GTCCCAGCTGGGAGTATGGGTGTGAGCTCTATAGACCATCCCTCTCTGCAATCAATAAACACTTG
CCTGTGAAAAA
```

FIGURE 78

MAGPWTFTLLCGLLAATLIQATLSPTAVLILGPKVIKEKLTQELKDHNATSILQQLPLLSAMREK
PAGGIPVLGSLVNTVLKHIIWLKVITANILQLQVKPSANDQELLVKIPLDMVAGFNTPLVKTIVE
FHMTTEAQATIRMDTSASGPTRLVLSDCATSHGSLRIQLLYKLSFLVNALAKQVMNLLVPSLPNL
VKNQLCPVIEASFNGMYADLLQLVKVPISLSIDRLEFDLLYPAIKGDTIQLYLGAKLLDSQGKVT
KWFNNSAASLTMPTLDNIPFSLIVSQDVVKAAVAAVLSPEEFMVLLDSVLPESAHRLKSSIGLIN
EKAADKLGSTQIVKILTQDTPEFFIDQGHAKVAQLIVLEVFPSSEALRPLFTLGIEASSEAQFYT
KGDQLILNLNNISSDRIQLMNSGIGWFQPDVLKNIITEIIHSILLPNQNGKLRSGVPVSLVKALG
FEAAESSLTKDALVLTPASLWKPSSPVSQ

Important features of the protein:
Signal peptide:
amino acids 1-21

N-glycosylation sites.
amino acids 48-51, 264-267, 401-404

Glycosaminoglycan attachment site.
amino acids 412-415

LBP / BPI / CETP family proteins.
amino acids 407-457

FIGURE 79

GAGAGAAGTCAGCCTGGCAGAGAGACTCTGAAATGAGGGATTAGAGGTGTTCAAGGAGCAAGAGC
TTCAGCCTGAAGACAAGGGAGCAGTCCCTGAAGACGCTTCTACTGAGAGGTCTGCC<u>ATG</u>GCCTCT
CTTGGCCTCCAACTTGTGGGCTACATCCTAGGCCTTCTGGGGCTTTTGGGCACACTGGTTGCCAT
GCTGCTCCCCAGCTGGAAAACAAGTTCTTATGTCGGTGCCAGCATTGTGACAGCAGTTGGCTTCT
CCAAGGGCCTCTGGATGGAATGTGCCACACACAGCACAGGCATCACCCAGTGTGACATCTATAGC
ACCCTTCTGGGCCTGCCCGCTGACATCCAGGCTGCCCAGGCCATGATGGTGACATCCAGTGCAAT
CTCCTCCCTGGCCTGCATTATCTCTGTGGTGGGCATGAGATGCACAGTCTTCTGCCAGGAATCCC
GAGCCAAAGACAGAGTGGCGGTAGCAGGTGGAGTCTTTTCATCCTTGGAGGCCTCCTGGGATTC
ATTCCTGTTGCCTGGAATCTTCATGGGATCCTACGGGACTTCTACTCACCACTGGTGCCTGACAG
CATGAAATTTGAGATTGGAGAGGCTCTTTACTTGGGCATTATTTCTTCCCTGTTCTCCCTGATAG
CTGGAATCATCCTCTGCTTTTCCTGCTCATCCCAGAGAAATCGCTCCAACTACTACGATGCCTAC
CAAGCCCAACCTCTTGCCACAAGGAGCTCTCCAAGGCCTGGTCAACCTCCCAAAGTCAAGAGTGA
GTTCAATTCCTACAGCCTGACAGGGTATGTG<u>TGA</u>AGAACCAGGGGCCAGAGCTGGGGGGTGGCTG
GGTCTGTGAAAAACAGTGGACAGCACCCCGAGGGCCACAGGTGAGGGACACTACCACTGGATCGT
GTCAGAAGGTGCTGCTGAGGATAGACTGACTTTGGCCATTGGATTGAGCAAAGGCAGAAATGGGG
GCTAGTGTAACAGCATGCAGGTTGAATTGCCAAGGATGCTCGCCATGCCAGCCTTTCTGTTTTCC
TCACCTTGCTGCTCCCCTGCCCTAAGTCCCCAACCCTCAACTTGAAACCCCATTCCCTTAAGCCA
GGACTCAGAGGATCCCTTTGCCCTCTGGTTTACCTGGGACTCCATCCCCAAACCCACTAATCACA
TCCCACTGACTGACCCTCTGTGATCAAAGACCCTCTCTCTGGCTGAGGTTGGCTCTTAGCTCATT
GCTGGGGATGGGAAGGAGAAGCAGTGGCTTTTGTGGGCATTGCTCTAACCTACTTCTCAAGCTTC
CCTCCAAAGAAACTGATTGGCCCTGGAACCTCCATCCCACTCTTGTTATGACTCCACAGTGTCCA
GACTAATTTGTGCATGAACTGAAATAAAACCATCCTACGGTATCCAGGGAACAGAAAGCAGGATG
CAGGATGGGAGGACAGGAAGGCAGCCTGGGACATTTAAAAAAATA

FIGURE 8o

MASLGLQLVGYILGLLGLLGTLVAMLLPSWKTSSYVGASIVTAVGFSKGLWMECATHSTGITQCD
IYSTLLGLPADIQAAQAMMVTSSAISSLACIISVVGMRCTVFCQESRAKDRVAVAGGVFFILGGL
LGFIPVAWNLHGILRDFYSPLVPDSMKFEIGEALYLGIISSLFSLIAGIILCFSCSSQRNRSNYY
DAYQAQPLATRSSPRPGQPPKVKSEFNSYSLTGYV

Important features of the protein:

Signal peptide:

amino acids 1-24

Transmembrane domains:

amino acids 82-102, 117-140, 163-182

N-glycosylation site.

amino acids 190-193

PMP-22 / EMP / MP20 family proteins.

amino acids 46-59

FIGURE 81

CCCACGCGTCCGCGCCTCTCCCTTCTGCTGGACCTTCCTTCGTCTCTCCATCTCTCCCTCCTTTC
CCCGCGTTCTCTTTCCACCTTTCTCTTCTTCCCACCTTAGACCTCCCTTCCTGCCCTCCTTTCCT
GCCCACCGCTGCTTCCTGGCCCTTCTCCGACCCCGCTCTAGCAGCAGACCTCCTGGGGTCTGTGG
GTTGATCTGTGGCCCTGTGCCTCCGTGTCCTTTTCGTCTCCCTTCCTCCCGACTCCGCTCCCGG
ACCAGCGGCCTGACCCTGGGGAAAGG<u>ATG</u>GTTCCCGAGGTGAGGGTCCTCTCCTCCTTGCTGGGA
CTCGCGCTGCTCTGGTTCCCCCTGGACTCCCACGCTCGAGCCCGCCCAGACATGTTCTGCCTTTT
CCATGGGAAGAGATACTCCCCGGCGAGAGCTGGCACCCCTACTTGGAGCCACAAGGCCTGATGT
ACTGCCTGCGCTGTACCTGCTCAGAGGGCGCCCATGTGAGTTGTTACCGCCTCCACTGTCCGCCT
GTCCACTGCCCCAGCCTGTGACGGAGCCACAGCAATGCTGTCCCAAGTGTGTGGAACCTCACAC
TCCCTCTGGACTCCGGGCCCCACCAAAGTCCTGCCAGCACAACGGGACCATGTACCAACACGGAG
AGATCTTCAGTGCCCATGAGCTGTTCCCCTCCCGCCTGCCCAACCAGTGTGTCCTCTGCAGCTGC
ACAGAGGGCCAGATCTACTGCGGCCTCACAACCTGCCCCGAACCAGGCTGCCCAGCACCCCTCCC
ACTGCCAGACTCCTGCTGCCAAGCCTGCAAAGATGAGGCAAGTGAGCAATCGGATGAAGAGGACA
GTGTGCAGTCGCTCCATGGGGTGAGACATCCTCAGGATCCATGTTCCAGTGATGCTGGGAGAAAG
AGAGGCCCGGGCACCCCAGCCCCACTGGCCTCAGCGCCCTCTGAGCTTCATCCCTCGCCACTT
CAGACCCAAGGGAGCAGGCAGCACAACTGTCAAGATCGTCCTGAAGGAGAAACATAAGAAAGCCT
GTGTGCATGGCGGGAAGACGTACTCCCACGGGGAGGTGTGGCACCCGGCCTTCCGTGCCTTCGGC
CCCTTGCCCTGCATCCTATGCACCTGTGAGGATGGCCGCCAGGACTGCCAGCGTGTGACCTGTCC
CACCGAGTACCCCTGCCGTCACCCCGAGAAAGTGGCTGGGAAGTGCTGCAAGATTTGCCCAGAGG
ACAAAGCAGACCCTGGCCACAGTGAGATCAGTTCTACCAGGTGTCCCAAGGCACCGGGCCGGGTC
CTCGTCCACACATCGGTATCCCCAAGCCCAGACAACCTGCGTCGCTTTGCCCTGGAACACGAGGC
CTCGGACTTGGTGGAGATCTACCTCTGGAAGCTGGTAAAAGATGAGGAAACTGAGGCTCAGAGAG
GTGAAGTACCTGGCCCAAGGCCACACAGCCAGAATCTTCCACTTGACTCAGATCAAGAAAGTCAG
GAAGCAAGACTTCCAGAAAGAGGCACAGCACTTCCGACTGCTCGCTGGCCCCACGAAGGTCACT
GGAACGTCTTCCTAGCCCAGACCCTGGAGCTGAAGGTCACGGCCAGTCCAGACAAAGTGACCAAG
ACATAACAAGACC<u>TAA</u>CAGTTGCAGATATGAGCTGTATAATTGTTGTTATTATATATTAATAAA
TAAGAAGTTGCATTACCCTCAAAAAAAAAAAAAAAAAAAAAA

FIGURE 82

MVPEVRVLSSLLGLALLWFPLDSHARARPDMFCLFHGKRYSPGESWHPYLEPQGLMYCLRCTCSE
GAHVSCYRLHCPPVHCPQPVTEPQQCCPKCVEPHTPSGLRAPPKSCQHNGTMYQHGEIFSAHELF
PSRLPNQCVLCSCTEGQIYCGLTTCPEPGCPAPLPLPDSCCQACKDEASEQSDEEDSVQSLHGVR
HPQDPCSSDAGRKRGPGTPAPTGLSAPLSFIPRHFRPKGAGSTTVKIVLKEKHKKACVHGGKTYS
HGEVWHPAFRAFGPLPCILCTCEDGRQDCQRVTCPTEYPCRHPEKVAGKCCKICPEDKADPGHSE
ISSTRCPKAPGRVLVHTSVSPSPDNLRRFALEHEASDLVEIYLWKLVKDEETEAQRGEVPGPRPH
SQNLPLDSDQESQEARLPERGTALPTARWPPRRSLERLPSPDPGAEGHGQSRQSDQDITKT

Signal peptide:
amino acids 1-25

FIGURE 83

GACAGCTGTGTCTCGATGGAGTAGACTCTCAGAACAGCGCAGTTTGCCCTCCGCTCACGCAGAGCCTCTCC
GTGGCTTCCGCACCTTGAGCATTAGGCCAGTTCTCCTCTTCTCTCTAATCCATCCGTCACCTCTCCTGTCA
TCCGTTTCCATGCCGTGAGGTCCATTCACAGAACACATCCATGGCTCTCATGCTCAGTTTGGTTCTGAGTC
TCCTCAAGCTGGGATCAGGGCAGTGGCAGGTGTTTGGGCCAGACAAGCCTGTCCAGGCCTTGGTGGGGAG
GACGCAGCATTCTCCTGTTTCCTGTCTCCTAAGACCAATGCAGAGGCCATGGAAGTGCGGTTCTTCAGGGG
CCAGTTCTCTAGCGTGGTCCACCTCTACAGGGACGGGAAGGACCAGCCATTTATGCAGATGCCACAGTATC
AAGGCAGGACAAAACTGGTGAAGGATTCTATTGCGGAGGGGCGCATCTCTCTGAGGCTGGAAAACATTACT
GTGTTGGATGCTGGCCTCTATGGGTGCAGGATTAGTTCCCAGTCTTACTACCAGAAGGCCATCTGGGAGCT
ACAGGTGTCAGCACTGGGCTCAGTTCCTCTCATTTCCATCACGGGATATGTTGATAGAGACATCCAGCTAC
TCTGTCAGTCCTCGGGCTGGTTCCCCCGGCCCACAGCGAAGTGGAAAGGTCCACAAGGACAGGATTTGTCC
ACAGACTCCAGGACAAACAGAGACATGCATGGCCTGTTTGATGTGGAGATCTCTCTGACCGTCCAAGAGAA
CGCCGGGAGCATATCCTGTTCCATGCGGCATGCTCATCTGAGCCGAGAGGTGGAATCCAGGGTACAGATAG
GAGATACCTTTTTCGAGCCTATATCGTGGCACCTGGCTACCAAAGTACTGGGAATACTCTGCTGTGGCCTA
TTTTTTGGCATTGTTGGACTGAAGATTTTCTTCTCCAAATTCCAGTGGAAAATCCAGGCGGAACTGGACTG
GAGAAGAAAGCACGGACAGGCAGAATTGAGAGACGCCCGGAAACACGCAGTGGAGGTGACTCTGGATCCAG
AGACGGCTCACCCGAAGCTCTGCGTTTCTGATCTGAAAACTGTAACCCATAGAAAAGCTCCCCAGGAGGTG
CCTCACTCTGAGAAGAGATTTACAAGGAAGAGTGTGGTGGCTTCTCAGAGTTTCCAAGCAGGGAAACATTA
CTGGGAGGTGGACGGAGGACACAATAAAAGGTGGCGCGTGGGAGTGTGCCGGGATGATGTGGACAGGAGGA
AGGAGTACGTGACTTTGTCTCCCGATCATGGGTACTGGGTCCTCAGACTGAATGGAGAACATTTGTATTTC
ACATTAAATCCCCGTTTTATCAGCGTCTTCCCCAGGACCCCACCTACAAAAATAGGGGTCTTCCTGGACTA
TGAGTGTGGGACCATCTCCTTCTTCAACATAAATGACCAGTCCCTTATTTATACCCTGACATGTCGGTTTG
AAGGCTTATTGAGGCCCTACATTGAGTATCCGTCCTATAATGAGCAAAATGGAACTCCCATAGTCATCTGC
CCAGTCACCCAGGAATCAGAGAAAGAGGCCTCTTGGCAAAGGGCCTCTGCAATCCCAGAGACAAGCAACAG
TGAGTCCTCCTCACAGGCAACCACGCCCTTCCTCCCCAGGGGTGAAATGTAGGATGAATCACATCCCACAT
TCTTCTTTAGGGATATTAAGGTCTCTCTCCCAGATCCAAAGTCCGCAGCAGCCGGCCAAGGTGGCTTCCA
GATGAAGGGGGACTGGCCTGTCCACATGGGAGTCAGGTGTCATGGCTGCCCTGAGCTGGGAGGGAAGAAGG
CTGACATTACATTTAGTTTGCTCTCACTCCATCTGGCTAAGTGATCTTGAAATACCACCTCTCAGGTGAAG
AACCGTCAGGAATTCCCATCTCACAGGCTGTGGTGTAGATTAAGTAGACAAGGAATGTGAATAATGCTTAG
ATCTTATTGATGACAGAGTGTATCCTAATGGTTTGTTCATTATATTACACTTTCAGTAAAAAAA

FIGURE 84

MALMLSLVLSLLKLGSGQWQVFGPDKPVQALVGEDAAFSCFLSPKTNAEAMEVRFFRGQFSSVVH
LYRDGKDQPFMQMPQYQGRTKLVKDSIAEGRISLRLENITVLDAGLYGCRISSQSYYQKAIWELQ
VSALGSVPLISITGYVDRDIQLLCQSSGWFPRPTAKWKGPQGQDLSTDSRTNRDMHGLFDVEISL
TVQENAGSISCSMRHAHLSREVESRVQIGDTFFEPISWHLATKVLGILCCGLFFGIVGLKIFFSK
FQWKIQAELDWRRKHGQAELRDARKHAVEVTLDPETAHPKLCVSDLKTVTHRKAPQEVPHSEKRF
TRKSVVASQSFQAGKHYWEVDGGHNKRWRVGVCRDDVDRRKEYVTLSPDHGYWVLRLNGEHLYFT
LNPRFISVFPRTPPTKIGVFLDYECGTISFFNINDQSLIYTLTCRFEGLLRPYIEYPSYNEQNGT
PIVICPVTQESEKEASWQRASAIPETSNSESSSQATTPFLPRGEM

Signal peptide:

amino acids 1-17

Transmembrane domain:

amino acids 239-255

FIGURE 85

AACAGACGTTCCCTCGCGGCCCTGGCACCTCTAACCCCAGAC<u>ATG</u>CTGCTGCTGCTGCCCCT
GCTCTGGGGGAGGGAGAGGGCGGAAGGACAGACAAGTAAACTGCTGACGATGCAGAGTTCCGTGA
CGGTGCAGGAAGGCCTGTGTGTCCATGTGCCCTGCTCCTTCTCCTACCCCTCGCATGGCTGGATT
TACCCTGGCCCAGTAGTTCATGGCTACTGGTTCCGGGAAGGGGCCAATACAGACCAGGATGCTCC
AGTGGCCACAAACAACCCAGCTCGGGCAGTGTGGGAGGAGACTCGGGACCGATTCCACCTCCTTG
GGGACCCACATACCAAGAATTGCACCCTGAGCATCAGAGATGCCAGAAGAAGTGATGCGGGGAGA
TACTTCTTTCGTATGGAGAAAGGAAGTATAAAATGGAATTATAAACATCACCGGCTCTCTGTGAA
TGTGACAGCCTTGACCCACAGGCCCAACATCCTCATCCCAGGCACCCTGGAGTCCGGCTGCCCCC
AGAATCTGACCTGCTCTGTGCCCTGGGCCTGTGAGCAGGGGACACCCCTATGATCTCCTGGATA
GGGACCTCCGTGTCCCCCCTGGACCCCTCCACCACCCGCTCCTCGGTGCTCACCCTCATCCCACA
GCCCCAGGACCATGGCACCAGCCTCACCTGTCAGGTGACCTTCCCTGGGGCCAGCGTGACCACGA
ACAAGACCGTCCATCTCAACGTGTCCTACCCGCCTCAGAACTTGACCATGACTGTCTTCCAAGGA
GACGGCACAGTATCCACAGTCTTGGGAAATGGCTCATCTCTGTCACTCCCAGAGGGCCAGTCTCT
GCGCCTGGTCTGTGCAGTTGATGCAGTTGACAGCAATCCCCCTGCCAGGCTGAGCCTGAGCTGGA
GAGGCCTGACCCTGTGCCCCTCACAGCCCTCAAACCCGGGGGTGCTGGAGCTGCCTTGGGTGCAC
CTGAGGGATGCAGCTGAATTCACCTGCAGAGCTCAGAACCCTCTCGGCTCTCAGCAGGTCTACCT
GAACGTCTCCCTGCAGAGCAAAGCCACATCAGGAGTGACTCAGGGGGTGGTCGGGGGAGCTGGAG
CCACAGCCCTGGTCTTCCTGTCCTTCTGCGTCATCTTCGTTGTAGTGAGGTCCTGCAGGAAGAAA
TCGGCAAGGCCAGCAGCGGGCGTGGGAGATACGGGCATAGAGGATGCAAACGCTGTCAGGGGTTC
AGCCTCTCAGGGGCCCCTGACTGAACCTTGGGCAGAAGACAGTCCCCCAGACCAGCCTCCCCCAG
CTTCTGCCCGCTCCTCAGTGGGGGAAGGAGAGCTCCAGTATGCATCCCTCAGCTTCCAGATGGTG
AAGCCTTGGGACTCGCGGGGACAGGAGGCCACTGACACCGAGTACTCGGAGATCAAGATCCACAG
A<u>TGA</u>GAAACTGCAGAGACTCACCCTGATTGAGGGATCACAGCCCCTCCAGGCAAGGGAGAAGTCA
GAGGCTGATTCTTGTAGAATTAACAGCCCTCAACGTGATGAGCTATGATAACACTATGAATTATG
TGCAGAGTGAAAAGCACACAGGCTTTAGAGTCAAAGTATCTCAAACCTGAATCCACACTGTGCCC
TCCCTTTTATTTTTTTAACTAAAAGACAGACAAATTCCTA

FIGURE 86

MLLLLLPLLWGRERAEGQTSKLLTMQSSVTVQEGLCVHVPCSFSYPSHGWIYPGPVVHGYWFREG
ANTDQDAPVATNNPARAVWEETRDRFHLLGDPHTKNCTLSIRDARRSDAGRYFFRMEKGSIKWNY
KHHRLSVNVTALTHRPNILIPGTLESGCPQNLTCSVPWACEQGTPPMISWIGTSVSPLDPSTTRS
SVLTLIPQPQDHGTSLTCQVTFPGASVTTNKTVHLNVSYPPQNLTMTVFQGDGTVSTVLGNGSSL
SLPEGQSLRLVCAVDAVDSNPPARLSLSWRGLTLCPSQPSNPGVLELPWVHLRDAAEFTCRAQNP
LGSQQVYLNVSLQSKATSGVTQGVVGGAGATALVFLSFCVIFVVVRSCRKKSARPAAGVGDTGIE
DANAVRGSASQGPLTEPWAEDSPPDQPPPASARSSVGEGELQYASLSFQMVKPWDSRGQEATDTE
YSEIKIHR

Signal peptide:
amino acids 1-15

Transmembrane domain:
amino acids 351-370

FIGURE 87

AGAAAGCTGCACTCTGTTGAGCTCCAGGGCGCAGTGGAGGGAGGGAGTGAAGGAGCTCTCTGTAC
CCAAGGAAAGTGCAGCTGAGACTCAGACAAGATTACAATGAACCAACTCAGCTTCCTGCTGTTTC
TCATAGCGACCACCAGAGGATGGAGTACAGATGAGGCTAATACTTACTTCAAGGAATGGACCTGT
TCTTCGTCTCCATCTCTGCCCAGAAGCTGCAAGGAAATCAAAGACGAATGTCCTAGTGCATTTGA
TGGCCTGTATTTTCTCCGCACTGAGAATGGTGTTATCTACCAGACCTTCTGTGACATGACCTCTG
GGGGTGGCGGCTGGACCCTGGTGGCCAGCGTGCATGAGAATGACATGCGTGGGAAGTGCACGGTG
GGCGATCGCTGGTCCAGTCAGCAGGGCAGCAAAGCAGACTACCCAGAGGGGGACGGCAACTGGGC
CAACTACAACACCTTTGGATCTGCAGAGGCGGCCACGAGCGATGACTACAAGAACCCTGGCTACT
ACGACATCCAGGCCAAGGACCTGGGCATCTGGCACGTGCCCAATAAGTCCCCCATGCAGCACTGG
AGAAACAGCTCCCTGCTGAGGTACCGCACGGACACTGGCTTCCTCCAGACACTGGGACATAATCT
GTTTGGCATCTACCAGAAATATCCAGTGAAATATGGAGAAGGAAAGTGTTGGACTGACAACGGCC
CGGTGATCCCTGTGGTCTATGATTTTGGCGACGCCCAGAAAACAGCATCTTATTACTCACCCTAT
GGCCAGCGGGAATTCACTGCGGGATTTGTTCAGTTCAGGGTATTTAATAACGAGAGAGCAGCCAA
CGCCTTGTGTGCTGGAATGAGGGTCACCGGATGTAACACTGAGCATCACTGCATTGGTGGAGGAG
GATACTTTCCAGAGGCCAGTCCCCAGCAGTGTGGAGATTTTCTGGTTTTGATTGGAGTGGATAT
GGAACTCATGTTGGTTACAGCAGCAGCCGTGAGATAACTGAGGCAGCTGTGCTTCTATTCTATCG
TTGAGAGTTTTGTGGGAGGGAACCCAGACCTCTCCTCCCAACCATGAGATCCCAAGGATGGAGAA
CAACTTACCCAGTAGCTAGAATGTTAATGGCAGAAGAGAAAACAATAAATCATATTGACTCAAGA
AAAAAA

FIGURE 88

MNQLSFLLFLIATTRGWSTDEANTYFKEWTCSSSPSLPRSCKEIKDECPSAFDGLYFLRTENGVI
YQTFCDMTSGGGGWTLVASVHENDMRGKCTVGDRWSSQQGSKADYPEGDGNWANYNTFGSAEAAT
SDDYKNPGYYDIQAKDLGIWHVPNKSPMQHWRNSSLLRYRTDTGFLQTLGHNLFGIYQKYPVKYG
EGKCWTDNGPVIPVVYDFGDAQKTASYYSPYGQREFTAGFVQFRVFNNERAANALCAGMRVTGCN
TEHHCIGGGGYFPEASPQQCGDFSGFDWSGYGTHVGYSSSREITEAAVLLFYR

Important features:

Signal peptide:

amino acids 1-16

N-glycosylation site.

amino acids 163-167

Glycosaminoglycan attachment sites.

amino acids 74-78, 289-293

N-myristoylation sites.

amino acids 76-82, 115-121, 124-130, 253-259, 292-298

FIGURE 89

CTAGATTTGTCGGCTTGCGGGGAGACTTCAGGAGTCGCTGTCTCTGAACTTCCAGCCTCAGAGAC
CGCCGCCCTTGTCCCCGAGGGCATGGGCCGGGTCTCAGGGCTTGTGCCCTCTCGCTTCCTGACG
CTCCTGGCGCATCTGGTGGTCGTCATCACCTTATTCTGGTCCCGGGACAGCAACATACAGGCCTG
CCTGCCTCTCACGTTCACCCCGAGGAGTATGACAAGCAGGACATTCAGCTGGTGGCCGCGCTCT
CTGTCACCCTGGGCCTCTTTGCAGTGGAGCTGGCCGGTTTCCTCTCAGGAGTCTCCATGTTCAAC
AGCACCCAGAGCCTCATCTCCATTGGGGCTCACTGTAGTGCATCCGTGGCCCTGTCCTTCTTCAT
ATTCGAGCGTTGGGAGTGCACTACGTATTGGTACATTTTTGTCTTCTGCAGTGCCCTTCCAGCTG
TCACTGAAATGGCTTTATTCGTCACCGTCTTTGGGCTGAAAAAGAAACCCTTCTGATTACCTTCA
TGACGGGAACCTAAGGACGAAGCCTACAGGGGCAAGGGCCGCTTCGTATTCCTGGAAGAAGGAAG
GCATAGGCTTCGGTTTTCCCCTCGGAAACTGCTTCTGCTGGAGGATATGTGTTGGAATAATTACG
TCTTGAGTCTGGGATTATCCGCATTGTATTTAGTGCTTTGTAATAAAATATGTTTGTAGTAACA
TTAAGACTTATATACAGTTTTAGGGGACAATTAAAAAAAAAAAA

FIGURE 90

MGRVSGLVPSRFLTLLAHLVVVITLFWSRDSNIQACLPLTFTPEEYDKQDIQLVAALSVTLGLFA
VELAGFLSGVSMFNSTQSLISIGAHCSASVALSFFIFERWECTTYWYIFVFCSALPAVTEMALFV
TVFGLKKKPF

Transmembrane domain:
amino acids 12-28 (type II), 51-66, 107-124

FIGURE 91

CTGGGACCCCGAAAAGAGAAGGGGAGAGCGAGGGGACGAGAGCGGAGGAGGAAG<u>ATG</u>CAACTGAC
TCGCTGCTGCTTCGTGTTCCTGGTGCAGGGTAGCCTCTATCTGGTCATCTGTGGCCAGGATGATG
GTCCTCCCGGCTCAGAGGACCCTGAGCGTGATGACCACGAGGGCCAGCCCCGGCCCCGGGTGCCT
CGGAAGCGGGGCCACATCTCACCTAAGTCCCGCCCCATGGCCAATTCCACTCTCCTAGGGCTGCT
GGCCCCGCCTGGGGAGGCTTGGGGCATTCTTGGGCAGCCCCCAACCGCCCGAACCACAGCCCCC
CACCCTCAGCCAAGGTGAAGAAAATCTTTGGCTGGGGCGACTTCTACTCCAACATCAAGACGGTG
GCCCTGAACCTGCTCGTCACAGGGAAGATTGTGGACCATGGCAATGGGACCTTCAGCGTCCACTT
CCAACACAATGCCACAGGCCAGGGAAACATCTCCATCAGCCTCGTGCCCCCAGTAAAGCTGTAG
AGTTCCACCAGGAACAGCAGATCTTCATCGAAGCCAAGGCCTCCAAAATCTTCAACTGCCGGATG
GAGTGGGAGAAGGTAGAACGGGGCCGCCGGACCTCGCTTTGCACCCACGACCCAGCCAAGATCTG
CTCCCGAGACCACGCTCAGAGCTCAGCCACCTGGAGCTGCTCCCAGCCCTTCAAAGTCGTCTGTG
TCTACATCGCCTTCTACAGCACGGACTATCGGCTGGTCCAGAAGGTGTGCCCAGATTACAACTAC
CATAGTGATACCCCCTACTACCCATCTGGG<u>TGA</u>CCCGGGGCAGGCCACAGAGGCCAGGCCAGGGC
TGGAAGGACAGGCCTGCCCATGCAGGAGACCATCTGGACACCGGGCAGGGAAGGGGTTGGGCCTC
AGGCAGGGAGGGGGGTGGAGACGAGGAGATGCCAAGTGGGGCCAGGGCCAAGTCTCAAGTGGCAG
AGAAAGGGTCCCAAGTGCTGGTCCCAACCTGAAGCTGTGGAGTGACTAGATCACAGGAGCACTGG
AGGAGGAGTGGGCTCTCTGTGCAGCCTCACAGGGCTTTGCCACGGAGCCACAGAGAGATGCTGGG
TCCCCGAGGCCTGTGGGCAGGCCGATCAGTGTGGCCCCAGATCAAGTCATGGGAGGAAGCTAAGC
CCTTGGTTCTTGCCATCCTGAGGAAAGATAGCAACAGGGAGGGGGAGATTTCATCAGTGTGGACA
GCCTGTCAACTTAGGATGGATGGCTGAGAGGGCTTCCTAGGAGCCAGTCAGCAGGGTGGGGTGGG
GCCAGAGGAGCTCTCCAGCCCTGCCTAGTGGGCGCCCTGAGCCCCTTGTCGTGTGCTGAGCATGG
CATGAGGCTGAAGTGGCAACCCTGGGGTCTTTGATGTCTTGACAGATTGACCATCTGTCTCCAGC
CAGGCCACCCCTTTCCAAAATTCCCTCTTCTGCCAGTACTCCCCCTGTACCACCCATTGCTGATG
GCACACCCATCCTTAAGCTAAGACAGGACGATTGTGGTCCTCCCACACTAAGGCCACAGCCCATC
CGCGTGCTGTGTGTCCCTCTTCCACCCCAACCCCTGCTGGCTCCTCTGGGAGCATCCATGTCCCG
GAGAGGGGTCCCTCAACAGTCAGCCTCACCTGTCAGACCGGGGTTCTCCCGGATCTGGATGGCGC
CGCCCTCTCAGCAGCGGGCACGGGTGGGGCGGGGCCGGGCCGCAGAGCATGTGCTGGATCTGTTC
TGTGTGTCTGTCTGTGGGTGGGGGGAGGGGAGGGAAGTCTTGTGAAACCGCTGATTGCTGACTTT
TGTGTGAAGAATCGTGTTCTTGGAGCAGGAAATAAAGCTTGCCCCGGGGCA

FIGURE 92

MQLTRCCFVFLVQGSLYLVICGQDDGPPGSEDPERDDHEGQPRPRVPRKRGHISPKSRPMANSTL
LGLLAPPGEAWGILGQPPNRPNHSPPPSAKVKKIFGWGDFYSNIKTVALNLLVTGKIVDHGNGTF
SVHFQHNATGQGNISISLVPPSKAVEFHQEQQIFIEAKASKIFNCRMEWEKVERGRRTSLCTHDP
AKICSRDHAQSSATWSCSQPFKVVCVYIAFYSTDYRLVQKVCPDYNYHSDTPYYPSG

Important features of the protein:

Signal peptide:

amino acids 1-14

N-glycosylation sites.

amino acids 62-65, 127-130, 137-140, 143-146

2-oxo acid dehydrogenases acyltransferase amino acids 61-71

FIGURE 93

CGGTGGCC<u>ATG</u>ACTGCGGCCGTGTTCTTCGGCTGCGCCTTCATTGCCTTCGGGCCTGCGCTCGCC
CTTTATGTCTTCACCATCGCCATCGAGCCGTTGCGTATCATCTTCCTCATCGCCGGAGCTTTCTT
CTGGTTGGTGTCTCTACTGATTTCGTCCCTTGTTTGGTTCATGGCAAGAGTCATTATTGACAACA
AAGATGGACCAACACAGAAATATCTGCTGATCTTTGGAGCGTTTGTCTCTGTCTATATCCAAGAA
ATGTTCCGATTTGCATATTATAAACTCTTAAAAAAAGCCAGTGAAGGTTTGAAGAGTATAAACCC
AGGTGAGACAGCACCCTCTATGCGACTGCTGGCCTATGTTTCTGGCTTGGGCTTTGGAATCATGA
GTGGAGTATTTTCCTTTGTGAATACCCTATCTGACTCCTTGGGGCCAGGCACAGTGGGCATTCAT
GGAGATTCTCCTCAATTCTTCCTTTATTCAGCTTTCATGACGCTGGTCATTATCTTGCTGCATGT
ATTCTGGGGCATTGTATTTTTTGATGGCTGTGAGAAGAAAAAGTGGGGCATCCTCCTTATCGTTC
TCCTGACCCACCTGCTGGTGTCAGCCCAGACCTTCATAAGTTCTTATTATGGAATAAACCTGGCG
TCAGCATTTATAATCCTGGTGCTCATGGGCACCTGGGCATTCTTAGCTGCGGGAGGCAGCTGCCG
AAGCCTGAAACTCTGCCTGCTCTGCCAAGACAAGAACTTTCTTCTTTACAACCAGCGCTCCAGA<u>T</u>
<u>AA</u>CCTCAGGGAACCAGCACTTCCCAAACCGCAGACTACATCTTTAGAGGAAGCACAACTGTGCCT
TTTTCTGAAAATCCCTTTTTCTGGTGGAATTGAGAAAGAAATAAAACTATGCAGATA

FIGURE 94

MTAAVFFGCAFIAFGPALALYVFTIAIEPLRIIFLIAGAFFWLVSLLISSLVWFMARVIIDNKDG
PTQKYLLIFGAFVSVYIQEMFRFAYYKLLKKASEGLKSINPGETAPSMRLLAYVSGLGFGIMSGV
FSFVNTLSDSLGPGTVGIHGDSPQFFLYSAFMTLVIILLHVFWGIVFFDGCEKKKWGILLIVLLT
HLLVSAQTFISSYYGINLASAFIILVLMGTWAFLAAGGSCRSLKLCLLCQDKNFLLYNQRSR

Important features of the protein:

Signal peptide:

amino acids 1-19

Transmembrane domains:

amino acids 32-51, 119-138, 152-169, 216-235

Glycosaminoglycan attachment site.

amino acids 120-123

Sodium:neurotransmitter symporter family protein amino acids 31-65

FIGURE 95

AATTTTTCACCAGAGTAAACTTGAGAAACCAACTGGACCTTGAGTATTGTACATTTTGCCTCGTG
GACCCAAAGGTAGCAATCTGAAAC<u>ATG</u>AGGAGTACGATTCTACTGTTTTGTCTTCTAGGATCAAC
TCGGTCATTACCACAGCTCAAACCTGCTTTGGGACTCCCTCCCACAAAACTGGCTCCGGATCAGG
GAACACTACCAAACCAACAGCAGTCAAATCAGGTCTTTCCTTCTTTAAGTCTGATACCATTAACA
CAGATGCTCACACTGGGGCCAGATCTGCATCTGTTAAATCCTGCTGCAGGAATGACACCTGGTAC
CCAGACCCACCCATTGACCCTGGGAGGGTTGAATGTACAACAGCAACTGCACCCACATGTGTTAC
CAATTTTTGTCACACAACTTGGAGCCCAGGGCACTATCCTAAGCTCAGAGGAATTGCCACAAATC
TTCACGAGCCTCATCATCCATTCCTTGTTCCCGGGAGGCATCCTGCCCACCAGTCAGGCAGGGGC
TAATCCAGATGTCCAGGATGGAAGCCTTCCAGCAGGAGGAGCAGGTGTAAATCCTGCCACCCAGG
GAACCCCAGCAGGCCGCCTCCCAACTCCCAGTGGCACAGATGACGACTTTGCAGTGACCACCCCT
GCAGGCATCCAAAGGAGCACACATGCCATCGAGGAAGCCACCACAGAATCAGCAAATGGAATTCA
G<u>TAA</u>GCTGTTTCAAATTTTTCAACTAAGCTGCCTCGAATTTGGTGATACATGTGAATCTTTATC
ATTGATTATATTATGGAATAGATTGAGACACATTGGATAGTCTTAGAAGAAATTAATTCTTAATT
TACCTGAAAATATTCTTGAAATTTCAGAAAATATGTTCTATGTAGAGAATCCCAACTTTTAAAAA
CAATAATTCAATGGATAAATCTGTCTTTGAAATATAACATTATGCTGCCTGGATGATATGCATAT
TAAAACATATTTGGAAAACTGGAAAAAAAAAAAAAAAAAAAAAAAAAAAAAAAAAAAAAAAAAAA
AAAAAAAAAAAAAAAAAAAAAAAAAAAAAA

FIGURE 96

MRSTILLFCLLGSTRSLPQLKPALGLPPTKLAPDQGTLPNQQQSNQVFPSLSLIPLTQM
LTLGPDLHLLNPAAGMTPGTQTHPLTLGGLNVQQQLHPHVLPIFVTQLGAQGTILSSEE
LPQIFTSLIIHSLFPGGILPTSQAGANPDVQDGSLPAGGAGVNPATQGTPAGRLPTPSG
TDDDFAVTTPAGIQRSTHAIEEATTESANGIQ

Signal peptide:

amino acids 1-16

FIGURE 97

```
GCTCAAGTGCCCTGCCTTGCCCCACCCAGCCCAGCCTGGCCAGAGCCCCCTGGAGAAGGAGCTCT
CTTCTTGCTTGGCAGCTGGACCAAGGGAGCCAGTCTTGGGCGCTGGAGGGCCTGTCCTGACCATG
GTCCCTGCCTGGCTGTGGCTGCTTTGTGTCTCCGTCCCCCAGGCTCTCCCCAAGGCCCAGCCTGC
AGAGCTGTCTGTGGAAGTTCCAGAAAACTATGGTGGAAATTTCCCTTTATACCTGACCAAGTTGC
CGCTGCCCCGTGAGGGGCTGAAGGCCAGATCGTGCTGTCAGGGGACTCAGGCAAGGCAACTGAG
GGCCCATTTGCTATGGATCCAGATTCTGGCTTCCTGCTGGTGACCAGGGCCCTGGACCGAGAGGA
GCAGGCAGAGTACCAGCTACAGGTCACCCTGGAGATGCAGGATGGACATGTCTTGTGGGGTCCAC
AGCCTGTGCTTGTGCACGTGAAGGATGAGAATGACCAGGTGCCCCATTTCTCTCAAGCCATCTAC
AGAGCTCGGCTGAGCCGGGGTACCAGGCCTGGCATCCCCTTCCTCTTCCTTGAGGCTTCAGACCG
GGATGAGCCAGGCACAGCCAACTCGGATCTTCGATTCCACATCCTGAGCCAGGCTCCAGCCCAGC
CTTCCCCAGACATGTTCCAGCTGGAGCCTCGGCTGGGGCTCTGGCCCTCAGCCCCAAGGGGAGC
ACCAGCCTTGACCACGCCCTGGAGAGGACCTACCAGCTGTTGGTACAGGTCAAGGACATGGGTGA
CCAGGCCTCAGGCCACCAGGCCACTGCCACCGTGGAAGTCTCCATCATAGAGAGCACCTGGGTGT
CCCTAGAGCCTATCCACCTGGCAGAGAATCTCAAAGTCCTATACCCGCACCACATGGCCCAGGTA
CACTGGAGTGGGGGTGATGTGCACTATCACCTGGAGAGCCATCCCCCGGGACCCTTTGAAGTGAA
TGCAGAGGGAAACCTCTACGTGACCAGAGAGCTGGACAGAGAAGCCCAGGCTGAGTACCTGCTCC
AGGTGCGGGCTCAGAATTCCCATGGCGAGGACTATGCGGCCCTCTGGAGCTGCACGTGCTGGTG
ATGGATGAGAATGACAACGTGCCTATCTGCCCTCCCCGTGACCCCACAGTCAGCATCCCTGAGCT
CAGTCCACCAGGTACTGAAGTGACTAGACTGTCAGCAGAGGATGCAGATGCCCCCGGCTCCCCCA
ATTCCCACGTTGTGTATCAGCTCCTGAGCCCTGAGCCTGAGGATGGGGTAGAGGGGAGAGCCTTC
CAGGTGGACCCCACTTCAGGCAGTGTGACGCTGGGGGTGCTCCCACTCCGAGCAGGCCAGAACAT
CCTGCTTCTGGTGCTGGCCATGGACCTGGCAGGCGCAGAGGGTGGCTTCAGCAGCACGTGTGAAG
TCGAAGTCGCAGTCACAGATATCAATGATCACGCCCCTGAGTTCATCACTTCCCAGATTGGGCCT
ATAAGCCTCCCTGAGGATGTGGAGCCCGGGACTCTGGTGGCCATGCTAACAGCCATTGATGCTGA
CCTCGAGCCCGCCTTCCGCCTCATGGATTTTGCCATTGAGAGGGGAGACACAGAAGGGACTTTTG
GCCTGGATTGGGAGCCAGACTCTGGGCATGTTAGACTCAGACTCTGCAAGAACCTCAGTTATGAG
GCAGCTCCAAGTCATGAGGTGGTGGTGGTGCAGAGTGTGGCGAAGCTGGTGGGGCCAGGCCC
AGGCCCTGGAGCCACCGCCACGGTGACTGTGCTAGTGGAGAGAGTGATGCCACCCCCAAGTTGG
ACCAGGAGAGCTACGAGGCCAGTGTCCCCATCAGTGCCCCAGCCGGCTCTTTCCTGCTGACCATC
CAGCCCTCCGACCCCATCAGCCGAACCCTCAGGTTCTCCCTAGTCAATGACTCAGAGGGCTGGCT
CTGCATTGAGAAATTCTCCGGGGAGGTGCACACCGCCCAGTCCCTGCAGGGCGCCCAGCCTGGGG
ACACCTACACGGTGCTTGTGGAGGCCCAGGATACAGCCCTGACTCTTGCCCCTGTGCCCTCCCAA
TACCTCTGCACACCCCGCCAAGACCATGGCTTGATCGTGAGTGGACCCAGCAAGGACCCCGATCT
GGCCAGTGGGCACGGTCCCTACAGCTTCACCCTTGGTCCCAACCCCACGGTGCAACGGGATTGGC
GCCTCCAGACTCTCAATGGTTCCCATGCCTACCTCACCTTGGCCCTGCATTGGGTGGAGCCACGT
GAACACATAATCCCCGTGGTGGTCAGCCACAATGCCCAGATGTGGCAGCTCCTGGTTCGAGTGAT
CGTGTGTCGCTGCAACGTGGAGGGGCAGTGCATGCGCAAGGTGGGCCGCATGAAGGGCATGCCCA
CGAAGCTGTCGGCAGTGGGCATCCTTGTAGGCACCCTGGTAGCAATAGGAATCTTCCTCATCCTC
ATTTTCACCCACTGGACCATGTCAAGGAAGAAGGACCCGGATCAACCAGCAGACAGCGTGCCCCT
GAAGGCGACTGTCTGAATGGCCCAGGCAGCTCTAGCTGGGAGCTTGGCCTCTGGCTCCATCTGAG
TCCCCTGGGAGAGAGCCCAGCACCCAAGATCCAGCAGGGGACAGGACAGAGTAGAAGCCCCTCCA
TCTGCCCTGGGGTGGAGGCACCATCACCATCACCAGGCATGTCTGCAGAGCCTGGACACCAACTT
TATGGACTGCCCATGGGAGTGCTCCAAATGTCAGGGTGTTTGCCCAATAATAAAGCCCCAGAGAA
CTGGGCTGGGCCCTATGGGAAAAAAAAAAAAAAAAAAAAAAAAAAAAAAAAAAAG
```

FIGURE 98

MVPAWLWLLCVSVPQALPKAQPAELSVEVPENYGGNFPLYLTKLPLPREGAEGQIVLSGDSGKAT
EGPFAMDPDSGFLLVTRALDREEQAEYQLQVTLEMQDGHVLWGPQPVLVHVKDENDQVPHFSQAI
YRARLSRGTRPGIPFLFLEASDRDEPGTANSDLRFHILSQAPAQPSPDMFQLEPRLGALALSPKG
STSLDHALERTYQLLVQVKDMGDQASGHQATATVEVSIIESTWVSLEPIHLAENLKVLYPHHMAQ
VHWSGGDVHYHLESHPPGPFEVNAEGNLYVTRELDREAQAEYLLQVRAQNSHGEDYAAPLELHVL
VMDENDNVPICPPRDPTVSIPELSPPGTEVTRLSAEDADAPGSPNSHVVYQLLSPEPEDGVEGRA
FQVDPTSGSVTLGVLPLRAGQNILLLVLAMDLAGAEGGFSSTCEVEVAVTDINDHAPEFITSQIG
PISLPEDVEPGTLVAMLTAIDADLEPAFRLMDFAIERGDTEGTFGLDWEPDSGHVRLRLCKNLSY
EAAPSHEVVVVVQSVAKLVGPGPGPGATATVTVLVERVMPPPKLDQESYEASVPISAPAGSFLLT
IQPSDPISRTLRFSLVNDSEGWLCIEKFSGEVHTAQSLQGAQPGDTYTVLVEAQDTALTLAPVPS
QYLCTPRQDHGLIVSGPSKDPDLASGHGPYSFTLGPNPTVQRDWRLQTLNGSHAYLTLALHWVEP
REHIIPVVVSHNAQMWQLLVRVIVCRCNVEGQCMRKVGRMKGMPTKLSAVGILVGTLVAIGIFLI
LIFTHWTMSRKKDPDQPADSVPLKATV

Signal peptide:
amino acids 1-18

Transmembrane domain:
amino acids 762-784

FIGURE 99

```
GGCTGACCGTGCTACATTGCCTGGAGGAAGCCTAAGGAACCCAGGCATCCAGCTGCCCACGCCTG
AGTCCAAGATTCTTCCCAGGAACACAAACGTAGGAGACCCACGCTCCTGGAAGCACCAGCCTTTA
TCTCTTCACCTTCAAGTCCCCTTTCTCAAGAATCCTCTGTTCTTTGCCCTCTAAAGTCTTGGTAC
ATCTAGGACCCAGGCATCTTGCTTTCCAGCCACAAAGAGACAG<u>ATG</u>AAGATGCAGAAAGGAAATG
TTCTCCTTATGTTTGGTCTACTATTGCATTTAGAAGCTGCAACAAATTCCAATGAGACTAGCACC
TCTGCCAACACTGGATCCAGTGTGATCTCCAGTGGAGCCAGCACAGCCACCAACTCTGGGTCCAG
TGTGACCTCCAGTGGGGTCAGCACAGCCACCATCTCAGGGTCCAGCGTGACCTCCAATGGGGTCA
GCATAGTCACCAACTCTGAGTTCCATACAACCTCCAGTGGGATCAGCACAGCCACCAACTCTGAG
TTCAGCACAGCGTCCAGTGGGATCAGCATAGCCACCAACTCTGAGTCCAGCACAACCTCCAGTGG
GGCCAGCACAGCCACCAACTCTGAGTCCAGCACACCCTCCAGTGGGGCCAGCACAGTCACCAACT
CTGGGTCCAGTGTGACCTCCAGTGGAGCCAGCACTGCCACCAACTCTGAGTCCAGCACAGTGTCC
AGTAGGGCCAGCACTGCCACCAACTCTGAGTCTAGCACACTCTCCAGTGGGGCCAGCACAGCCAC
CAACTCTGACTCCAGCACAACCTCCAGTGGGGCTAGCACAGCCACCAACTCTGAGTCCAGCACAA
CCTCCAGTGGGGCCAGCACAGCCACCAACTCTGAGTCCAGCACAGTGTCCAGTAGGGCCAGCACT
GCCACCAACTCTGAGTCCAGCACAACCTCCAGTGGGGCCAGCACAGCCACCAACTCTGAGTCCAG
AACGACCTCCAATGGGGCTGGCACAGCCACCAACTCTGAGTCCAGCACGACCTCCAGTGGGGCCA
GCACAGCCACCAACTCTGACTCCAGCACAGTGTCCAGTGGGGCCAGCACTGCCACCAACTCTGAG
TCCAGCACGACCTCCAGTGGGGCCAGCACAGCCACCAACTCTGAGTCCAGCACGACCTCCAGTGG
GGCTAGCACAGCCACCAACTCTGACTCCAGCACAACCTCCAGTGGGGCCGGCACAGCCACCAACT
CTGAGTCCAGCACAGTGTCCAGTGGGATCAGCACAGTCACCAATTCTGAGTCCAGCACACCCTCC
AGTGGGGCCAACACAGCCACCAACTCTGAGTCCAGTACGACCTCCAGTGGGGCCAACACAGCCAC
CAACTCTGAGTCCAGCACAGTGTCCAGTGGGGCCAGCACTGCCACCAACTCTGAGTCCAGCACAA
CCTCCAGTGGGGTCAGCACAGCCACCAACTCTGAGTCCAGCACAACCTCCAGTGGGGCTAGCACA
GCCACCAACTCTGACTCCAGCACAACCTCCAGTGAGGCCAGCACAGCCACCAACTCTGAGTCTAG
CACAGTGTCCAGTGGGATCAGCACAGTCACCAATTCTGAGTCCAGCACAACCTCCAGTGGGGCCA
ACACAGCCACCAACTCTGGGTCCAGTGTGACCTCTGCAGGCTCTGGAACAGCAGCTCTGACTGGA
ATGCACACAACTTCCCATAGTGCATCTACTGCAGTGAGTGAGGCAAAGCCTGGTGGGTCCCTGGT
GCCGTGGGAAATCTTCCTCATCACCCTGGTCTCGGTTGTGGCGGCCGTGGGGCTCTTTGCTGGGC
TCTTCTTCTGTGTGAGAAACAGCCTGTCCCTGAGAAACACCTTTAACACAGCTGTCTACCACCCT
CATGGCCTCAACCATGGCCTTGGTCCAGGCCCTGGAGGGAATCATGGAGCCCCCACAGGCCCAG
GTGGAGTCCTAACTGGTTCTGGAGGAGACCAGTATCATCGATAGCCATGGAGATGAGCGGGAGGA
ACAGCGGGCCC<u>TGA</u>GCAGCCCCGGAAGCAAGTGCCGCATTCTTCAGGAAGGAAGAGACCTGGGCA
CCCAAGACCTGGTTTCCTTTCATTCATCCCAGGAGACCCCTCCCAGCTTTGTTTGAGATCCTGAA
AATCTTGAAGAAGGTATTCCTCACCTTTCTTGCCTTTACCAGACACTGGAAAGAGAATACTATAT
TGCTCATTTAGCTAAGAAATAAATACATCTCATCTAACACACACGACAAAGAGAAGCTGTGCTTG
CCCCGGGGTGGGTATCTAGCTCTGAGATGAACTCAGTTATAGGAGAAAACCTCCATGCTGGACTC
CATCTGGCATTCAAAATCTCCACAGTAAAATCCAAAGACCTCAAAAAAAAAAAAAAAAAAAAAAA
AAAAAAAAAAAAAAAAAAAAAAAAAAAAA
```

FIGURE 100

MKMQKGNVLLMFGLLLHLEAATNSNETSTSANTGSSVISSGASTATNSGSSVTSSGVSTATISGS
SVTSNGVSIVTNSEFHTTSSGISTATNSEFSTASSGISIATNSESSTTSSGASTATNSESSTPSS
GASTVTNSGSSVTSSGASTATNSESSTVSSRASTATNSESSTLSSGASTATNSDSSTTSSGASTA
TNSESSTTSSGASTATNSESSTVSSRASTATNSESSTTSSGASTATNSESRTTSNGAGTATNSES
STTSSGASTATNSDSSTVSSGASTATNSESSTTSSGASTATNSESSTTSSGASTATNSDSSTTSS
GAGTATNSESSTVSSGISTVTNSESSTPSSGANTATNSESSTTSSGANTATNSESSTVSSGASTA
TNSESSTTSSGVSTATNSESSTTSSGASTATNSDSSTTSSEASTATNSESSTVSSGISTVTNSES
STTSSGANTATNSGSSVTSAGSGTAALTGMHTTSHSASTAVSEAKPGGSLVPWEIFLITLVSVVA
AVGLFAGLFFCVRNSLSLRNTFNTAVYHPGLNHGLGPGPGGNHGAPHRPRWSPNWFWRRPVSSI
AMEMSGRNSGP

Signal peptide:
amino acids 1-20

Transmembrane domain:
amino acids 510-532

FIGURE 101

GGCCGGACGCCTCCGCGTTACGGGATGAATTAACGGCGGGTTCCGCACGGAGGTTGTGACCCCTA
CGGAGCCCCAGCTTGCCCACGCACCCCACTCGGCGTCGCGCGGCGTGCCCTGCTTGTCACAGGTG
GGAGGCTGGAACTATCAGGCTGAAAAACAGAGTGGGTACTCTCTTCTGGGAAGCTGGCAACAAAT
GGATGATGTGATATAATGCATTCCAGGGGAAGGGAAATTGTGGTGCTTCTGAACCCATGGTCAATT
AACGAGGCAGTTTCTAGCTACTGCACGTACTTCATAAAGCAGGACTCTAAAAGCTTTGGAATCAT
GGTGTCATGGAAAGGGATTTACTTTATACTGACTCTGTTTTGGGGAAGCTTTTTGGAAGCATTT
TCATGCTGAGTCCCTTTTTACCTTTGATGTTTGTAAACCCATCTTGGTATCGCTGGATCAACAAC
CGCCTTGTGGCAACATGGCTCACCCTACCTGTGGCATTATTGGAGACCATGTTTGGTGTAAAAGT
GATTATAACTGGGGATGCATTTGTTCCTGGAGAAAGAAGTGTCATTATCATGAACCATCGGACAA
GAATGGACTGGATGTTCCTGTGGAATTGCCTGATGCGATATAGCTACCTCAGATTGGAGAAAATT
TGCCTCAAAGCGAGTCTCAAAGGTGTTCCTGGATTTGGTTGGGCCATGCAGGCTGCTGCCTATAT
CTTCATTCATAGGAAATGGAAGGATGACAAGAGCCATTTCGAAGACATGATTGATTACTTTTGTG
ATATTCACGAACCACTTCAACTCCTCATATTCCCAGAAGGGACTGATCTCACAGAAACAGCAAG
TCTCGAAGTAATGCATTTGCTGAAAAAATGGACTTCAGAAATATGAATATGTTTTACATCCAAG
AACTACAGGCTTTACTTTTGTGGTAGACCGTCTAAGAGAAGGTAAGAACCTTGATGCTGTCCATG
ATATCACTGTGGCGTATCCTCACAACATTCCTCAATCAGAGAAGCACCTCCTCCAAGGAGACTTT
CCCAGGGAAATCCACTTTCACGTCCACCGGTATCCAATAGACACCCTCCCCACATCCAAGGAGGA
CCTTCAACTCTGGTGCCACAAACGGTGGGAAGAGAAAGAAGAGAGGCTGCGTTCCTTCTATCAAG
GGGAGAAGAATTTTTATTTTACCGGACAGAGTGTCATTCCACCTTGCAAGTCTGAACTCAGGGTC
CTTGTGGTCAAATTGCTCTCTATACTGTATTGGACCCTGTTCAGCCCTGCAATGTGCCTACTCAT
ATATTTGTACAGTCTTGTTAAGTGGTATTTTATAATCACCATTGTAATCTTTGTGCTGCAAGAGA
GAATATTTGGTGGACTGGAGATCATAGAACTTGCATGTTACCGACTTTTACACAAACAGCCACAT
TTAAATTCAAAGAAAATGAGTAAGATTATAAGGTTTGCCATGTGAAAACCTAGAGCATATTTTG
GAAATGTTCTAAACCTTTCTAAGCTCAGATGCATTTTTGCATGACTATGTCGAATATTTCTTACT
GCCATCATTATTTGTTAAAGATATTTTGCACTTAATTTTGTGGGAAAAATATTGCTACAATTTTT
TTTAATCTCTGAATGTAATTTCGATACTGTGTACATAGCAGGGAGTGATCGGGGTGAAATAACTT
GGGCCAGAATATTATTAAACAATCATCAGGCTTTTAAA

FIGURE 102

MHSRGREIVVLLNPWSINEAVSSYCTYFIKQDSKSFGIMVSWKGIYFILTLFWGSFFGSIFMLSP
FLPLMFVNPSWYRWINNRLVATWLTLPVALLETMFGVKVIITGDAFVPGERSVIIMNHRTRMDWM
FLWNCLMRYSYLRLEKICLKASLKGVPGFGWAMQAAAYIFIHRKWKDDKSHFEDMIDYFCDIHEP
LQLLIFPEGTDLTENSKSRSNAFAEKNGLQKYEYVLHPRTTGFTFVVDRLREGKNLDAVHDITVA
YPHNIPQSEKHLLQGDFPREIHFHVHRYPIDTLPTSKEDLQLWCHKRWEEKEERLRSFYQGEKNF
YFTGQSVIPPCKSELRVLVVKLLSILYWTLFSPAMCLLIYLYSLVKWYFIITIVIFVLQERIFGG
LEIIELACYRLLHKQPHLNSKKNE

Important features of the protein:
Signal peptide:
amino acids 1-22

Transmembrane domains:
amino acids 44-63, 90-108; 354-377

FIGURE 103

CGGCTCGAGCGGCTCGAGTGAAGAGCCTCTCCACGGCTCCTGCGCCTGAGACAGCTGGCCTGACC
TCCAAATCATCCATCCACCCCTGCTGTCATCTGTTTTCATAGTGTGAGATCAACCCACAGGAATA
TCC<u>ATG</u>GCTTTTGTGCTCATTTTGGTTCTCAGTTTCTACGAGCTGGTGTCAGGACAGTGGCAAGT
CACTGGACCGGGCAAGTTTGTCCAGGCCTTGGTGGGGGAGGACGCCGTGTTCTCCTGCTCCCTCT
TTCCTGAGACCAGTGCAGAGGCTATGGAAGTGCGGTTCTTCAGGAATCAGTTCCATGCTGTGGTC
CACCTCTACAGAGATGGGGAAGACTGGGAATCTAAGCAGATGCCACAGTATCGAGGGAGAACTGA
GTTTGTGAAGGACTCCATTGCAGGGGGGCGTGTCTCTCTAAGGCTAAAAAACATCACTCCCTCGG
ACATCGGCCTGTATGGGTGCTGGTTCAGTTCCCAGATTTACGATGAGGAGGCCACCTGGGAGCTG
CGGGTGGCAGCACTGGGCTCACTTCCTCTCATTTCCATCGTGGGATATGTTGACGGAGGTATCCA
GTTACTCTGCCTGTCCTCAGGCTGGTTCCCCCAGCCCACAGCCAAGTGGAAAGGTCCACAAGGAC
AGGATTTGTCTTCAGACTCCAGAGCAAATGCAGATGGGTACAGCCTGTATGATGTGGAGATCTCC
ATTATAGTCCAGGAAAATGCTGGGAGCATATTGTGTTCCATCCACCTTGCTGAGCAGAGTCATGA
GGTGGAATCCAAGGTATTGATAGGAGAGACGTTTTCCAGCCCTCACCTTGGCGCCTGGCTTCTA
TTTTACTCGGGTTACTCTGTGGTGCCCTGTGTGGTGTTGTCATGGGGATGATAATTGTTTTCTTC
AAATCCAAAGGGAAAATCCAGGCGGAACTGGACTGGAGAAGAAAGCACGGACAGGCAGAATTGAG
AGACGCCCGGAAACACGCAGTGGAGGTGACTCTGGATCCAGAGACGGCTCACCCGAAGCTCTGCG
TTTCTGATCTGAAAACTGTAACCCATAGAAAAGCTCCCCAGGAGGTGCCTCACTCTGAGAAGAGA
TTTACAAGGAAGAGTGTGGTGGCTTCTCAGGGTTTCCAAGCAGGGAGACATTACTGGGAGGTGGA
CGTGGGACAAAATGTAGGGTGGTATGTGGGAGTGTGTCGGGATGACGTAGACAGGGGGAAGAACA
ATGTGACTTTGTCTCCCAACAATGGGTATTGGGTCCTCAGACTGACAACAGAACATTTGTATTTC
ACATTCAATCCCCATTTTATCAGCCTCCCCCCCAGCACCCCTCCTACACGAGTAGGGGTCTTCCT
GGACTATGAGGGTGGGACCATCTCCTTCTTCAATACAAATGACCAGTCCCTTATTTATACCCTGC
TGACATGTCAGTTTGAAGGCTTGTTGAGACCCTATATCCAGCATGCGATGTATGACGAGGAAAAG
GGGACTCCCATATTCATATGTCCAGTGTCCTGGGGA<u>TGA</u>GACAGAGAAGACCCTGCTTAAAGGGC
CCCACACCACAGACCCAGACACAGCCAAGGGAGAGTGCTCCCGACAGGTGGCCCCAGCTTCCTCT
CCGGAGCCTGCGCACAGAGAGTCACGCCCCCACTCTCCTTTAGGGAGCTGAGGTTCTTCTGCCC
TGAGCCCTGCAGCAGCGGCAGTCACAGCTTCCAGATGAGGGGGGATTGGCCTGACCCTGTGGGAG
TCAGAAGCCATGGCTGCCCTGAAGTGGGGACGGAATAGACTCACATTAGGTTTAGTTTGTGAAAA
CTCCATCCAGCTAAGCGATCTTGAACAAGTCACAACCTCCCAGGCTCCTCATTTGCTAGTCACGG
ACAGTGATTCCTGCCTCACAGGTGAAGATTAAAGAGACAACGAATGTGAATCATGCTTGCAGGTT
TGAGGGCACAGTGTTTGCTAATGATGTGTTTTTATATTATACATTTTCCCACCATAAACTCTGTT
TGCTTATTCCACATTAATTTACTTTTCTCTATACCAAATCACCCATGGAATAGTTATTGAACACC
TGCTTTGTGAGGCTCAAAGAATAAAGAGGAGGTAGGATTTTTCACTGATTCTATAAGCCCAGCAT
TACCTGATACCAAAACCAGGCAAAGAAAACAGAAGAAGAGGAAGGAAAACTACAGGTCCATATCC
CTCATTAACACAGACACAAAATTCTAAATAAATTTTAACAAATTAAACTAAACAATATATTTA
AAGATGATATATAACTACTCAGTGTGGTTTGTCCCACAAATGCAGAGTTGGTTTAATATTTAAAT
ATCAACCAGTGTAATTCAGCACATTAATAAAGTAAAAAGAAAACCATAAAAAAAAAAAAAAA

FIGURE 104

MAFVLILVLSFYELVSGQWQVTGPGKFVQALVGEDAVFSCSLFPETSAEAMEVRFFRNQFHAVVH
LYRDGEDWESKQMPQYRGRTEFVKDSIAGGRVSLRLKNITPSDIGLYGCWFSSQIYDEEATWELR
VAALGSLPLISIVGYVDGGIQLLCLSSGWFPQPTAKWKGPQGQDLSSDSRANADGYSLYDVEISI
IVQENAGSILCSIHLAEQSHEVESKVLIGETFFQPSPWRLASILLGLLCGALCGVVMGMIIVFFK
SKGKIQAELDWRRKHGQAELRDARKHAVEVTLDPETAHPKLCVSDLKTVTHRKAPQEVPHSEKRF
TRKSVVASQGFQAGRHYWEVDVGQNVGWYVGVCRDDVDRGKNNVTLSPNNGYWVLRLTTEHLYFT
FNPHFISLPPSTPPTRVGVFLDYEGGTISFFNTNDQSLIYTLLTCQFEGLLRPYIQHAMYDEEKG
TPIFICPVSWG

Signal peptide:

amino acids 1-17

Transmembrane domains:

amino acids 131-150, 235-259

FIGURE 105

```
CCTTCACAGGACTCTTCATTGCTGGTTGGCAATGATGTATCGGCCAGATGTGGTGAGGGCTAGGAAAAGAG
TTTGTTGGGAACCCTGGGTTATCGGCCTCGTCATCTTCATATCCCTGATTGTCCTGGCAGTGTGCATTGGA
CTCACTGTTCATTATGTGAGATATAATCAAAAGAAGACCTACAATTACTATAGCACATTGTCATTTACAAC
TGACAAACTATATGCTGAGTTTGGCAGAGAGGCTTCTAACAATTTTACAGAAATGAGCCAGAGACTTGAAT
CAATGGTGAAAAATGCATTTTATAAATCTCCATTAAGGGAAGAATTTGTCAAGTCTCAGGTTATCAAGTTC
AGTCAACAGAAGCATGGAGTGTTGGCTCATATGCTGTTGATTTGTAGATTTCACTCTACTGAGGATCCTGA
AACTGTAGATAAAATTGTTCAACTTGTTTTACATGAAAAGCTGCAAGATGCTGTAGGACCCCCTAAAGTAG
ATCCTCACTCAGTTAAAATTAAAAAAATCAACAAGACAGAAACAGACAGCTATCTAAACCATTGCTGCGGA
ACACGAAGAAGTAAAACTCTAGGTCAGAGTCTCAGGATCGTTGGTGGGACAGAAGTAGAAGAGGGTGAATG
GCCCTGGCAGGCTAGCCTGCAGTGGGATGGGAGTCATCGCTGTGGAGCAACCTTAATTAATGCCACATGGC
TTGTGAGTGCTGCTCACTGTTTTACAACATATAAGAACCCTGCCAGATGGACTGCTTCCTTTGGAGTAACA
ATAAAACCTTCGAAAATGAAACGGGGTCTCCGGAGAATAATTGTCCATGAAAAATACAAACACCCATCACA
TGACTATGATATTTCTCTTGCAGAGCTTTCTAGCCCTGTTCCCTACACAAATGCAGTACATAGAGTTTGTC
TCCCTGATGCATCCTATGAGTTTCAACCAGGTGATGTGATGTTTGTGACAGGATTTGGAGCACTGAAAAAT
GATGGTTACAGTCAAAATCATCTTCGACAAGCACAGGTGACTCTCATAGACGCTACAACTTGCAATGAACC
TCAAGCTTACAATGACGCCATAACTCCTAGAATGTTATGTGCTGGCTCCTTAGAAGGAAAAACAGATGCAT
GCCAGGGTGACTCTGGAGGACCACTGGTTAGTTCAGATGCTAGAGATATCTGGTACCTTGCTGGAATAGTG
AGCTGGGGAGATGAATGTGCGAAACCCAACAAGCCTGGTGTTTATACTAGAGTTACGGCCTTGCGGGACTG
GATTACTTCAAAAACTGGTATCTAAGAGACAAAAGCCTCATGGAACAGATAACATTTTTTTTGTTTTTG
GGTGTGGAGGCCATTTTTAGAGATACAGAATTGGAGAAGACTTGCAAAACAGCTAGATTTGACTGATCTCA
ATAAACTGTTTGCTTGATGCATGTATTTTCTTCCCAGCTCTGTTCCGCACGTAAGCATCCTGCTTCTGCCA
GATCAACTCTGTCATCTGTGAGCAATAGTTGAAACTTTATGTACATAGAGAAATAGATAATACAATATTAC
ATTACAGCCTGTATTCATTTGTTCTCTAGAAGTTTTGTCAGAATTTTGACTTGTTGACATAAATTTGTAAT
GCATATATACAATTTGAAGCACTCCTTTTCTTCAGTTCCTCAGCTCCTCTCATTTCAGCAAATATCCATTT
TCAAGGTGCAGAACAAGGAGTGAAAGAAAATATAAGAAGAAAAAAATCCCCTACATTTTATTGGCACAGAA
AAGTATTAGGTGTTTTTCTTAGTGGAATATTAGAAATGATCATATTCATTATGAAAGGTCAAGCAAAGACA
GCAGAATACCAATCACTTCATCATTTAGGAAGTATGGGAACTAAGTTAAGGAAGTCCAGAAAGAAGCCAAG
ATATATCCTTATTTTCATTTCCAAACAACTACTATGATAAATGTGAAGAAGATTCTGTTTTTTTGTGACCT
ATAATAATTATACAAACTTCATGCAATGTACTTGTTCTAAGCAAATTAAAGCAAATATTTATTTAACATTG
TTACTGAGGATGTCAACATATAACAATAAAATATAAATCACCCA
```

FIGURE 106

```
MMYRPDVVRARKRVCWEPWVIGLVIFISLIVLAVCIGLTVHYVRYNQKKTYNYYSTLSFTTDKLY
AEFGREASNNFTEMSQRLESMVKNAFYKSPLREEFVKSQVIKFSQQKHGVLAHMLLICRFHSTED
PETVDKIVQLVLHEKLQDAVGPPKVDPHSVKIKKINKTETDSYLNHCCGTRRSKTLGQSLRIVGG
TEVEEGEWPWQASLQWDGSHRCGATLINATWLVSAAHCFTTYKNPARWTASFGVTIKPSKMKRGL
RRIIVHEKYKHPSHDYDISLAELSSPVPYTNAVHRVCLPDASYEFQPGDVMFVTGFGALKNDGYS
QNHLRQAQVTLIDATTCNEPQAYNDAITPRMLCAGSLEGKTDACQGDSGGPLVSSDARDIWYLAG
IVSWGDECAKPNKPGVYTRVTALRDWITSKTGI
```

Transmembrane domain:
amino acids 21-40 (type II)

FIGURE 107

AGAGAAAGAAGCGTCTCCAGCTGAAGCCAATGCAGCCCTCCGGCTCTCCGCGAAGAAGTTCCCTG
CCCCGATGAGCCCCGCCGTGCGTCCCGACTATCCCCAGGCGGGCGTGGGGCACCGGGCCCAGC
GCCGACGATCGCTGCCGTTTTGCCCTTGGGAGTAGGATGTGGTGAAAGGATGGGGCTTCTCCCTT
ACGGGGCTCACAATGGCCAGAGAAGATTCCGTGAAGTGTCTGCGCTGCCTGCTCTACGCCCTCAA
TCTGCTCTTTTGGTTAATGTCCATCAGTGTGTTGGCAGTTTCTGCTTGGATGAGGGACTACCTAA
ATAATGTTCTCACTTTAACTGCAGAAACGAGGGTAGAGGAAGCAGTCATTTTGACTTACTTTCCT
GTGGTTCATCCGGTCATGATTGCTGTTTGCTGTTTCCTTATCATTGTGGGATGTTAGGATATTG
TGGAACGGTGAAAAGAAATCTGTTGCTTCTTGCATGGTACTTTGGAAGTTTGCTTGTCATTTTCT
GTGTAGAACTGGCTTGTGGCGTTTGGACATATGAACAGGAACTTATGGTTCCAGTACAATGGTCA
GATATGGTCACTTTGAAAGCCAGGATGACAAATTATGGATTACCTAGATATCGGTGGCTTACTCA
TGCTTGGAATTTTTTTCAGAGAGAGTTTAAGTGCTGTGGAGTAGTATATTTCACTGACTGGTTGG
AAATGACAGAGATGGACTGGCCCCCAGATTCCTGCTGTGTTAGAGAATTCCCAGGATGTTCCAAA
CAGGCCCACCAGGAAGATCTCAGTGACCTTTATCAAGAGGGTTGTGGGAAGAAAATGTATTCCTT
TTTGAGAGGAACCAAACAACTGCAGGTGCTGAGGTTTCTGGGAATCTCCATTGGGGTGACACAAA
TCCTGGCCATGATTCTCACCATTACTCTGCTCTGGGCTCTGTATTATGATAGAAGGGAGCCTGGG
ACAGACCAAATGATGTCCTTGAAGAATGACAACTCTCAGCACCTGTCATGTCCCTCAGTAGAACT
GTTGAAACCAAGCCTGTCAAGAATCTTTGAACACACATCCATGGCAAACAGCTTTAATACACACT
TTGAGATGGAGGAGTTATAAAAGAAATGTCACAGAAGAAAACCACAAACTTGTTTTATTGGACT
TGTGAATTTTTGAGTACATACTATGTGTTTCAGAAATATGTAGAAATAAAAATGTTGCCATAAAA
TAACACCTAAGCATATACTATTCTATGCTTTAAAATGAGGATGGAAAAGTTTCATGTCATAAGTC
ACCACCTGGACAATAATTGATGCCCTTAAAATGCTGAAGACAGATGTCATACCCACTGTGTAGCC
TGTGTATGACTTTTACTGAACACAGTTATGTTTTGAGGCAGCATGGTTTGATTAGCATTTCCGCA
TCCATGCAAACGAGTCACATATGGTGGGACTGGAGCCATAGTAAAGGTTGATTTACTTCTACCAA
CTAGTATATAAAGTACTAATTAAATGCTAACATAGGAAGTTAGAAAATACTAATAACTTTTATTA
CTCAGCGATCTATTCTTCTGATGCTAAATAAATTATATATCAGAAAACTTTCAATATTGGTGACT
ACCTAAATGTGATTTTTGCTGGTTACTAAAATATTCTTACCACTTAAAAGAGCAAGCTAACACAT
TGTCTTAAGCTGATCAGGGATTTTTTGTATATAAGTCTGTGTTAAATCTGTATAATTCAGTCGAT
TTCAGTTCTGATAATGTTAAGAATAACCATTATGAAAGGAAAATTTGTCCTGTATAGCATCATT
ATTTTTAGCCTTTCCTGTTAATAAAGCTTTACTATTCTGTCCTGGCTTATATTACACATATAAC
TGTTATTTAAATACTTAACCACTAATTTTGAAAATTACCAGTGTGATACATAGGAATCATTATTC
AGAATGTAGTCTGGTCTTTAGGAAGTATTAATAAGAAAATTTGCACATAACTTAGTTGATTCAGA
AAGGACTTGTATGCTGTTTTTCTCCCAAATGAAGACTCTTTTTGACACTAAACACTTTTTAAAAA
GCTTATCTTTGCCTTCTCCAAACAAGAAGCAATAGTCTCCAAGTCAATATAAATTCTACAGAAAA
TAGTGTTCTTTTTCTCCAGAAAAATGCTTGTGAGAATCATTAAAACATGTGACAATTTAGAGATT
CTTTGTTTATTTCACTGATTAATATACTGTGGCAAATTACACAGATTATTAAATTTTTTTACAA
GAGTATAGTATATTTATTTGAAATGGGAAAGTGCATTTTACTGTATTTTGTGTATTTTGTTTAT
TTCTCAGAATATGGAAAGAAAATTAAAATGTGTCAATAAATATTTTCTAGAGAGTAA

FIGURE 108

MAREDSVKCLRCLLYALNLLFWLMSISVLAVSAWMRDYLNNVLTLTAETRVEEAVILTYFPVVHP
VMIAVCCFLIIVGMLGYCGTVKRNLLLLAWYFGSLLVIFCVELACGVWTYEQELMVPVQWSDMVT
LKARMTNYGLPRYRWLTHAWNFFQREFKCCGVVYFTDWLEMTEMDWPPDSCCVREFPGCSKQAHQ
EDLSDLYQEGCGKKMYSFLRGTKQLQVLRFLGISIGVTQILAMILTITLLWALYYDRREPGTDQM
MSLKNDNSQHLSCPSVELLKPSLSRIFEHTSMANSFNTHFEMEEL

Signal peptide:

amino acids 1-33

Transmembrane domains:

amino acids 12-35, 57-86, 94-114, 226-248

FIGURE 109

```
CCAAGGCCAGAGCTGTGGACACCTTATCCCACTCATCCTCATCCTCTTCCTCTGATAAAGCCCCTACCAGTGCT
GATAAAGTCTTTCTCGTGAGAGCCTAGAGGCCTTAAAAAAAAAAGTGCTTGAAAGAGAAGGGGACAAAGGAACA
CCAGTATTAAGAGGATTTTCCAGTGTTTCTGGCAGTTGGTCCAGAAGGATGCCTCCATTCCTGCTTCTCACCTG
CCTCTTCATCACAGGCACCTCCGTGTCACCCGTGGCCCTAGATCCTTGTTCTGCTTACATCAGCCTGAATGAGC
CCTGGAGGAACACTGACCACCAGTTGGATGAGTCTCAAGGTCCTCCTCTATGTGACAACCATGTGAATGGGGAG
TGGTACCACTTCACGGGCATGGCGGGAGATGCCATGCCTACCTTCTGCATACCAGAAAACCACTGTGGAACCCA
CGCACCTGTCTGGCTCAATGGCAGCCACCCCTAGAAGGCGACGGCATTGTGCAACGCCAGGCTTGTGCCAGCT
TCAATGGGAACTGCTGTCTCTGGAACACCACGGTGGAAGTCAAGGCTTGCCCTGGAGGCTACTATGTGTATCGT
CTGACCAAGCCCAGCGTCTGCTTCCACGTCTACTGTGGTCATTTTTATGACATCTGCGACGAGGACTGCCATGG
CAGCTGCTCAGATACCAGCGAGTGCACATGCGCTCCAGGAACTGTGCTAGGCCCTGACAGGCAGACATGCTTTG
ATGAAAATGAATGTGAGCAAAACAACGGTGGCTGCAGTGAGATCTGTGTGAACCTCAAAAACTCCTACCGCTGT
GAGTGTGGGGTTGGCCGTGTGCTAAGAAGTGATGGCAAGACTTGTGAAGACGTTGAAGGATGCCACAATAACAA
TGGTGGCTGCAGCCACTCTTGCCTTGGATCTGAGAAAGGCTACCAGTGTGAATGTCCCCGGGGCCTGGTGCTGT
CTGAGGATAACCACACTTGCCAAGTCCCTGTGTTGTGCAAATCAAATGCCATTGAAGTGAACATCCCCAGGGAG
CTGGTTGGTGGCCTGGAGCTCTTCCTGACCAACACCTCCTGCCGAGGAGTGTCCAACGGCACCCATGTCAACAT
CCTCTTCTCTCAAGACATGTGGTACAGTGGTCGATGTGGTGAATGACAAGATTGTGGCCAGCAACCTCGTGA
CAGGTCTACCCAAGCAGACCCCGGGGAGCAGCGGGGACTTCATCATCCGAACCAGCAAGCTGCTGATCCCGGTG
ACCTGCGAGTTTCCACGCCTGTACACCATTTCTGAAGGATACGTTCCCAACCTTCGAAACTCCCCACTGGAAAT
CATGAGCCGAAATCATGGGATCTTCCCATTCACTCTGGAGATCTTCAAGGACAATGAGTTTGAAGAGCCTTACC
GGGAAGCTCTGCCCACCCTCAAGCTTCGTGACTCCCTCTACTTTGGCATTGAGCCCGTGGTGCACGTGAGCGGC
TTGGAAAGCTTGGTGGAGAGCTGCTTTGCCACCCCCACCTCCAAGATCGACGAGGTCCTGAAATACTACCTCAT
CCGGGATGGCTGTGTTTCAGATGACTCGGTAAAGCAGTACACATCCCGGGATCACCTAGCAAAGCACTTCCAGG
TCCCTGTCTTCAAGTTTGTGGGCAAAGACCACAAGGAAGTGTTTCTGCACTGCCGGGTTCTTGTCTGTGGAGTG
TTGGACGAGCGTTCCCGCTGTGCCCAGGGTTGCCACCGGCGAATGCGTCGTGGGGCAGGAGGAGAGGACTCAGC
CGGTCTACAGGGCCAGACGCTAACAGGCGGCCCGATCCGCATCGACTGGGAGGACTAGTTCGTAGCCATACCTC
GAGTCCCTGCATTGGACGGCTCTGCTCTTTGGAGCTTCTCCCCCCACCGCCCTCTAAGAACATCTGCCAACAGC
TGGGTTCAGACTTCACACTGTGAGTTCAGACTCCAGCACCAACTCACTCTGATTCTGGTCCATTCAGTGGGCA
CAGGTCACAGCACTGCTGAACAATGTGGCCTGGGTGGGGTTTCATCTTTCTAGGGTTGAAAACTAAACTGTCCA
CCCAGAAAGACACTCACCCCATTTCCCTCATTTCTTTCCTACACTTAAATACCTCGTGTATGGTGCAATCAGAC
CACAAAATCAGAAGCTGGGTATAATATTTCAAGTTACAAACCCTAGAAAAATTAAACAGTTACTGAAATTATGA
CTTAAATACCCAATGACTCCTTAAATATGTAAATTATAGTTATACCTTGAAATTTCAATTCAAATGCAGACTAA
TTATAGGGAATTTGGAAGTGTATCAATAAAACAGTATATAATTTT
```

FIGURE 110

MPPFLLLTCLFITGTSVSPVALDPCSAYISLNEPWRNTDHQLDESQGPPLCDNHVNGEWYHFTGMAGDAMP
TFCIPENHCGTHAPVWLNGSHPLEGDGIVQRQACASFNGNCCLWNTTVEVKACPGGYYVYRLTKPSVCFHV
YCGHFYDICDEDCHGSCSDTSECTCAPGTVLGPDRQTCFDENECEQNNGGCSEICVNLKNSYRCECGVGRV
LRSDGKTCEDVEGCHNNNGGCSHSCLGSEKGYQCECPRGLVLSEDNHTCQVPVLCKSNAIEVNIPRELVGG
LELFLTNTSCRGVSNGTHVNILFSLKTCGTVVDVVNDKIVASNLVTGLPKQTPGSSGDFIIRTSKLLIPVT
CEFPRLYTISEGYVPNLRNSPLEIMSRNHGIFPFTLEIFKDNEFEEPYREALPTLKLRDSLYFGIEPVVHV
SGLESLVESCFATPTSKIDEVLKYYLIRDGCVSDDSVKQYTSRDHLAKHFQVPVFKFVGKDHKEVFLHCRV
LVCGVLDERSRCAQGCHRRMRRGAGGEDSAGLQGQTLTGGPIRIDWED

Important features of the protein:

Signal peptide:

amino acids 1-16

N-glycosylation sites.

amino acids 89-93, 116-120, 259-263, 291-295, 299-303

Tyrosine kinase phosphorylation sites.

amino acids 411-418, 443-451

N-myristoylation sites.

amino acids 226-232, 233-239, 240-246, 252-258, 296-302, 300-306, 522-528, 531-537

Aspartic acid and asparagine hydroxylation site.

amino acids 197-209

ZP domain proteins.

amino acids 431-457

Calcium-binding EGF-like proteins.

amino acids 191-212, 232-253

FIGURE 111

```
GAGAGAGGCAGCAGCTTGCTCAGCGGACAAGGATGCTGGGCGTGAGGGACCAAGGCCTGCCCTGCACTCGG
GCCTCCTCCAGCCAGTGCTGACCAGGGACTTCTGACCTGCTGGCCAGCCAGGACCTGTGTGGGGAGGCCCT
CCTGCTGCCTTGGGGTGACAATCTCAGCTCCAGGCTACAGGGAGACCGGGAGGATCACAGAGCCAGATGT
TACAGGATCCTGACAGTGATCAACCTCTGAACAGCCTCGATGTCAAACCCCTGCGCAAACCCCGTATCCCC
ATGGAGACCTTCAGAAAGGTGGGGATCCCCATCATCATAGCACTACTGAGCCTGGCGAGTATCATCATTGT
GGTTGTCCTCATCAAGGTGATTCTGGATAAATACTACTTCCTCTGCGGGCAGCCTCTCCACTTCATCCCGA
GGAAGCAGCTGTGTGACGGAGAGCTGGACTGTCCCTTGGGGGAGGACGAGGAGCACTGTGTCAAGAGCTTC
CCCGAAGGGCCTGCAGTGGCAGTCCGCCTCTCCAAGGACCGATCCACACTGCAGGTGCTGGACTCGGCCAC
AGGGAACTGGTTCTCTGCCTGTTTCGACAACTTCACAGAAGCTCTCGCTGAGACAGCCTGTAGGCAGATGG
GCTACAGCAGAGCTGTGGAGATTGGCCCAGACCAGGATCTGGATGTTGTTGAAATCACAGAAAACAGCCAG
GAGCTTCGCATGCGGAACTCAAGTGGGCCCTGTCTCTCAGGCTCCCTGGTCTCCCTGCACTGTCTTGCCTG
TGGGAAGAGCCTGAAGACCCCCCGTGTGGTGGGTGGGGAGGAGGCCTCTGTGGATTCTTGGCCTTGGCAGG
TCAGCATCCAGTACGACAAACAGCACGTCTGTGGAGGGAGCATCCTGGACCCCCACTGGGTCCTCACGGCA
GCCCACTGCTTCAGGAAACATACCGATGTGTTCAACTGGAAGGTGCGGGCAGGCTCAGACAAACTGGGCAG
CTTCCCATCCCTGGCTGTGGCCAAGATCATCATCATTGAATTCAACCCCATGTACCCCAAAGACAATGACA
TCGCCCTCATGAAGCTGCAGTTCCCACTCACTTTCTCAGGCACAGTCAGGCCCATCTGTCTGCCCTTCTTT
GATGAGGAGCTCACTCCAGCCACCCCACTCTGGATCATTGGATGGGGCTTTACGAAGCAGAATGGAGGGAA
GATGTCTGACATACTGCTGCAGGCGTCAGTCCAGGTCATTGACAGCACACGGTGCAATGCAGACGATGCGT
ACCAGGGGGAAGTCACCGAGAAGATGATGTGTGCAGGCATCCCGGAAGGGGGTGTGGACACCTGCCAGGGT
GACAGTGGTGGGCCCCTGATGTACCAATCTGACCAGTGGCATGTGGTGGGCATCGTTAGCTGGGGCTATGG
CTGCGGGGGCCCGAGCACCCCAGGAGTATACACCAAGGTCTCAGCCTATCTCAACTGGATCTACAATGTCT
GGAAGGCTGAGCTGTAATGCTGCTGCCCCTTTGCAGTGCTGGGAGCCGCTTCCTTCCTGCCCTGCCCACCT
GGGGATCCCCCAAAGTCAGACACAGAGCAAGAGTCCCCTTGGGTACACCCCTCTGCCCACAGCCTCAGCAT
TTCTTGGAGCAGCAAAGGGCCTCAATTCCTGTAAGAGACCCTCGCAGCCCAGAGGCGCCCAGAGGAAGTCA
GCAGCCCTAGCTCGGCCACACTTGGTGCTCCCAGCATCCCAGGGAGAGACACAGCCCACTGAACAAGGTCT
CAGGGGTATTGCTAAGCCAAGAAGGAACTTTCCCACACTACTGAATGGAAGCAGGCTGTCTTGTAAAAGCC
CAGATCACTGTGGGCTGGAGAGGAGAAGGAAAGGGTCTGCGCCAGCCCTGTCCGTCTTCACCCATCCCCAA
GCCTACTAGAGCAAGAAACCAGTTGTAATATAAAATGCACTGCCCTACTGTTGGTATGACTACCGTTACCT
ACTGTTGTCATTGTTATTACAGCTATGGCCACTATTATTAAAGAGCTGTGTAACATCTCTGGCAAAAAAA
AAAA
```

FIGURE 112

MLQDPDSDQPLNSLDVKPLRKPRIPMETFRKVGIPIIIALLSLASIIIVVVLIKVILDKYYFLCG
QPLHFIPRKQLCDGELDCPLGEDEEHCVKSFPEGPAVAVRLSKDRSTLQVLDSATGNWFSACFDN
FTEALAETACRQMGYSRAVEIGPDQDLDVVEITENSQELRMRNSSGPCLSGSLVSLHCLACGKSL
KTPRVVGGEEASVDSWPWQVSIQYDKQHVCGGSILDPHWVLTAAHCFRKHTDVFNWKVRAGSDKL
GSFPSLAVAKIIIIEFNPMYPKDNDIALMKLQFPLTFSGTVRPICLPFFDEELTPATPLWIIGWG
FTKQNGGKMSDILLQASVQVIDSTRCNADDAYQGEVTEKMMCAGIPEGGVDTCQGDSGGPLMYQS
DQWHVVGIVSWGYGCGGPSTPGVYTKVSAYLNWIYNVWKAEL

Transmembrane domain:
amino acids 32-53 (typeII)

FIGURE 113

GGCTGGACTGGAACTCCTGGTCCCAAGTGATCCACCCGCCTCAGCCTCCCAAGGTGCTGTGATTA
TAGGTGTAAGCCACCGTGTCTGGCCTCTGAACAACTTTTTCAGCAACTAAAAAAGCCACAGGAGT
TGAACTGCTAGGATTCTGACT<u>ATG</u>CTGTGGTGGCTAGTGCTCCTACTCCTACCTACATTAAAATC
TGTTTTTTGTTCTCTTGTAACTAGCCTTTACCTTCCTAACACAGAGGATCTGTCACTGTGGCTCT
GGCCCAAACCTGACCTTCACTCTGGAACGAGAACAGAGGTTTCTACCCACACCGTCCCCTCGAAG
CCGGGGACAGCCTCACCTTGCTGGCCTCTCGCTGGAGCAGTGCCCTCACCAACTGTCTCACGTCT
GGAGGCACTGACTCGGGCAGTGCAGGTAGCTGAGCCTCTTGGTAGCTGCGGCTTTCAAGGTGGGC
CTTGCCCTGGCCGTAGAAGGGAT<u>TGA</u>CAAGCCCGAAGATTTCATAGGCGATGGCTCCCACTGCCC
AGGCATCAGCCTTGCTGTAGTCAATCACTGCCCTGGGGCCAGGACGGGCCGTGGACACCTGCTCA
GAAGCAGTGGGTGAGACATCACGCTGCCCGCCCATCTAACCTTTTCATGTCCTGCACATCACCTG
ATCCATGGCTAATCTGAACTCTGTCCCAAGGAACCCAGAGCTTGAGTGAGCTGTGGCTCAGACC
CAGAAGGGGTCTGCTTAGACCACCTGGTTTATGTGACAGGACTTGCATTCTCCTGGAACATGAGG
GAACGCCGGAGGAAAGCAAAGTGGCAGGGAAGGAACTTGTGCCAAATTATGGGTCAGAAAAGATG
GAGGTGTTGGGTTATCACAAGGCATCGAGTCTCCTGCATTCAGTGGACATGTGGGGAAGGGCTG
CCGATGGCGCATGACACACTCGGGACTCACCTCTGGGGCCATCAGACAGCCGTTTCCGCCCCGAT
CCACGTACCAGCTGCTGAAGGGCAACTGCAGGCCGATGCTCTCATCAGCCAGGCAGCAGCCAAAA
TCTGCGATCACCAGCCAGGGGCAGCCGTCTGGGAAGGAGCAAGCAAAGTGACCATTTCTCCTCCC
CTCCTTCCCTCTGAGAGGCCCTCCTATGTCCCTACTAAAGCCACCAGCAAGACATAGCTGACAGG
GGCTAATGGCTCAGTGTTGGCCCAGGAGGTCAGCAAGGCCTGAGAGCTGATCAGAAGGGCCTGCT
GTGCGAACACGGAAATGCCTCCAGTAAGCACAGGCTGCAAAATCCCCAGGCAAAGGACTGTGTGG
CTCAATTTAAATCATGTTCTAGTAATTGGAGCTGTCCCCAAGACCAAAGGAGCTAGAGCTTGGTT
CAAATGATCTCCAAGGGCCCTTATACCCCAGGAGACTTTGATTTGAATTTGAAACCCCAAATCCA
AACCTAAGAACCAGGTGCATTAAGAATCAGTTATTGCCGGGTGTGGTGGCCTGTAATGCCAACAT
TTTGGGAGGCCGAGGCGGGTAGATCACCTGAGGTCAGGAGTTCAAGACCAGCCTGGCCAACATGG
TGAAACCCCTGTCTCTACTAAAAATACAAAAAAACTAGCCAGGCATGGTGGTGTGTGCCTGTATC
CCAGCTACTCGGGAGGCTGAGACAGGAGAATTACTTGAACCTGGGAGGTGAAGGAGGCTGAGACA
GGAGAATCACTTCAGCCTGAGCAACACAGCGAGACTCTGTCTCAGAAAAAATAAAAAAGAATTA
TGGTTATTTGTAA

FIGURE 114

MLWWLVLLLLPTLKSVFCSLVTSLYLPNTEDLSLWLWPKPDLHSGTRTEVSTHTVPSKPGTASPC
WPLAGAVPSPTVSRLEALTRAVQVAEPLGSCGFQGGPCPGRRRD

Signal peptide:

amino acids 1-15

FIGURE 115

CAGCAGTGGTCTCTCAGTCCTCTCAAAGCAAGGAAAGAGTACTGTGTGCTGAGAGACCATGGCAA

AGAATCCTCCAGAGAATTGTGAAGACTGTCACATTCTAAATGCAGAAGCTTTTAAATCCAAGAAA

ATATGTAAATCACTTAAGATTTGTGGACTGGTGTTTGGTATCCTGGCCCTAACTCTAATTGTCCT

GTTTTGGGGGAGCAAGCACTTCTGGCCGGAGGTACCCAAAAAAGCCTATGACATGGAGCACACTT

TCTACAGCAATGGAGAGAAGAAGAAGATTTACATGGAATTGATCCTGTGACCAGAACTGAAATA

TTCAGAAGCGGAAATGGCACTGATGAAACATTGGAAGTGCACGACTTTAAAAACGGATACACTGG

CATCTACTTCGTGGGTCTTCAAAAATGTTTTATCAAAACTCAGATTAAAGTGATTCCTGAATTTT

CTGAACCAGAAGAGGAAATAGATGAGAATGAAGAAATTACCACAACTTTCTTTGAACAGTCAGTG

ATTTGGGTCCCAGCAGAAAAGCCTATTGAAAACCGAGATTTTCTTAAAAATTCCAAAATTCTGGA

GATTTGTGATAACGTGACCATGTATTGGATCAATCCCACTCTAATATCAGTTTCTGAGTTACAAG

ACTTTGAGGAGGAGGGAGAAGATCTTCACTTTCCTGCCAACGAAAAAAAGGGATTGAACAAAAT

GAACAGTGGGTGGTCCCTCAAGTGAAAGTAGAGAAGACCCGTCACGCCAGACAAGCAAGTGAGGA

AGAACTTCCAATAAATGACTATACTGAAAATGGAATAGAATTTGATCCATGCTGGATGAGAGAG

GTTATTGTTGTATTTACTGCCGTCGAGGCAACCGCTATTGCCGCCGCGTCTGTGAACCTTTACTA

GGCTACTACCCATATCCATACTGCTACCAAGGAGGACGAGTCATCTGTCGTGTCATCATGCCTTG

TAACTGGTGGGTGGCCCGCATGCTGGGGAGGGTCTAATAGGAGGTTTGAGCTCAAATGCTTAAAC

TGCTGGCAACATATAATAAATGCATGCTATTCAATGAATTTCTGCCTATGAGGCATCTGGCCCCT

GGTAGCCAGCTCTCCAGAATTACTTGTAGGTAATTCCTCTCTTCATGTTCTAATAAACTTCTACA

TTATCACCAAAAAAAAAAAAAAAAAAA

FIGURE 116

MAKNPPENCEDCHILNAEAFKSKKICKSLKICGLVFGILALTLIVLFWGSKHFWPEVPKKAYDME
HTFYSNGEKKKIYMEIDPVTRTEIFRSGNGTDETLEVHDFKNGYTGIYFVGLQKCFIKTQIKVIP
EFSEPEEEIDENEEITTTFFFEQSVIWVPAEKPIENRDFLKNSKILEICDNVTMYWINPTLISVSE
LQDFEEEGEDLHFPANEKKGIEQNEQWVVPQVKVEKTRHARQASEEELPINDYTENGIEFDPMLD
ERGYCCIYCRRGNRYCRRVCEPLLGYYPYPYCYQGGRVICRVIMPCNWWVARMLGRV

Important features of the protein:

Signal peptide:

amino acids 1-40

Transmembrane domain:

amino acids 25-47 (type II)

N-glycosylation sites.

amino acids 94-97, 180-183

Glycosaminoglycan attachment sites.

amino acids 92-95, 70-73, 85-88, 133-136, 148-151, 192-195, 239-242

N-myristoylation sites.

amino acids 33-38, 95-100, 116-121, 215-220, 272-277

Microbodies C-terminal targeting signal.

amino acids 315-317

Cytochrome c family heme-binding site signature.

amino acids 9-14

FIGURE 117

GAGCTCCCCTCAGGAGCGCGTTAGCTTCACACCTTCGGCAGCAGGAGGGCGGCAGCTTCTCGCAGGCGGCA
GGGCGGGCGGCCAGGATCATGTCCACCACCACATGCCAAGTGGTGGCGTTCCTCCTGTCCATCCTGGGGCT
GGCCGGCTGCATCGCGGCCACCGGGATGGACATGTGGAGCACCCAGGACCTGTACGACAACCCCGTCACCT
CCGTGTTCCAGTACGAAGGGCTCTGGAGGAGCTGCGTGAGGCAGAGTTCAGGCTTCACCGAATGCAGGCCC
TATTTCACCATCCTGGGACTTCCAGCCATGCTGCAGGCAGTGCGAGCCCTGATGATCGTAGGCATCGTCCT
GGGTGCCATTGGCCTCCTGGTATCCATCTTTGCCCTGAAATGCATCCGCATTGGCAGCATGGAGGACTCTG
CCAAAGCCAACATGACACTGACCTCCGGGATCATGTTCATTGTCTCAGGTCTTTGTGCAATTGCTGGAGTG
TCTGTGTTTGCCAACATGCTGGTGACTAACTTCTGGATGTCCACAGCTAACATGTACACCGGCATGGGTGG
GATGGTGCAGACTGTTCAGACCAGGTACACATTTGGTGCGGCTCTGTTCGTGGGCTGGGTCGCTGGAGGCC
TCACACTAATTGGGGGTGTGATGATGTGCATCGCCTGCCGGGGCCTGGCACCAGAAGAAACCAACTACAAA
GCCGTTTCTTATCATGCCTCAGGCCACAGTGTTGCCTACAAGCCTGGAGGCTTCAAGGCCAGCACTGGCTT
TGGGTCCAACACCAAAAACAAGAAGATATACGATGGAGGTGCCCGCACAGAGGACGAGGTACAATCTTATC
CTTCCAAGCACGACTATGTGTAATGCTCTAAGACCTCTCAGCACGGGCGGAAGAAACTCCCGGAGAGCTCA
CCCAAAAAACAAGGAGATCCCATCTAGATTTCTTCTTGCTTTTGACTCACAGCTGGAAGTTAGAAAAGCCT
CGATTTCATCTTTGGAGAGGCCAAATGGTCTTAGCCTCAGTCTCTGTCTCTAAATATTCCACCATAAAACA
GCTGAGTTATTTATGAATTAGAGGCTATAGCTCACATTTTCAATCCTCTATTTCTTTTTTAAATATAACT
TTCTACTCTGATGAGAGAATGTGGTTTTAATCTCTCTCTCACATTTTGATGATTTAGACAGACTCCCCCTC
TTCCTCCTAGTCAATAAACCCATTGATGATCTATTTCCCAGCTTATCCCCAAGAAAACTTTTGAAAGGAAA
GAGTAGACCCAAAGATGTTATTTTCTGCTGTTTGAATTTTGTCTCCCCACCCCCAACTTGGCTAGTAATAA
ACACTTACTGAAGAAGAAGCAATAAGAGAAAGATATTTGTAATCTCTCCAGCCCATGATCTCGGTTTTCTT
ACACTGTGATCTTAAAAGTTACCAAACCAAAGTCATTTTCAGTTTGAGGCAACCAAACCTTTCTACTGCTG
TTGACATCTTCTTATTACAGCAACACCATTCTAGGAGTTTCCTGAGCTCTCCACTGGAGTCCTCTTTCTGT
CGCGGGTCAGAAATTGTCCCTAGATGAATGAGAAAATTATTTTTTTTAATTTAAGTCCTAAATATAGTTAA
AATAAATAATGTTTTAGTAAAATGATACACTATCTCTGTGAAATAGCCTCACCCCTACATGTGGATAGAAG
GAAATGAAAAAATAATTGCTTTGACATTGTCTATATGGTACTTTGTAAAGTCATGCTTAAGTACAAATTCC
ATGAAAAGCTCACACCTGTAATCCTAGCACTTTGGGAGGCTGAGGAGGAAGGATCACTTGAGCCCAGAAGT
TCGAGACTAGCCTGGGCAACATGGAGAAGCCCTGTCTCTACAAAATACAGAGAGAAAAAATCAGCCAGTCA
TGGTGGCATACACCTGTAGTCCCAGCATTCCGGGAGGCTGAGGTGGGAGGATCACTTGAGCCCAGGGAGGT
TGGGGCTGCAGTGAGCCATGATCACACCACTGCACTCCAGCCAGGTGACATAGCGAGATCCTGTCTAAAAA
AATAAAAAATAAATAATGGAACACAGCAAGTCCTAGGAAGTAGGTTAAAACTAATTCTTTAA

FIGURE 118

MSTTTCQVVAFLLSILGLAGCIAATGMDMWSTQDLYDNPVTSVFQYEGLWRSCVRQSSGFTECRP
YFTILGLPAMLQAVRALMIVGIVLGAIGLLVSIFALKCIRIGSMEDSAKANMTLTSGIMFIVSGL
CAIAGVSVFANMLVTNFWMSTANMYTGMGGMVQTVQTRYTFGAALFVGWVAGGLTLIGGVMMCIA
CRGLAPEETNYKAVSYHASGHSVAYKPGGFKASTGFGSNTKNKKIYDGGARTEDEVQSYPSKHDY
V

Signal peptide:
amino acids 1-23

Transmembrane domains:
amino acids 81-100, 121-141, 173-194

FIGURE 119

```
GGAAAAACTGTTCTCTTCTGTGGCACAGAGAACCCTGCTTCAAAGCAGAAGTAGCAGTTCCGGAGTCC
AGCTGGCTAAAACTCATCCCAGAGGATAATGGCAACCCATGCCTTAGAAATCGCTGGGCTGTTTCTTG
GTGGTGTTGGAATGGTGGGCACAGTGGCTGTCACTGTCATGCCTCAGTGGAGAGTGTCGGCCTTCATT
GAAAACAACATCGTGGTTTTTGAAAACTTCTGGGAAGGACTGTGGATGAATTGCGTGAGGCAGGCTAA
CATCAGGATGCAGTGCAAATCTATGATTCCCTGCTGGCTCTTTCTCCGGACCTACAGGCAGCCAGAG
GACTGATGTGTGCTGCTTCCGTGATGTCCTTCTTGGCTTTCATGATGGCCATCCTTGGCATGAAATGC
ACCAGGTGCACGGGGACAATGAGAAGGTGAAGGCTCACATTCTGCTGACGGCTGGAATCATCTTCAT
CATCACGGGCATGGTGGTGCTCATCCCTGTGAGCTGGGTTGCCAATGCCATCATCAGAGATTTCTATA
ACTCAATAGTGAATGTTGCCCAAAAACGTGAGCTTGGAGAAGCTCTCTACTTAGGATGGACCACGGCA
CTGGTGCTGATTGTTGGAGGAGCTCTGTTCTGCTGCGTTTTTTGTTGCAACGAAAAGAGCAGTAGCTA
CAGATACTCGATACCTTCCCATCGCACAACCCAAAAAAGTTATCACACCGGAAAGAAGTCACCGAGCG
TCTACTCCAGAAGTCAGTATGTGTAGTTGTGTATGTTTTTTAACTTTACTATAAAGCCATGCAAATG
ACAAAAATCTATATTACTTTCTCAAAATGGACCCCAAAGAAACTTTGATTTACTGTTCTTAACTGCCT
AATCTTAATTACAGGAACTGTGCATCAGCTATTTATGATTCTATAAGCTATTTCAGCAGAATGAGATA
TTAAACCCAATGCTTTGATTGTTCTAGAAAGTATAGTAATTTGTTTTCTAAGGTGGTTCAAGCATCTA
CTCTTTTTATCATTTACTTCAAAATGACATTGCTAAAGACTGCATTATTTTACTACTGTAATTTCTCC
ACGACATAGCATTATGTACATAGATGAGTGTAACATTTATATCTCACATAGAGACATGCTTATATGGT
TTTATTTAAAATGAAATGCCAGTCCATTACACTGAATAAATAGAACTCAACTATTGCTTTTCAGGGAA
ATCATGGATAGGGTTGAAGAAGGTTACTATTAATTGTTTAAAAACAGCTTAGGGATTAATGTCCTCCA
TTTATAATGAAGATTAAAATGAAGGCTTTAATCAGCATTGTAAAGGAAATTGAATGGCTTTCTGATAT
GCTGTTTTTAGCCTAGGAGTTAGAAATCCTAACTTCTTTATCCTCTTCTCCCAGAGGCTTTTTTTTT
CTTGTGTATTAAATTAACATTTTTAAAACGCAGATATTTTGTCAAGGGGCTTTGCATTCAAACTGCTT
TTCCAGGGCTATACTCAGAAGAAAGATAAAAGTGTGATCTAAGAAAAAGTGATGGTTTTAGGAAAGTG
AAAATATTTTTGTTTTTGTATTTGAAGAAGAATGATGCATTTTGACAAGAAATCATATATGTATGGAT
ATATTTTAATAAGTATTTGAGTACAGACTTTGAGGTTTCATCAATATAAATAAAAGAGCAGAAAAATA
TGTCTTGGTTTTCATTTGCTTACCAAAAAAACAACAACAAAAAAAGTTGTCCTTTGAGAACTTCACCT
GCTCCTATGTGGGTACCTGAGTCAAAATTGTCATTTTGTTCTGTGAAAAATAAATTTCCTTCTTGTA
CCATTTCTGTTTAGTTTTACTAAAATCTGTAAATACTGTATTTTCTGTTTATTCCAAATTTGATGAA
ACTGACAATCCAATTTGAAAGTTTGTGTCGACGTCTGTCTAGCTTAAATGAATGTGTTCTATTTGCTT
TATACATTTATATTAATAAATTGTACATTTTTCTAATT
```

FIGURE 120

MATHALEIAGLFLGGVGMVGTVAVTVMPQWRVSAFIENNIVVFENFWEGLWMNCVRQANIRMQCK
IYDSLLALSPDLQAARGLMCAASVMSFLAFMMAILGMKCTRCTGDNEKVKAHILLTAGIIFIITG
MVVLIPVSWVANAIIRDFYNSIVNVAQKRELGEALYLGWTTALVLIVGGALFCCVFCCNEKSSSY
RYSIPSHRTTQKSYHTGKKSPSVYSRSQYV

Signal peptide:

amino acids 1-17

Transmembrane domains:

amino acids 82-101, 118-145, 164-188

FIGURE 121

GGAGAGAGGCGCGCGGGTGAAAGGCGCATTGATGCAGCCTGCGGCGGCCTCGGAGCGCGGCGGAG
CCAGACGCTGACCACGTTCCTCTCCTCGGTCTCCTCCGCCTCCAGCTCCGCGCTGCCCGGCAGCC
GGGAGCCATGCGACCCCAGGGCCCCGCCGCCTCCCCGCAGCGGCTCCGCGGCCTCCTGCTGCTCC
TGCTGCTGCAGCTGCCCGCGCCGTCGAGCGCCTCTGAGATCCCCAAGGGGAAGCAAAAGGCGCAG
CTCCGGCAGAGGGAGGTGGTGGACCTGTATAATGGAATGTGCTTACAAGGGCCAGCAGGAGTGCC
TGGTCGAGACGGGAGCCCTGGGGCCAATGTTATTCCGGGTACACCTGGGATCCCAGGTCGGGATG
GATTCAAAGGAGAAAAGGGGGAATGTCTGAGGGAAAGCTTTGAGGAGTCCTGGACACCCAACTAC
AAGCAGTGTTCATGGAGTTCATTGAATTATGGCATAGATCTTGGGAAAATTGCGGAGTGTACATT
TACAAAGATGCGTTCAAATAGTGCTCTAAGAGTTTTGTTCAGTGGCTCACTTCGGCTAAAATGCA
GAAATGCATGCTGTCAGCGTTGGTATTTCACATTCAATGGAGCTGAATGTTCAGGACCTCTTCCC
ATTGAAGCTATAATTTATTTGGACCAAGGAAGCCCTGAAATGAATTCAACAATTAATATTCATCG
CACTTCTTCTGTGGAAGGACTTTGTGAAGGAATTGGTGCTGGATTAGTGGATGTTGCTATCTGGG
TTGGCACTTGTTCAGATTACCCAAAAGGAGATGCTTCTACTGGATGGAATTCAGTTTCTCGCATC
ATTATTGAAGAACTACCAAAATAAATGCTTTAATTTTCATTTGCTACCTCTTTTTTTATTATGCC
TTGGAATGGTTCACTTAAATGACATTTTAAATAAGTTTATGTATACATCTGAATGAAAAGCAAAG
CTAAATATGTTTACAGACCAAAGTGTGATTTCACACTGTTTTTAAATCTAGCATTATTCATTTTG
CTTCAATCAAAAGTGGTTTCAATATTTTTTTTAGTTGGTTAGAATACTTTCTTCATAGTCACATT
CTCTCAACCTATAATTTGGAATATTGTTGTGGTCTTTTGTTTTTTCTCTTAGTATAGCATTTTTA
AAAAAATATAAAAGCTACCAATCTTTGTACAATTTGTAAATGTTAAGAATTTTTTTATATCTGT
TAAATAAAAATTATTTCCAACA

FIGURE 122

MRPQGPAASPQRLRGLLLLLLLQLPAPSSASEIPKGKQKAQLRQREVVDLYNGMCLQGPAGVPGR
DGSPGANVIPGTPGIPGRDGFKGEKGECLRESFEESWTPNYKQCSWSSLNYGIDLGKIAECTFTK
MRSNSALRVLFSGSLRLKCRNACCQRWYFTFNGAECSGPLPIEAIIYLDQGSPEMNSTINIHRTS
SVEGLCEGIGAGLVDVAIWVGTCSDYPKGDASTGWNSVSRIIIEELPK

Signal peptide:
amino acids 1-30

Transmembrane domain:
amino acids 195-217

FIGURE 123

```
GCTGAGCGTGTGCGCGGTACGGGGCTCTCCTGCCTTCTGGGCTCCAACGCAGCTCTGTGGCTGAA
CTGGGTGCTCATCACGGGAACTGCTGGGCTATGGAATACAGATGTGGCAGCTCAGGTAGCCCCAA
ATTGCCTGGAAGAATACATCATGTTTTCGATAAGAAGAAATTGTAGGATCCAGTTTTTTTTTA
ACCGCCCCCTCCCCACCCCCAAAAAAACTGTAAAGATGCAAAAACGTAATATCCATGAAGATCC
TATTACCTAGGAAGATTTTGATGTTTTGCTGCGAATGCGGTGTTGGGATTTATTTGTTCTTGGAG
TGTTCTGCGTGGCTGGCAAAGAATAATGTTCCAAAATCGGTCCATCTCCCAAGGGGTCCAATTTT
TCTTCCTGGGTGTCAGCGAGCCCTGACTCACTACAGTGCAGCTGACAGGGGCTGTCATGCAACTG
GCCCCTAAGCCAAAGCAAAAGACCTAAGGACGACCTTTGAACAATACAAAGATGGGTTTCAATG
TAATTAGGCTACTGAGCGGATCAGCTGTAGCACTGGTTATAGCCCCACTGTCTTACTGACAATG
CTTTCTTCTGCCGAACGAGGATGCCCTAAGGGCTGTAGGTGTGAAGGCAAAATGGTATATTGTGA
ATCTCAGAAATTACAGGAGATACCCTCAAGTATATCTGCTGGTTGCTTAGGTTTGTCCCTTCGCT
ATAACAGCCTTCAAAAACTTAAGTATAATCAATTTAAAGGGCTCAACCAGCTCACCTGGCTATAC
CTTGACCATAACCATATCAGCAATATTGACGAAAATGCTTTTAATGGAATACGCAGACTCAAAGA
GCTGATTCTTAGTTCCAATAGAATCTCCTATTTTCTTAACAATACCTTCAGACCTGTGACAAATT
TACGGAACTTGGATCTGTCCTATAATCAGCTGCATTCTCTGGGATCTGAACAGTTTCGGGGCTTG
CGGAAGCTGCTGAGTTTACATTTACGGTCTAACTCCCTGAGAACCATCCCTGTGCAATATTCCA
AGACTGCCGCAACCTGGAACTTTTGGACCTGGGATATAACCGGATCCGAAGTTTAGCCAGGAATG
TCTTTGCTGGCATGATCAGACTCAAAGAACTTCACCTGGAGCACAATCAATTTTCCAAGCTCAAC
CTGGCCCTTTTTCCAAGGTTGGTCAGCCTTCAGAACCTTTACTTGCAGTGGAATAAAATCAGTGT
CATAGGACAGACCATGTCCTGGACCTGGAGCTCCTTACAAAGGCTTGATTTATCAGGCAATGAGA
TCGAAGCTTTCAGTGGACCCAGTGTTTTCCAGTGTGTCCCGAATCTGCAGCGCCTCAACCTGGAT
TCCAACAAGCTCACATTTATTGGTCAAGAGATTTGGATTCTTGGATATCCCTCAATGACATCAG
TCTTGCTGGGAATATATGGGAATGCAGCAGAAATATTTGCTCCCTTGTAAACTGGCTGAAAAGTT
TTAAAGGTCTAAGGGAGAATACAATTATCTGTGCCAGTCCCAAAGAGCTGCAAGGAGTAAATGTG
ATCGATGCAGTGAAGAACTACAGCATCTGTGGCAAAAGTACTACAGAGAGGTTTGATCTGGCCAG
GGCTCTCCCAAAGCCGACGTTTAAGCCCAAGCTCCCCAGGCCGAAGCATGAGAGCAAACCCCCTT
TGCCCCCGACGGTGGGAGCCACAGAGCCCGGCCCAGAGACCGATGCTGACGCCGAGCACATCTCT
TTCCATAAAATCATCGCGGGCAGCGTGGCGCTTTTCCTGTCCGTGCTCGTCATCCTGCTGGTTAT
CTACGTGTCATGGAAGCGGTACCCTGCGAGCATGAAGCAGCTGCAGCAGCGCTCCCTCATGCGAA
GGCACAGGAAAAGAAAGACAGTCCCTAAAGCAAATGACTCCCAGCACCCAGGAATTTTATGTA
GATTATAAACCCACCAACACGGAGACCAGCGAGATGCTGCTGAATGGGACGGGACCCTGCACCTA
TAACAAATCGGGCTCCAGGGAGTGTGAGGTATGAACCATTGTGATAAAAAGAGCTCTTAAAAGCT
GGGAAATAAGTGGTGCTTTATTGAACTCTGGTGACTATCAAGGGAACGCGATGCCCCCCTCCCC
TTCCCTCTCCCTCTCACTTTGGTGGCAAGATCCTTCCTTGTCCGTTTTAGTGCATTCATAATACT
GGTCATTTTCCTCTCATACATAATCAACCCATTGAAATTTAAATACCACAATCAATGTGAAGCTT
GAACTCCGGTTTAATATAATACCTATTGTATAAGACCCTTTACTGATTCCATTAATGTCGCATTT
GTTTTAAGATAAAACTTCTTTCATAGGTAAAAAAAAAA
```

FIGURE 124

```
MGFNVIRLLSGSAVALVIAPTVLLTMLSSAERGCPKGCRCEGKMVYCESQKLQEIPSSISAGCLG
LSLRYNSLQKLKYNQFKGLNQLTWLYLDHNHISNIDENAFNGIRRLKELILSSNRISYFLNNTFR
PVTNLRNLDLSYNQLHSLGSEQFRGLRKLLSLHLRSNSLRTIPVRIFQDCRNLELLDLGYNRIRS
LARNVFAGMIRLKELHLEHNQFSKLNLALFPRLVSLQNLYLQWNKISVIGQTMSWTWSSLQRLDL
SGNEIEAFSGPSVFQCVPNLQRLNLDSNKLTFIGQEILDSWISLNDISLAGNIWECSRNICSLVN
WLKSFKGLRENTIICASPKELQGVNVIDAVKNYSICGKSTTERFDLARALPKPTFKPKLPRPKHE
SKPPLPPTVGATEPGPETDADAEHISFHKIIAGSVALFLSVLVILLVIYVSWKRYPASMKQLQQR
SLMRRHRKKKRQSLKQMTPSTQEFYVDYKPTNTETSEMLLNGTGPCTYNKSGSRECEV
```

Important features of the protein:

Signal peptide:

amino acids 1-33

Transmembrane domain:

amino acids 420-442

N-glycosylation sites.

amino acids 126-129, 357-360, 496-499, 504-507 cAMP- and cGMP-dependent protein kinase phosphorylation site.

amino acids 465-468

Tyrosine kinase phosphorylation site.

amino acids 136-142

N-myristoylation sites.

amino acids 11-16, 33-38, 245-250, 332-337, 497-502, 507-512

FIGURE 125

CCGTTATCGTCTTGCGCTACTGCTGAATGTCCGTCCCGGAGGAGGAGGAGAGGCTTTTGCCGCTG
ACCCAGAGATGGCCCCGAGCGAGCAAATTCCTACTGTCCGGCTGCGCGGCTACCGTGGCCGAGCT
AGCAACCTTTCCCCTGGATCTCACAAAAACTCGACTCCAAATGCAAGGAGAAGCAGCTCTTGCTC
GGTTGGGAGACGGTGCAAGAGAATCTGCCCCCTATAGGGGAATGGTGCGCACAGCCCTAGGGATC
ATTGAAGAGGAAGGCTTTCTAAAGCTTTGGCAAGGAGTGACACCCGCCATTTACAGACACGTAGT
GTATTCTGGAGGTCGAATGGTCACATATGAACATCTCCGAGAGGTTGTGTTTGGCAAAAGTGAAG
ATGAGCATTATCCCCTTTGGAAATCAGTCATTGGAGGGATGATGGCTGGTGTTATTGGCCAGTTT
TTAGCCAATCCAACTGACCTAGTGAAGGTTCAGATGCAAATGGAAGGAAAAGGAAACTGGAAGG
AAAACCATTGCGATTTCGTGGTGTACATCATGCATTTGCAAAAATCTTAGCTGAAGGAGGAATAC
GAGGGCTTTGGGCAGGCTGGGTACCCAATATACAAAGAGCAGCACTGGTGAATATGGGAGATTTA
ACCACTTATGATACAGTGAAACACTACTTGGTATTGAATACACCACTTGAGGACAATATCATGAC
TCACGGTTTATCAAGTTTATGTTCTGGACTGGTAGCTTCTATTCTGGGAACACCAGCCGATGTCA
TCAAAAGCAGAATAATGAATCAACCACGAGATAAACAAGGAAGGGGACTTTTGTATAAATCATCG
ACTGACTGCTTGATTCAGGCTGTTCAAGGTGAAGGATTCATGAGTCTATATAAAGGCTTTTTACC
ATCTTGGCTGAGAATGACCCCTTGGTCAATGGTGTTCTGGCTTACTTATGAAAAAATCAGAGAGA
TGAGTGGAGTCAGTCCATTTTAA

FIGURE 126

MSVPEEEERLLPLTQRWPRASKFLLSGCAATVAELATFPLDLTKTRLQMQGEAALARLGDGARES
APYRGMVRTALGIIEEEGFLKLWQGVTPAIYRHVVYSGGRMVTYEHLREVVFGKSEDEHYPLWKS
VIGGMMAGVIGQFLANPTDLVKVQMQMEGKRKLEGKPLRFRGVHHAFAKILAEGGIRGLWAGWVP
NIQRAALVNMGDLTTYDTVKHYLVLNTPLEDNIMTHGLSSLCSGLVASILGTPADVIKSRIMNQP
RDKQGRGLLYKSSTDCLIQAVQGEGFMSLYKGFLPSWLRMTPWSMVFWLTYEKIREMSGVSPF

Transmembrane domains:

amino acids 25-38, 130-147, 233-248

FIGURE 127

CGCGGATCGGACCCAAGCAGGTCGGCGGCGGCGGCAGGAGAGCGGCCGGGCGTCAGCTCCTCGAC
CCCCGTGTCGGGCTAGTCCAGCGAGGCGGACGGGCGGCGTGGGCCCATGGCCAGGCCCGGCATGG
AGCGGTGGCGCGACCGGCTGGCGCTGGTGACGGGGGCCTCGGGGGGCATCGGCGCGGCCGTGGCC
CGGGCCCTGGTCCAGCAGGGACTGAAGGTGGTGGGCTGCGCCCGCACTGTGGGCAACATCGAGGA
GCTGGCTGCTGAATGTAAGAGTGCAGGCTACCCCGGGACTTTGATCCCCTACAGATGTGACCTAT
CAAATGAAGAGGACATCCTCTCCATGTTCTCAGCTATCCGTTCTCAGCACAGCGGTGTAGACATC
TGCATCAACAATGCTGGCTTGGCCCGGCCTGACACCCTGCTCTCAGGCAGCACCAGTGGTTGGAA
GGACATGTTCAATGTGAACGTGCTGGCCCTCAGCATCTGCACACGGGAAGCCTACCAGTCCATGA
AGGAGCGGAATGTGGACGATGGGCACATCATTAACATCAATAGCATGTCTGGCCACCGAGTGTTA
CCCCTGTCTGTGACCCACTTCTATAGTGCCACCAAGTATGCCGTCACTGCGCTGACAGAGGGACT
GAGGCAAGAGCTTCGGGAGGCCCAGACCCACATCCGAGCCACGTGCATCTCTCCAGGTGTGGTGG
AGACACAATTCGCCTTCAAACTCCACGACAAGGACCCTGAGAAGGCAGCTGCCACCTATGAGCAA
ATGAAGTGTCTCAAACCCGAGGATGTGGCCGAGGCTGTTATCTACGTCCTCAGCACCCCGCACA
CATCCAGATTGGAGACATCCAGATGAGGCCCACGGAGCAGGTGACCTAGTGACTGTGGGAGCTCC
TCCTTCCCTCCCCACCCTTCATGGCTTGCCTCCTGCCTCTGGATTTTAGGTGTTGATTTCTGGAT
CACGGGATACCACTTCCTGTCCACACCCCGACCAGGGGCTAGAAAATTTGTTTGAGATTTTTATA
TCATCTTGTCAAATTGCTTCAGTTGTAAATGTGAAAAATGGGCTGGGGAAAGGAGGTGGTGTCCC
TAATTGTTTTACTTGTTAACTTGTTCTTGTGCCCTGGGCACTTGGCCTTTGTCTGCTCTCAGTG
TCTTCCCTTTGACATGGGAAGGAGTTGTGGCCAAAATCCCCATCTTCTTGCACCTCAACGTCTG
TGGCTCAGGGCTGGGGTGGCAGAGGGAGGCCTTCACCTTATATCTGTGTTGTTATCCAGGGCTCC
AGACTTCCTCCTCTGCCTGCCCACTGCACCCTCTCCCCTTATCTATCTCCTTCTCGGCTCCCC
AGCCCAGTCTTGGCTTCTTGTCCCCTCCTGGGGTCATCCCTCCACTCTGACTCTGACTATGGCAG
CAGAACACCAGGGCCTGGCCCAGTGGATTTCATGGTGATCATTAAAAAAGAAAAATCGCAACCAA
AAAAAAAAA

FIGURE 128

MARPGMERWRDRLALVTGASGGIGAAVARALVQQGLKVVGCARTVGNIEELAAECKSAGYPGTLI
PYRCDLSNEEDILSMFSAIRSQHSGVDICINNAGLARPDTLLSGSTSGWKDMFNVNVLALSICTR
EAYQSMKERNVDDGHIININSMSGHRVLPLSVTHFYSATKYAVTALTEGLRQELREAQTHIRATC
ISPGVVETQFAFKLHDKDPEKAAATYEQMKCLKPEDVAEAVIYVLSTPAHIQIGDIQMRPTEQVT

Important features of the protein:

Signal peptide:

amino acids 1-17

N-myristoylation sites.

amino acids 18-24, 21-27, 22-28, 24-30, 40-46, 90-96, 109-115, 199-205

Short-chain alcohol dehyrogenase.

amino acids 30-42, 104-114

FIGURE 129

AACTTCTAC<u>ATG</u>GGCCTCCTGCTGCTGGTGCTCTTCCTCAGCCTCCTGCCGGTGGCCTACACCAT
CATGTCCCTCCCACCCTCCTTTGACTGCGGGCCGTTCAGGTGCAGAGTCTCAGTTGCCCGGGAGC
ACCTCCCCTCCCGAGGCAGTCTGCTCAGAGGGCCTCGGCCCAGAATTCCAGTTCTGGTTTCATGC
CAGCCTGTAAAAGGCCATGGAACTTTGGGTGAATCACCGATGCCATTTAAGAGGGTTTTCTGCCA
GGATGGAAATGTTAGGTCGTTCTGTGTCTGCGCTGTTCATTTCAGTAGCCACCAGCCACCTGTGG
CCGTTGAGTGCTTGAAA<u>TGA</u>GGAACTGAGAAAATTAATTTCTCATGTATTTTCTCATTTATTTA
TTAATTTTTAACTGATAGTTGTACATATTTGGGGGTACATGTGATATTTGGATACATGTATACAA
TATATAATGATCAAATCAGGGTAACTGGGATATCCATCACATCAAACATTTATTTTTATTCTTT
TTAGACAGAGTCTCACTCTGTCACCCAGGCTGGAGTGCAGTGGTGCCATCTCAGCTTACTGCAAC
CTCTGCCTGCCAGGTTCAAGCGATTCTCATGCCTCCACCTCCCAAGTAGCTGGGACTACAGGCAT
GCACCACAATGCCCAACTAATTTTTGTATTTTTAGTAGAGACGGGGTTTTGCCATGTTGCCCAGG
CTGGCCTTGAACTCCTGGCCTCAAACAATCCACTTGCCTCGGCCTCCCAAAGTGTTATGATTACA
GGCGTGAGCCACCGTGCCTGGCCTAAACATTTATCTTTTCTTTGTGTTGGGAACTTTGAAATTAT
ACAATGAATTATTGTTAACTGTCATCTCCTGCTGTGCTATGGAACACTGGGACTTCTTCCCTCT
ATCTAACTGTATATTTGTACCAGTTAACCAACCGTACTTCATCCCCACTCCTCTCTATCCTTCCC
AACCTCTGATCACCTCATTCTACTCTCTACCTCCATGAGATCCACTTTTTAGCTCCCACATGTG
AGTAAGAAAATGCAATATTTGTCTTTCTGTGCCTGGCTTATTTCACTTAACATAATGACTTCCTG
TTCCATCCATGTTGCTGCAAATGACAGGATTTCGTTCTTAATTTCAATTAAAATAACCACACATG
GCAAAAA

FIGURE 130

MGLLLLVLFLSLLPVAYTIMSLPPSFDCGPFRCRVSVAREHLPSRGSLLRGPRPRIPVLVSCQPV
KGHGTLGESPMPFKRVFCQDGNVRSFCVCAVHFSSHQPPVAVECLK

Important features of the protein:

Signal peptide:

amino acids 1-18

N-myristoylation site.

amino acids 86-92

Zinc carboxypeptidases, zinc-binding region 2 signature.

amino acids 68-79

FIGURE 131

TTCTGAAGTAACGGAAGCTACCTTGTATAAAGACCTCAACACTGCTGACCATGATCAGCGCAGCCTGGAGC
ATCTTCCTCATCGGGACTAAAATTGGGCTGTTCCTTCAAGTAGCACCTCTATCAGTTATGGCTAAATCCTG
TCCATCTGTGTGTCGCTGCGATGCGGGTTTCATTTACTGTAATGATCGCTTTCTGACATCCATTCCAACAG
GAATACCAGAGGATGCTACAACTCTCTACCTTCAGAACAACCAAATAAATAATGCTGGGATTCCTTCAGAT
TTGAAAAACTTGCTGAAAGTAGAAAGAATATACCTATACCACAACAGTTTAGATGAATTTCCTACCAACCT
CCCAAAGTATGTAAAAGAGTTACATTTGCAAGAAAATAACATAAGGACTATCACTTATGATTCACTTTCAA
AAATTCCCTATCTGGAAGAATTACATTTAGATGACAACTCTGTCTCTGCAGTTAGCATAGAAGAGGGAGCA
TTCCGAGACAGCAACTATCTCCGACTGCTTTTCCTGTCCCGTAATCACCTTAGCACAATTCCCTGGGGTTT
GCCCAGGACTATAGAAGAACTACGCTTGGATGATAATCGCATATCCACTATTTCATCACCATCTCTTCAAG
GTCTCACTAGTCTAAAACGCCTGGTTCTAGATGGAAACCTGTTAACAATCATGGTTTAGGTGACAAAGTT
TTCTTCAACCTAGTTAATTTGACAGAGCTGTCCCTGGTGCGGAATTCCCTGACTGCTGCACCAGTAAACCT
TCCAGGCACAAACCTGAGGAAGCTTTATCTTCAAGATAACCACATCAATCGGGTGCCCCCAAATGCTTTTT
CTTATCTAAGGCAGCTCTATCGACTGGATATGTCCAATAATAACCTAAGTAATTTACCTCAGGGTATCTTT
GATGATTTGGACAATATAACACAACTGATTCTTCGCAACAATCCCTGGTATTGCGGGTGCAAGATGAAATG
GGTACGTGACTGGTTACAATCACTACCTGTGAAGGTCAACGTGCGTGGGCTCATGTGCCAAGCCCCAGAAA
AGGTTCGTGGGATGGCTATTAAGGATCTCAATGCAGAACTGTTTGATTGTAAGGACAGTGGGATTGTAAGC
ACCATTCAGATAACCACTGCAATACCCAACACAGTGTATCCTGCCCAAGGACAGTGGCCAGCTCCAGTGAC
CAAACAGCCAGATATTAAGAACCCCAAGCTCACTAAGGATCAACAAACCACAGGGAGTCCCTCAAGAAAAA
CAATTACAATTACTGTGAAGTCTGTCACCTCTGATACCATTCATATCTCTTGGAAACTTGCTCTACCTATG
ACTGCTTTGAGACTCAGCTGGCTTAAACTGGGCCATAGCCCGGCATTTGGATCTATAACAGAAACAATTGT
AACAGGGGAACGCAGTGAGTACTTGGTCACAGCCCTGGAGCCTGATTCACCCTATAAAGTATGCATGGTTC
CCATGGAAACCAGCAACCTCTACCTATTTGATGAAACTCCTGTTTGTATTGAGACTGAAACTGCACCCCTT
CGAATGTACAACCCTACAACCACCCTCAATCGAGAGCAAGAGAAAGAACCTTACAAAAACCCCAATTTACC
TTTGGCTGCCATCATTGGTGGGCTGTGGCCCTGGTTACCATTGCCCTTCTTGCTTTAGTGTGTTGGTATG
TTCATAGGAATGGATCGCTCTTCTCAAGGAACTGTGCATATAGCAAAGGGAGGAGAAGAAAGGATGACTAT
GCAGAAGCTGGCACTAAGAAGGACAACTCTATCCTGGAAATCAGGGAAACTTCTTTTCAGATGTTACCAAT
AAGCAATGAACCCATCTCGAAGGAGGAGTTTGTAATACACACCATATTTCCTCCTAATGGAATGAATCTGT
ACAAAAACAATCACAGTGAAAGCAGTAGTAACCGAAGCTACAGAGACAGTGGTATTCCAGACTCAGATCAC
TCACACTCATGATGCTGAAGGACTCACAGCAGACTTGTGTTTTGGGTTTTTTAAACCTAAGGGAGGTGATG
GT

FIGURE 132

```
MISAAWSIFLIGTKIGLFLQVAPLSVMAKSCPSVCRCDAGFIYCNDRFLTSIPTGIPEDATTLYL
QNNQINNAGIPSDLKNLLKVERIYLYHNSLDEFPTNLPKYVKELHLQENNIRTITYDSLSKIPYL
EELHLDDNSVSAVSIEEGAFRDSNYLRLLFLSRNHLSTIPWGLPRTIEELRLDDNRISTISSPSL
QGLTSLKRLVLDGNLLNNHGLGDKVFFNLVNLTELSLVRNSLTAAPVNLPGTNLRKLYLQDNHIN
RVPPNAFSYLRQLYRLDMSNNNLSNLPQGIFDDLDNITQLILRNNPWYCGCKMKWVRDWLQSLPV
KVNVRGLMCQAPEKVRGMAIKDLNAELFDCKDSGIVSTIQITTAIPNTVYPAQGQWPAPVTKQPD
IKNPKLTKDQQTTGSPSRKTITITVKSVTSDTIHISWKLALPMTALRLSWLKLGHSPAFGSITET
IVTGERSEYLVTALEPDSPYKVCMVPMETSNLYLFDETPVCIETETAPLRMYNPTTTLNREQEKE
PYKNPNLPLAAIIGGAVALVTIALLALVCWYVHRNGSLFSRNCAYSKGRRRKDDYAEAGTKKDNS
ILEIRETSFQMLPISNEPISKEEFVIHTIFPPNGMNLYKNNHSESSSNRSYRDSGIPDSDHSHS
```

Important features of the protein:

Signal peptide:

amino acids 1-28

Transmembrane domain:

amino acids 531-552

N-glycosylation sites.

amino acids 226-229, 282-285, 296-299, 555-558, 626-629, 633-636

Tyrosine kinase phosphorylation site.

amino acids 515-522

N-myristoylation sites.

amino acids 12-17, 172-177, 208-213, 359-364, 534-539, 556-561, 640-645

Amidation site.

amino acids 567-570

Leucine zipper pattern.

amino acids 159-180

Phospholipase A2 aspartic acid active site.

amino acids 34-44

FIGURE 133

CCGTCATCCCCCTGCAGCCACCCTTCCCAGAGTCCTTTGCCCAGGCCACCCCAGGCTTCTTGGCA
GCCCTGCCGGGCCACTTGTCTTC<u>ATG</u>TCTGCCAGGGGGAGGTGGGAAGGAGGTGGGAGGAGGGCG
TGCAGAGGCAGTCTGGGCTTGGCCAGAGCTCAGGGTGCTGAGCGTGTGACCAGCAGTGAGCAGAG
GCCGGCCATGGCCAGCCTGGGGCTGCTGCTCCTGCTCTTACTGACAGCACTGCCACCGCTGTGGT
CCTCCTCACTGCCTGGGCTGGACACTGCTGAAAGTAAAGCCACCATTGCAGACCTGATCCTGTCT
GCGCTGGAGAGAGCCACCGTCTTCCTAGAACAGAGGCTGCCTGAAATCAACCTGGATGGCATGGT
GGGGGTCCGAGTGCTGGAAGAGCAGCTAAAAAGTGTCCGGGAGAAGTGGGCCCAGGAGCCCTGC
TGCAGCCGCTGAGCCTGCGCGTGGGGATGCTGGGGGAGAAGCTGGAGGCTGCCATCCAGAGATCC
CTCCACTACCTCAAGCTGAGTGATCCCAAGTACCTAAGAGAGTTCCAGCTGACCCTCCAGCCCGG
GTTTTGGAAGCTCCCACATGCCTGGATCCACACTGATGCCTCCTTGGTGTACCCCACGTTCGGGC
CCCAGGACTCATTCTCAGAGGAGAAGTGACGTGTGCCTGGTGCAGCTGCTGGGAACCGGGACG
GACAGCAGCGAGCCCTGCGGCCTCTCAGACCTCTGCAGGAGCCTCATGACCAAGCCCGGCTGCTC
AGGCTACTGCCTGTCCCACCAACTGCTCTTCTTCCTCTGGGCCAGAATGAGGGGATGCACACAGG
GACCACTCCAACAGAGCCAGGACTATATCAACCTCTTCTGCGCCAACATGATGGACTTGAACCGC
AGAGCTGAGGCCATCGGATACGCCTACCCTACCCGGGACATCTTCATGGAAAACATCATGTTCTG
TGGAATGGGCGGCTTCTCCGACTTCTACAAGCTCCGGTGGCTGGAGGCCATTCTCAGCTGGCAGA
AACAGCAGGAAGGATGCTTCGGGGAGCCTGATGCTGAAGATGAAGAATTATCTAAAGCTATTCAA
TATCAGCAGCATTTTTCGAGGAGAGTGAAGAGGCGAGAAAAACAATTTCCAGATTCTCGCTCTGT
TGCTCAGGCTGGAGTACAGTGGCGCAATCTCGGCTCACTGCAACCTTTGCCTCCTGGGTTCAAGC
AATTCTCTTGCCTCATCCTCCCGAGTAGCTGGGACTACAGGAGCGTGCCACCATACCTGGCTAAT
TTTTATATTTTTTAGTAGAGACAGGGTTTCATCATGTTGCTCATGCTGGTCTCGAACTCCTGAT
CTCAAGAGATCCGCCCACCTCAGGCTCCCAAAGTGTGGGATTA<u>TAG</u>GTGTGAGCCACCGTGTCTG
GCTGAAAAGCACTTTCAAAGAGACTGTGTTGAATAAAGGGCCAAGGTTCTTGCCACCCAGCACTC
ATGGGGGCTCTCTCCCCTAGATGGCTGCTCCTCCCACAACACAGCCACAGCAGTGGCAGCCCTGG
GTGGCTTCCTATACATCCTGGCAGAATACCCCCCAGCAAACAGAGAGCCACACCCATCCACACCG
CCACCACCAAGCAGCCGCTGAGACGGACGGTTCCATGCCAGCTGCCTGGAGGAGAACAGACCCC
TTTAGTCCTCATCCCTTAGATCCTGGAGGGCACGGATCACATCCTGGGAAGAAGGCATCTGGAGG
ATAAGCAAAGCCACCCCGACACCCAATCTTGGAAGCCCTGAGTAGGCAGGGCCAGGGTAGGTGGG
GGCCGGGAGGGACCCAGGTGTGAACGGATGAATAAAGTTCAACTGCAACTGAAAAAAAAAA

FIGURE 134

MSARGRWEGGGRRACRGSLGLARAQGAERVTSSEQRPAMASLGLLLLLLLTALPPLWSSSLPGLD
TAESKATIADLILSALERATVFLEQRLPEINLDGMVGVRVLEEQLKSVREKWAQEPLLQPLSLRV
GMLGEKLEAAIQRSLHYLKLSDPKYLREFQLTLQPGFWKLPHAWIHTDASLVYPTFGPQDSFSEE
RSDVCLVQLLGTGTDSSEPCGLSDLCRSLMTKPGCSGYCLSHQLLFFLWARMRGCTQGPLQQSQD
YINLFCANMMDLNRRAEAIGYAYPTRDIFMENIMFCGMGGFSDFYKLRWLEAILSWQKQQEGCFG
EPDAEDEELSKAIQYQQHFSRRVKRREKQFPDSRSVAQAGVQWRNLGSLQPLPPGFKQFSCLILP
SSWDYRSVPPYLANFYIFLVETGFHHVAHAGLELLISRDPPTSGSQSVGL

Important features of the protein:

Signal peptide:

amino acids 1-26

Transmembrane domain:

amino acids 39-56

Tyrosine kinase phosphorylation sites.

amino acids 149-156, 274-282

N-myristoylation sites.

amino acids 10-16, 20-26, 63-69, 208-214

Amidation site.

amino acids 10-14

Glycoprotein hormones beta chain signature 1.

amino acids 230-237

FIGURE 135

GGTCTGAGTGCAGAGCTGCTGTCATGGCGGCCGCTCTGTGGGGCTTCTTTCCCGTCCTGCTGCTG
CTGCTGCTATCGGGGGATGTCCAGAGCTCGGAGGTGCCCGGGGCTGCTGCTGAGGGATCGGGAGG
GAGTGGGGTCGGCATAGGAGATCGCTTCAAGATTGAGGGGCGTGCAGTTGTTCCAGGGGTGAAGC
CTCAGGACTGGATCTCGGCGGCCCGAGTGCTGGTAGACGGAGAAGAGCACGTCGGTTTCCTTAAG
ACAGATGGGAGTTTTGTGGTTCATGATATACCTTCTGGATCTTATGTAGTGGAAGTTGTATCTCC
AGCTTACAGATTTGATCCCGTTCGAGTGGATATCACTTCGAAAGGAAAAATGAGAGCAAGATATG
TGAATTACATCAAAACATCAGAGGTTGTCAGACTGCCCTATCCTCTCCAAATGAAATCTTCAGGT
CCACCTTCTTACTTTATTAAAGGGAATCGTGGGGCTGGACAGACTTTCTAATGAACCCAATGGT
TATGATGATGGTTCTTCCTTTATTGATATTTGTGCTTCTGCCTAAAGTGGTCAACACAAGTGATC
CTGACATGAGACGGGAAATGGAGCAGTCAATGAATATGCTGAATTCCAACCATGAGTTGCCTGAT
GTTTCTGAGTTCATGACAAGACTCTTCTCTTCAAAATCATCTGGCAAATCTAGCAGCGGCAGCAG
TAAAACAGGCAAAGTGGGGCTGGCAAAAGGAGGTAGTCAGGCCGTCCAGAGCTGGCATTTGCAC
AAACACGGCAACACTGGGTGGCATCCAAGTCTTGGAAAACCGTGTGAAGCAACTACTATAAACTT
GAGTCATCCCGACGTTGATCTCTTACAACTGTGTATGTT
AACTTTTTAGCACATGTTTTGTACTTGGTACACGAGAAAACCCAGCTTTCATCTTTTGTCTGTAT
GAGGTCAATATTGATGTCACTGAATTAATTACAGTGTCCTATAGAAATGCCATTAATAAATTAT
ATGAACTACTATACATTATGTATATTAATTAAAACATCTTAATCCAGAAATCAAAAAAAAAAAA
AAAAAAAAAAAAAA

FIGURE 136

MAAALWGFFPVLLLLLLSGDVQSSEVPGAAAEGSGGSGVGIGDRFKIEGRAVVPGVKPQDWISAA
RVLVDGEEHVGFLKTDGSFVVHDIPSGSYVVEVVSPAYRFDPVRVDITSKGKMRARYVNYIKTSE
VVRLPYPLQMKSSGPPSYFIKRESWGWTDFLMNPMVMMMVLPLLIFVLLPKVVNTSDPDMRREME
QSMNMLNSNHELPDVSEFMTRLFSSKSSGKSSSGSSKTGKSGAGKRR

Important features of the protein:

Signal sequence:

amino acids 1-23

Transmembrane domain:

amino acids 161-182

N-glycosylation site.

amino acids 184-187

Glycosaminoglycan attachment sites.

amino acids 37-40, 236-239 cAMP- and cGMP-dependent protein kinase phosphorylation site.

amino acids 151-154

N-myristoylation sites.

amino acids 33-38, 36-41, 38-44, 229-234

Amidation site.

amino acids 238-241

ATP/GTP-binding site motif A (P-loop).

amino acids 229-236

FIGURE 137

```
GATGGCGCAGCCACAGCTTCTGTGAGATTCGATTTCTCCCCAGTTCCCCTGTGGGTCTGAGGGGA
CCAGAAGGGTGAGCTACGTTGGCTTTCTGGAAGGGGAGGCTATATGCGTCAATTCCCCAAAACAA
GTTTTGACATTTCCCCTGAAATGTCATTCTCTATCTATTCACTGCAAGTGCCTGCTGTTCCAGGC
CTTACCTGCTGGGCACTAACGGCGGAGCCAGGATGGGGACAGAATAAAGGAGCCACGACCTGTGC
CACCAACTCGCACTCAGACTCTGAACTCAGACCTGAAATCTTCTCTTCACGGGAGGCTTGGCAGT
TTTTCTTACTCCTGTGGTCTCCAGATTTCAGGCCTAAGATGAAAGCCTCTAGTCTTGCCTTCAGC
CTTCTCTCTGCTGCGTTTTATCTCCTATGGACTCCTTCCACTGGACTGAAGACACTCAATTTGGG
AAGCTGTGTGATCGCCACAAACCTTCAGGAAATACGAATGGATTTTCTGAGATACGGGGCAGTG
TGCAAGCCAAAGATGGAAACATTGACATCAGAATCTTAAGGAGGACTGAGTCTTTGCAAGACACA
AAGCCTGCGAATCGATGCTGCCTCCTGCGCCATTTGCTAAGACTCTATCTGGACAGGGTATTTAA
AAACTACCAGACCCCTGACCATTATACTCTCCGGAAGATCAGCAGCCTCGCCAATTCCTTTCTTA
CCATCAAGAAGGACCTCCGGCTCTCATGCCCACATGACATGCCATTGTGGGGAGGAAGCAATG
AAGAAATACAGCCAGATTCTGAGTCACTTTGAAAAGCTGGAACCTCAGGCAGCAGTTGTGAAGGC
TTTGGGGGAACTAGACATTCTTCTGCAATGGATGGAGGAGACAGAATAGGAGGAAAGTGATGCTG
CTGCTAAGAATATTCGAGGTCAAGAGCTCCAGTCTTCAATACCTGCAGAGGAGGCATGACCCCAA
ACCACCATCTCTTTACTGTACTAGTCTTGTGCTGGTCACAGTGTATCTTATTTATGCATTACTTG
CTTCCTTGCATGATTGTCTTTATGCATCCCCAATCTTAATTGAGACCATACTTGTATAAGATTTT
TGTAATATCTTTCTGCTATTGGATATATTTATTAGTTAATATATTTATTTATTTTTTGCTATTTA
ATGTATTTATTTTTTTACTTGGACATGAAACTTTAAAAAAATTCACAGATTATATTTATAACCTG
ACTAGAGCAGGTGATGTATTTTTATACAGTAAAAAAAAAAACCTTGTAAATTCTAGAAGAGTGG
CTAGGGGGGTTATTCATTTGTATTCAACTAAGGACATATTTACTCATGCTGATGCTCTGTGAGAT
ATTTGAAATTGAACCAATGACTACTTAGGATGGGTTGTGGAATAAGTTTTGATGTGGAATTGCAC
ATCTACCTTACAATTACTGACCATCCCCAGTAGACTCCCCAGTCCCATAATTGTGTATCTTCCAG
CCAGGAATCCTACACGGCCAGCATGTATTTCTACAAATAAAGTTTTCTTTGCATACCAAAAAAA
AAAAAAAAAA
```

FIGURE 138

MRQFPKTSFDISPEMSFSIYSLQVPAVPGLTCWALTAEPGWGQNKGATTCATNSHSDSELRPEIF
SSREAWQFFLLLWSPDFRPKMKASSLAFSLLSAAFYLLWTPSTGLKTLNLGSCVIATNLQEIRNG
FSEIRGSVQAKDGNIDIRILRRTESLQDTKPANRCCLLRHLLRLYLDRVFKNYQTPDHYTLRKIS
SLANSFLTIKKDLRLSHAHMTCHCGEEAMKKYSQILSHFEKLEPQAAVVKALGELDILLQWMEET
E

Important features of the protein:
Signal peptide:
amino acids 1-42 cAMP- and cGMP-dependent protein kinase phosphorylation sites.
amino acids 192-195, 225-228

N-myristoylation sites.
amino acids 42-47, 46-51, 136-141

FIGURE 139

```
CCTGGAGCCGGAAGCGCGGCTGCAGCAGGGCGAGGCTCCAGGTGGGGTCGGTTCCGCATCCAGCC
TAGCGTGTCCACGATGCGGCTGGGCTCCGGGACTTTCGCTACCTGTTGCGTAGCGATCGAGGTGC
TAGGGATCGCGGTCTTCCTTCGGGGATTCTTCCCGGCTCCCGTTCGTTCCTCTGCCAGAGCGGAA
CACGGAGCGGAGCCCCCAGCGCCCGAACCCTCGGCTGGAGCCAGTTCTAACTGGACCACGCTGCC
ACCACCTCTCTTCAGTAAAGTTGTTATTGTTCTGATAGATGCCTTGAGAGATGATTTTGTGTTTG
GGTCAAAGGGTGTGAAATTTATGCCCTACACAACTTACCTTGTGGAAAAAGGAGCATCTCACAGT
TTTGTGGCTGAAGCAAAGCCACCTACAGTTACTATGCCTCGAATCAAGGCATTGATGACGGGGAG
CCTTCCTGGCTTTGTCGACGTCATCAGGAACCTCAATTCTCCTGCACTGCTGGAAGACAGTGTGA
TAAGACAAGCAAAAGCAGCTGGAAAAAGAATAGTCTTTTATGGAGATGAAACCTGGGTTAAATTA
TTCCCAAAGCATTTTGTGGAATATGATGGAACAACCTCATTTTTCGTGTCAGATTACACAGAGGT
GGATAATAATGTCACGAGGCATTTGGATAAAGTATTAAAAGAGGAGATTGGGACATATTAATCC
TCCACTACCTGGGGCTGGACCACATTGGCCACATTTCAGGGCCCAACAGCCCCCTGATTGGGCAG
AAGCTGAGCGAGATGGACAGCGTGCTGATGAAGATCCACACCTCACTGCAGTCGAAGGAGAGAGA
GACGCCTTTACCCAATTTGCTGGTTCTTTGTGGTGACCATGGCATGTCTGAAACAGGAAGTCACG
GGGCCTCCTCCACCGAGGAGGTGAATACACCTCTGATTTTAATCAGTTCTGCGTTTGAAAGGAAA
CCCGGTGATATCCGACATCCAAAGCACGTCCAATAGACGGATGTGGCTGCGACACTGGCGATAGC
ACTTGGCTTACCGATTCCAAAAGACAGTGTAGGGAGCCTCCTATTCCCAGTTGTGGAAGGAAGAC
CAATGAGAGAGCAGTTGAGATTTTTACATTTGAATACAGTGCAGCTTAGTAAACTGTTGCAAGAG
AATGTGCCGTCATATGAAAAGATCCTGGGTTTGAGCAGTTTAAAATGTCAGAAAGATTGCATGG
GAACTGGATCAGACTGTACTTGGAGGAAAAGCATTCAGAAGTCCTATTCAACCTGGGCTCCAAGG
TTCTCAGGCAGTACCTGGATGCTCTGAAGACGCTGAGCTTGTCCTGAGTGCACAAGTGGCCCAG
TTCTCACCCTGCTCCTGCTCAGCGTCCCACAGGCACTGCACAGAAAGGCTGAGCTGGAAGTCCCA
CTGTCATCTCCTGGGTTTTCTCTGCTCTTTTATTTGGTGATCCTGGTTCTTTCGGCCGTTCACGT
CATTGTGTGCACCTCAGCTGAAAGTTCGTGCTACTTCTGTGGCCTCTCGTGGCTGGCGGCAGGCT
GCCTTTCGTTTACCAGACTCTGGTTGAACACCTGGTGTGTGCCAAGTGCTGGCAGTGCCCTGGAC
AGGGGGCCTCAGGGAAGGACGTGGAGCAGCCTTATCCCAGGCCTCTGGGTGTCCCGACACAGGTG
TTCACATCTGTGCTGTCAGGTCAGATGCCTCAGTTCTTGGAAAGCTAGGTTCCTGCGACTGTTAC
CAAGGTGATTGTAAAGAGCTGGCGGTCACAGAGGAACAAGCCCCCAGCTGAGGGGTGTGTGAA
TCGGACAGCCTCCCAGCAGAGGTGTGGGAGCTGCAGCTGAGGGAAGAAGAGACAATCGGCCTGGA
CACTCAGGAGGGTCAAAAGGAGACTTGGTCGCACCACTCATCCTGCCACCCCAGAATGCATCCT
GCCTCATCAGGTCCAGATTTCTTTCCAAGGCGGACGTTTTCTGTTGGAATTCTTAGTCCTTGGCC
TCGGACACCTTCATTCGTTAGCTGGGGAGTGGTGGTGAGGCAGTGAAGAAGAGGCGGATGGTCAC
ACTCAGATCCACAGAGCCCAGGATCAAGGGACCCACTGCAGTGGCAGCAGGACTGTTGGGCCCCC
ACCCCAACCCTGCACAGCCCTCATCCCTCTTGGCTTGAGCCGTCAGAGGCCCTGTGCTGAGTGT
CTGACCGAGACACTCACAGCTTTGTCATCAGGGCACAGGCTTCCTCGGAGCCAGGATGATCTGTG
CCACGCTTGCACCTCGGGCCCATCTGGGCTCATGCTCTCTCCTGCTATTGAATTAGTACCTAG
CTGCACACAGTATGTAGTTACCAAAAGAATAAACGGCAATAATTGAGAAAAAAA
```

FIGURE 140

MRLGSGTFATCCVAIEVLGIAVFLRGFFPAPVRSSARAEHGAEPPAPEPSAGASSNWTTLPPPLF
SKVVIVLIDALRDDFVFGSKGVKFMPYTTYLVEKGASHSFVAEAKPPTVTMPRIKALMTGSLPGF
VDVIRNLNSPALLEDSVIRQAKAAGKRIVFYGDETWVKLFPKHFVEYDGTTSFFVSDYTEVDNNV
TRHLDKVLKRGDWDILILHYLGLDHIGHISGPNSPLIGQKLSEMDSVLMKIHTSLQSKERETPLP
NLLVLCGDHGMSETGSHGASSTEEVNTPLILISSAFERKPGDIRHPKHVQ

Important features of the protein:
Signal peptide:
amino acids 1-34

Transmembrane domain:
amino acids 58-76

N-glycosylation sites.
amino acids 56-60, 194-198

N-myristoylation sites.
amino acids 6-12, 52-58, 100-106, 125-131, 233-239, 270-276, 275-281, 278-284

Amidation site.
amino acids 154-158

Cell attachment sequence.
amino acids 205-208

FIGURE 141

GGCACGAGGCAAGCCTTCCAGGTTATCGTGACGCACCTTGAAAGTCTGAGAGCTACTGCCCTACA
GAAAGTTACTAGTGCCCTAAAGCTGGCGCTGGCACTG<u>ATG</u>TTACTGCTGCTGTTGGAGTACAACT
TCCCTATAGAAAACAACTGCCAGCACCTTAAGACCACTCACACCTTCAGAGTGAAGAACTTAAAC
CCGAAGAAATTCAGCATTCATGACCAGGATCACAAAGTACTGGTCCTGGACTCTGGGAATCTCAT
AGCAGTTCCAGATAAAAACTACATACGCCCAGAGATCTTCTTTGCATTAGCCTCATCCTTGAGCT
CAGCCTCTGCGGAGAAAGGAAGTCCGATTCTCCTGGGGGTCTCTAAAGGGGAGTTTTGTCTCTAC
TGTGACAAGGATAAAGGACAAAGTCATCCATCCCTTCAGCTGAAGAAGGAGAAACTGATGAAGCT
GGCTGCCCAAAAGGAATCAGCACGCCGGCCCTTCATCTTTTATAGGGCTCAGGTGGGCTCCTGGA
ACATGCTGGAGTCGGCGGCTCACCCCGGATGGTTCATCTGCACCTCCTGCAATTGTAATGAGCCT
GTTGGGGTGACAGATAAATTTGAGAACAGGAAACACATTGAATTTTCATTTCAACCAGTTTGCAA
AGCTGAAATGAGCCCCAGTGAGGTCAGCGAT<u>TAG</u>GAAACTGCCCCATTGAACGCCTTCCTCGCTA
ATTTGAACTAATTGTATAAAAACACCAAACCTGCTCACT

FIGURE 142

MLLLLLEYNFPIENNCQHLKTTHTFRVKNLNPKKFSIHDQDHKVLVLDSGNLIAVPDKNYIRPEI
FFALASSLSSASAEKGSPILLGVSKGEFCLYCDKDKGQSHPSLQLKKEKLMKLAAQKESARRPFI
FYRAQVGSWNMLESAAHPGWFICTSCNCNEPVGVTDKFENRKHIEFSFQPVCKAEMSPSEVSD cAMP- and cGMP-dependent protein kinase phosphorylation site.
amino acids 33-36

N-myristoylation site.
amino acids 50-55, 87-92

Interleukin-1
amino acids 37-182

FIGURE 143

CTAGAGAGTATAGGGCAGAAGGATGGCAGATGAGTGACTCCACATCCAGAGCTGCCTCCCTTTAA
TCCAGGATCCTGTCCTTCCTGTCCTGTAGGAGTGCCTGTTGCCAGTGTGGGGTGAGACAAGTTTG
TCCCACAGGGCTGTCTGAGCAGATAAGATTAAGGGCTGGGTCTGTGCTCAATTAACTCCTGTGGG
CACGGGGGCTGGGAAGAGCAAAGTCAGCGGTGCCTACAGTCAGCACCATGCTGGGCCTGCCGTGG
AAGGGAGGTCTGTCCTGGGCGCTGCTGCTGCTTCTCTTAGGCTCCCAGATCCTGCTGATCTATGC
CTGGCATTTCCACGAGCAAAGGGACTGTGATGAACACAATGTCATGGCTCGTTACCTCCCTGCCA
CAGTGGAGTTTGCTGTCCACACATTCAACCAACAGAGCAAGGACTACTATGCCTACAGACTGGGG
CACATCTTGAATTCCTGGAAGGAGCAGGTGGAGTCCAAGACTGTATTCTCAATGGAGCTACTGCT
GGGGAGAACTAGGTGTGGGAAATTTGAAGACGACATTGACAACTGCCATTTCCAAGAAAGCACAG
AGCTGAACAATACTTTCACCTGCTTCTTCACCATCAGCACCAGGCCCTGGATGACTCAGTTCAGC
CTCCTGAACAAGACCTGCTTGGAGGGATTCCACTGAGTGAAACCCACTCACAGGCTTGTCCATGT
GCTGCTCCCACATTCCGTGGACATCAGCACTACTCTCCTGAGGACTCTTCAGTGGCTGAGCAGCT
TTGGACTTGTTTGTTATCCTATTTTGCATGTGTTTGAGATCTCAGATCAGTGTTTTAGAAAATCC
ACACATCTTGAGCCTAATCATGTAGTGTAGATCATTAAACATCAGCATTTTAAGAAAAAAAAAAA
AAAAAAAAAAAAAAAAAAAAAAAAAAAAAAAAAAAAAAAAAAAAAAAAA

FIGURE 144

MLGLPWKGGLSWALLLLLLGSQILLIYAWHFHEQRDCDEHNVMARYLPATVEFAVHTFNQQSKDY
YAYRLGHILNSWKEQVESKTVFSMELLLGRTRCGKFEDDIDNCHFQESTELNNTFTCFFTISTRP
WMTQFSLLNKTCLEGFH

Important features of the protein:
Signal peptide:
amino acids 1-25

N-glycosylation sites.
amino acids 117-121, 139-143

N-myristoylation site.
amino acids 9-15

FIGURE 145

CTGTGCAGCTCGAGGCTCCAGAGGCACACTCCAGAGAGAGCCAAGGTTCTGACGCGATGAGGAAG
CACCTGAGCTGGTGGTGGCTGGCCACTGTCTGCATGCTGCTCTTCAGCCACCTCTCTGCGGTCCA
GACGAGGGGCATCAAGCACAGAATCAAGTGGAACCGGAAGGCCCTGCCCAGCACTGCCCAGATCA
CTGAGGCCCAGGTGGCTGAGAACCGCCCGGGAGCCTTCATCAAGCAAGGCCGCAAGCTCGACATT
GACTTCGGAGCCGAGGGCAACAGGTACTACGAGGCCAACTACTGGCAGTTCCCCGATGGCATCCA
CTACAACGGCTGCTCTGAGGCTAATGTGACCAAGGAGGCATTTGTCACCGGCTGCATCAATGCCA
CCCAGGCGGCGAACCAGGGGGAGTTCCAGAAGCCAGACAACAAGCTCCACCAGCAGGTGCTCTGG
CGGCTGGTCCAGGAGCTCTGCTCCCTCAAGCATTGCGAGTTTTGGTTGGAGAGGGGCGCAGGACT
TCGGGTCACCATGCACCAGCCAGTGCTCCTCTGCCTTCTGGCTTTGATCTGGCTCATGGTGAAAT
AAGCTTGCCAGGAGGCTGGCAGTACAGAGCGCAGCAGCGAGCAAATCCTGGCAAGTGACCCAGCT
CTTCTCCCCCAAACCCACGCGTGTTCTGAAGGTGCCCAGGAGCGGCGATGCACTCGCACTGCAAA
TGCCGCTCCCACGTATGCGCCCTGGTATGTGCCTGCGTTCTGATAGATGGGGACTGTGGCTTCT
CCGTCACTCCATTCTCAGCCCCTAGCAGAGCGTCTGGCACACTAGATTAGTAGTAAATGCTTGAT
GAGAAGAACACATCAGGCACTGCGCCACCTGCTTCACAGTACTTCCCAACAACTCTTAGAGGTAG
GTGTATTCCCGTTTTACAGATAAGGAAACTGAGGCCCAGAGAGCTGAAGTACTGCACCCAGCATC
ACCAGCTAGAAAGTGGCAGAGCCAGGATTCAACCCTGGCTTGTCTAACCCCAGGTTTTCTGCTCT
GTCCAATTCCAGAGCTGTCTGGTGATCACTTTATGTCTCACAGGGACCCACATCCAAACATGTAT
CTCTAATGAAATTGTGAAAGCTCCATGTTTAGAAATAAATGAAAACACCTGA

FIGURE 146

MRKHLSWWWLATVCMLLFSHLSAVQTRGIKHRIKWNRKALPSTAQITEAQVAENRPGAFIKQGRK
LDIDFGAEGNRYYEANYWQFPDGIHYNGCSEANVTKEAFVTGCINATQAANQGEFQKPDNKLHQQ
VLWRLVQELCSLKHCEFWLERGAGLRVTMHQPVLLCLLALIWLMVK

Important features of the protein:

Signal peptide:

amino acids 1-26

Transmembrane domain:

amino acids 157-171

N-glycosylation sites.

amino acids 98-102, 110-114

Tyrosine kinase phosphorylation site.

amino acids 76-83

N-myristoylation sites.

amino acids 71-77, 88-94, 93-99, 107-113, 154-160

Amidation site.

amino acids 62-66

FIGURE 147

GCCTTGGCCTCCCAAAGGGCTGGGATTATAGGCGTGACCACCATGTCTGGTCCAGAGTCTCATTT
CCTGATGATTTATAGACTCAAAGAAAACTC<u>ATG</u>TTCAGAAGCTCTCTTCTCTTCTGGCCTCCTCT
CTGTCTTCTTTCCCTCTTTCTTCTTATTTTAATTAGTAGCATCTACTCAGAGTCATGCAAGCTGG
AAATCTTTCATTTTGCTTGTCAGTGGGGTAGGTCACTGAGTCTTAGTTTTTATTTTTTGAAATTT
CAACTTTCAGATTCAGGGGGTACATGTGAAGGTTTGTTTTATGAGTATATTGCA<u>TGA</u>TGCTGAGG
TTTGGGGT

FIGURE 148

MFRSSLLFWPPLCLLSLFLLILISSIYSESCKLEIFHFACQWGRSLSLSFYFLKFQLSDSGGTCE
GLFYEYIA

Important features of the protein:

Signal peptide:

amino acids 1-25

N-myristoylation site.

amino acids 62-68

FIGURE 149

```
GTCTCCGCGTCACAGGAACTTCAGCACCCACAGGGCGGACAGCGCTCCCCTCTACCTGGAGACTTGAC
TCCCGCGCGCCCCAACCCTGCTTATCCCTTGACCGTCGAGTGTCAGAGATCCTGCAGCCGCCCAGTCC
CGGCCCCTCTCCCGCCCCACACCCACCCTCCTGGCTCTTCCTGTTTTTACTCCTCCTTTTCATTCATA
ACAAAAGCTACAGCTCCAGGAGCCCAGCGCCGGGCTGTGACCCAAGCCGAGCGTGGAAGAATGGGGTT
CCTCGGGACCGGCACTTGGATTCTGGTGTTAGTGCTCCCGATTCAAGCTTTCCCCAAACCTGGAGGAA
GCCAAGACAAATCTCTACATAATAGAGAATTAAGTGCAGAAAGACCTTTGAATGACAGATTGCTGAA
GCAGAAGAAGACAAGATTAAAAAAACATATCCTCCAGAAAACAAGCCAGGTCAGAGCAACTATTCTTT
TGTTGATAACTTGAACCTGCTAAAGGCAATAACAGAAAAGGAAAAAATTGAGAAAGAAAGACAATCTA
TAAGAAGCTCCCCACTTGATAATAAGTTGAATGTGGAAGATGTTGATTCAACCAAGAATCGAAAACTG
ATCGATGATTATGACTCTACTAAGAGTGGATTGGATCATAAATTTCAAGATGATCCAGATGGTCTTCA
TCAACTAGACGGGACTCCTTTAACCGCTGAAGACATTGTCCATAAAATCGCTGCCAGGATTTATGAAG
AAAATGACAGAGCCGTGTTTGACAAGATTGTTTCTAAACTACTTAATCTCGGCCTTATCACAGAAAGC
CAAGCACATACACTGGAAGATGAAGTAGCAGAGGTTTTACAAAAATTAATCTCAAAGGAAGCCAACAA
TTATGAGGAGGATCCCAATAAGCCCACAAGCTGGACTGAGAATCAGGCTGGAAAAATACCAGAGAAAG
TGACTCCAATGGCAGCAATTCAAGATGGTCTTGCTAAGGGAGAAAACGATGAAACAGTATCTAACACA
TTAACCTTGACAAATGGCTTGGAAAGGAGAACTAAAACCTACAGTGAAGACAACTTTGAGGAACTCCA
ATATTTCCCAAATTTCTATGCGCTACTGAAAGTATTGATTCAGAAAAAGAAGCAAAAGAGAAAGAAA
CACTGATTACTATCATGAAAACACTGATTGACTTTGTGAAGATGATGGTGAAATATGGAACAATATCT
CCAGAAGAAGGTGTTTCCTACCTTGAAAACTTGGATGAAATGATTGCTCTTCAGACCAAAAACAAGCT
AGAAAAAAATGCTACTGACAATATAAGCAAGCTTTTCCCAGCACCATCAGAGAAGAGTCATGAAGAAA
CAGACAGTACCAAGGAAGAAGCAGCTAAGATGGAAAAGGAATATGGAAGCTTGAAGGATTCCACAAAA
GATGATAACTCCAACCCAGGAGGAAAGACAGATGAACCCAAAGGAAAAACAGAAGCCTATTTGGAAGC
CATCAGAAAAATATTGAATGGTTGAAGAAACATGACAAAAGGGAATAAAGAAGATTATGACCTTT
CAAAGATGAGAGACTTCATCAATAAACAAGCTGATGCTTATGTGGAGAAAGGCATCCTTGACAAGGAA
GAAGCCGAGGCCATCAAGCGCATTTATAGCAGCCTGTAAAAATGGCAAAAGATCCAGGAGTCTTTCAA
CTGTTTCAGAAAACATAATATAGCTTAAAACACTTCTAATTCTGTGATTAAAATTTTTTGACCCAAGG
GTTATTAGAAAGTGCTGAATTTACAGTAGTTAACCTTTTACAAGTGGTTAAAACATAGCTTTCTTCCC
GTAAAAACTATCTGAAAGTAAAGTTGTATGTAAGCTGAAAAAAAAAAAAAAAAAAA
```

FIGURE 150

MGFLGTGTWILVLVLPIQAFPKPGGSQDKSLHNRELSAERPLNEQIAEAEEDKIKKTYPPENKPG
QSNYSFVDNLNLLKAITEKEKIEKERQSIRSSPLDNKLNVEDVDSTKNRKLIDDYDSTKSGLDHK
FQDDPDGLHQLDGTPLTAEDIVHKIAARIYEENDRAVFDKIVSKLLNLGLITESQAHTLEDEVAE
VLQKLISKEANNYEEDPNKPTSWTENQAGKIPEKVTPMAAIQDGLAKGENDETVSNTLTLTNGLE
RRTKTYSEDNFEELQYFPNFYALLKSIDSEKEAKEKETLITIMKTLIDFVKMMVKYGTISPEEGV
SYLENLDEMIALQTKNKLEKNATDNISKLFPAPSEKSHEETDSTKEEAAKMEKEYGSLKDSTKDD
NSNPGGKTDEPKGKTEAYLEAIRKNIEWLKKHDKKGNKEDYDLSKMRDFINKQADAYVEKGILDK
EEAEAIKRIYSSL

N-glycosylation sites:

amino acids 68-71, 346-349, 350-353

Casein kinase II phosphorylation site:

amino acids 70-73, 82-85, 97-100, 125-128, 147-150, 188-191, 217-220, 265-268, 289-292, 305-308, 320-323, 326-329, 362-365, 368-341, 369-372, 382-385, 386-389, 387-390

N-myristoylation sites:

amino acids 143-148, 239-244

FIGURE 151

CGGCTCGAGGCTCCCGCCAGGAGAAAGGAACATTCTGAGGGGAGTCTACACCCTGTGGAGCTCAA
GATGGTCCTGAGTGGGGCGCTGTGCTTCCGAATGAAGGACTCGGCATTGAAGGTGCTTTATCTGC
ATAATAACCAGCTTCTAGCTGGAGGGCTGCATGCAGGGAAGGTCATTAAAGGTGAAGAGATCAGC
GTGGTCCCCAATCGGTGGCTGGATGCCAGCCTGTCCCCGTCATCCTGGGTGTCCAGGGTGGAAG
CCAGTGCCTGTCATGTGGGGTGGGGCAGGAGCCGACTCTAACACTAGAGCCAGTGAACATCATGG
AGCTCTATCTTGGTGCCAAGGAATCCAAGAGCTTCACCTTCTACCGGCGGGACATGGGGCTCACC
TCCAGCTTCGAGTCGGCTGCCTACCCGGGCTGGTTCCTGTGCACGGTGCCTGAAGCCGATCAGCC
TGTCAGACTCACCCAGCTTCCCGAGAATGGTGGCTGGAATGCCCCCATCACAGACTTCTACTTCC
AGCAGTGTGACTAGGGCAACGTGCCCCCAGAACTCCCTGGGCAGAGCCAGCTCGGGTGAGGGGT
GAGTGGAGGAGACCCATGGCGGACAATCACTCTCTGCTCTCAGGACCCCCACGTCTGACTTAG
TGGGCACCTGACCACTTTGTCTTCTGGTTCCAGTTTGGATAAATTCTGAGATTTGGAGCTCAGT
CCACGGTCCTCCCCACTGGATGGTGCTACTGCTGTGGAACCTTGTAAAAACCATGTGGGGTAAA
CTGGGAATAACATGAAAAGATTTCTGTGGGGGTGGGGTGGGGGAGTGGTGGGAATCATTCCTGCT
TAATGGTAACTGACAAGTGTTACCCTGAGCCCCGCAGGCCAACCCATCCCCAGTTGAGCCTTATA
GGGTCAGTAGCTCTCCACATGAAGTCCTGTCACTCACCACTGTGCAGGAGAGGGAGGTGGTCATA
GAGTCAGGGATCTATGGCCCTTGGCCCAGCCCCACCCCCTTCCCTTTAATCCTGCCACTGTCATA
TGCTACCTTTCCTATCTCTTCCCTCATCATCTTGTTGTGGGCATGAGGAGGTGGTGATGTCAGAA
GAAATGGCTCGAGCTCAGAAGATAAAGATAAGTAGGGTATGCTGATCCTCTTTTAAAAACCCAA
GATACAATCAAAATCCCAGATGCTGGTCTCTATTCCCATGAAAAGTGCTCATGACATATTGAGA
AGACCTACTTACAAAGTGGCATATATTGCAATTTATTTAATTAAAAGATACCTATTTATATATT
TCTTTATAGAAAAAGTCTGGAAGAGTTTACTTCAATTGTAGCAATGTCAGGGTGGTGGCAGTAT
AGGTGATTTTCTTTTAATTCTGTTAATTTATCTGTATTTCCTAATTTTTCTACAATGAAGATGA
ATTCCTTGTATAAAAATAAGAAAAGAAATTAATCTTGAGGTAAGCAGAGCAGACATCATCTCTGA
TTGTCCTCAGCCTCCACTTCCCCAGAGTAAATTCAAATTGAATCGAGCTCTGCTGCTCTGGTTGG
TTGTAGTAGTGATCAGGAAACAGATCTCAGCAAAGCCACTGAGGAGGAGGCTGTGCTGAGTTTGT
GTGGCTGGAATCTCTGGGTAAGGAACTTAAAGAACAAAATCATCTGGTAATTCTTTCCTAGAAG
GATCACAGCCCCTGGGATTCCAAGGCATTGGATCCAGTCTCTAAGAAGGCTGCTGTACTGGTTGA
ATTGTGTCCCCCTCAAATTCACATCCTTCTTGGAATCTCAGTCTGTGAGTTTATTTGGAGATAAG
GTCTCTGCAGATGTAGTTAGTTAAGACAAGGTCATGCTGGATGAAGGTAGACCTAAATTCAATAT
GACTGGTTTCCTTGTATGAAAGGAGAGGACACAGAGACAGAGGAGACGCGGGGAAGACTATGTA
AAGATGAAGGCAGAGATCGGAGTTTTGCAGCCACAAGCTAAGAAACACCAAGGATTGTGGCAACC
ATCAGAAGCTTGGAAGAGGCAAAGAAGAATTCTTCCCTAGAGGCTTTAGAGGGATAACGGCTCTG
CTGAAACCTTAATCTCAGACTTCCAGCCTCCTGAACGAAGAAAGAATAAATTTCGGCTGTTTAA
GCCACCAAGGATAATTGGTTACAGCAGCTCTAGGAAACTAATACAGCTGCTAAAATGATCCCTGT
CTCCTCGTGTTTACATTCTGTGTGTGTCCCCTCCCACAATGTACCAAAGTTGTCTTTGTGACCAA
TAGAATATGGCAGAAGTGATGGCATGCCACTTCCAAGATTAGGTTATAAAAGACACTGCAGCTTC
TACTTGAGCCCTCTCTCTCTGCCACCCACCGCCCCAATCTATCTTGGCTCACTCGCTCTGGGGG
AAGCTAGCTGCCATGCTATGAGCAGGCCTATAAAGAGACTTACGTGGTAAAAAATGAAGTCTCCT
GCCCACAGCCACATTAGTGAACCTAGAAGCAGAGACTCTGTGAGATAATCGATGTTTGTTGTTTT
AAGTTGCTCAGTTTTGGTCTAACTTGTTATGCAGCAATAGATAAATAATATGCAGAGAAAGAG

FIGURE 152

MVLSGALCFRMKDSALKVLYLHNNQLLAGGLHAGKVIKGEEISVVPNRWLDASLSPVILGVQGGS
QCLSCGVGQEPTLTLEPVNIMELYLGAKESKSFTFYRRDMGLTSSFESAAYPGWFLCTVPEADQP
VRLTQLPENGGWNAPITDFYFQQCD

N-myristoylation sites.

amino acids 29-34, 30-35, 60-65, 63-68, 73-78, 91-96, 106-111

Interleukin-1 signature.

amino acids 111-131

Interleukin-1 proteins.

amino acids 8-29, 83-120, 95-134, 64-103

FIGURE 153

CTTCAGAACAGGTTCTCCTTCCCCAGTCACCAGTTGCTCGAGTTAGAATTGTCTGCAATGGCCGC
CCTGCAGAAATCTGTGAGCTCTTTCCTTATGGGGACCCTGGCCACCAGCTGCCTCCTTCTCTTGG
CCCTCTTGGTACAGGGAGGAGCAGCTGCGCCCATCAGCTCCCACTGCAGGCTTGACAAGTCCAAC
TTCCAGCAGCCCTATATCACCAACCGCACCTTCATGCTGGCTAAGGAGGCTAGCTTGGCTGATAA
CAACACAGACGTTCGTCTCATTGGGGAGAAACTGTTCCACGGAGTCAGTATGAGTGAGCGCTGCT
ATCTGATGAAGCAGGTGCTGAACTTCACCCTTGAAGAAGTGCTGTTCCCTCAATCTGATAGGTTC
CAGCCTTATATGCAGGAGGTGGTGCCCTTCCTGGCCAGGCTCAGCAACAGGCTAAGCACATGTCA
TATTGAAGGTGATGACCTGCATATCCAGAGGAATGTGCAAAAGCTGAAGGACACAGTGAAAAAGC
TTGGAGAGAGTGGAGAGATCAAAGCAATTGGAGAACTGGATTTGCTGTTTATGTCTCTGAGAAAT
GCCTGCATTTGACCAGAGCAAAGCTGAAAAATGAATAACTAACCCCCTTTCCCTGCTAGAAATAA
CAATTAGATGCCCCAAAGCGATTTTTTTTAACCAAAAGGAAGATGGGAAGCCAAACTCCATCATG
ATGGGTGGATTCCAAATGAACCCCTGCGTTAGTTACAAAGGAAACCAATGCCACTTTTGTTTATA
AGACCAGAAGGTAGACTTTCTAAGCATAGATATTTATTGATAACATTTCATTGTAACTGGTGTTC
TATACACAGAAAACAATTTATTTTTTAAATAATTGTCTTTTTCCATAAAAAAGATTACTTTCCAT
TCCTTTAGGGGAAAAAACCCCTAAATAGCTTCATGTTTCCATAATCAGTACTTTATATTTATAAA
TGTATTTATTATTATTATAAGACTGCATTTTATTTATATCATTTATTAATATGGATTTATTTAT
AGAAACATCATTCGATATTGCTACTTGAGTGTAAGGCTAATATTGATATTTATGACAATAATTAT
AGAGCTATAACATGTTTATTTGACCTCAATAAACACTTGGATATCCC

FIGURE 154

MAALQKSVSSFLMGTLATSCLLLLALLVQGGAAAPISSHCRLDKSNFQQPYITNRTFMLAKEASL
ADNNTDVRLIGEKLFHGVSMSERCYLMKQVLNFTLEEVLFPQSDRFQPYMQEVVPFLARLSNRLS
TCHIEGDDLHIQRNVQKLKDTVKKLGESGEIKAIGELDLLFMSLRNACI

Important features of the protein:

Signal peptide:

amino acids 1-33

N-glycosylation sites.

amino acids 54-58, 68-72, 97-101

N-myristoylation sites.

amino acids 14-20, 82-88

Prokaryotic membrane lipoprotein lipid attachment site.

amino acids 10-21

FIGURE 155

GGCTTGCTGAAAATAAAATCAGGACTCCTAACCTGCTCCAGTCAGCCTGCTTCCACGAGGCCTGT
CAGTCAGTGCCCGACTTGTGACTGAGTGTGCAGTGCCCAGCATGTACCAGGTCAGTGCAGAGGGC
TGCCTGAGGGCTGTGCTGAGAGGGAGAGGAGCAGAGATGCTGCTGAGGGTGGAGGGAGGCCAAGC
TGCCAGGTTTGGGGCTGGGGGCCAAGTGGAGTGAGAAACTGGGATCCCAGGGGGAGGGTGCAGAT
GAGGGAGCGACCCAGATTAGGTGAGGACAGTTCTCTCATTAGCCTTTTCCTACAGGTGGTTGCAT
TCTTGGCAATGGTCATGGGAACCCACACCTACAGCCACTGGCCCAGCTGCTGCCCCAGCAAGGG
CAGGACACCTCTGAGGAGCTGCTGAGGTGGAGCACTGTGCCTGTGCCTCCCTAGAGCCTGCTAG
GCCCAACCGCCACCCAGAGTCCTGTAGGGCCAGTGAAGATGGACCCCTCAACAGCAGGGCATCT
CCCCCTGGAGATATGAGTTGGACAGAGACTTGAACCGGCTCCCCCAGGACCTGTACCACGCCCGT
TGCCTGTGCCCGCACTGCGTCAGCCTACAGACAGGCTCCCACATGGACCCCCGGGGCAACTCGGA
GCTGCTCTACCACAACCAGACTGTCTTCTACAGGCGGCCATGCCATGGCGAGAAGGGCACCCACA
AGGGCTACTGCCTGGAGCGCAGGCTGTACCGTGTTTCCTTAGCTTGTGTGTGTGCGGCCCCGT
GTGATGGGCTAGCCGGACCTGCTGGAGGCTGGTCCCTTTTGGGAAACCTGGAGCCAGGTGTACA
ACCACTTGCCATGAAGGGCCAGGATGCCCAGATGCTTGGCCCCTGTGAAGTGCTGTCTGGAGCAG
CAGGATCCCGGGACAGGATGGGGGGCTTTGGGGAAAACCTGCACTTCTGCACATTTTGAAAAGAG
CAGCTGCTGCTTAGGGCCGCCGGAAGCTGGTGTCCTGTCATTTTCTCTCAGGAAAGGTTTTCAAA
GTTCTGCCCATTTCTGGAGGCCACCACTCCTGTCTCTTCCTCTTTTCCCATCCCTGCTACCCTG
GCCCAGCACAGGCACTTTCTAGATATTTCCCCCTTGCTGGAGAAGAAAGAGCCCCTGGTTTATT
TGTTTGTTTACTCATCACTCAGTGAGCATCTACTTTGGGTGCATTCTAGTGTAGTTACTAGTCTT
TTGACATGGATGATTCTGAGGAGGAAGCTGTTATTGAATGTATAGAGATTTATCCAAATAAATAT
CTTTATTTAAAAATGAAAAA

FIGURE 156

MRERPRLGEDSSLISLFLQVVAFLAMVMGTHTYSHWPSCCPSKGQDTSEELLRWSTVPVPPLEPA
RPNRHPESCRASEDGPLNSRAISPWRYELDRDLNRLPQDLYHARCLCPHCVSLQTGSHMDPRGNS
ELLYHNQTVFYRRPCHGEKGTHKGYCLERRLYRVSLACVCVRPRVMG

Important features of the protein:

Signal peptide:

amino acids 1-32

N-glycosylation site.

amino acids 136-140

Tyrosine kinase phosphorylation site.

amino acids 127-135

N-myristoylation sites.

amino acids 44-50, 150-156

FIGURE 157

CCGGC<u>ATG</u>TCGCTCGTGCTGCTAAGCCTGGCCGCGCTGTGCAGGAGCGCCGTACCCCGAGAGCC
GACCGTTCAATGTGGCTCTGAAACTGGGCCATCTCCAGAGTGGATGCTACAACATGATCTAATCC
CCGGAGACTTGAGGGACCTCCGAGTAGAACCTGTTACAACTAGTGTTGCAACAGGGGACTATTCA
ATTTTGATGAATGTAAGCTGGGTACTCCGGGCAGATGCCAGCATCCGCTTGTTGAAGGCCACCAA
GATTTGTGTGACGGGCAAAAGCAACTTCCAGTCCTACAGCTGTGTGAGGTGCAATTACACAGAGG
CCTTCCAGACTCAGACCAGACCCTCTGGTGGTAAATGGACATTTTCCTACATCGGCTTCCCTGTA
GAGCTGAACACAGTCTATTTCATTGGGGCCCATAATATTCCTAATGCAAATATGAATGAAGATGG
CCCTTCCATGTCTGTGAATTTCACCTCACCAGGCTGCCTAGACCACATAATGAAATATAAAAAAA
AGTGTGTCAAGGCCGGAAGCCTGTGGGATCCGAACATCACTGCTTGTAAGAAGAATGAGGAGACA
GTAGAAGTGAACTTCACAACCACTCCCCTGGGAAACAGATACATGGCTCTTATCCAACACAGCAC
TATCATCGGGTTTTCTCAGGTGTTTGAGCCACACCAGAAGAAACAAACGCGAGCTTCAGTGGTGA
TTCCAGTGACTGGGGATAGTGAAGGTGCTACGGTGCAGCTGACTCCATATTTTCCTACTTGTGGC
AGCGACTGCATCCGACATAAAGGAACAGTTGTGCTCTGCCCACAAACAGGCGTCCCTTTCCCTCT
GGATAACAACAAAAGCAAGCCGGGAGGCTGGCTGCCTCTCCTCCTGCTGTCTCTGCTGGTGGCCA
CATGGGTGCTGGTGGCAGGGATCTATCTAATGTGGAGGCACGAAAGGATCAAGAAGACTTCCTTT
TCTACCACCACACTACTGCCCCCATTAAGGTTCTTGTGGTTTACCCATCTGAAATATGTTTCCA
TCACACAATTTGTTACTTCACTGAATTTCTTCAAAACCATTGCAGAAGTGAGGTCATCCTTGAAA
AGTGGCAGAAAAGAAAATAGCAGAGATGGGTCCAGTGCAGTGGCTTGCCACTCAAAAGAAGGCA
GCAGACAAAGTCGTCTTCCTTCTTTCCAATGACGTCAACAGTGTGTGCGATGGTACCTGTGGCAA
GAGCGAGGGCAGTCCCAGTGAGAACTCTCAAGACCTCTTCCCCCTTGCCTTTAACCTTTTCTGCA
GTGATCTAAGAAGCCAGATTCATCTGCACAAATACGTGGTGGTCTACTTTAGAGAGATTGATACA
AAAGACGATTACAATGCTCTCAGTGTCTGCCCCAAGTACCACCTCATGAAGGATGCCACTGCTTT
CTGTGCAGAACTTCTCCATGTCAAGCAGCAGGTGTCAGCAGGAAAAGATCACAAGCCTGCCACG
ATGGCTGCTGCTCCTTG<u>TAG</u>

FIGURE 158

```
MSLVLLSLAALCRSAVPREPTVQCGSETGPSPEWMLQHDLIPGDLRDLRVEPVTTSVATGDYSILMNVSWV
LRADASIRLLKATKICVTGKSNFQSYSCVRCNYTEAFQTQTRPSGGKWTFSYIGFPVELNTVYFIGAHNIP
NANMNEDGPSMSVNFTSPGCLDHIMKYKKKCVKAGSLWDPNITACKKNEETVEVNFTTTPLGNRYMALIQH
STIIGFSQVFEPHQKKQTRASVVIPVTGDSEGATVQLTPYFPTCGSDCIRHKGTVVLCPQTGVPFPLDNNK
SKPGGWLPLLLLSLLVATWVLVAGIYLMWRHERIKKTSFSTTTLLPPIKVLVVYPSEICFHHTICYFTEFL
QNHCRSEVILEKWQKKKIAEMGPVQWLATQKKAADKVVFLLSNDVNSVCDGTCGKSEGSPSENSQDLFPLA
FNLFCSDLRSQIHLHKYVVVYFREIDTKDDYNALSVCPKYHLMKDATAFCAELLHVKQQVSAGKRSQACHD
GCCSL
```

Important features of the protein:

Signal peptide:

amino acids 1-14

Transmembrane domain:

amino acids 290-309

N-glycosylation sites.

amino acids 67 - 71, 103 - 107, 156 - 160, 183 - 187, 197 - 201 and 283 - 287 cAMP- and cGMP-dependent protein kinase phosphorylation sites.

amino acids 228 - 232 and 319 - 323

Casein kinase II phosphorylation sites.

amino acids 178 - 182, 402 - 406, 414 - 418 and 453 - 457

N-myristoylation site.

amino acids 116-122

Amidation site.

amino acids 488-452

FIGURE 159

AGCCACCAGCGCAACATGACAGTGAAGACCCTGCATGGCCCAGCCATGGTCAAGTACTTGCTGCT
GTCGATATTGGGGCTTGCCTTTCTGAGTGAGGCGGCAGCTCGGAAAATCCCCAAAGTAGGACATA
CTTTTTTCCAAAAGCCTGAGAGTTGCCCGCCTGTGCCAGGAGGTAGTATGAAGCTTGACATTGGC
ATCATCAATGAAAACCAGCGCGTTTCCATGTCACGTAACATCGAGAGCCGCTCCACCTCCCCCTG
GAATTACACTGTCACTTGGGACCCCAACCGGTACCCTCGGAAGTTGTACAGGCCCAGTGTAGGA
ACTTGGGCTGCATCAATGCTCAAGGAAAGGAAGACATCTCCATGAATTCCGTTCCCATCCAGCAA
GAGACCCTGGTCGTCCGGAGGAAGCACCAAGGCTGCTCTGTTTCTTTCCAGTTGGAGAAGGTGCT
GGTGACTGTTGGCTGCACCTGCGTCACCCCTGTCATCCACCATGTGCAGTAAGAGGTGCATATCC
ACTCAGCTGAAGAAG

FIGURE 160

MTVKTLHGPAMVKYLLLSILGLAFLSEAAARKIPKVGHTFFQKPESCPPVPGGSMKLDIGIINEN
QRVSMSRNIESRSTSPWNYTVTWDPNRYPSEVVQAQCRNLGCINAQGKEDISMNSVPIQQETLVV
RRKHQGCSVSFQLEKVLVTVGCTCVTPVIHHVQ

Signal sequence:
amino acids 1-30

N-glycosylation site.
amino acids 83-87

N-myristoylation sites.
amino acids 106-111, 136-141

FIGURE 161

```
ACACTGGCCAAACAAAAACGAAAGCACTCCGTGCTGGAAGTAGGAGGAGAGTCAGGACTCCCAGG
ACAGAGAGTGCACAAACTACCCAGCACAGCCCCTCCGCCCCCTCTGGAGGCTGAAGAGGGATTC
CAGCCCCTGCCACCCACAGACACGGGCTGACTGGGGTGTCTGCCCCCCTTGGGGGGGGGCAGCAC
AGGGCCTCAGGCCTGGGTGCCACCTGGCACCTAGAAGATGCCTGTGCCCTGGTTCTTGCTGTCCT
TGGCACTGGGCCGAAGCCCAGTGGTCCTTTCTCTGGAGAGGCTTGTGGGCCTCAGGACGCTACC
CACTGCTCTCCGGGCCTCTCCTGCCGCCTCTGGGACAGTGACATACTCTGCCTGCCTGGGGACAT
CGTGCCTGCTCCGGGCCCCGTGCTGGCGCCTACGCACCTGCAGACAGAGCTGGTGCTGAGGTGCC
AGAAGGAGACCGACTGTGACCTCTGTCTGCGTGTGGCTGTCCACTTGGCCGTGCATGGGCACTGG
GAAGAGCCTGAAGATGAGGAAAAGTTTGGAGGAGCAGCTGACTCAGGGGTGGAGGAGCCTAGGAA
TGCCTCTCTCCAGGCCCAAGTCGTGCTCTCCTTCCAGGCCTACCCTACTGCCCGCTGCGTCCTGC
TGGAGGTGCAAGTGCCTGCTGCCCTTGTGCAGTTTGGTCAGTCTGTGGGCTCTGTGGTATATGAC
TGCTTCGAGGCTGCCCTAGGGAGTGAGGTACGAATCTGGTCCTATACTCAGCCCAGGTACGAGAA
GGAACTCAACCACACACAGCAGCTGCCTGCCCTGCCCTGGCTCAACGTGTCAGCAGATGGTGACA
ACGTGCATCTGGTTCTGAATGTCTCTGAGGAGCAGCACTTCGGCCTCTCCCTGTACTGGAATCAG
GTCCAGGGCCCCCCAAAACCCCGGTGGCACAAAAACCTGACTGGACCGCAGATCATTACCTTGAA
CCACACAGACCTGGTTCCCTGCCTCTGTATTCAGGTGTGGCCTCTGGAACCTGACTCCGTTAGGA
CGAACATCTGCCCCTTCAGGGAGGACCCCGCGCACACCAGAACCTCTGGCAAGCCGCCCGACTG
CGACTGCTGACCCTGCAGAGCTGGCTGCTGGACGCACCGTGCTCGCTGCCCGCAGAAGCGGCACT
GTGCTGGCGGGCTCCGGGTGGGGGACCCCTGCCAGCCACTGGTCCCACCGCTTTCCTGGGAGAACG
TCACTGTGGACAAGGTTCTCGAGTTCCCATTGCTGAAAGGCCACCCTAACCTCTGTGTTCAGGTG
AACAGCTCGGAGAAGCTGCAGCTGCAGGAGTGCTTGTGGGCTGACTCCCTGGGGCCTCTCAAAGA
CGATGTGCTACTGTTGGAGACACGAGGCCCCCAGGACAACAGATCCCTCTGTGCCTTGGAACCCA
GTGGCTGTACTTCACTACCCAGCAAAGCCTCCACGAGGGCAGCTCGCCTTGGAGAGTACTTACTA
CAAGACCTGCAGTCAGGCCAGTGTCTGCAGCTATGGGACGATGACTTGGGAGCGCTATGGGCCTG
CCCCATGGACAAATACATCCACAAGCGCTGGGCCCTCGTGTGGCTGGCCTGCCTACTCTTTGCCG
CTGCGCTTTCCCTCATCCTCCTTCTCAAAAAGGATCACGCGAAAGGGTGGCTGAGGCTCTTGAAA
CAGGACGTCCGCTCGGGGCGGCCGCCAGGGCCGCGCGGCTCTGCTCCTCTACTCAGCCGATGA
CTCGGGTTTCGAGCGCCTGGTGGGCGCCCTGGCGTCGGCCCTGTGCCAGCTGCCGCTGCGCGTGG
CCGTAGACCTGTGGAGCCGTCGTGAACTGAGCGCGCAGGGGCCCGTGGCTTGGTTTCACGCGCAG
CGGCGCCAGACCCTGCAGGAGGGCGGCGTGGTGGTCTTGCTCTTCTCTCCCGGTGCGGTGGCGCT
GTGCAGCGAGTGGCTACAGGATGGGGTGTCCGGGCCCGGGGCGCACGGCCCGCACGACGCCTTCC
GCGCCTCGCTCAGCTGCGTGCTGCCCGACTTCTTGCAGGGCCGGGCGCCCGGCAGCTACGTGGGG
GCCTGCTTCGACAGGCTGCTCCACCCGGACGCCGTACCCGCCCTTTTCCGCACCGTGCCCGTCTT
CACACTGCCCTCCCAACTGCCAGACTTCCTGGGGGCCCTGCAGCAGCCTCGCGCCCCGCGTTCCG
GGCGGCTCCAAGAGAGAGCGGAGCAAGTGTCCCGGGCCCTTCAGCCAGCCCTGGATAGCTACTTC
CATCCCCGGGGACTCCCGCGCCGGGACGCGGGGTGGGACCAGGGGCGGGACCTGGGGCGGGGGA
CGGGACTTAAATAAAGGCAGACGCTGTTTTTCTAAAAAAA
```

FIGURE 162

```
MPVPWFLLSLALGRSPVVLSLERLVGPQDATHCSPGLSCRLWDSDILCLPGDIVPAPGPVLAPTHLQTELV
LRCQKETDCDLCLRVAVHLAVHGHWEEPEDEEKFGGAADSGVEEPRNASLQAQVVLSFQAYPTARCVLLEV
QVPAALVQFGQSVGSVVYDCFEAALGSEVRIWSYTQPRYEKELNHTQQLPALPWLNVSADGDNVHLVLNVS
EEQHFGLSLYWNQVQGPPKPRWHKNLTGPQIITLNHTDLVPCLCIQVWPLEPDSVRTNICPFREDPRAHQN
LWQAARLRLLTLQSWLLDAPCSLPAEAALCWRAPGGDPCQPLVPPLSWENVTVDKVLEFPLLKGHPNLCVQ
VNSSEKLQLQECLWADSLGPLKDDVLLLETRGPQDNRSLCALEPSGCTSLPSKASTRAARLGEYLLQDLQS
GQCLQLWDDDLGALWACPMDKYIHKRWALVWLACLLFAAALSLILLLKKDHAKGWLRLLKQDVRSGAAARG
RAALLLYSADDSGFERLVGALASALCQLPLRVAVDLWSRRELSAQGPVAWFHAQRRQTLQEGGVVVLLFSP
GAVALCSEWLQDGVSGPGAHGPHDAFRASLSCVLPDFLQGRAPGSYVGACFDRLLHPDAVPALFRTVPVFT
LPSQLPDFLGALQQPRAPRSGRLQERAEQVSRALQPALDSYFHPPGTPAPGRGVGPGAGPGAGDGT
```

Signal sequence:

amino acids 1-20

Transmembrane domain.

amino acids 453-475

N-glycosylation sites.

amino acids 118-121, 186-189, 198-201, 211-214, 238-241, 248-251, 334-337, 357-360, 391-394

Glycosaminoglycan attachment site.

amino acids 583-586 cAMP- and cGMP-dependent protein kinase phosphorylation site.

amino acids 552-555

N-myristoylation sites.

amino acids 107-112, 152-157, 319-324, 438-443, 516-521, 612-617, 692-697, 696-701, 700-705

FIGURE 163

```
GGGAGGGCTCTGTGCCAGCCCCGATGAGGACGCTGCTGACCATCTTGACTGTGGGATCCCTGGCT
GCTCACGCCCCTGAGGACCCCTCGGATCTGCTCCAGCACGTGAATTCCAGTCCAGCAACTTTGA
AAACATCCTGACGTGGGACAGCGGGCCAGAGGGCACCCCAGACACGGTCTACAGCATCGAGTATA
AGACGTACGGAGAGAGGGACTGGGTGGCAAAGAAGGGCTGTCAGCGGATCACCCGGAAGTCCTGC
AACCTGACGGTGGAGACGGGCAACCTCACGGAGCTCTACTATGCCAGGGTCACCGCT
GTCAGTGCGGGAGGCCGGTCAGCCACCAAGATGACTGACAGGTTCAGCTCTCTGCAGCACACTAC
CCTCAAGCCACCTGATGTGACCTGTATCTCCAAAGTGAGATCGATTCAGATGATTGTTCATCCTA
CCCCCACGCCAATCCGTGCAGGCGATGGCCACCGGCTAACCCTGGAAGACATCTTCCATGACCTG
TTCTACCACTTAGAGCTCCAGGTCAACCGCACCTACCAAATGCACCTTGGAGGGAAGCAGAGAGA
ATATGAGTTCTTCGGCCTGACCCCTGACACAGAGTTCCTTGGCACCATCATGATTTGCGTTCCCA
CCTGGGCCAAGGAGAGTGCCCCCTACATGTGCCGAGTGAAGACACTGCCAGACCGGACATGGACC
TACTCCTTCTCCGGAGCCTTCCTGTTCTCCATGGGCTTCCTCGTCGCAGTACTCTGCTACCTGAG
CTACAGATATGTCACCAAGCCGCCTGCACCTCCCAACTCCCTGAACGTCCAGCGAGTCCTGACTT
TCCAGCCGCTGCGCTTCATCCAGGAGCACGTCCTGATCCCTGTCTTTGACCTCAGCGGCCCCAGC
AGTCTGGCCCAGCCTGTCCAGTACTCCCAGATCAGGGTGTCTGGACCCAGGGAGCCCGCAGGAGC
TCCACAGCGGCATAGCCTGTCCGAGATCACCTACTTAGGGCAGCCAGACATCTCCATCCTCCAGC
CCTCCAACGTGCCACCTCCCCAGATCCTCTCCCCACTGTCCTATGCCCCAAACGCTGCCCTGAG
GTCGGGCCCCATCCTATGCACCTCAGGTGACCCCGAAGCTCAATTCCCATTCTACGCCCCACA
GGCCATCTCTAAGGTCCAGCCTTCCTCCTATGCCCCTCAAGCCACTCCGGACAGCTGGCCTCCCT
CCTATGGGGTATGCATGGAAGGTTCTGGCAAAGACTCCCCACTGGGACACTTTCTAGTCCTAAA
CACCTTAGGCCTAAAGGTCAGCTTCAGAAAGAGCCACCAGCTGGAAGCTGCATGTTAGGTGGCCT
TTCTCTGCAGGAGGTGACCTCCTTGGCTATGGAGGAATCCCAAGAAGCAAAATCATTGCACCAGC
CCCTGGGGATTTGCACAGACAGAACATCTGACCCAAATGTGCTACACAGTGGGGAGGAAGGGACA
CCACAGTACCTAAAGGGCCAGCTCCCCCTCCTCTCCTCAGTCCAGATCGAGGGCCACCCCATGTC
CCTCCCTTTGCAACCTCCTTCCGGTCCATGTTCCCCCTCGGACCAAGGTCCAAGTCCCTGGGGCC
TGCTGGAGTCCCTTGTGTGTCCCAAGGATGAAGCCAAGAGCCCAGCCCCTGAGACCTCAGACCTG
GAGCAGCCCACAGAACTGGATTCTCTTTTCAGAGGCCTGGCCCTGACTGTGCAGTGGGAGTCCTG
AGGGGAATGGGAAAGGCTTGGTGCTTCCTCCCTGTCCCTACCCAGTGTCACATCCTTGGCTGTCA
ATCCCATGCCTGCCCATGCCACACACTCTGCGATCTGGCCTCAGACGGGTGCCCTTGAGAGAAGC
AGAGGGAGTGGCATGCAGGGCCCCTGCCATGGGTGCGCTCCTCACCGGAACAAAGCAGCATGATA
AGGACTGCAGCGGGGGAGCTCTGGGGAGCAGCTTGTGTAGACAAGCGCGTGCTCGCTGAGCCCTG
CAAGGCAGAAATGACAGTGCAAGGAGGAAATGCAGGGAAACTCCCGAGGTCCAGAGCCCCACCTC
CTAACACCATGGATTCAAAGTGCTCAGGGAATTTGCCTCTCCTTGCCCCATTCCTGGCCAGTTTC
ACAATCTAGCTCGACAGAGCATGAGGCCCCTGCCTCTTCTGTCATTGTTCAAAGGTGGGAAGAGA
GCCTGGAAAAGAACCAGGCCTGGAAAAGAACCAGAAGGAGGCTGGGCAGAACCAGAACAACCTGC
ACTTCTGCCAAGGCCAGGGCCAGCAGGACGGCAGGACTCTAGGGAGGGGTGTGGCCTGCAGCTCA
TTCCCAGCCAGGGCAACTGCCTGACGTTGCACGATTTCAGCTTCATTCCTCTGATAGAACAAAGC
GAAATGCAGGTCCACCAGGGAGGGAGACACACAAGCCTTTCTGCAGGCAGGAGTTTCAGACCCT
ATCCTGAGAATGGGGTTTGAAAGGAAGGTGAGGGCTGTGGCCCCTGGACGGGTACAATAACACAC
TGTACTGATGTCACAACTTTGCAAGCTCTGCCTTGGGTTCAGCCCATCTGGGCTCAAATTCCAGC
CTCACCACTCACAAGCTGTGTGACTTCAAACAAATGAAATCAGTGCCCAGAACCTCGGTTTCCTC
ATCTGTAATGTGGGGATCATAACACCTACCTCATGGAGTTGTGGTGAAGATGAAATGAAGTCATG
TCTTTAAAGTGCTTAATAGTGCCTGGTACATGGGCAGTGCCCAATAAACGGTAGCTATTTAAAAA
AAAAAAA
```

FIGURE 164

MRTLLTILTVGSLAAHAPEDPSDLLQHVKFQSSNFENILTWDSGPEGTPDTVYSIEYKTYGERDW
VAKKGCQRITRKSCNLTVETGNLTELYYARVTAVSAGGRSATKMTDRFSSLQHTTLKPPDVTCIS
KVRSIQMIVHPTPTPIRAGDGHRLTLEDIFHDLFYHLELQVNRTYQMHLGGKQREYEFFGLTPDT
EFLGTIMICVPTWAKESAPYMCRVKTLPDRTWTYSFSGAFLFSMGFLVAVLCYLSYRYVTKPPAP
PNSLNVQRVLTFQPLRFIQEHVLIPVFDLSGPSSLAQPVQYSQIRVSGPREPAGAPQRHSLSEIT
YLGQPDISILQPSNVPPPQILSPLSYAPNAAPEVGPPSYAPQVTPEAQFPFYAPQAISKVQPSSY
APQATPDSWPPSYGVCMEGSGKDSPTGTLSSPKHLRPKGQLQKEPPAGSCMLGGLSLQEVTSLAM
EESQEAKSLHQPLGICTDRTSDPNVLHSGEEGTPQYLKGQLPLLSSVQIEGHPMSLPLQPPSGPC
SPSDQGPSPWGLLESLVCPKDEAKSPAPETSDLEQPTELDSLFRGLALTVQWES

Signal sequence.
amino acids 1-17

Transmembrane domain.
amino acids 233-250

N-glycosylation sites.
amino acids 80-83, 87-90, 172-175

N-myristoylation sites.
amino acids 11-16, 47-52, 102-107, 531-536, 565-570

FIGURE 165

TGGCCTACTGGAAAAAAAAAAAAAAAAAAAAAAGTCACCCGGGCCCGCGGTGGCCACAACATGG
CTGCGGCGCCGGGGCTGCTCTTCTGGCTGTTCGTGCTGGGGGCGCTCTGGTGGGTCCCGGGCCAG
TCGGATCTCAGCCACGGACGGCGTTTCTCGGACCTCAAAGTGTGCGGGGACGAAGAGTGCAGCAT
GTTAATGTACCGTGGGAAAGCTCTTGAAGACTTCACGGGCCCTGATTGTCGTTTTGTGAATTTTA
AAAAGGTGACGATGTATATGTCTACTACAAACTGGCAGGGGGATCCCTTGAACTTTGGGCTGGA
AGTGTTAACACAGTTTTGGATATTTTCCAAAAGATTTGATCAAGGTACTTCATAAATACACGGA
AGAAGAGCTACATATTCCAGCAGATGAGACAGACTTTGTCTGCTTTGAAGGAGGAAGAGATGATT
TTAATAGTTATAATGTAGAAGAGCTTTTAGGATCTTTGGAACTGGAGGACTCTGTACCTGAAGAG
TCGAAGAAAGCTGAAGAAGTTTCTCAGCACAGAGAGAAATCTCCTGAGGAGTCTCGGGGGCGTGA
ACTTGACCCTGTGCCTGAGCCCGAGGCATTCAGAGCTGATTCAGAGGATGGAGAAGGTGCTTTCT
CAGAGAGCACCGAGGGGCTGCAGGGACAGCCCTCAGCTCAGGAGAGCCACCCTCACACCAGCGGT
CCTGCGGCTAACGCTCAGGGAGTGCAGTCTTCGTTGGACACTTTTGAAGAAATTCTGCACGATAA
ATTGAAAGTGCCGGGAAGCGAAAGCAGAACTGGCAATAGTTCTCCTGCCTCGGTGGAGCGGGAGA
AGACAGATGCTTACAAAGTCCTGAAAACAGAAATGAGTCAGAGAGGAAGTGGACAGTGCGTTATT
CATTACAGCAAAGGATTTCGTTGGCATCAAAATCTAAGTTTGTTTTACAAAGATTGTTTTTAGTA
CTAAGCTGCCTTGGCAGTTTGCATTTTGAGCCAAACAAAATATATTATTTTCCCTTCTAAGTA
AAAAAAAAAAAAAAAAAA

FIGURE 166

MAAAPGLLFWLFVLGALWWVPGQSDLSHGRRFSDLKVCGDEECSMLMYRGKALEDFTGPDCRFVN
FKKGDDVYVYYKLAGGSLELWAGSVEHSFGYFPKDLIKVLHKYTEEELHIPADETDFVCFEGGRD
DFNSYNVEELLGSLELEDSVPEESKKAEEVSQHREKSPEESRGRELDPVPEPEAFRADSEDGEGA
FSESTEGLQGQPSAQESHPHTSGPAANAQGVQSSLDTFEEILHDKLKVPGSESRTGNSSPASVER
EKTDAYKVLKTEMSQRGSGQCVIHYSKGFRWHQNLSLFYKDCF

Important features of the protein:
Signal peptide:
amino acids 1-22

N-glycosylation site.
amino acids 294-298 cAMP- and cGMP-dependent protein kinase phosphorylation site.
amino acids 30-34

Tyrosine kinase phosphorylation site.
amino acids 67-76

N-myristoylation sites.
amino acids 205-211, 225-231, 277-283

Amidation site.
amino acids 28-32

FIGURE 167

```
CCAGGACCAGGGCGCACCGGCTCAGCCTCTCACTTGTCAGAGGCCGGGGAAGAGAAGCAAAGCGC
AACGGTGTGGTCCAAGCCGGGGCTTCTGCTTCGCCTCTAGGACATACACGGGACCCCCTAACTTC
AGTCCCCCAAACGCGCACCCTCGAAGTCTTGAACTCCAGCCCCGCACATCCACGCGCGGCACAGG
CGCGGCAGGCGGCAGGTCCCGGCCGAAGGCGATGCGCGCAGGGGGTCGGGCAGCTGGGCTCGGGC
GGCGGGAGTAGGGCCCGGCAGGGAGGCAGGGAGGCTGCATATTCAGAGTCGCGGGCTGCGCCCTG
GGCAGAGGCCGCCCTCGCTCCACGCAACACCTGCTGCTGCCACCGCGCCGCGATGAGCCGCGTGG
TCTCGCTGCTGCTGGGCGCCGCGCTGCTCTGCGGCACGGAGCCTTCTGCCGCCGCGTGGTCAGC
GGCCAAAAGGTGTGTTTTGCTGACTTCAAGCATCCCTGCTACAAAATGGCCTACTTCCATGAACT
GTCCAGCCGAGTGAGCTTTCAGGAGGCACGCCTGGCTTGTGAGAGTGAGGGAGGAGTCCTCCTCA
GCCTTGAGAATGAAGCAGAACAGAAGTTAATAGAGAGCATGTTGCAAAACCTGACAAAACCCGGG
ACAGGGATTTCTGATGGTGATTTCTGGATAGGGCTTTGGAGGAATGGAGATGGGCAAACATCTGG
TGCCTGCCCAGATCTCTACCAGTGGTCTGATGGAAGCAATTCCCAGTACCGAAACTGGTACACAG
ATGAACCTTCCTGCGGAAGTGAAAAGTGTGTTGTGATGTATCACCAACCAACTGCCAATCCTGGC
CTTGGGGGTCCCTACCTTTACCAGTGGAATGATGACAGGTGTAACATGAAGCACAATTATATTTG
CAAGTATGAACCAGAGATTAATCCAACAGCCCTGTAGAAAAGCCTTATCTTACAAATCAACCAG
GAGACACCCATCAGAATGTGGTTGTTACTGAAGCAGGTATAATTCCCAATCTAATTTATGTTGTT
ATACCAACAATACCCCTGCTCTTACTGATACTGGTTGCTTTTGGAACCTGTTGTTTCCAGATGCT
GCATAAAAGTAAAGGAAGAACAAAAACTAGTCCAAACCAGTCTACACTGTGGATTTCAAAGAGTA
CCAGAAAAGAAAGTGGCATGGAAGTATAATAACTCATTGACTTGGTTCCAGAATTTTGTAATTCT
GGATCTGTATAAGGAATGGCATCAGAACAATAGCTTGGAATGGCTTGAAATCACAAAGGATCTGC
AAGATGAACTGTAAGCTCCCCCTTGAGGCAAATATTAAAGTAATTTTTATATGTCTATTATTTCA
TTTAAAGAATATGCTGTGCTAATAATGGAGTGAGACATGCTTATTTTGCTAAAGGATGCACCCAA
ACTTCAAACTTCAAGCAAATGAAATGGACAATGCAGATAAAGTTGTTATCAACACGTCGGGAGTA
TGTGTGTTAGAAGCAATTCCTTTTATTTCTTTCACCTTTCATAAGTTGTTATCTAGTCAATGTAA
TGTATATTGTATTGAAATTTACAGTGTGCAAAAGTATTTTACCTTTGCATAAGTGTTTGATAAAA
ATGAACTGTTCTAATATTTATTTTTATGGCATCTCATTTTTCAATACATGCTCTTTTGATTAAAG
AAACTTATTACTGTTGTCAACTGAATTCACACACACACAAATATAGTACCATAGAAAAGTTTGT
TTTCTCGAAATAATTCATCTTTCAGCTTCTCTGCTTTTGGTCAATGTCTAGGAAATCTCTTCAGA
AATAAGAAGCTATTTCATTAAGTGTGATATAAACCTCCTCAAACATTTTACTTAGAGGCAAGGAT
TGTCTAATTTCAATTGTGCAAGACATGTGCCTTATAATTATTTTTAGCTTAAAATTAAACAGATT
TTGTAATAATGTAACTTTGTTAATAGGTGCATAAACACTAATGCAGTCAATTTGAACAAAAGAAG
TGACATACACAATATAAATCATATGTCTTCACACGTTGCCTATATAATGAGAAGCAGCTCTCTGA
GGGTTCTGAAATCAATGTGGTCCCTCTCTTGCCCACTAAACAAAGATGGTTGTTCGGGGTTTGGG
ATTGACACTGGAGGCAGATAGTTGCAAAGTTAGTCTAAGGTTTCCCTAGCTGTATTTAGCCTCTG
ACTATATTAGTATACAAAGAGGTCATGTGGTTGAGACCAGGTGAATAGTCACTATCAGTGTGGAG
ACAAGCACAGCACACAGACATTTTAGGAAGGAAAGGAACTACGAAATCGTGTGAAAATGGGTTGG
AACCCATCAGTGATCGCATATTCATTGATGAGGGTTTGCTTGAGATAGAAAATGGTGGCTCCTTT
CTGTCTTATCTCCTAGTTTCTTCAATGCTTACGCCTTGTTCTTCTCAAGAGAAAGTTGTAACTCT
CTGGTCTTCATATGTCCCTGTGCTCCTTTTAACCAAATAAAGAGTTCTTGTTTCTGGGGGAAAAA
AAAAAAAAAAAAAAAAAAAAAAAAAAAAAAAAAA
```

FIGURE 168

MSRVVSLLLGAALLCGHGAFCRRVVSGQKVCFADFKHPCYKMAYFHELSSRVSFQEARLACESE
GGVLLSLENEAEQKLIESMLQNLTKPGTGISDGDFWIGLWRNGDGQTSGACPDLYQWSDGSNSQ
YRNWYTDEPSCGSEKCVVMYHQPTANPGLGGPYLYQWNDDRCNMKHNYICKYEPEINPTAPVEK
PYLTNQPGDTHQNVVVTEAGIIPNLIYVVIPTIPLLLLILVAFGTCCFQMLHKSKGRTKTSPNQ
STLWISKSTRKESGMEV

Important features of the protein:
Signal peptide:
amino acids 1-21

Transmembrane domain:
amino acids 214-235

N-glycosylation sites.
amino acids 86-89, 255-258 cAMP- and cGMP-dependent protein kinase phosphorylation site.
amino acids 266-269

N-myristoylation sites.
amino acids 27-32, 66-71, 91-96, 93-98, 102-107, 109-114, 140-145, 212-217

US 7,202,335 B2

PRO300 POLYPEPTIDES

RELATED APPLICATIONS

This application is a continuation of, and claims priority under 35 USC §120 to, U.S. application Ser. No. 10/006,867 filed Dec. 6, 2001, which is a continuation of, and claims priority under 35 USC §120 to, PCT Application PCT/US00/23328 filed Aug. 24, 2000, which is a continuation-in part of, and claims priority under 35 USC §120 to, U.S. application Ser. No. 09/380,138 filed Aug. 25, 1999, now abandoned, which is the National Stage filed under 35 USC §371 of PCT Application PCT/US99/05028 filed Mar. 8, 1999, which claims priority under 35 USC §119 to U.S. Provisional Application 60/082,797 filed Apr. 22, 1998.

FIELD OF THE INVENTION

The present invention relates generally to the identification and isolation of novel DNA and to the recombinant production of novel polypeptides.

BACKGROUND OF THE INVENTION

Extracellular proteins play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. These secreted polypeptides or signaling molecules normally pass through the cellular secretory pathway to reach their site of action in the extracellular environment.

Secreted proteins have various industrial applications, including as pharmaceuticals, diagnostics, biosensors and bioreactors. Most protein drugs available at present, such as thrombolytic agents, interferons, interleukins, erythropoietins, colony stimulating factors, and various other cytokines, are secretory proteins. Their receptors, which are membrane proteins, also have potential as therapeutic or diagnostic agents. Efforts are being undertaken by both industry and academia to identify new, native secreted proteins. Many efforts are focused on the screening of mammalian recombinant DNA libraries to identify the coding sequences for novel secreted proteins. Examples of screening methods and techniques are described in the literature [see, for example, Klein et al., Proc. Natl. Acad. Sci. 93:7108–7113 (1996); U.S. Pat. No. 5,536,637)].

Membrane-bound proteins and receptors can play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. Such membrane-bound proteins and cell receptors include, but are not limited to, cytokine receptors, receptor kinases, receptor phosphatases, receptors involved in cell—cell interactions, and cellular adhesin molecules like selectins and integrins. For instance, transduction of signals that regulate cell growth and differentiation is regulated in part by phosphorylation of various cellular proteins. Protein tyrosine kinases, enzymes that catalyze that process, can also act as growth factor receptors. Examples include fibroblast growth factor receptor and nerve growth factor receptor.

Membrane-bound proteins and receptor molecules have various industrial applications, including as pharmaceutical and diagnostic agents. Receptor immunoadhesins, for instance, can be employed as therapeutic agents to block receptor-ligand interactions. The membrane-bound proteins can also be employed for screening of potential peptide or small molecule inhibitors of the relevant receptor/ligand interaction.

Efforts are being undertaken by both industry and academia to identify new, native receptor or membrane-bound proteins. Many efforts are focused on the screening of mammalian recombinant DNA libraries to identify the coding sequences for novel receptor or membrane-bound proteins.

SUMMARY OF THE INVENTION

In one embodiment, the invention provides an isolated nucleic acid molecule comprising a nucleotide sequence that encodes a PRO polypeptide.

In one aspect, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule encoding a PRO polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein, or (b) the complement of the DNA molecule of (a).

In other aspects, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule comprising the coding sequence of a full-length PRO polypeptide cDNA as disclosed herein, the coding sequence of a PRO polypeptide lacking the signal peptide as disclosed herein, the coding sequence of an extracellular domain of a transmembrane PRO polypeptide, with or without the signal peptide, as disclosed herein or the coding sequence of any other specifically defined fragment of the full-length amino acid sequence as disclosed herein, or (b) the complement of the DNA molecule of (a).

In a further aspect, the invention concerns an isolated nucleic acid molecule comprising a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule that encodes the same mature polypeptide encoded by any of the human protein cDNAs deposited with the ATCC as disclosed herein, or (b) the complement of the DNA molecule of (a).

Another aspect the invention provides an isolated nucleic acid molecule comprising a nucleotide sequence encoding a PRO polypeptide which is either transmembrane domain-deleted or transmembrane domain-inactivated, or is complementary to such encoding nucleotide sequence, wherein the transmembrane domain(s) of such polypeptide are disclosed herein. Therefore, soluble extracellular domains of the herein described PRO polypeptides are contemplated.

Another embodiment is directed to fragments of a PRO polypeptide coding sequence, or the complement thereof, that may find use as, for example, hybridization probes, for encoding fragments of a PRO polypeptide that may optionally encode a polypeptide comprising a binding site for an anti-PRO antibody or as antisense oligonucleotide probes. Such nucleic acid fragments are usually at least about 20 nucleotides in length, alternatively at least about 30 nucleotides in length, alternatively at least about 40 nucleotides in length, alternatively at least about 50 nucleotides in length, alternatively at least about 60 nucleotides in length, alternatively at least about 70 nucleotides in length, alternatively at least about 80 nucleotides in length, alternatively at least about 90 nucleotides in length, alternatively at least about 100 nucleotides in length, alternatively at least about 110 nucleotides in length, alternatively at least about 120 nucleotides in length, alternatively at least about 130 nucleotides in length, alternatively at least about 140 nucleotides in length, alternatively at least about 150 nucleotides in length, alternatively at least about 160 nucleotides in length, alternatively at least about 170 nucleotides in length, alternatively at least about 180 nucleotides in length, alternatively at least about 190 nucleotides in length, alternatively at least about 200 nucleotides in length, alternatively at least about 250 nucleotides in length, alternatively at least about 300 nucleotides in length, alternatively at least about 350 nucleotides in length, alternatively at least about 400 nucleotides in length, alternatively at least about 450 nucleotides in length, alternatively at least about 500 nucleotides in length, alternatively at least about 600 nucleotides in length, alternatively at least about 700 nucleotides in length, alternatively at least about 800 nucleotides in length, alternatively at least about 900 nucleotides in length and alternatively at least about 1000 nucleotides in length, wherein in this context the term "about" means the referenced nucleotide sequence length plus or minus 10% of that referenced length. It is noted that novel fragments of a PRO polypeptide-encoding nucleotide sequence may be determined in a routine manner by aligning the PRO polypeptide-encoding nucleotide sequence with other known nucleotide sequences using any of a number of well known sequence alignment programs and determining which PRO polypeptide-encoding nucleotide sequence fragment(s) are novel. All of such PRO polypeptide-encoding nucleotide sequences are contemplated herein. Also contemplated are the PRO polypeptide fragments encoded by these nucleotide molecule fragments, preferably those PRO polypeptide fragments that comprise a binding site for an anti-PRO antibody.

In another embodiment, the invention provides isolated PRO polypeptide encoded by any of the isolated nucleic acid sequences hereinabove identified.

In a certain aspect, the invention concerns an isolated PRO polypeptide, comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a PRO polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein.

In a further aspect, the invention concerns an isolated PRO polypeptide comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to an amino acid sequence encoded by any of the human protein cDNAs deposited with the ATCC as disclosed herein.

In a specific aspect, the invention provides an isolated PRO polypeptide without the N-terminal signal sequence and/or the initiating methionine and is encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of the PRO polypeptide and recovering the PRO polypeptide from the cell culture.

Another aspect the invention provides an isolated PRO polypeptide which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the PRO polypeptide and recovering the PRO polypeptide from the cell culture.

In yet another embodiment, the invention concerns agonists and antagonists of a native PRO polypeptide as defined herein. In a particular embodiment, the agonist or antagonist is an anti-PRO antibody or a small molecule.

In a further embodiment, the invention concerns a method of identifying agonists or antagonists to a PRO polypeptide which comprise contacting the PRO polypeptide with a candidate molecule and monitoring a biological activity mediated by said PRO polypeptide. Preferably, the PRO polypeptide is a native PRO polypeptide.

In a still further embodiment, the invention concerns a composition of matter comprising a PRO polypeptide, or an agonist or antagonist of a PRO polypeptide as herein described, or an anti-PRO antibody, in combination with a carrier. Optionally, the carrier is a pharmaceutically acceptable carrier.

Another embodiment of the present invention is directed to the use of a PRO polypeptide, or an agonist or antagonist thereof as hereinbefore described, or an anti-PRO antibody, for the preparation of a medicament useful in the treatment of a condition which is responsive to the PRO polypeptide, an agonist or antagonist thereof or an anti-PRO antibody.

In other embodiments of the present invention, the invention provides vectors comprising DNA encoding any of the herein described polypeptides. Host cell comprising any such vector are also provided. By way of example, the host cells may be CHO cells, *E. Coli*, or yeast. A process for producing any of the herein described polypeptides is further provided and comprises culturing host cells under conditions suitable for expression of the desired polypeptide and recovering the desired polypeptide from the cell culture.

In other embodiments, the invention provides chimeric molecules comprising any of the herein described polypeptides fused to a heterologous polypeptide or amino acid sequence. Example of such chimeric molecules comprise any of the herein described polypeptides fused to an epitope tag sequence or a Fc region of an immunoglobulin.

In another embodiment, the invention provides an antibody which binds, preferably specifically, to any of the above or below described polypeptides. Optionally, the antibody is a monoclonal antibody, humanized antibody, antibody fragment or single-chain antibody.

In yet other embodiments, the invention provides oligonucleotide probes useful for isolating genomic and cDNA nucleotide sequences or as antisense probes, wherein those probes may be derived from any of the above or below described nucleotide sequences.

In yet other embodiments, the present invention is directed to methods of using the PRO polypeptides of the present invention for a variety of uses based upon the functional biological assay data presented in the Examples below.

BRIEF DESCRIPTION OF THE DRAWINGS

FIG. 1 shows a nucleotide sequence (SEQ ID NO:1) of a native sequence PRO180 cDNA, wherein SEQ ID NO:1 is a clone designated herein as "DNA26843-1389".

FIG. 2 shows the amino acid sequence (SEQ ID NO:2) derived from the coding sequence of SEQ ID NO:1 shown in FIG. 1.

FIG. 3 shows a nucleotide sequence (SEQ ID NO:3) of a native sequence PRO218 cDNA, wherein SEQ ID NO:3 is a clone designated herein as "DNA30867-1335".

FIG. 4 shows the amino acid sequence (SEQ ID NO:4) derived from the coding sequence of SEQ ID NO:3 shown in FIG. 3.

FIG. 5 shows a nucleotide sequence (SEQ ID NO:5) of a native sequence PRO263 cDNA, wherein SEQ ID NO:5 is a clone designated herein as "DNA34431-1177".

FIG. 6 shows the amino acid sequence (SEQ ID NO:6) derived from the coding sequence of SEQ ID NO:5 shown in FIG. 5.

FIG. 7 shows a nucleotide sequence (SEQ ID NO:7) of a native sequence PRO295 cDNA, wherein SEQ ID NO:7 is a clone designated herein as "DNA38268-1188".

FIG. 8 shows the amino acid sequence (SEQ ID NO:8) derived from the coding sequence of SEQ ID NO:7 shown in FIG. 7.

FIG. 9 shows a nucleotide sequence (SEQ ID NO:9) of a native sequence PRO874 cDNA, wherein SEQ ID NO:9 is a clone designated herein as "DNA40621-1440".

FIG. 10 shows the amino acid sequence (SEQ ID NO:10) derived from the coding sequence of SEQ ID NO:9 shown in FIG. 9.

FIG. 11 shows a nucleotide sequence (SEQ ID NO:11) of a native sequence PRO300 cDNA, wherein SEQ ID NO:11 is a clone designated herein as "DNA40625-1189".

FIG. 12 shows the amino acid sequence (SEQ ID NO:12) derived from the coding sequence of SEQ ID NO:11 shown in FIG. 11.

FIG. 13 shows a nucleotide sequence (SEQ ID NO:13) of a native sequence PRO1864 cDNA, wherein SEQ ID NO:13 is a clone designated herein as "DNA45409-2511".

FIG. 14 shows the amino acid sequence (SEQ ID NO:14) derived from the coding sequence of SEQ ID NO:13 shown in FIG. 13.

FIG. 15 shows a nucleotide sequence (SEQ ID NO:15) of a native sequence PRO1282 cDNA, wherein SEQ ID NO:15 is a clone designated herein as "DNA45495-1550".

FIG. 16 shows the amino acid sequence (SEQ ID NO:16) derived from the coding sequence of SEQ ID NO:15 shown in FIG. 15.

FIG. 17 shows a nucleotide sequence (SEQ ID NO:17) of a native sequence PRO1063 cDNA, wherein SEQ ID NO:17 is a clone designated herein as "DNA49820-1427".

FIG. 18 shows the amino acid sequence (SEQ ID NO:18) derived from the coding sequence of SEQ ID NO:17 shown in FIG. 17.

FIG. 19 shows a nucleotide sequence (SEQ ID NO:19) of a native sequence PRO1773 cDNA, wherein SEQ ID NO:19 is a clone designated herein as "DNA56406-1704".

FIG. 20 shows the amino acid sequence (SEQ ID NO:20) derived from the coding sequence of SEQ ID NO:19 shown in FIG. 19.

FIG. 21 shows a nucleotide sequence (SEQ ID NO:21) of a native sequence PRO1013 cDNA, wherein SEQ ID NO:21 is a clone designated herein as "DNA56410-1414".

FIG. 22 shows the amino acid sequence (SEQ ID NO:22) derived from the coding sequence of SEQ ID NO:21 shown in FIG. 21.

FIG. 23 shows a nucleotide sequence (SEQ ID NO:23) of a native sequence PRO937 cDNA, wherein SEQ ID NO:23 is a clone designated herein as "DNA56436-1448".

FIG. 24 shows the amino acid sequence (SEQ ID NO:24) derived from the coding sequence of SEQ ID NO:23 shown in FIG. 23.

FIG. 25 shows a nucleotide sequence (SEQ ID NO:25) of a native sequence PRO842 cDNA, wherein SEQ ID NO:25 is a clone designated herein as "DNA56855-1447".

FIG. 26 shows the amino acid sequence (SEQ ID NO:26) derived from the coding sequence of SEQ ID NO:25 shown in FIG. 25.

FIG. 27 shows a nucleotide sequence (SEQ ID NO:27) of a native sequence PRO1180 cDNA, wherein SEQ ID NO:27 is a clone designated herein as "DNA56860-1510".

FIG. 28 shows the amino acid sequence (SEQ ID NO:28) derived from the coding sequence of SEQ ID NO:27 shown in FIG. 27.

FIG. 29 shows a nucleotide sequence (SEQ ID NO:29) of a native sequence PRO831 cDNA, wherein SEQ ID NO:29 is a clone designated herein as "DNA56862-1343".

FIG. 30 shows the amino acid sequence (SEQ ID NO:30) derived from the coding sequence of SEQ ID NO:29 shown in FIG. 29.

FIG. 31 shows a nucleotide sequence (SEQ ID NO:31) of a native sequence PRO1115 cDNA, wherein SEQ ID NO:31 is a clone designated herein as "DNA56868-1478".

FIG. 32 shows the amino acid sequence (SEQ ID NO:32) derived from the coding sequence of SEQ ID NO:31 shown in FIG. 31.

FIG. 33 shows a nucleotide sequence (SEQ ID NO:33) of a native sequence PRO1277 cDNA, wherein SEQ ID NO:33 is a clone designated herein as "DNA56869-1545".

FIG. 34 shows the amino acid sequence (SEQ ID NO:34) derived from the coding sequence of SEQ ID NO:33 shown in FIG. 33.

FIG. 35 shows a nucleotide sequence (SEQ ID NO:35) of a native sequence PRO1074 cDNA, wherein SEQ ID NO:35 is a clone designated herein as "DNA57704-1452".

FIG. 36 shows the amino acid sequence (SEQ ID NO:36) derived from the coding sequence of SEQ ID NO:35 shown in FIG. 35.

FIG. 37 shows a nucleotide sequence (SEQ ID NO:37) of a native sequence PRO1344 cDNA, wherein SEQ ID NO:37 is a clone designated herein as "DNA58723-1588".

FIG. 38 shows the amino acid sequence (SEQ ID NO:38) derived from the coding sequence of SEQ ID NO:37 shown in FIG. 37.

FIG. 39 shows a nucleotide sequence (SEQ ID NO:39) of a native sequence PRO1136 cDNA, wherein SEQ ID NO:39 is a clone designated herein as "DNA57827-1493".

FIG. 40 shows the amino acid sequence (SEQ ID NO:40) derived from the coding sequence of SEQ ID NO:39 shown in FIG. 39.

FIG. 41 shows a nucleotide sequence (SEQ ID NO:41) of a native sequence PRO1109 cDNA, wherein SEQ ID NO:41 is a clone designated herein as "DNA58737-1473".

FIG. 42 shows the amino acid sequence (SEQ ID NO:42) derived from the coding sequence of SEQ ID NO:41 shown in FIG. 41.

FIG. 43 shows a nucleotide sequence (SEQ ID NO:43) of a native sequence PRO1003 cDNA, wherein SEQ ID NO:43 is a clone designated herein as "DNA58846-1409".

FIG. 44 shows the amino acid sequence (SEQ ID NO:44) derived from the coding sequence of SEQ ID NO:43 shown in FIG. 43.

FIG. 45 shows a nucleotide sequence (SEQ ID NO:45) of a native sequence PRO1138 cDNA, wherein SEQ ID NO:45 is a clone designated herein as "DNA58850-1495".

FIG. 46 shows the amino acid sequence (SEQ ID NO:46) derived from the coding sequence of SEQ ID NO:45 shown in FIG. 45.

FIG. 47 shows a nucleotide sequence (SEQ ID NO:47) of a native sequence PRO994 cDNA, wherein SEQ ID NO:47 is a clone designated herein as "DNA58855-1422".

FIG. 48 shows the amino acid sequence (SEQ ID NO:48) derived from the coding sequence of SEQ ID NO:47 shown in FIG. 47.

FIG. 49 shows a nucleotide sequence (SEQ ID NO:49) of a native sequence PRO1069 cDNA, wherein SEQ ID NO:49 is a clone designated herein as "DNA59211-1450".

FIG. 50 shows the amino acid sequence (SEQ ID NO:50) derived from the coding sequence of SEQ ID NO:49 shown in FIG. 49.

FIG. 51 shows a nucleotide sequence (SEQ ID NO:51) of a native sequence PRO1411 cDNA, wherein SEQ ID NO:51 is a clone designated herein as "DNA59212-1627".

FIG. 52 shows the amino acid sequence (SEQ ID NO:52) derived from the coding sequence of SEQ ID NO:51 shown in FIG. 51.

FIG. 53 shows a nucleotide sequence (SEQ ID NO:53) of a native sequence PRO1129 cDNA, wherein SEQ ID NO:53 is a clone designated herein as "DNA59213-1487".

FIG. 54 shows the amino acid sequence (SEQ ID NO:54) derived from the coding sequence of SEQ ID NO:53 shown in FIG. 53.

FIG. 55 shows a nucleotide sequence (SEQ ID NO:55) of a native sequence PRO1027 cDNA, wherein SEQ ID NO:55 is a clone designated herein as "DNA59605-1418".

FIG. 56 shows the amino acid sequence (SEQ ID NO:56) derived from the coding sequence of SEQ ID NO:55 shown in FIG. 55.

FIG. 57 shows a nucleotide sequence (SEQ ID NO:57) of a native sequence PRO1106 cDNA, wherein SEQ ID NO:57 is a clone designated herein as "DNA59609-1470".

FIG. 58 shows the amino acid sequence (SEQ ID NO:58) derived from the coding sequence of SEQ ID NO:57 shown in FIG. 57.

FIG. 59 shows a nucleotide sequence (SEQ ID NO:59) of a native sequence PRO1291 cDNA, wherein SEQ ID NO:59 is a clone designated herein as "DNA59610-1556".

FIG. 60 shows the amino acid sequence (SEQ ID NO:60) derived from the coding sequence of SEQ ID NO:59 shown in FIG. 59.

FIG. 61 shows a nucleotide sequence (SEQ ID NO:61) of a native sequence PRO3573 cDNA, wherein SEQ ID NO:61 is a clone designated herein as "DNA59837-2545".

FIG. 62 shows the amino acid sequence (SEQ ID NO:62) derived from the coding sequence of SEQ ID NO:61 shown in FIG. 61.

FIG. 63 shows a nucleotide sequence (SEQ ID NO:63) of a native sequence PRO3566 cDNA, wherein SEQ ID NO:63 is a clone designated herein as "DNA59844-2542".

FIG. 64 shows the amino acid sequence (SEQ ID NO:64) derived from the coding sequence of SEQ ID NO:63 shown in FIG. 63.

FIG. 65 shows a nucleotide sequence (SEQ ID NO:65) of a native sequence PRO1098 cDNA, wherein SEQ ID NO:65 is a clone designated herein as "DNA59854-1459".

FIG. 66 shows the amino acid sequence (SEQ ID NO:66) derived from the coding sequence of SEQ ID NO:65 shown in FIG. 65.

FIG. 67 shows a nucleotide sequence (SEQ ID NO:67) of a native sequence PRO1158 cDNA, wherein SEQ ID NO:67 is a clone designated herein as "DNA60625-1507".

FIG. 68 shows the amino acid sequence (SEQ ID NO:68) derived from the coding sequence of SEQ ID NO:67 shown in FIG. 67.

FIG. 69 shows a nucleotide sequence (SEQ ID NO:69) of a native sequence PRO1124 cDNA, wherein SEQ ID NO:69 is a clone designated herein as "DNA60629-1481".

FIG. 70 shows the amino acid sequence (SEQ ID NO:70) derived from the coding sequence of SEQ ID NO:69 shown in FIG. 69.

FIG. 71 shows a nucleotide sequence (SEQ ID NO:71) of a native sequence PRO1287 cDNA, wherein SEQ ID NO:71 is a clone designated herein as "DNA61755-1554".

FIG. 72 shows the amino acid sequence (SEQ ID NO:72) derived from the coding sequence of SEQ ID NO:71 shown in FIG. 71.

FIG. 73 shows a nucleotide sequence (SEQ ID NO:73) of a native sequence PRO1335 cDNA, wherein SEQ ID NO:73 is a clone designated herein as "DNA62812-1594".

FIG. 74 shows the amino acid sequence (SEQ ID NO:74) derived from the coding sequence of SEQ ID NO:73 shown in FIG. 73.

FIG. 75 shows a nucleotide sequence (SEQ ID NO:75) of a native sequence PRO1315 cDNA, wherein SEQ ID NO:75 is a clone designated herein as "DNA62815-1576".

FIG. 76 shows the amino acid sequence (SEQ ID NO:76) derived from the coding sequence of SEQ ID NO:75 shown in FIG. 75.

FIG. 77 shows a nucleotide sequence (SEQ ID NO:77) of a native sequence PRO1357 cDNA, wherein SEQ ID NO:77 is a clone designated herein as "DNA64881-1602".

FIG. 78 shows the amino acid sequence (SEQ ID NO:78) derived from the coding sequence of SEQ ID NO:77 shown in FIG. 77.

FIG. 79 shows a nucleotide sequence (SEQ ID NO:79) of a native sequence PRO1356 cDNA, wherein SEQ ID NO:79 is a clone designated herein as "DNA64886-1601".

FIG. 80 shows the amino acid sequence (SEQ ID NO:80) derived from the coding sequence of SEQ ID NO:79 shown in FIG. 79.

FIG. 81 shows a nucleotide sequence (SEQ ID NO:81) of a native sequence PRO1557 cDNA, wherein SEQ ID NO:81 is a clone designated herein as "DNA64902-1667".

FIG. 82 shows the amino acid sequence (SEQ ID NO:82) derived from the coding sequence of SEQ ID NO:81 shown in FIG. 81.

FIG. 83 shows a nucleotide sequence (SEQ ID NO:83) of a native sequence PRO1347 cDNA, wherein SEQ ID NO:83 is a clone designated herein as "DNA64950-1590".

FIG. 84 shows the amino acid sequence (SEQ ID NO:84) derived from the coding sequence of SEQ ID NO:83 shown in FIG. 83.

FIG. 85 shows a nucleotide sequence (SEQ ID NO:85) of a native sequence PRO1302 cDNA, wherein SEQ ID NO:85 is a clone designated herein as "DNA65403-1565".

FIG. 86 shows the amino acid sequence (SEQ ID NO:86) derived from the coding sequence of SEQ ID NO:85 shown in FIG. 85.

FIG. 87 shows a nucleotide sequence (SEQ ID NO:87) of a native sequence PRO1270 cDNA, wherein SEQ ID NO:87 is a clone designated herein as "DNA66308-1537".

FIG. 88 shows the amino acid sequence (SEQ ID NO:88) derived from the coding sequence of SEQ ID NO:87 shown in FIG. 87.

FIG. 89 shows a nucleotide sequence (SEQ ID NO:89) of a native sequence PRO1268 cDNA, wherein SEQ ID NO:89 is a clone designated herein as "DNA66519-1535".

FIG. 90 shows the amino acid sequence (SEQ ID NO:90) derived from the coding sequence of SEQ ID NO:89 shown in FIG. 89.

FIG. 91 shows a nucleotide sequence (SEQ ID NO:91) of a native sequence PRO1327 cDNA, wherein SEQ ID NO:91 is a clone designated herein as "DNA66521-1583".

FIG. 92 shows the amino acid sequence (SEQ ID NO:92) derived from the coding sequence of SEQ ID NO:91 shown in FIG. 91.

FIG. 93 shows a nucleotide sequence (SEQ ID NO:93) of a native sequence PRO1328 cDNA, wherein SEQ ID NO:93 is a clone designated herein as "DNA66658-1584".

FIG. 94 shows the amino acid sequence (SEQ ID NO:94) derived from the coding sequence of SEQ ID NO:93 shown in FIG. 93.

FIG. 95 shows a nucleotide sequence (SEQ ID NO:95) of a native sequence PRO1329 cDNA, wherein SEQ ID NO:95 is a clone designated herein as "DNA66660-1585".

FIG. 96 shows the amino acid sequence (SEQ ID NO:96) derived from the coding sequence of SEQ ID NO:95 shown in FIG. 95.

FIG. 97 shows a nucleotide sequence (SEQ ID NO:97) of a native sequence PRO1340 cDNA, wherein SEQ ID NO:97 is a clone designated herein as "DNA66663-1598".

FIG. 98 shows the amino acid sequence (SEQ ID NO:98) derived from the coding sequence of SEQ ID NO:97 shown in FIG. 97.

FIG. 99 shows a nucleotide sequence (SEQ ID NO:99) of a native sequence PRO1342 cDNA, wherein SEQ ID NO:99 is a clone designated herein as "DNA66674-1599".

FIG. 100 shows the amino acid sequence (SEQ ID NO:100) derived from the coding sequence of SEQ ID NO:99 shown in FIG. 99.

FIG. 101 shows a nucleotide sequence (SEQ ID NO:101) of a native sequence PRO3579 cDNA, wherein SEQ ID NO:101 is a clone designated herein as "DNA68862-2546".

FIG. 102 shows the amino acid sequence (SEQ ID NO:102) derived from the coding sequence of SEQ ID NO:101 shown in FIG. 101.

FIG. 103 shows a nucleotide sequence (SEQ ID NO:103) of a native sequence PRO1472 cDNA, wherein SEQ ID NO:103 is a clone designated herein as "DNA68866-1644".

FIG. 104 shows the amino acid sequence (SEQ ID NO:104) derived from the coding sequence of SEQ ID NO:103 shown in FIG. 103.

FIG. 105 shows a nucleotide sequence (SEQ ID NO:105) of a native sequence PRO1461 cDNA, wherein SEQ ID NO:105 is a clone designated herein as "DNA68871-1638".

FIG. 106 shows the amino acid sequence (SEQ ID NO:106) derived from the coding sequence of SEQ ID NO:105 shown in FIG. 105.

FIG. 107 shows a nucleotide sequence (SEQ ID NO:107) of a native sequence PRO1568 cDNA, wherein SEQ ID NO:107 is a clone designated herein as "DNA68880-1676".

FIG. 108 shows the amino acid sequence (SEQ ID NO:108) derived from the coding sequence of SEQ ID NO:107 shown in FIG. 107.

FIG. 109 shows a nucleotide sequence (SEQ ID NO:109) of a native sequence PRO1753 cDNA, wherein SEQ ID NO:109 is a clone designated herein as "DNA68883-1691".

FIG. 110 shows the amino acid sequence (SEQ ID NO:110) derived from the coding sequence of SEQ ID NO:109 shown in FIG. 109.

FIG. 111 shows a nucleotide sequence (SEQ ID NO:111) of a native sequence PRO1570 cDNA, wherein SEQ ID NO:111 is a clone designated herein as "DNA68885-1678".

FIG. 112 shows the amino acid sequence (SEQ ID NO:112) derived from the coding sequence of SEQ ID NO:111 shown in FIG. 111.

FIG. 113 shows a nucleotide sequence (SEQ ID NO:113) of a native sequence PRO1446 cDNA, wherein SEQ ID NO:113 is a clone designated herein as "DNA71277-1636".

FIG. 114 shows the amino acid sequence (SEQ ID NO:114) derived from the coding sequence of SEQ ID NO:113 shown in FIG. 113.

FIG. 115 shows a nucleotide sequence (SEQ ID NO:115) of a native sequence PRO1565 cDNA, wherein SEQ ID NO:115 is a clone designated herein as "DNA73727-1673".

FIG. 116 shows the amino acid sequence (SEQ ID NO:116) derived from the coding sequence of SEQ ID NO:115 shown in FIG. 115.

FIG. 117 shows a nucleotide sequence (SEQ ID NO:117) of a native sequence PRO1572 cDNA, wherein SEQ ID NO:117 is a clone designated herein as "DNA73734-1680".

FIG. 118 shows the amino acid sequence (SEQ ID NO: 118) derived from the coding sequence of SEQ ID NO:117 shown in FIG. 117.

FIG. 119 shows a nucleotide sequence (SEQ ID NO:119) of a native sequence PRO1573 cDNA, wherein SEQ ID NO:119 is a clone designated herein as "DNA73735-1681".

FIG. 120 shows the amino acid sequence (SEQ ID NO:120) derived from the coding sequence of SEQ ID NO:119 shown in FIG. 119.

FIG. 121 shows a nucleotide sequence (SEQ ID NO:121) of a native sequence PRO1550 cDNA, wherein SEQ ID NO:121 is a clone designated herein as "DNA76393-1664".

FIG. 122 shows the amino acid sequence (SEQ ID NO:122) derived from the coding sequence of SEQ ID NO:121 shown in FIG. 121.

FIG. 123 shows a nucleotide sequence (SEQ ID NO:123) of a native sequence PRO1693 cDNA, wherein SEQ ID NO:123 is a clone designated herein as "DNA77301-1708".

FIG. 124 shows the amino acid sequence (SEQ ID NO:124) derived from the coding sequence of SEQ ID NO:123 shown in FIG. 123.

FIG. 125 shows a nucleotide sequence (SEQ ID NO:125) of a native sequence PRO1566 cDNA, wherein SEQ ID NO:125 is a clone designated herein as "DNA77568-1626".

FIG. 126 shows the amino acid sequence (SEQ ID NO:126) derived from the coding sequence of SEQ ID NO:125 shown in FIG. 125.

FIG. 127 shows a nucleotide sequence (SEQ ID NO:127) of a native sequence PRO1774 cDNA, wherein SEQ ID NO:127 is a clone designated herein as "DNA77626-1705".

FIG. 128 shows the amino acid sequence (SEQ ID NO:128) derived from the coding sequence of SEQ ID NO:127 shown in FIG. 127.

FIG. 129 shows a nucleotide sequence (SEQ ID NO:129) of a native sequence PRO1928 cDNA, wherein SEQ ID NO:129 is a clone designated herein as "DNA81754-2532".

FIG. 130 shows the amino acid sequence (SEQ ID NO:130) derived from the coding sequence of SEQ ID NO:129 shown in FIG. 129.

FIG. 131 shows a nucleotide sequence (SEQ ID NO:131) of a native sequence PRO1865 cDNA, wherein SEQ ID NO:131 is a clone designated herein as "DNA81757-2512".

FIG. 132 shows the amino acid sequence (SEQ ID NO:132) derived from the coding sequence of SEQ ID NO:131 shown in FIG. 131.

FIG. 133 shows a nucleotide sequence (SEQ ID NO:133) of a native sequence PRO1925 cDNA, wherein SEQ ID NO:133 is a clone designated herein as "DNA82302-2529".

FIG. 134 shows the amino acid sequence (SEQ ID NO:134) derived from the coding sequence of SEQ ID NO:133 shown in FIG. 133.

FIG. 135 shows a nucleotide sequence (SEQ ID NO:135) of a native sequence PRO1926 cDNA, wherein SEQ ID NO:135 is a clone designated herein as "DNA82340-2530".

FIG. 136 shows the amino acid sequence (SEQ ID NO:136) derived from the coding sequence of SEQ ID NO:135 shown in FIG. 135.

FIG. 137 shows a nucleotide sequence (SEQ ID NO:137) of a native sequence PRO1801 cDNA, wherein SEQ ID NO:137 is a clone designated herein as "DNA83500-2506".

FIG. 138 shows the amino acid sequence (SEQ ID NO:138) derived from the coding sequence of SEQ ID NO:137 shown in FIG. 137.

FIG. 139 shows a nucleotide sequence (SEQ ID NO:139) of a native sequence PRO4405 cDNA, wherein SEQ ID NO:139 is a clone designated herein as "DNA84920-2614".

FIG. 140 shows the amino acid sequence (SEQ ID NO:140) derived from the coding sequence of SEQ ID NO:139 shown in FIG. 139.

FIG. 141 shows a nucleotide sequence (SEQ ID NO:141) of a native sequence PRO3435 cDNA, wherein SEQ ID NO:141 is a clone designated herein as "DNA85066-2534".

FIG. 142 shows the amino acid sequence (SEQ ID NO:142) derived from the coding sequence of SEQ ID NO:141 shown in FIG. 141.

FIG. 143 shows a nucleotide sequence (SEQ ID NO:143) of a native sequence PRO3543 cDNA, wherein SEQ ID NO:143 is a clone designated herein as "DNA86571-2551".

FIG. 144 shows the amino acid sequence (SEQ ID NO:144) derived from the coding sequence of SEQ ID NO:143 shown in FIG. 143.

FIG. 145 shows a nucleotide sequence (SEQ ID NO:145) of a native sequence PRO3443 cDNA, wherein SEQ ID NO:145 is a clone designated herein as "DNA87991-2540".

FIG. 146 shows the amino acid sequence (SEQ ID NO:146) derived from the coding sequence of SEQ ID NO:145 shown in FIG. 145.

FIG. 147 shows a nucleotide sequence (SEQ ID NO:147) of a native sequence PRO3442 cDNA, wherein SEQ ID NO:147 is a clone designated herein as "DNA92238-2539".

FIG. 148 shows the amino acid sequence (SEQ ID NO:148) derived from the coding sequence of SEQ ID NO:147 shown in FIG. 147.

FIG. 149 shows a nucleotide sequence (SEQ ID NO:149) of a native sequence PRO5990 cDNA, wherein SEQ ID NO:149 is a clone designated herein as "DNA96042-2682".

FIG. 150 shows the amino acid sequence (SEQ ID NO:150) derived from the coding sequence of SEQ ID NO:149 shown in FIG. 149.

FIG. 151 shows a nucleotide sequence (SEQ ID NO:151) of a native sequence PRO4342 cDNA, wherein SEQ ID NO:151 is a clone designated herein as "DNA96787-2534".

FIG. 152 shows the amino acid sequence (SEQ ID NO:152) derived from the coding sequence of SEQ ID NO:151 shown in FIG. 151.

FIG. 153 shows a nucleotide sequence (SEQ ID NO:153) of a native sequence PRO10096 cDNA, wherein SEQ ID NO:153 is a clone designated herein as "DNA125185-2806".

FIG. 154 shows the amino acid sequence (SEQ ID NO:154) derived from the coding sequence of SEQ ID NO:153 shown in FIG. 153.

FIG. 155 shows a nucleotide sequence (SEQ ID NO:155) of a native sequence PRO10272 cDNA, wherein SEQ ID NO:155 is a clone designated herein as "DNA147531-2821".

FIG. 156 shows the amino acid sequence (SEQ ID NO:156) derived from the coding sequence of SEQ ID NO:155 shown in FIG. 155.

FIG. 157 shows a nucleotide sequence (SEQ ID NO:157) of a native sequence PRO5801 cDNA, wherein SEQ ID NO:157 is a clone designated herein as "DNA115291-2681".

FIG. 158 shows the amino acid sequence (SEQ ID NO:158) derived from the coding sequence of SEQ ID NO:157 shown in FIG. 157.

FIG. 159 shows a nucleotide sequence (SEQ ID NO:159) of a native sequence PRO20110 cDNA, wherein SEQ ID NO:159 is a clone designated herein as "DNA166819".

FIG. 160 shows the amino acid sequence (SEQ ID NO:160) derived from the coding sequence of SEQ ID NO:159 shown in FIG. 159.

FIG. 161 shows a nucleotide sequence (SEQ ID NO:161) of a native sequence PRO20040 cDNA, wherein SEQ ID NO:161 is a clone designated herein as "DNA 164625-2890".

FIG. 162 shows the amino acid sequence (SEQ ID NO:162) derived from the coding sequence of SEQ ID NO:161 shown in FIG. 161.

FIG. 163 shows a nucleotide sequence (SEQ ID NO:163) of a native sequence PRO20233 cDNA, wherein SEQ ID NO:163 is a clone designated herein as "DNA165608".

FIG. 164 shows the amino acid sequence (SEQ ID NO:164) derived from the coding sequence of SEQ ID NO:163 shown in FIG. 163.

FIG. 165 shows a nucleotide sequence (SEQ ID NO:165) of a native sequence PRO19670 cDNA, wherein SEQ ID NO:165 is a clone designated herein as "DNA131639-2874".

FIG. 166 shows the amino acid sequence (SEQ ID NO:166) derived from the coding sequence of SEQ ID NO:165 shown in FIG. 165.

FIG. 167 shows a nucleotide sequence (SEQ ID NO:167) of a native sequence PRO1890 cDNA, wherein SEQ ID NO:167 is a clone designated herein as "DNA79230-2525".

FIG. 168 shows the amino acid sequence (SEQ ID NO:168) derived from the coding sequence of SEQ ID NO:167 shown in FIG. 167.

DETAILED DESCRIPTION OF THE PREFERRED EMBODIMENTS

I. Definitions

The terms "PRO polypeptide" and "PRO" as used herein and when immediately followed by a numerical designation refer to various polypeptides, wherein the complete designation (i.e., PRO/number) refers to specific polypeptide sequences as described herein. The terms "PRO/number polypeptide" and "PRO/number" wherein the term "number" is provided as an actual numerical designation as used herein encompass native sequence polypeptides and polypeptide variants (which are further defined herein). The PRO polypeptides described herein may be isolated from a variety of sources, such as from human tissue types or from another source, or prepared by recombinant or synthetic methods. The term "PRO polypeptide" refers to each individual PRO/number polypeptide disclosed herein. All disclosures in this specification which refer to the "PRO polypeptide" refer to each of the polypeptides individually as well as jointly. For example, descriptions of the preparation of, purification of, derivation of, formation of antibodies to or against, administration of, compositions containing, treatment of a disease with, etc., pertain to each polypeptide of the invention individually. The term "PRO polypeptide" also includes variants of the PRO/number polypeptides disclosed herein.

A "native sequence PRO polypeptide" comprises a polypeptide having the same amino acid sequence as the corresponding PRO polypeptide derived from nature. Such native sequence PRO polypeptides can be isolated from nature or can be produced by recombinant or synthetic means. The term "native sequence PRO polypeptide" specifically encompasses naturally-occurring truncated or secreted forms of the specific PRO polypeptide (e.g., an extracellular domain sequence), naturally-occurring variant forms (e.g., alternatively spliced forms) and naturally-occurring allelic variants of the polypeptide. In various embodiments of the invention, the native sequence PRO polypeptides disclosed herein are mature or full-length native sequence polypeptides comprising the full-length amino acids sequences shown in the accompanying figures. Start and stop codons are shown in bold font and underlined in the figures. However, while the PRO polypeptide disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the PRO polypeptides.

The PRO polypeptide "extracellular domain" or "ECD" refers to a form of the PRO polypeptide which is essentially free of the transmembrane and cytoplasmic domains. Ordinarily, a PRO polypeptide ECD will have less than 1% of such transmembrane and/or cytoplasmic domains and preferably, will have less than 0.5% of such domains. It will be understood that any transmembrane domains identified for the PRO polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified herein. Optionally, therefore, an extracellular domain of a PRO polypeptide may contain from about 5 or fewer amino acids on either side of the transmembrane domain/extracellular domain boundary as identified in the Examples or specification and such polypeptides, with or without the associated signal peptide, and nucleic acid encoding them, are comtemplated by the present invention.

The approximate location of the "signal peptides" of the various PRO polypeptides disclosed herein are shown in the present specification and/or the accompanying figures. It is noted, however, that the C-terminal boundary of a signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., *Prot. Eng.* 10:1–6 (1997) and von Heinje et al., *Nucl. Acids. Res.* 14:4683–4690 (1986)). Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

"PRO polypeptide variant" means an active PRO polypeptide as defined above or below having at least about 80% amino acid sequence identity with a full-length native sequence PRO polypeptide sequence as disclosed herein, a PRO polypeptide sequence lacking the signal peptide as disclosed herein, an extracellular domain of a PRO polypeptide, with or without the signal peptide, as disclosed herein or any other fragment of a full-length PRO polypeptide sequence as disclosed herein. Such PRO polypeptide variants include, for instance, PRO polypeptides wherein one or more amino acid residues are added, or deleted, at the N- or C-terminus of the full-length native amino acid sequence. Ordinarily, a PRO polypeptide variant will have at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a full-length native sequence PRO polypeptide sequence as disclosed herein, a PRO polypeptide sequence lacking the signal peptide as disclosed herein, an extracellular domain of a PRO polypeptide, with or without the signal peptide, as disclosed herein or any other specifically defined fragment of a full-length PRO polypeptide sequence as disclosed herein. Ordinarily, PRO variant polypeptides are at least about 10 amino acids in length, alternatively at least about 20 amino acids in length, alternatively at least about 30 amino acids in length, alternatively at least about 40 amino acids in length, alternatively at least about 50 amino acids in length, alternatively at least about 60 amino acids in length, alternatively at least about 70 amino acids in length, alternatively at least about 80 amino acids in length, alternatively at least about 90 amino acids in length, alternatively at least about 100 amino acids in length, alternatively at least about 150 amino acids in length, alternatively at least about 200 amino acids in length, alternatively at least about 300 amino acids in length, or more.

"Percent (%) amino acid sequence identity" with respect to the PRO polypeptide sequences identified herein is defined as the percentage of amino acid residues in a candidate sequence that are identical with the amino acid residues in the specific PRO polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence designated "PRO", wherein "PRO" represents the amino acid sequence of a hypothetical PRO polypeptide of interest, "Comparison Protein" represents the amino acid sequence of a polypeptide against which the "PRO" polypeptide of interest is being compared, and "X," "Y" and "Z" each represent different hypothetical amino acid residues.

Unless specifically stated otherwise, all % amino acid sequence identity values used herein are obtained as described in the immediately preceding paragraph using the ALIGN-2 computer program. However, % amino acid sequence identity values may also be obtained as described below by using the WU-BLAST-2 computer program (Altschul et al., *Methods in Enzymology* 266:460–480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % amino acid sequence identity value is determined by dividing (a) the number of matching identical amino acid residues between the amino acid sequence of the PRO polypeptide of interest having a sequence derived from the native PRO polypeptide and the comparison amino acid sequence of interest (i.e., the sequence against which the PRO polypeptide of interest is being compared which may be a PRO variant polypeptide) as determined by WU-BLAST-2 by (b) the total number of amino acid residues of the PRO polypeptide of interest. For example, in the statement "a polypeptide comprising an the amino acid sequence A which has or having at least 80% amino acid sequence identity to the amino acid sequence B", the amino acid sequence A is the comparison amino acid sequence of interest and the amino acid sequence B is the amino acid sequence of the PRO polypeptide of interest.

Percent amino acid sequence identity may also be determined using the sequence comparison program NCBI-BLAST2 (Altschul et al., *Nucleic Acids Res.* 25:3389–3402 (1997)). The NCBI-BLAST2 sequence comparison program may be downloaded from the National Institutes of Health website or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

"PRO variant polynucleotide" or "PRO variant nucleic acid sequence" means a nucleic acid molecule which encodes an active PRO polypeptide as defined below and which has at least about 80% nucleic acid sequence identity with a nucleotide acid sequence encoding a full-length native sequence PRO polypeptide sequence as disclosed herein, a full-length native sequence PRO polypeptide sequence lacking the signal peptide as disclosed herein, an extracellular domain of a PRO polypeptide, with or without the signal peptide, as disclosed herein or any other fragment of a full-length PRO polypeptide sequence as disclosed herein. Ordinarily, a PRO variant polynucleotide will have at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity with a nucleic acid sequence encoding a full-length native sequence PRO polypeptide sequence as disclosed herein, a full-length native sequence PRO polypeptide sequence lacking the signal peptide as disclosed herein, an extracellular domain of a PRO polypeptide, with or without the signal sequence, as disclosed herein or any other fragment of a full-length PRO polypeptide sequence as disclosed herein. Variants do not encompass the native nucleotide sequence.

Ordinarily, PRO variant polynucleotides are at least about 30 nucleotides in length, alternatively at least about 60 nucleotides in length, alternatively at least about 90 nucleotides in length, alternatively at least about 120 nucleotides in length, alternatively at least about 150 nucleotides in length, alternatively at least about 180 nucleotides in length, alternatively at least about 210 nucleotides in length, alternatively at least about 240 nucleotides in length, alternatively at least about 270 nucleotides in length, alternatively at least about 300 nucleotides in length, alternatively at least about 450 nucleotides in length, alternatively at least about 600 nucleotides in length, alternatively at least about 900 nucleotides in length, or more.

"Percent (%) nucleic acid sequence identity" with respect to PRO-encoding nucleic acid sequences identified herein is defined as the percentage of nucleotides in a candidate sequence that are identical with the nucleotides in the PRO nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5, demonstrate how to calculate the % nucleic acid sequence identity of the nucleic acid sequence designated "Comparison DNA" to the nucleic acid sequence designated "PRO-DNA", wherein "PRO-DNA" represents a hypothetical PRO-encoding nucleic acid sequence of interest, "Comparison DNA" represents the nucleotide sequence of a nucleic acid molecule against which the "PRO-DNA" nucleic acid molecule of interest is being compared, and "N", "L" and "V" each represent different hypothetical nucleotides.

Unless specifically stated otherwise, all % nucleic acid sequence identity values used herein are obtained as described in the immediately preceding paragraph using the ALIGN-2 computer program. However, % nucleic acid sequence identity values may also be obtained as described below by using the WU-BLAST-2 computer program (Altschul et al., *Methods in Enzymology* 266:460–480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % nucleic acid sequence identity value is determined by dividing (a) the number of matching identical nucleotides between the nucleic acid sequence of the PRO polypeptide-encoding nucleic acid molecule of interest having a sequence derived from the native sequence PRO polypeptide-encoding nucleic acid and the comparison nucleic acid molecule of interest (i.e., the sequence against which the PRO polypeptide-encoding nucleic acid molecule of interest is being compared which may be a variant PRO polynucleotide) as determined by WU-BLAST-2 by (b) the total number of nucleotides of the PRO polypeptide-encoding nucleic acid molecule of interest. For example, in the statement "an isolated nucleic acid molecule comprising a nucleic acid sequence A which has or having at least 80% nucleic acid sequence identity to the nucleic acid sequence B", the nucleic acid sequence A is the comparison nucleic acid molecule of interest and the nucleic acid sequence B is the nucleic acid sequence of the PRO polypeptide-encoding nucleic acid molecule of interest.

Percent nucleic acid sequence identity may also be determined using the sequence comparison program NCBI-BLAST2 (Altschul et al., *Nucleic Acids Res.* 25:3389–3402 (1997)). The NCBI-BLAST2 sequence comparison program may be downloaded from the National Institutes of Health website or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program NCBI-BLAST2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

In other embodiments, PRO variant polynucleotides are nucleic acid molecules that encode an active PRO polypeptide and which are capable of hybridizing, preferably under stringent hybridization and wash conditions, to nucleotide sequences encoding a full-length PRO polypeptide as disclosed herein. PRO variant polypeptides may be those that are encoded by a PRO variant polynucleotide.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the PRO polypeptide natural environment will not be present. Ordinarily, however, isolated polypeptide will be prepared by at least one purification step.

An "isolated" PRO polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers, for example, single anti-PRO monoclonal antibodies (including agonist, antagonist, and neutralizing antibodies), anti-PRO antibody compositions with polyepitopic specificity, single chain anti-PRO antibodies, and fragments of anti-PRO antibodies (see below). The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/ml denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

The term "epitope tagged" when used herein refers to a chimeric polypeptide comprising a PRO polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

"Active" or "activity" for the purposes herein refers to form(s) of a PRO polypeptide which retain a biological and/or an immunological activity of native or naturally-occurring PRO, wherein "biological" activity refers to a biological function (either inhibitory or stimulatory) caused by a native or naturally-occurring PRO other than the ability to induce the production of an antibody against an antigenic epitope possessed by a native or naturally-occurring PRO and an "immunological" activity refers to the ability to induce the production of an antibody against an antigenic epitope possessed by a native or naturally-occurring PRO.

The term "antagonist" is used in the broadest sense, and includes any molecule that partially or fully blocks, inhibits, or neutralizes a biological activity of a native PRO polypeptide disclosed herein. In a similar manner, the term "agonist" is used in the broadest sense and includes any molecule that mimics a biological activity of a native PRO polypeptide disclosed herein. Suitable agonist or antagonist molecules specifically include agonist or antagonist antibodies or antibody fragments, fragments or amino acid sequence variants of native PRO polypeptides, peptides, antisense oligonucleotides, small organic molecules, etc. Methods for identifying agonists or antagonists of a PRO polypeptide may comprise contacting a PRO polypeptide with a candidate agonist or antagonist molecule and measuring a detectable change in one or more biological activities normally associated with the PRO polypeptide.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

"Antibody fragments" comprise a portion of an intact antibody, preferably the antigen binding or variable region of the intact antibody. Examples of antibody fragments include Fab, Fab', $F(ab')_2$, and Fv fragments; diabodies; linear antibodies (Zapata et al., *Protein Eng.* 8(10): 1057–1062 [1995]); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an $F(ab')_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269–315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444–6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a PRO polypeptide or antibody thereto) to a mammal. The components of the liposome are commonly arranged in a bilayer formation, similar to the lipid arrangement of biological membranes.

A "small molecule" is defined herein to have a molecular weight below about 500 Daltons.

Table 1

```
/*
 *
 * C-C increased from 12 to 15
 * Z is average of EQ
 * B is average of ND
 * match with stop is _M; stop-stop = 0; J (joker) match = 0
 */
define _M      -8      /* value of a match with a stop */ int     _day[26][26] = {
/*       A  B  C  D  E  F  G  H  I  J  K  L  M  N  O  P  Q  R  S  T  U  V  W  X  Y  Z */
/* A */  { 2, 0,-2, 0, 0,-4, 1,-1,-1, 0,-1,-2,-1, 0,_M, 1, 0,-2, 1, 1, 0, 0,-6, 0,-3, 0},
/* B */  { 0, 3,-4, 3, 2,-5, 0, 1,-2, 0, 0,-3,-2, 2,_M,-1, 1, 0, 0, 0, 0,-2,-5, 0,-3, 1},
/* C */  {-2,-4,15,-5,-5,-4,-3,-3,-2, 0,-5,-6,-5,-4,_M,-3,-5,-4, 0,-2, 0,-2,-8, 0, 0,-5},
/* D */  { 0, 3,-5, 4, 3,-6, 1, 1,-2, 0, 0,-4,-3, 2,_M,-1, 2,-1, 0, 0, 0,-2,-7, 0,-4, 2},
/* E */  { 0, 2,-5, 3, 4,-5, 0, 1,-2, 0, 0,-3,-2, 1,_M,-1, 2,-1, 0, 0, 0,-2,-7, 0,-4, 3},
/* F */  {-4,-5,-4,-6,-5, 9,-5,-2, 1, 0,-5, 2, 0,-4,_M,-5,-5,-4,-3,-3, 0,-1, 0, 0, 7,-5},
/* G */  { 1, 0,-3, 1, 0,-5, 5,-2,-3, 0,-2,-4,-3, 0,_M,-1,-1,-3, 1, 0, 0,-1,-7, 0,-5, 0},
/* H */  {-1, 1,-3, 1, 1,-2,-2, 6,-2, 0, 0,-2,-2, 2,_M, 0, 3, 2,-1,-1, 0,-2,-3, 0, 0, 2},
/* I */  {-1,-2,-2,-2,-2, 1,-3,-2, 5, 0,-2, 2, 2,-2,_M,-2,-2,-2,-1, 0, 0, 4,-5, 0,-1,-2},
/* J */  { 0, 0, 0, 0, 0, 0, 0, 0, 0, 0, 0, 0, 0, 0,_M, 0, 0, 0, 0, 0, 0, 0, 0, 0, 0, 0},
/* K */  {-1, 0,-5, 0, 0,-5,-2, 0,-2, 0, 5,-3, 0, 1,_M,-1, 1, 3, 0, 0, 0,-2,-3, 0,-4, 0},
/* L */  {-2,-3,-6,-4,-3, 2,-4,-2, 2, 0,-3, 6, 4,-3,_M,-3,-2,-3,-3,-1, 0, 2,-2, 0,-1,-2},
/* M */  {-1,-2,-5,-3,-2, 0,-3,-2, 2, 0, 0, 4, 6,-2,_M,-2,-1, 0,-2,-1, 0, 2,-4, 0,-2,-1},
/* N */  { 0, 2,-4, 2, 1,-4, 0, 2,-2, 0, 1,-3,-2, 2,_M,-1, 1, 0, 1, 0, 0,-2,-4, 0,-2, 1},
/* O */  {_M,_M,_M,_M,_M,_M,_M,_M,_M,_M,_M,_M,_M,_M, 0,_M,_M,_M,_M,_M,_M,_M,_M,_M,_M,_M},
/* P */  { 1,-1,-3,-1,-1,-5,-1, 0,-2, 0,-1,-3,-2,-1,_M, 6, 0, 0, 1, 0, 0,-1,-6, 0,-5, 0},
/* Q */  { 0, 1,-5, 2, 2,-5,-1, 3,-2, 0, 1,-2,-1, 1,_M, 0, 4, 1,-1,-1, 0,-2,-5, 0,-4, 3},
/* R */  {-2, 0,-4,-1,-1,-4,-3, 2,-2, 0, 3,-3, 0, 0,_M, 0, 1, 6, 0,-1, 0,-2, 2, 0,-4, 0},
/* S */  { 1, 0, 0, 0, 0,-3, 1,-1,-1, 0, 0,-3,-2, 1,_M, 1,-1, 0, 2, 1, 0,-1,-2, 0,-3, 0},
/* T */  { 1, 0,-2, 0, 0,-3, 0,-1, 0, 0, 0,-1,-1, 0,_M, 0,-1,-1, 1, 3, 0, 0,-5, 0,-3, 0},
/* U */  { 0, 0, 0, 0, 0, 0, 0, 0, 0, 0, 0, 0, 0, 0,_M, 0, 0, 0, 0, 0, 0, 0, 0, 0, 0, 0},
/* V */  { 0,-2,-2,-2,-2,-1,-1,-2, 4, 0,-2, 2, 2,-2,_M,-1,-2,-2,-1, 0, 0, 4,-6, 0,-2,-2},
/* W */  {-6,-5,-8,-7,-7, 0,-7,-3,-5, 0,-3,-2,-4,-4,_M,-6,-5, 2,-2,-5, 0,-6,17, 0, 0,-6},
/* X */  { 0, 0, 0, 0, 0, 0, 0, 0, 0, 0, 0, 0, 0, 0,_M, 0, 0, 0, 0, 0, 0, 0, 0, 0, 0, 0},
/* Y */  {-3,-3, 0,-4,-4, 7,-5, 0,-1, 0,-4,-1,-2,-2,_M,-5,-4,-4,-3,-3, 0,-2, 0, 0,10,-4},
/* Z */  { 0, 1,-5, 2, 3,-5, 0, 2,-2, 0, 0,-2,-1, 1,_M, 0, 3, 0, 0, 0, 0,-2,-6, 0,-4, 4}
};
```

Table 1 (cont')

```
/*
*/
#include <stdio.h>
include <ctype.h> define MAXJMP    16      /* max jumps in a diag */
define MAXGAP    24      /* don't continue to penalize gaps larger than this */
#define JMPS      1024    /* max jmps in an path */
define MX        4       /* save if there's at least MX-1 bases since last jmp */ define DMAT      3       /* value of matching bases */
define DMIS      0       /* penalty for mismatched bases */
#define DINS0     8       /* penalty for a gap */
#define DINS1     1       /* penalty per base */
#define PINS0     8       /* penalty for a gap */
define PINS1     4       /* penalty per residue */ struct jmp {
        short          n[MAXJMP];         /* size of jmp (neg for dely) */
        unsigned short x[MAXJMP];         /* base no. of jmp in seq x */
};                                        /* limits seq to 2^16 -1 */ struct diag {
        int            score;             /* score at last jmp */
        long           offset;            /* offset of prev block */
        short          ijmp;              /* current jmp index */
        struct jmp     jp;                /* list of jmps */
};

struct path {
        int            spc;               /* number of leading spaces */
        short          n[JMPS];           /* size of jmp (gap) */
        int            x[JMPS];           /* loc of jmp (last elem before gap) */
};

char          *ofile;                     /* output file name */
char          *namex[2];                  /* seq names: getseqs() */
char          *prog;                      /* prog name for err msgs */
char          *seqx[2];                   /* seqs: getseqs() */
int           dmax;                       /* best diag: nw() */
int           dmax0;                      /* final diag */
int           dna;                        /* set if dna: main() */
int           endgaps;                    /* set if penalizing end gaps */
int           gapx, gapy;                 /* total gaps in seqs */
int           len0, len1;                 /* seq lens */
int           ngapx, ngapy;               /* total size of gaps */
int           smax;                       /* max score: nw() */
int           *xbm;                       /* bitmap for matching */
long          offset;                     /* current offset in jmp file */
struct diag   *dx;                        /* holds diagonals */
struct path   pp[2];                      /* holds path for seqs */ char          *calloc(), *malloc(), *index(), *strcpy();
char          *getseq(), *g_calloc();
```

Table 1 (cont')

```
/* Needleman-Wunsch alignment program
 *
 * usage: progs file1 file2
 *    where file1 and file2 are two dna or two protein sequences.
 *    The sequences can be in upper- or lower-case an may contain ambiguity
 *    Any lines beginning with ';', '>' or '<' are ignored
 *    Max file length is 65535 (limited by unsigned short x in the jmp struct)
 *    A sequence with 1/3 or more of its elements ACGTU is assumed to be DNA
 *    Output is in the file "align.out"
 *
 * The program may create a tmp file in /tmp to hold info about traceback.
 * Original version developed under BSD 4.3 on a vax 8650
 */
include "nw.h"
#include "day.h"

static   _dbval[26] = {
    1,14,2,13,0,0,4,11,0,0,12,0,3,15,0,0,0,5,6,8,8,7,9,0,10,0
};

static   _pbval[26] = {
    1, 2|(1<<('D'-'A'))|(1<<('N'-'A')), 4, 8, 16, 32, 64,
    128, 256, 0xFFFFFFFF, 1<<10, 1<<11, 1<<12, 1<<13, 1<<14,
    1<<15, 1<<16, 1<<17, 1<<18, 1<<19, 1<<20, 1<<21, 1<<22,
    1<<23, 1<<24, 1<<25|(1<<('E'-'A'))|(1<<('Q'-'A'))
};

main(ac, av)                                                                    main
        int     ac;
        char    *av[ ];
{
        prog = av[0];
        if (ac != 3) {
                fprintf(stderr,"usage: %s file1 file2\n", prog);
                fprintf(stderr,"where file1 and file2 are two dna or two protein sequences.\n");
                fprintf(stderr,"The sequences can be in upper- or lower-case\n");
                fprintf(stderr,"Any lines beginning with ';' or '<' are ignored\n");
                fprintf(stderr,"Output is in the file \"align.out\"\n");
                exit(1);
        }
        namex[0] = av[1];
        namex[1] = av[2];
        seqx[0] = getseq(namex[0], &len0);
        seqx[1] = getseq(namex[1], &len1);
        xbm = (dna)? _dbval : _pbval;

endgaps = 0;            /* 1 to penalize endgaps */
        ofile = "align.out";    /* output file */ nw();           /* fill in the matrix, get the possible jmps */
        readjmps();     /* get the actual jmps */
        print();        /* print stats, alignment */ cleanup(0);     /* unlink any tmp files */
}
```

Table 1 (cont')

```
/* do the alignment, return best score: main()
 * dna: values in Fitch and Smith, PNAS, 80, 1382-1386, 1983
 * pro: PAM 250 values
 * When scores are equal, we prefer mismatches to any gap, prefer
 * a new gap to extending an ongoing gap, and prefer a gap in seqx
 * to a gap in seq y.
 */
nw()                                                                              nw
{
        char            *px, *py;       /* seqs and ptrs */
        int             *ndely, *dely;  /* keep track of dely */
        int             ndelx, delx;    /* keep track of delx */
        int             *tmp;           /* for swapping row0, row1 */
        int             mis;            /* score for each type */
        int             ins0, ins1;     /* insertion penalties */
        register        id;             /* diagonal index */
        register        ij;             /* jmp index */
        register        *col0, *col1;   /* score for curr, last row */
        register        xx, yy;         /* index into seqs */ dx = (struct diag *)g_calloc("to get diags", len0+len1+1, sizeof(struct diag));

ndely = (int *)g_calloc("to get ndely", len1+1, sizeof(int));
        dely = (int *)g_calloc("to get dely", len1+1, sizeof(int));
        col0 = (int *)g_calloc("to get col0", len1+1, sizeof(int));
        col1 = (int *)g_calloc("to get col1", len1+1, sizeof(int));
        ins0 = (dna)? DINS0 : PINS0;
        ins1 = (dna)? DINS1 : PINS1;

smax = -10000;
        if (endgaps) {
                for (col0[0] = dely[0] = -ins0, yy = 1; yy <= len1; yy++) {
                        col0[yy] = dely[yy] = col0[yy-1] - ins1;
                        ndely[yy] = yy;
                }
                col0[0] = 0;    /* Waterman Bull Math Biol 84 */
        }
        else
                for (yy = 1; yy <= len1; yy++)
                        dely[yy] = -ins0;

/* fill in match matrix
        */
        for (px = seqx[0], xx = 1; xx <= len0; px++, xx++) {
                /* initialize first entry in col
                */
                if (endgaps) {
                        if (xx == 1)
                                col1[0] = delx = -(ins0+ins1);
                        else
                                col1[0] = delx = col0[0] - ins1;
                        ndelx = xx;
                }
                else {
                        col1[0] = 0;
                        delx = -ins0;
                        ndelx = 0;
                }
```

Table 1 (cont')

...nw

```
for (py = seqx[1], yy = 1; yy <= len1; py++, yy++) {
        mis = col0[yy-1];
        if (dna)
                mis += (xbm[*px-'A']&xbm[*py-'A'])? DMAT : DMIS;
        else
                mis += _day[*px-'A'][*py-'A'];

/* update penalty for del in x seq;
         * favor new del over ongong del
         * ignore MAXGAP if weighting endgaps
         */
        if (endgaps || ndely[yy] < MAXGAP) {
                if (col0[yy] - ins0 >= dely[yy]) {
                        dely[yy] = col0[yy] - (ins0+ins1);
                        ndely[yy] = 1;
                } else {
                        dely[yy] -= ins1;
                        ndely[yy]++;
                }
        } else {
                if (col0[yy] - (ins0+ins1) >= dely[yy]) {
                        dely[yy] = col0[yy] - (ins0+ins1);
                        ndely[yy] = 1;
                } else
                        ndely[yy]++;
        }

/* update penalty for del in y seq;
         * favor new del over ongong del
         */
        if (endgaps || ndelx < MAXGAP) {
                if (col1[yy-1] - ins0 >= delx) {
                        delx = col1[yy-1] - (ins0+ins1);
                        ndelx = 1;
                } else {
                        delx -= ins1;
                        ndelx++;
                }
        } else {
                if (col1[yy-1] - (ins0+ins1) >= delx) {
                        delx = col1[yy-1] - (ins0+ins1);
                        ndelx = 1;
                } else
                        ndelx++;
        }

/* pick the maximum score; we're favoring
         * mis over any del and delx over dely
         */
```

Table 1 (cont')

...nw

```
                        id = xx - yy + len1 - 1;
                        if (mis >= delx && mis >= dely[yy])
                                col1[yy] = mis;
                        else if (delx >= dely[yy]) {
                                col1[yy] = delx;
                                ij = dx[id].ijmp;
                                if (dx[id].jp.n[0] && (!dna || (ndelx >= MAXJMP
                                        && xx > dx[id].jp.x[ij]+MX) || mis > dx[id].score+DINS0)) {
                                        dx[id].ijmp++;
                                        if (++ij >= MAXJMP) {
                                                writejmps(id);
                                                ij = dx[id].ijmp = 0;
                                                dx[id].offset = offset;
                                                offset += sizeof(struct jmp) + sizeof(offset);
                                        }
                                }
                                dx[id].jp.n[ij] = ndelx;
                                dx[id].jp.x[ij] = xx;
                                dx[id].score = delx;
                        }
                        else {
                                col1[yy] = dely[yy];
                                ij = dx[id].ijmp;
if (dx[id].jp.n[0] && (!dna || (ndely[yy] >= MAXJMP
                                        && xx > dx[id].jp.x[ij]+MX) || mis > dx[id].score+DINS0)) {
                                        dx[id].ijmp++;
                                        if (++ij >= MAXJMP) {
                                                writejmps(id);
                                                ij = dx[id].ijmp = 0;
                                                dx[id].offset = offset;
                                                offset += sizeof(struct jmp) + sizeof(offset);
                                        }
                                }
                                dx[id].jp.n[ij] = -ndely[yy];
                                dx[id].jp.x[ij] = xx;
                                dx[id].score = dely[yy];
                        }
                        if (xx == len0 && yy < len1) {
                                /* last col
                                */
                                if (endgaps)
                                        col1[yy] -= ins0+ins1*(len1-yy);
                                if (col1[yy] > smax) {
                                        smax = col1[yy];
                                        dmax = id;
                                }
                        }
                }
                if (endgaps && xx < len0)
                        col1[yy-1] -= ins0+ins1*(len0-xx);
                if (col1[yy-1] > smax) {
                        smax = col1[yy-1];
                        dmax = id;
                }
        }
        tmp = col0; col0 = col1; col1 = tmp;
}
(void) free((char *)ndely);
(void) free((char *)dely);
```

Table 1 (cont')

```
            (void) free((char *)col0);
            (void) free((char *)col1);                  }
/*
 *
 * print() -- only routine visible outside this module
 *
 * static:
 * getmat() -- trace back best path, count matches: print()
 * pr_align() -- print alignment of described in array p[ ]: print()
 * dumpblock() -- dump a block of lines with numbers, stars: pr_align()
 * nums() -- put out a number line: dumpblock()
 * putline() -- put out a line (name, [num], seq, [num]): dumpblock()
 * stars() --put a line of stars: dumpblock()
 * stripname() -- strip any path and prefix from a seqname
 */ include "nw.h"

define SPC      3
#define P_LINE   256      /* maximum output line */
define P_SPC    3        /* space between name or num and seq */ extern   _day[26][26];
int      olen;            /* set output line length */
FILE     *fx;             /* output file */ print()                                                                         print
{
            int      lx, ly, firstgap, lastgap;      /* overlap */ if ((fx = fopen(ofile, "w")) == 0) {
                     fprintf(stderr,"%s: can't write %s\n", prog, ofile);
                     cleanup(1);
            }
            fprintf(fx, "<first sequence: %s (length = %d)\n", namex[0], len0);
            fprintf(fx, "<second sequence: %s (length = %d)\n", namex[1], len1);
            olen = 60;
            lx = len0;
            ly = len1;
            firstgap = lastgap = 0;
            if (dmax < len1 - 1) {        /* leading gap in x */
                     pp[0].spc = firstgap = len1 - dmax - 1;
                     ly -= pp[0].spc;
            }
            else if (dmax > len1 - 1) {   /* leading gap in y */
                     pp[1].spc = firstgap = dmax - (len1 - 1);
                     lx -= pp[1].spc;
            }
            if (dmax0 < len0 - 1) {       /* trailing gap in x */
                     lastgap = len0 - dmax0 -1;
                     lx -= lastgap;
            }
            else if (dmax0 > len0 - 1) {/* trailing gap in y */
                     lastgap = dmax0 - (len0 - 1);
                     ly -= lastgap;
            }
            getmat(lx, ly, firstgap, lastgap);
            pr_align();
}
```

Table 1 (cont')

```
/*
 * trace back the best path, count matches
 */
static
getmat(lx, ly, firstgap, lastgap)
        int     lx, ly;                 /* "core" (minus endgaps) */
        int     firstgap, lastgap;      /* leading trailing overlap */
{
        int             nm, i0, i1, siz0, siz1;
        char            outx[32];
        double          pct;
        register        n0, n1;
        register char   *p0, *p1;

/* get total matches, score
         */
        i0 = i1 = siz0 = siz1 = 0;
        p0 = seqx[0] + pp[1].spc;
        p1 = seqx[1] + pp[0].spc;
        n0 = pp[1].spc + 1;
        n1 = pp[0].spc + 1;

nm = 0;
        while ( *p0 && *p1 ) {
                if (siz0) {
                        p1++;
                        n1++;
                        siz0--;
                }
                else if (siz1) {
                        p0++;
                        n0++;
                        siz1--;
                }
                else {
                        if (xbm[*p0-'A']&xbm[*p1-'A'])
                                nm++;
                        if (n0++ == pp[0].x[i0])
                                siz0 = pp[0].n[i0++];
                        if (n1++ == pp[1].x[i1])
                                siz1 = pp[1].n[i1++];
                        p0++;
                        p1++;
                }
        }

/* pct homology:
         * if penalizing endgaps, base is the shorter seq
         * else, knock off overhangs and take shorter core
         */
        if (endgaps)
                lx = (len0 < len1)? len0 : len1;
        else
                lx = (lx < ly)? lx : ly;
        pct = 100.*(double)nm/(double)lx;
        fprintf(fx, "\n");
        fprintf(fx, "<%d match%s in an overlap of %d: %.2f percent similarity\n",
                nm, (nm == 1)? "" : "es", lx, pct);
``` getmat

Table 1 (cont')

```
            fprintf(fx, "<gaps in first sequence: %d", gapx);                               ...getmat
            if (gapx) {
                    (void) sprintf(outx, " (%d %s%s)",
                            ngapx, (dna)? "base":"residue", (ngapx == 1)? "":"s");
                    fprintf(fx,"%s", outx);

fprintf(fx, ", gaps in second sequence: %d", gapy);
            if (gapy) {
                    (void) sprintf(outx, " (%d %s%s)",
                            ngapy, (dna)? "base":"residue", (ngapy == 1)? "":"s");
                    fprintf(fx,"%s", outx);
            }
            if (dna)
                    fprintf(fx,
                    "\n<score: %d (match = %d, mismatch = %d, gap penalty = %d + %d per base)\n",
                    smax, DMAT, DMIS, DINS0, DINS1);
            else
                    fprintf(fx,
                    "\n<score: %d (Dayhoff PAM 250 matrix, gap penalty = %d + %d per residue)\n",
                    smax, PINS0, PINS1);
            if (endgaps)
                    fprintf(fx,
                    "<endgaps penalized. left endgap: %d %s%s, right endgap: %d %s%s\n",
                    firstgap, (dna)? "base" : "residue", (firstgap == 1)? "" : "s",
                    lastgap, (dna)? "base" : "residue", (lastgap == 1)? "" : "s");
            else
                    fprintf(fx, "<endgaps not penalized\n");
} static          nm;             /* matches in core -- for checking */
static          lmax;           /* lengths of stripped file names */
static          ij[2];          /* jmp index for a path */
static          nc[2];          /* number at start of current line */
static          ni[2];          /* current elem number -- for gapping */
static          siz[2];
static char     *ps[2];         /* ptr to current element */
static char     *po[2];         /* ptr to next output char slot */
static char     out[2][P_LINE]; /* output line */
static char     star[P_LINE];   /* set by stars() */

/*
* print alignment of described in struct path pp [ ]
*/
static
pr_align()                                                                                  pr_align
{
        int             nn;     /* char count */
        int             more;
        register        i;

for (i = 0, lmax = 0; i < 2; i++) {
                nn = stripname(namex[i]);
                if (nn > lmax)
                        lmax = nn;

nc[i] = 1;
                ni[i] = 1;
                siz[i] = ij[i] = 0;
```

Table 1 (cont')

...pr_align

```
                ps[i] = seqx[i];
                po[i] = out[i];                    }
        for (nn = nm = 0, more = 1; more; ) {
                for (i = more = 0; i < 2; i++) {
                        /*
                         * do we have more of this sequence?
                         */
                        if (!*ps[i])
                                continue;

more++;

if (pp[i].spc) {    /* leading space */
                                *po[i]++ = ' ';
                                pp[i].spc--;
                        }
                        else if (siz[i]) {    /* in a gap */
                                *po[i]++ = '-';
                                siz[i]--;
                        }
                        else {              /* we're putting a seq element
                                             */
                                *po[i] = *ps[i];
                                if (islower(*ps[i]))
                                        *ps[i] = toupper(*ps[i]);
                                po[i]++;
                                ps[i]++;

/*
                                 * are we at next gap for this seq?
                                 */
                                if (ni[i] == pp[i].x[ij[i]]) {
                                        /*
                                         * we need to merge all gaps
                                         * at this location
                                         */
                                        siz[i] = pp[i].n[ij[i]++];
                                        while (ni[i] == pp[i].x[ij[i]])
                                                siz[i] += pp[i].n[ij[i]++];
                                }
                                ni[i]++;
                        }
                }
                if (++nn == olen || !more && nn) {
                        dumpblock();
                        for (i = 0; i < 2; i++)
                                po[i] = out[i];
                        nn = 0;
                }
            }
        }
}
/*
 * dump a block of lines, including numbers, stars: pr_align()
 */
static
```

Table 1 (cont')

```
dumpblock()                                                              dumpblock
{
        register i;

for (i = 0; i < 2; i++)
                *po[i]-- = '\0';
        (void) putc('\n', fx);
        for (i = 0; i < 2; i++) {
                if (*out[i] && (*out[i] != ' ' || *(po[i]) != ' ')) {
                        if (i == 0)
                                nums(i);
                        if (i == 0 && *out[1])
                                stars();
                        putline(i);
                        if (i == 0 && *out[1])
                                fprintf(fx, star);
                        if (i == 1)
                                nums(i);
                }
        }
}

/*
 * put out a number line: dumpblock()
 */
static
nums(ix)                                                                 nums
        int     ix;     /* index in out[] holding seq line */
{
        char            nline[P_LINE];
        register        i, j;
        register char   *pn, *px, *py;

for (pn = nline, i = 0; i < lmax+P_SPC; i++, pn++)
                *pn = ' ';
        for (i = nc[ix], py = out[ix]; *py; py++, pn++) {
                if (*py == ' ' || *py == '-')
                        *pn = ' ';
                else {
                        if (i%10 == 0 || (i == 1 && nc[ix] != 1)) {
                                j = (i < 0)? -i : i;
                                for (px = pn; j; j /= 10, px--)
                                        *px = j%10 + '0';
                                if (i < 0)
                                        *px = '-';
                        }
                        else
                                *pn = ' ';
                        i++;
                }
        }
        *pn = '\0';
        nc[ix] = i;
        for (pn = nline; *pn; pn++)
                (void) putc(*pn, fx);
        (void) putc('\n', fx);
}

/*
```

Table 1 (cont')

```
* put out a line (name, [num], seq, [num]): dumpblock()
*/
static
putline(ix)
        int     ix;                     {
        int     i;
        register char   *px;

for (px = namex[ix], i = 0; *px && *px != ':'; px++, i++)
                (void) putc(*px, fx);
        for (; i < lmax+P_SPC; i++)
                (void) putc(' ', fx);

/* these count from 1:
        * ni[] is current element (from 1)
        * nc[] is number at start of current line
        */
        for (px = out[ix]; *px; px++)
                (void) putc(*px&0x7F, fx);
        (void) putc('\n', fx);
}

/*
* put a line of stars (seqs always in out[0], out[1]): dumpblock()
*/
static
stars()
{
        int     i;
        register char   *p0, *p1, cx, *px;

if (!*out[0] || (*out[0] == ' ' && *(po[0]) == ' ') ||
            !*out[1] || (*out[1] == ' ' && *(po[1]) == ' '))
                return;
        px = star;
        for (i = lmax+P_SPC; i; i--)
                *px++ = ' ';

for (p0 = out[0], p1 = out[1]; *p0 && *p1; p0++, p1++) {
                if (isalpha(*p0) && isalpha(*p1)) {
                        if (xbm[*p0-'A']&xbm[*p1-'A']) {
                                cx = '*';
                                nm++;
                        }
                        else if (!dna && _day[*p0-'A'][*p1-'A'] > 0)
                                cx = '.';
                        else
                                cx = ' ';
                }
                else
                        cx = ' ';
                *px++ = cx;
        }
        *px++ = '\n';
        *px = '\0';
}
``` putline stars

Table 1 (cont')

```
/*
 * strip path or prefix from pn, return len: pr_align()
 */
static
stripname(pn)                                                                    stripname
        char    *pn;       /* file name (may be path) */
{
        register char    *px, *py;

py = 0;
        for (px = pn; *px; px++)
                if (*px == '/')
                        py = px + 1;
        if (py)
                (void) strcpy(pn, py);
        return(strlen(pn));

}

/*
 * cleanup() -- cleanup any tmp file
 * getseq() -- read in seq, set dna, len, maxlen
 * g_calloc() -- calloc() with error checkin
 * readjmps() -- get the good jmps, from tmp file if necessary
 * writejmps() -- write a filled array of jmps to a tmp file: nw()
 */
include "nw.h"
include <sys/file.h> char    *jname = "/tmp/homgXXXXXX";          /* tmp file for jmps */
FILE    *fj;

int     cleanup();                           /* cleanup tmp file */
long    lseek();

/*
 * remove any tmp file if we blow
 */
cleanup(i)                                                                       cleanup
        int    i;
{
        if (fj)
                (void) unlink(jname);
        exit(i);
}

/*
 * read, return ptr to seq, set dna, len, maxlen
 * skip lines starting with ';', '<', or '>'
 * seq in upper or lower case
 */
char    *
```

Table 1 (cont')

getseq

```
getseq(file, len)
        char    *file;   /* file name */
        int     *len;    /* seq len */
{
        char            line[1024], *pseq;
        register char   *px, *py;
        int             natgc, tlen;
        FILE            *fp;

if ((fp = fopen(file,"r")) == 0) {
                fprintf(stderr,"%s: can't read %s\n", prog, file);
                exit(1);
        }
        tlen = natgc = 0;
        while (fgets(line, 1024, fp)) {
                if (*line == ';' || *line == '<' || *line == '>')
                        continue;
                for (px = line; *px != '\n'; px++)
                        if (isupper(*px) || islower(*px))
                                tlen++;
        }
        if ((pseq = malloc((unsigned)(tlen+6))) == 0) {
                fprintf(stderr,"%s: malloc() failed to get %d bytes for %s\n", prog, tlen+6, file);
                exit(1);
        }
        pseq[0] = pseq[1] = pseq[2] = pseq[3] = '\0';
        py = pseq + 4;
        *len = tlen;
        rewind(fp);

while (fgets(line, 1024, fp)) {
                if (*line == ';' || *line == '<' || *line == '>')
                        continue;
                for (px = line; *px != '\n'; px++) {
                        if (isupper(*px))
                                *py++ = *px;
                        else if (islower(*px))
                                *py++ = toupper(*px);
                        if (index("ATGCU",*(py-1)))
                                natgc++;
                }
        }
        *py++ = '\0';
        *py = '\0';
        (void) fclose(fp);
        dna = natgc > (tlen/3);
        return(pseq+4);
} char    *
```

Table 1 (cont')

g_calloc

```
g_calloc(msg, nx, sz)
        char    *msg;           /* program, calling routine */
        int     nx, sz;         /* number and size of elements */
{
        char            *px, *calloc();

if ((px = calloc((unsigned)nx, (unsigned)sz)) == 0) {
                if (*msg) {
                        fprintf(stderr, "%s: g_calloc() failed %s (n=%d, sz=%d)\n", prog, msg, nx, sz);
                        exit(1);
                }
        }
        return(px);
}

/*
 * get final jmps from dx[] or tmp file, set pp[], reset dmax: main()
 */
``` readjmps

```
readjmps()
{
        int             fd = -1;
        int             siz, i0, i1;
        register i, j, xx;

if (fj) {
                (void) fclose(fj);
                if ((fd = open(jname, O_RDONLY, 0)) < 0) {
                        fprintf(stderr, "%s: can't open() %s\n", prog, jname);
                        cleanup(1);
                }
        }
        for (i = i0 = i1 = 0, dmax0 = dmax, xx = len0; ; i++) {
                while (1) {
                        for (j = dx[dmax].ijmp; j >= 0 && dx[dmax].jp.x[j] >= xx; j--)
                                ;
                        if (j < 0 && dx[dmax].offset && fj) {
                                (void) lseek(fd, dx[dmax].offset, 0);
                                (void) read(fd, (char *)&dx[dmax].jp, sizeof(struct jmp));
                                (void) read(fd, (char *)&dx[dmax].offset, sizeof(dx[dmax].offset));
                                dx[dmax].ijmp = MAXJMP-1;
                        }
                        else
                                break;
                }
                if (i >= JMPS) {
                        fprintf(stderr, "%s: too many gaps in alignment\n", prog);
                        cleanup(1);
```

Table 1 (cont')

...readjmps

```
            }
            if (j >= 0) {
                    siz = dx[dmax].jp.n[j];
                    xx = dx[dmax].jp.x[j];
                    dmax += siz;
                    if (siz < 0) {              /* gap in second seq */
                            pp[1].n[i1] = -siz;
                            xx += siz;
                            /* id = xx - yy + len1 - 1
                            */
                            pp[1].x[i1] = xx - dmax + len1 - 1;
                            gapy++;
                            ngapy -= siz;
/* ignore MAXGAP when doing endgaps */
                            siz = (-siz < MAXGAP || endgaps)? -siz : MAXGAP;
                            i1++;
                    }
                    else if (siz > 0) {  /* gap in first seq */
                            pp[0].n[i0] = siz;
                            pp[0].x[i0] = xx;
                            gapx++;
                            ngapx += siz;
/* ignore MAXGAP when doing endgaps */
                            siz = (siz < MAXGAP || endgaps)? siz : MAXGAP;
                            i0++;
                    }
            }
            else
                    break;
    }
    /* reverse the order of jmps
    */
    for (j = 0, i0--; j < i0; j++, i0--) {
            i = pp[0].n[j]; pp[0].n[j] = pp[0].n[i0]; pp[0].n[i0] = i;
            i = pp[0].x[j]; pp[0].x[j] = pp[0].x[i0]; pp[0].x[i0] = i;
    }
    for (j = 0, i1--; j < i1; j++, i1--) {
            i = pp[1].n[j]; pp[1].n[j] = pp[1].n[i1]; pp[1].n[i1] = i;
            i = pp[1].x[j]; pp[1].x[j] = pp[1].x[i1]; pp[1].x[i1] = i;
    }
    if (fd >= 0)
            (void) close(fd);
    if (fj) {
            (void) unlink(jname);
```

Table 1 (cont')

```
                fj = 0;
                offset = 0;
        }                               }
/*
 * write a filled jmp struct offset of the prev one (if any): nw()
 */
writejmps(ix)                                                           writejmps
        int     ix;
{
        char    *mktemp();

if (!fj) {
                if (mktemp(jname) < 0) {
                        fprintf(stderr, "%s: can't mktemp() %s\n", prog, jname);
                        cleanup(1);
                }
                if ((fj = fopen(jname, "w")) == 0) {
                        fprintf(stderr, "%s: can't write %s\n", prog, jname);
                        exit(1);
                }
        }
        (void) fwrite((char *)&dx[ix].jp, sizeof(struct jmp), 1, fj);
        (void) fwrite((char *)&dx[ix].offset, sizeof(dx[ix].offset), 1, fj);
}
```

TABLE 2

| | | |
|---|---|---|
| PRO | XXXXXXXXXXXXXXX | (Length = 15 amino acids) |
| Comparison Protein | XXXXXYYYYYYY | (Length = 12 amino acids) |

% amino acid sequence identity = (the number of identically matching amino acid residues between the two polypeptide sequences as determined by ALIGN-2) divided by (the total number of amino acid residues of the PRO polypeptide) = 5 divided by 15 = 33.3%

TABLE 3

| | | |
|---|---|---|
| PRO | XXXXXXXXXX (Length = 10 amino acids) | |
| Comparison Protein | XXXXXYYYYYYZZYZ (Length = 15 amino acids) | |

% amino acid sequence identity = (the number of identically matching amino acid residues between the two polypeptide sequences as determined by ALIGN-2) divided by (the total number of amino acid residues of the PRO polypeptide) = 5 divided by 10 = 50%

TABLE 4

| | | |
|---|---|---|
| PRO-DNA | NNNNNNNNNNNNNN | (Length = 14 nucleotides) |
| Comparison DNA | NNNNNNLLLLLLLLLL | (Length = 16 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 6 divided by 14 = 42.9%

TABLE 5

| | | |
|---|---|---|
| PRO-DNA | NNNNNNNNNNNN | (Length = 12 nucleotides) |
| Comparison DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 4 divided by 12 = 33.3%

II. Compositions and Methods of the Invention

A. Full-Length PRO Polypeptides

The present invention provides newly identified and isolated nucleotide sequences encoding polypeptides referred to in the present application as PRO polypeptides. In particular, cDNAs encoding various PRO polypeptides have been identified and isolated, as disclosed in further detail in the Examples below. It is noted that proteins produced in separate expression rounds may be given different PRO numbers but the UNQ number is unique for any given DNA and the encoded protein, and will not be changed. However, for sake of simplicity, in the present specification the protein encoded by the full length native nucleic acid molecules disclosed herein as well as all further native homologues and variants included in the foregoing definition of PRO, will be referred to as "PRO/number", regardless of their origin or mode of preparation.

As disclosed in the Examples below, various cDNA clones have been deposited with the ATCC. The actual nucleotide sequences of those clones can readily be determined by the skilled artisan by sequencing of the deposited clone using routine methods in the art. The predicted amino acid sequence can be determined from the nucleotide sequence using routine skill. For the PRO polypeptides and encoding nucleic acids described herein, Applicants have identified what is believed to be the reading frame best identifiable with the sequence information available at the time.

B. PRO Polypeptide Variants

In addition to the full-length native sequence PRO polypeptides described herein, it is contemplated that PRO variants can be prepared. PRO variants can be prepared by introducing appropriate nucleotide changes into the PRO DNA, and/or by synthesis of the desired PRO polypeptide. Those skilled in the art will appreciate that amino acid changes may alter post-translational processes of the PRO, such as changing the number or position of glycosylation sites or altering the membrane anchoring characteristics.

Variations in the native full-length sequence PRO or in various domains of the PRO described herein, can be made, for example, using any of the techniques and guidelines for conservative and non-conservative mutations set forth, for instance, in U.S. Pat. No. 5,364,934. Variations may be a substitution, deletion or insertion of one or more codons encoding the PRO that results in a change in the amino acid sequence of the PRO as compared with the native sequence PRO. Optionally the variation is by substitution of at least one amino acid with any other amino acid in one or more of the domains of the PRO. Guidance in determining which amino acid residue may be inserted, substituted or deleted without adversely affecting the desired activity may be found by comparing the sequence of the PRO with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

PRO polypeptide fragments are provided herein. Such fragments may be truncated at the N-terminus or C-terminus, or may lack internal residues, for example, when compared with a full length native protein. Certain fragments lack amino acid residues that are not essential for a desired biological activity of the PRO polypeptide.

PRO fragments may be prepared by any of a number of conventional techniques. Desired peptide fragments may be chemically synthesized. An alternative approach involves generating PRO fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, PRO polypeptide fragments share at least one biological and/or immunological activity with the native PRO polypeptide disclosed herein.

In particular embodiments, conservative substitutions of interest are shown in Table 6 under the heading of preferred substitutions. If such substitutions result in a change in biological activity, then more substantial changes, denominated exemplary substitutions in Table 6, or as further described below in reference to amino acid classes, are introduced and the products screened.

TABLE 6

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the PRO polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA*, 317:415 (1986)] or other known techniques can be performed on the cloned DNA to produce the PRO variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science*, 244: 1081–1085 (1989)]. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.*, 150:1 (1976)]. If alanine substitution does not yield adequate amounts of variant, an isoteric amino acid can be used.

C. Modifications of PRO

Covalent modifications of PRO are included within the scope of this invention. One type of covalent modification includes reacting targeted amino acid residues of a PRO polypeptide with an organic derivatizing agent that is capable of reacting with selected side chains or the N- or C-terminal residues of the PRO. Derivatization with bifunctional agents is useful, for instance, for crosslinking PRO to a water-insoluble support matrix or surface for use in the method for purifying anti-PRO antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79–86 (1983)], acetylation of the N-terminal amine, and amidation of any C-terminal carboxyl group.

Another type of covalent modification of the PRO polypeptide included within the scope of this invention comprises altering the native glycosylation pattern of the polypeptide. "Altering the native glycosylation pattern" is intended for purposes herein to mean deleting one or more carbohydrate moieties found in native sequence PRO (either by removing the underlying glycosylation site or by deleting the glycosylation by chemical and/or enzymatic means), and/or adding one or more glycosylation sites that are not present in the native sequence PRO. In addition, the phrase includes qualitative changes in the glycosylation of the native proteins, involving a change in the nature and proportions of the various carbohydrate moieties present.

Addition of glycosylation sites to the PRO polypeptide may be accomplished by altering the amino acid sequence. The alteration may be made, for example, by the addition of, or substitution by, one or more serine or threonine residues to the native sequence PRO (for O-linked glycosylation sites). The PRO amino acid sequence may optionally be altered through changes at the DNA level, particularly by mutating the DNA encoding the PRO polypeptide at preselected bases such that codons are generated that will translate into the desired amino acids.

Another means of increasing the number of carbohydrate moieties on the PRO polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259–306 (1981).

Removal of carbohydrate moieties present on the PRO polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal.*

*Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of PRO comprises linking the PRO polypeptide to one of a variety of nonproteinaceous polymers, e.g., polyethylene glycol (PEG), polypropylene glycol, or polyoxyalkylenes, in the manner set forth in U.S. Pat. No. 4,640,835; 4,496,689; 4,301,144; 4,670,417; 4,791,192 or 4,179,337.

The PRO of the present invention may also be modified in a way to form a chimeric molecule comprising PRO fused to another, heterologous polypeptide or amino acid sequence.

In one embodiment, such a chimeric molecule comprises a fusion of the PRO with a tag polypeptide which provides an epitope to which an anti-tag antibody can selectively bind. The epitope tag is generally placed at the amino- or carboxyl-terminus of the PRO. The presence of such epitope-tagged forms of the PRO can be detected using an antibody against the tag polypeptide. Also, provision of the epitope tag enables the PRO to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol*, 8:2159–2165 (1988)]; the c-myc tag and the 8F9, 3C7, 6E10, G4, B7 and 9E10 antibodies thereto [Evan et al., *Molecular and Cellular Biology*, 5:3610–3616 (1985)]; and the Herpes Simplex virus glycoprotein D (gD) tag and its antibody [Paborsky et al., *Protein Engineering*, 3(6):547–553 (1990)]. Other tag polypeptides include the Flag-peptide [Hopp et al., *BioTechnology*, 6:1204–1210 (1988)]; the KT3 epitope peptide [Martin et al., *Science*, 255:192–194 (1992)]; an α-tubulin epitope peptide [Skinner et al., *J. Biol. Chem.*, 266:15163–15166 (1991)]; and the T7 gene 10 protein peptide tag [Lutz-Freyermuth et al., *Proc. Natl. Acad. Sci. USA*, 87:6393–6397 (1990)].

In an alternative embodiment, the chimeric molecule may comprise a fusion of the PRO with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a PRO polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

D. Preparation of PRO

The description below relates primarily to production of PRO by culturing cells transformed or transfected with a vector containing PRO nucleic acid. It is, of course, contemplated that alternative methods, which are well known in the art, may be employed to prepare PRO. For instance, the PRO sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149–2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the PRO may be chemically synthesized separately and combined using chemical or enzymatic methods to produce the full-length PRO.

1. Isolation of DNA Encoding PRO

DNA encoding PRO may be obtained from a cDNA library prepared from tissue believed to possess the PRO mRNA and to express it at a detectable level. Accordingly, human PRO DNA can be conveniently obtained from a cDNA library prepared from human tissue, such as described in the Examples. The PRO-encoding gene may also be obtained from a genomic library or by known synthetic procedures (e.g., automated nucleic acid synthesis).

Libraries can be screened with probes (such as antibodies to the PRO or oligonucleotides of at least about 20–80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding PRO is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for PRO production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of eukaryotic cell transfection and prokaryotic cell transformation are known to the ordinarily skilled artisan, for example, CaCl$_2$, CaPO$_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456–457 (1978) can be employed. General aspects of mammalian cell host system transfections have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyomithine, may also be used. For various techniques for transforming mammalian cells, see Keown et al., *Methods in Enzymology*, 185:527–537 (1990) and Mansour et al., *Nature*, 336:348–352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kan$^r$; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 μg. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for PRO-encoding vectors. *Saccharomyces cerevisiae* is a commonly used lower eukaryotic host microorganism. Others include *Schizosaccharomyces pombe* (Beach and Nurse, *Nature*, 290: 140 [1981]; EP 139,383 published 2 May 1985); *Kluyveromyces* hosts (U.S. Pat. No. 4,943,529; Fleer et al., *Bio/Technology*, 9:968–975 (1991)) such as, e.g., *K. lactis* (MW98-8C, CBS683, CBS4574; Louvencourt et al., *J. Bacteriol.*, 154(2):737–742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology*, 8:135 (1990), *K. thermotolerans*, and *K. marxianus*; *yarrowia* (EP 402,226); *Pichia pastoris* (EP 183,070; Sreekrishna et al., *J. Basic Microbiol.*, 28:265–278 [1988]); *Candida*; *Trichoderma reesia* (EP 244,234); *Neurospora crassa* (Case et al., *Proc. Natl. Acad. Sci. USA*, 76:5259–5263 [1979]); *Schwanniomyces* such as *Schwanniomyces occidentalis* (EP 394,538 published 31 Oct. 1990); and filamentous fungi such as, e.g., *Neurospora*, *Penicillium*, *Tolypocladium* (WO 91/00357 published 10 Jan. 1991), and *Aspergillus* hosts such as *A. nidulans* (Ballance et al., *Biochem. Biophys. Res. Commun.*, 112:284–289 [1983]; Tilbum et al., *Gene*, 26:205–221 [1983]; Yelton et al., *Proc. Natl. Acad. Sci. USA*, 81: 1470–1474 [1984]) and *A. niger* (Kelly and Hynes, *EMBO J.*, 4:475–479 [1985]). Methylotropic yeasts are suitable herein and include, but are not limited to, yeast capable of growth on methanol selected from the genera consisting of *Hansenula*, *Candida*, *Kloeckera*, *Pichia*, *Saccharomyces*, *Torulopsis*, and *Rhodotorula*. A list of specific species that are exemplary of this class of yeasts may be found in C. Anthony, *The Biochemistry of Methylotrophs*, 269 (1982).

Suitable host cells for the expression of glycosylated PRO are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/-DHFR(CHO, Urlaub and Chasin, *Proc. Natl. Acad. Sci. USA*, 77:4216 (1980)); mouse sertoli cells (TM4, Mather, *Biol. Reprod.*, 23:243–251 (1980)); human lung cells (W138, ATCC CCL75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding PRO may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The PRO may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the PRO-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including Saccharomyces and Kluyveromyces α-factor leaders, the latter described in U.S. Pat. No. 5,010, 182), or acid phosphatase leader, the C. albicans glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the PRO-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the PRO-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21–25 (1983)]. Promoters for use in bacterial systems also will contain a Shine-Dalgarno (S.D.) sequence operably linked to the DNA encoding PRO.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

PRO transcription from vectors in mammalian host cells is controlled, for example, by promoters obtained from the genomes of viruses such as polyoma virus, fowlpox virus (UK 2,211,504 published 5 μl. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the PRO by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the PRO coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding PRO.

Still other methods, vectors, and host cells suitable for adaptation to the synthesis of PRO in recombinant vertebrate cell culture are described in Gething et al., *Nature*, 293: 620–625 (1981); Mantei et al., *Nature*, 281:40–46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201–5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence PRO polypeptide or against a synthetic peptide based on the DNA sequences provided herein or against exogenous sequence fused to PRO DNA and encoding a specific antibody epitope.

5. Purification of Polypeptide

Forms of PRO may be recovered from culture medium or from host cell lysates. If membrane-bound, it can be released from the membrane using a suitable detergent solution (e.g. Triton-X 100) or by enzymatic cleavage. Cells employed in expression of PRO can be disrupted by various physical or chemical means, such as freeze-thaw cycling, sonication, mechanical disruption, or cell lysing agents.

It may be desired to purify PRO from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the PRO. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular PRO produced.

E. Uses for PRO

Nucleotide sequences (or their complement) encoding PRO have various applications in the art of molecular biology, including uses as hybridization probes, in chromosome and gene mapping and in the generation of anti-sense RNA and DNA. PRO nucleic acid will also be useful for the preparation of PRO polypeptides by the recombinant techniques described herein.

The full-length native sequence PRO gene, or portions thereof, may be used as hybridization probes for a cDNA library to isolate the full-length PRO cDNA or to isolate still other cDNAs (for instance, those encoding naturally-occurring variants of PRO or PRO from other species) which have a desired sequence identity to the native PRO sequence disclosed herein. Optionally, the length of the probes will be about 20 to about 50 bases. The hybridization probes may be derived from at least partially novel regions of the full length native nucleotide sequence wherein those regions may be determined without undue experimentation or from genomic sequences including promoters, enhancer elements and introns of native sequence PRO. By way of example, a screening method will comprise isolating the coding region of the PRO gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the PRO gene of the present invention can be used to screen libraries of human cDNA, genomic DNA or mRNA to determine which members of such libraries the probe hybridizes to. Hybridization techniques are described in further detail in the Examples below.

Any EST sequences disclosed in the present application may similarly be employed as probes, using the methods disclosed herein.

Other useful fragments of the PRO nucleic acids include antisense or sense oligonucleotides comprising a singe-stranded nucleic acid sequence (either RNA or DNA) capable of binding to target PRO mRNA (sense) or PRO DNA (antisense) sequences. Antisense or sense oligonucleotides, according to the present invention, comprise a fragment of the coding region of PRO DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of PRO proteins. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Antisense or sense RNA or DNA molecules are generally at least about 5 bases in length, about 10 bases in length, about 15 bases in length, about 20 bases in length, about 25 bases in length, about 30 bases in length, about 35 bases in length, about 40 bases in length, about 45 bases in length, about 50 bases in length, about 55 bases in length, about 60 bases in length, about 65 bases in length, about 70 bases in length, about 75 bases in length, about 80 bases in length, about 85 bases in length, about 90 bases in length, about 95 bases in length, about 100 bases in length, or more.

The probes may also be employed in PCR techniques to generate a pool of sequences for identification of closely related PRO coding sequences.

Nucleotide sequences encoding a PRO can also be used to construct hybridization probes for mapping the gene which encodes that PRO and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for PRO encode a protein which binds to another protein (example, where the PRO is a receptor), the PRO can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor PRO can be used to isolate correlative ligand(s). Screening assays can be designed to find lead compounds that mimic the biological activity of a native PRO or a receptor for PRO. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein—protein binding assays, biochemical screening assays, immunoassays and cell based assays, which are well characterized in the art.

Nucleic acids which encode PRO or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding PRO can be used to clone genomic DNA encoding PRO in accordance with established techniques and the genomic sequences used to generate transgenic animals that contain cells which express DNA encoding PRO. Methods for generating transgenic animals, particularly animals such as mice or rats, have become conventional in the art and are described, for example, in U.S. Pat. Nos. 4,736,866 and 4,870,009. Typically, particular cells would be targeted for PRO transgene incorporation with tissue-specific enhancers. Transgenic animals that include a copy of a transgene encoding PRO introduced into the germ line of the animal at an embryonic stage can be used to examine the effect of increased expression of DNA encoding PRO. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of PRO can be used to construct a PRO "knock out" animal which has a defective or altered gene encoding PRO as a result of homologous recombination between the endogenous gene encoding PRO and altered genomic DNA encoding PRO introduced into an embryonic stem cell of the animal. For example, cDNA encoding PRO can be used to clone genomic DNA encoding PRO in accordance with established techniques. A portion of the genomic DNA encoding PRO can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell*, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell*, 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113–152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knock-out animals can be characterized for instance, for their ability to defend against certain pathological conditions and for their development of pathological conditions due to absence of the PRO polypeptide.

Nucleic acid encoding the PRO polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83:4143–4146

[1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205–210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429–4432 (1987); and Wagner et al., *Proc. Natl. Acad. Sci. USA* 87, 3410–3414 (1990). For review of gene marking and gene therapy protocols see Anderson et al., *Science* 256, 808–813 (1992).

The PRO polypeptides described herein may also be employed as molecular weight markers for protein electrophoresis purposes and the isolated nucleic acid sequences may be used for recombinantly expressing those markers.

The nucleic acid molecules encoding the PRO polypeptides or fragments thereof described herein are useful for chromosome identification. In this regard, there exists an ongoing need to identify new chromosome markers, since relatively few chromosome marking reagents, based upon actual sequence data are presently available. Each PRO nucleic acid molecule of the present invention can be used as a chromosome marker.

The PRO polypeptides and nucleic acid molecules of the present invention may also be used diagnostically for tissue typing, wherein the PRO polypeptides of the present invention may be differentially expressed in one tissue as compared to another, preferably in a diseased tissue as compared to a normal tissue of the same tissue type. PRO nucleic acid molecules will find use for generating probes for PCR, Northern analysis, Southern analysis and Western analysis.

The PRO polypeptides described herein may also be employed as therapeutic agents. The PRO polypeptides of the present invention can be formulated according to known methods to prepare pharmaceutically useful compositions, whereby the PRO product hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42–96.

When in vivo administration of a PRO polypeptide or agonist or antagonist thereof is employed, normal dosage amounts may vary from about 10 ng/kg to up to 100 mg/kg of mammal body weight or more per day, preferably about 1 µg/kg/day to 10 mg/kg/day, depending upon the route of administration. Guidance as to particular dosages and methods of delivery is provided in the literature; see, for example, U.S. Pat. No. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of a PRO polypeptide is desired in a formulation with release characteristics suitable for the treatment of any disease or disorder requiring administration of the PRO polypeptide, microencapsulation of the PRO polypeptide is contemplated. Microencapsulation of recombinant proteins for sustained release has been successfully performed with human growth hormone (rhGH), interferon- (rhIFN-), interleukin-2, and MN rgp120. Johnson et al., *Nat. Med.,* 2:795–799 (1996); Yasuda, *Biomed. Ther.,* 27:1221–1223 (1993); Hora et al., *Bio/Technology* 8:755–758 (1990); Cleland, "Design and Production of Single Immunization Vaccines Using Polylactide Polyglycolide Microsphere Systems," in *Vaccine Design: The Subunit and Adjuvant Approach*, Powell and Newman, eds, (Plenum Press: New York, 1995), pp. 439–462; WO 97/03692, WO 96/40072, WO 96/07399; and U.S. Pat. No. 5,654,010.

The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), *Biodegradable Polymers as Drug Delivery Systems* (Marcel Dekker: New York, 1990), pp. 1–41.

This invention encompasses methods of screening compounds to identify those that mimic the PRO polypeptide (agonists) or prevent the effect of the PRO polypeptide (antagonists). Screening assays for antagonist drug candidates are designed to identify compounds that bind or complex with the PRO polypeptides encoded by the genes identified herein, or otherwise interfere with the interaction of the encoded polypeptides with other cellular proteins. Such screening assays will include assays amenable to high-throughput screening of chemical libraries, making them particularly suitable for identifying small molecule drug candidates.

The assays can be performed in a variety of formats, including protein—protein binding assays, biochemical screening assays, immunoassays, and cell-based assays, which are well characterized in the art.

All assays for antagonists are common in that they call for contacting the drug candidate with a PRO polypeptide encoded by a nucleic acid identified herein under conditions and for a time sufficient to allow these two components to interact.

In binding assays, the interaction is binding and the complex formed can be isolated or detected in the reaction mixture. In a particular embodiment, the PRO polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the PRO polypeptide and drying. Alternatively, an immobilized antibody, e.g., a monoclonal antibody, specific for the PRO polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular PRO polypeptide encoded by a gene identified herein, its interaction with that polypeptide can be assayed by methods well known for detecting protein—protein interactions. Such assays include traditional approaches, such as, e.g., cross-linking, co-immunoprecipitation, and co-purification through gradients or chromatographic columns. In addition, protein—protein interactions can be monitored by using a yeast-based genetic system described by Fields and co-workers (Fields and Song, *Nature (London)*, 340:245–246 (1989); Chien et al., *Proc. Natl. Acad. Sci. USA*, 88:9578–9582 (1991)) as disclosed by Chevray and Nathans, *Proc. Natl. Acad. Sci. USA*, 89: 5789–5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein—protein interaction. Colonies containing interacting polypeptides are detected with a chromogenic substrate for β-galactosidase. A complete kit (MATCHMAKER™) for identifying protein—protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a PRO polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the PRO polypeptide may be added to a cell along with the compound to be screened for a particular activity and the ability of the compound to inhibit the activity of interest in the presence of the PRO polypeptide indicates that the compound is an antagonist to the PRO polypeptide. Alternatively, antagonists may be detected by combining the PRO polypeptide and a potential antagonist with membrane-bound PRO polypeptide receptors or recombinant receptors under appropriate conditions for a competitive inhibition assay. The PRO polypeptide can be labeled, such as by radioactivity, such that the number of PRO polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.*, 1(2): Chapter 5 (1991). Preferably, expression cloning is employed wherein polyadenylated RNA is prepared from a cell responsive to the PRO polypeptide and a cDNA library created from this RNA is divided into pools and used to transfect COS cells or other cells that are not responsive to the PRO polypeptide. Transfected cells that are grown on glass slides are exposed to labeled PRO polypeptide. The PRO polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled PRO polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

In another assay for antagonists, mammalian cells or a membrane preparation expressing the receptor would be incubated with labeled PRO polypeptide in the presence of the candidate compound. The ability of the compound to enhance or block this interaction could then be measured.

More specific examples of potential antagonists include an oligonucleotide that binds to the fusions of immunoglobulin with PRO polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the PRO polypeptide that recognizes the receptor but imparts no effect, thereby competitively inhibiting the action of the PRO polypeptide.

Another potential PRO polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature PRO polypeptides herein, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.,* 6:3073 (1979); Cooney et al., *Science,* 241: 456 (1988); Dervan et al., *Science,* 251:1360 (1991)), thereby preventing transcription and the production of the PRO polypeptide. The antisense RNA oligonucleotide hybridizes to the mRNA in vivo and blocks translation of the mRNA molecule into the PRO polypeptide (antisense—Okano, *Neurochem.,* 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the PRO polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the PRO polypeptide, thereby blocking the normal biological activity of the PRO polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology,* 4:469–471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

Diagnostic and therapeutic uses of the herein disclosed molecules may also be based upon the positive functional assay hits disclosed and described below.

F. Anti-PRO Antibodies

The present invention further provides anti-PRO antibodies. Exemplary antibodies include polyclonal, monoclonal, humanized, bispecific, and heteroconjugate antibodies.

1. Polyclonal Antibodies

The anti-PRO antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the PRO polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-PRO antibodies may, alternatively, be monoclonal antibodies. Monoclonal antibodies may be prepared using hybridoma methods, such as those described by Kohler and Milstein, *Nature,* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the PRO polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51–63].

The culture medium in which the hybridoma cells are cultured can then be assayed for the presence of monoclonal antibodies directed against PRO. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Human and Humanized Antibodies

The anti-PRO antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522–525 (1986); Riechmann et al., *Nature*, 332:323–329 (1988); and Presta, *Curr. Op. Struct. Biol.*, 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779–783 (1992); Lonberg et al., *Nature* 368 856–859 (1994); Morrison, *Nature* 368, 812–13 (1994); Fishwild et al., *Nature Biotechnology* 14, 845–51 (1996); Neuberger, *Nature Biotechnology* 14, 826 (1996); Lonberg and Huszar, *Intern. Rev. Immunol.* 13 65–93 (1995).

The antibodies may also be affinity matured using known selection and/or mutagenesis methods as described above. Preferred affinity matured antibodies have an affinity which is five times, more preferably 10 times, even more preferably 20 or 30 times greater than the starting antibody (generally murine, humanized or human) from which the matured antibody is prepared.

4. Bispecific Antibodies

Bispecific antibodies are monoclonal, preferably human or humanized, antibodies that have binding specificities for at least two different antigens. In the present case, one of the binding specificities is for the PRO, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature*, 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.*, 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175:217–225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various technique for making and isolating bispecific antibody fragments directly from recombinant cell culture have also been described. For example, bispecific antibodies have been produced using leucine zippers. Kostelny et al., *J. Immunol.* 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., *J. Immunol.* 152:5368 (1994).

Antibodies with more than two valencies are contemplated. For example, trispecific antibodies can be prepared. Tutt et al., *J. Immunol.* 147:60 (1991).

Exemplary bispecific antibodies may bind to two different epitopes on a given PRO polypeptide herein. Alternatively, an anti-PRO polypeptide arm may be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular PRO polypeptide. Bispecific antibodies may also be used to localize cytotoxic agents to cells which express a particular PRO polypeptide. These antibodies possess a PRO-binding arm and an arm which binds a cytotoxic agent or a radionuclide chelator, such as EOTUBE, DPTA, DOTA, or TETA. Another bispecific antibody of interest binds the PRO polypeptide and further binds tissue factor (TF).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

6. Effector Function Engineering

It may be desirable to modify the antibody of the invention with respect to effector function, so as to enhance, e.g., the effectiveness of the antibody in treating cancer. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.*, 176: 1191–1195 (1992) and Shopes, *J. Immunol.*, 148: 2918–2922 (1992). Homodimeric antibodies with enhanced anti-tumor activity may also be prepared using heterobifunctional cross-linkers as described in Wolff et al. *Cancer Research*, 53: 2560–2565 (1993). Alternatively, an antibody can be engineered that has dual Fc regions and may thereby have enhanced complement lysis and ADCC capabilities. See Stevenson et al., *Anti-Cancer Drug Design* 3: 219–230 (1989).

7. Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol)propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science*, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

8. Immunoliposomes

The antibodies disclosed herein may also be formulated as immunoliposomes. Liposomes containing the antibody are prepared by methods known in the art, such as described in Epstein et al., *Proc. Natl. Acad. Sci. USA*, 82: 3688 (1985); Hwang et al., *Proc. Natl. Acad. Sci. USA*, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.*, 257: 286–288 (1982) via a disulfide-interchange reaction. A chemotherapeutic agent (such as Doxorubicin) is optionally contained within the liposome. See Gabizon et al., *J. National Cancer Inst.*, 81(19): 1484 (1989).

9. Pharmaceutical Compositions of Antibodies

Antibodies specifically binding a PRO polypeptide identified herein, as well as other molecules identified by the screening assays disclosed hereinbefore, can be administered for the treatment of various disorders in the form of pharmaceutical compositions.

If the PRO polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA,* 90: 7889–7893 (1993).

The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's *Pharmaceutical Sciences,* supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

G. Uses for Anti-PRO Antibodies

The anti-PRO antibodies of the invention have various utilities. For example, anti-PRO antibodies may be used in diagnostic assays for PRO, e.g., detecting its expression (and in some cases, differential expression) in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques,* CRC Press, Inc. (1987) pp. 147–158]. The antibodies used in the diagnostic assays can be labeled with a detectable moiety. The detectable moiety should be capable of producing, either directly or indirectly, a detectable signal. For example, the detectable moiety may be a radioisotope, such as $^{3}H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature,* 144:945 (1962); David et al., *Biochemisty,* 13:1014 (1974); Pain et al., *J. Immunol. Meth.,* 40:219 (1981); and Nygren, *J. Histochem. and Cytochem.,* 30:407 (1982).

Anti-PRO antibodies also are useful for the affinity purification of PRO from recombinant cell culture or natural sources. In this process, the antibodies against PRO are immobilized on a suitable support, such a Sephadex resin or filter paper, using methods well known in the art. The immobilized antibody then is contacted with a sample containing the PRO to be purified, and thereafter the support is washed with a suitable solvent that will remove substantially all the material in the sample except the PRO, which is bound to the immobilized antibody. Finally, the support is washed with another suitable solvent that will release the PRO from the antibody.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Extracellular Domain Homology Screening to Identify Novel Polypeptides and cDNA Encoding Therefor The extracellular domain (ECD) sequences (including the secretion signal sequence, if any) from about 950 known secreted proteins from the Swiss-Prot public database were used to search EST databases. The EST databases included public databases (e.g., Dayhoff, GenBank), and proprietary databases (e.g. LIFESEQ™, Incyte Pharmaceuticals, Palo Alto, Calif.). The search was performed using the computer program BLAST or BLAST-2 (Altschul et al., *Methods in Enzymology* 266:460–480 (1996)) as a comparison of the ECD protein sequences to a 6 frame translation of the EST sequences. Those comparisons with a BLAST score of 70 (or in some cases 90) or greater that did not encode known proteins were clustered and assembled into consensus DNA sequences with the program "phrap" (Phil Green, University of Washington, Seattle, Wash.).

Using this extracellular domain homology screen, consensus DNA sequences were assembled relative to the other identified EST sequences using phrap. In addition, the consensus DNA sequences obtained were often (but not always) extended using repeated cycles of BLAST or BLAST-2 and phrap to extend the consensus sequence as far as possible using the sources of EST sequences discussed above.

Based upon the consensus sequences obtained as described above, oligonucleotides were then synthesized and used to identify by PCR a cDNA library that contained the sequence of interest and for use as probes to isolate a clone of the full-length coding sequence for a PRO polypeptide. Forward and reverse PCR primers generally range from 20 to 30 nucleotides and are often designed to give a PCR product of about 100–1000 bp in length. The probe sequences are typically 40–55 bp in length. In some cases, additional oligonucleotides are synthesized when the consensus sequence is greater than about 1–1.5 kbp. In order to screen several libraries for a full-length clone, DNA from the libraries was screened by PCR amplification, as per Ausubel et al., *Current Protocols in Molecular Biology*, with the PCR primer pair. A positive library was then used to isolate clones encoding the gene of interest using the probe oligonucleotide and one of the primer pairs.

The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or PRKD; pRK5B is a precursor of pRK5D that does not contain the SfiI site; see, Holmes et al., *Science*, 253:1278–1280 (1991)) in the unique XhoI and NotI sites.

Example 2

Isolation of cDNA Clones by Amylase Screening

1. Preparation of Oligo DT Primed cDNA Library mRNA was isolated from a human tissue of interest using reagents and protocols from Invitrogen, San Diego, Calif. (Fast Track 2). This RNA was used to generate an oligo dT primed cDNA library in the vector pRK5D using reagents and protocols from Life Technologies, Gaithersburg, Md. (Super Script Plasmid System). In this procedure, the double stranded cDNA was sized to greater than 1000 bp and the SalI/NotI linkered cDNA was cloned into XhoI/NotI cleaved vector. pRK5D is a cloning vector that has an sp6 transcription initiation site followed by an SfiI restriction enzyme site preceding the XhoI/NotI cDNA cloning sites.

2. Preparation of Random Primed cDNA Library

A secondary cDNA library was generated in order to preferentially represent the 5' ends of the primary cDNA clones. Sp6 RNA was generated from the primary library (described above), and this RNA was used to generate a random primed cDNA library in the vector pSST-AMY.0 using reagents and protocols from Life Technologies (Super Script Plasmid System, referenced above). In this procedure the double stranded cDNA was sized to 500–1000 bp, linkered with blunt to NotI adaptors, cleaved with SfiI, and cloned into SfiI/NotI cleaved vector. pSST-AMY.0 is a cloning vector that has a yeast alcohol dehydrogenase promoter preceding the cDNA cloning sites and the mouse amylase sequence (the mature sequence without the secretion signal) followed by the yeast alcohol dehydrogenase terminator, after the cloning sites. Thus, cDNAs cloned into this vector that are fused in frame with amylase sequence will lead to the secretion of amylase from appropriately transfected yeast colonies.

3. Transformation and Detection

DNA from the library described in paragraph 2 above was chilled on ice to which was added electrocompetent DH10B bacteria (Life Technologies, 20 ml). The bacteria and vector mixture was then electroporated as recommended by the manufacturer. Subsequently, SOC media (Life Technologies, 1 ml) was added and the mixture was incubated at 37° C. for 30 minutes. The transformants were then plated onto 20 standard 150 mm LB plates containing ampicillin and incubated for 16 hours (37° C.). Positive colonies were scraped off the plates and the DNA was isolated from the bacterial pellet using standard protocols, e.g. CsCl-gradient. The purified DNA was then carried on to the yeast protocols below.

The yeast methods were divided into three categories: (1) Transformation of yeast with the plasmid/cDNA combined vector; (2) Detection and isolation of yeast clones secreting amylase; and (3) PCR amplification of the insert directly from the yeast colony and purification of the DNA for sequencing and further analysis.

The yeast strain used was HD56-5A (ATCC-90785). This strain has the following genotype: MAT alpha, ura3-52, leu2-3, leu2-112, his3-11, his3-15, MAL$^+$, SUC$^+$, GAL$^+$. Preferably, yeast mutants can be employed that have deficient post-translational pathways. Such mutants may have translocation deficient alleles in sec71, sec72, sec62, with truncated sec71 being most preferred. Alternatively, antagonists (including antisense nucleotides and/or ligands) which interfere with the normal operation of these genes, other proteins implicated in this post translation pathway (e.g., SEC61p, SEC72p, SEC62p, SEC63p, TDJ1p or SSA1p-4p) or the complex formation of these proteins may also be preferably employed in combination with the amylase-expressing yeast.

Transformation was performed based on the protocol outlined by Gietz et al., *Nucl. Acid. Res.*, 20:1425 (1992). Transformed cells were then inoculated from agar into YEPD complex media broth (100 ml) and grown overnight at 30° C. The YEPD broth was prepared as described in Kaiser et al., *Methods in Yeast Genetics*, Cold Spring Harbor Press, Cold Spring Harbor, N.Y., p. 207 (1994). The overnight culture was then diluted to about $2\times10^6$ cells/ml (approx. OD$_{600}$=0.1) into fresh YEPD broth (500 ml) and regrown to $1\times10^7$ cells/ml (approx. OD$_{600}$=0.4–0.5).

The cells were then harvested and prepared for transformation by transfer into GS3 rotor bottles in a Sorval GS3 rotor at 5,000 rpm for 5 minutes, the supernatant discarded, and then resuspended into sterile water, and centrifuged again in 50 ml falcon tubes at 3,500 rpm in a Beckman GS-6KR centrifuge. The supernatant was discarded and the cells were subsequently washed with LiAc/TE (10 ml, 10 mM Tris-HCl, 1 mM EDTA pH 7.5, 100 mM Li$_2$OOCCH$_3$), and resuspended into LiAc/TE (2.5 ml).

Transformation took place by mixing the prepared cells (100 µl) with freshly denatured single stranded salmon testes DNA (Lofstrand Labs, Gaithersburg, Md.) and transforming DNA (1 µg, vol. <10 µl) in microfuge tubes. The mixture was mixed briefly by vortexing, then 40% PEG/TE (600 µl, 40% polyethylene glycol-4000, 10 mM Tris-HCl, 1 mM EDTA, 100 mM Li$_2$OOCCH$_3$, pH 7.5) was added. This mixture was gently mixed and incubated at 30° C. while agitating for 30 minutes. The cells were then heat shocked at 42° C. for 15 minutes, and the reaction vessel centrifuged in a microfuge at 12,000 rpm for 5–10 seconds, decanted and resuspended into TE (500 µl, 10 mM Tris-HCl, 1 mM EDTA pH 7.5) followed by recentrifugation. The cells were then diluted into TE (1 ml) and aliquots (200 µl) were spread onto the selective media previously prepared in 150 mm growth plates (VWR).

Alternatively, instead of multiple small reactions, the transformation was performed using a single, large scale reaction, wherein reagent amounts were scaled up accordingly.

The selective media used was a synthetic complete dextrose agar lacking uracil (SCD-Ura) prepared as described in Kaiser et al., *Methods in Yeast Genetics*, Cold Spring Harbor Press, Cold Spring Harbor, N.Y., p. 208–210 (1994). Transformants were grown at 30° C. for 2–3 days.

The detection of colonies secreting amylase was performed by including red starch in the selective growth media. Starch was coupled to the red dye (Reactive Red-120, Sigma) as per the procedure described by Biely et al., *Anal. Biochem.*, 172:176–179 (1988). The coupled starch was incorporated into the SCD-Ura agar plates at a final concentration of 0.15% (w/v), and was buffered with potassium phosphate to a pH of 7.0 (50–100 mM final concentration).

The positive colonies were picked and streaked across fresh selective media (onto 150 mm plates) in order to obtain well isolated and identifiable single colonies. Well isolated single colonies positive for amylase secretion were detected by direct incorporation of red starch into buffered SCD-Ura agar. Positive colonies were determined by their ability to break down starch resulting in a clear halo around the positive colony visualized directly.

4. Isolation of DNA by PCR Amplification

When a positive colony was isolated, a portion of it was picked by a toothpick and diluted into sterile water (30 µl) in a 96 well plate. At this time, the positive colonies were either frozen and stored for subsequent analysis or immediately amplified. An aliquot of cells (5 µl) was used as a template for the PCR reaction in a 25 µl volume containing: 0.5 µl KLENTAQ (a 5'-exo minus N-terminal deletion of Taq DNA polymerase available from Clontech, Palo Alto, Calif.); 4.0 µl 10 mM dNTP's (Perkin Elmer-Cetus); 2.5 µl Kentaq buffer (Clontech); 0.25 µl forward oligo 1; 0.25 µl reverse oligo 2; 12.5 µl distilled water. The sequence of the forward oligonucleotide 1 was:

5'-TGTAAAACGACGGCCAGT TAAATAGACCTGCAATTATTAATCT-3' (SEQ ID NO:169)

The sequence of reverse oligonucleotide 2 was:

5'-CAGGAAACAGCTATGACC ACCTGCACACCTGCAAATCCATT-3' (SEQ ID NO:170)

PCR was then performed as follows:

| a. | | Denature | 92° C., | 5 minutes |
|---|---|---|---|---|
| b. | 3 cycles of: | Denature | 92° C., | 30 seconds |
| | | Anneal | 59° C., | 30 seconds |
| | | Extend | 72° C., | 60 seconds |
| c. | 3 cycles of: | Denature | 92° C., | 30 seconds |
| | | Anneal | 57° C., | 30 seconds |
| | | Extend | 72° C., | 60 seconds |

-continued

| d. | 25 cycles of: | Denature | 92° C., | 30 seconds |
|---|---|---|---|---|
| | | Anneal | 55° C., | 30 seconds |
| | | Extend | 72° C., | 60 seconds |
| e. | | Hold | 4° C. | |

The underlined regions of the oligonucleotides annealed to the ADH promoter region and the amylase region, respectively, and amplified a 307 bp region from vector pSST-AMY.0 when no insert was present. Typically, the first 18 nucleotides of the 5' end of these oligonucleotides contained annealing sites for the sequencing primers. Thus, the total product of the PCR reaction from an empty vector was 343 bp. However, signal sequence-fused cDNA resulted in considerably longer nucleotide sequences.

Following the PCR, an aliquot of the reaction (5 µl) was examined by agarose gel electrophoresis in a 1% agarose gel using a Tris-Borate-EDTA (TBE) buffering system as described by Sambrook et al., supra. Clones resulting in a single strong PCR product larger than 400 bp were further analyzed by DNA sequencing after purification with a 96 QIAQUICK PCR clean-up column (Qiagen Inc., Chatsworth, Calif.).

Example 3

Isolation of cDNA Clones Using Signal Algorithm Analysis

Various polypeptide-encoding nucleic acid sequences were identified by applying a proprietary signal sequence finding algorithm developed by Genentech, Inc. (South San Francisco, Calif.) upon ESTs as well as clustered and assembled EST fragments from public (e.g., GenBank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals. Use of this algorithm resulted in the identification of numerous polypeptide-encoding nucleic acid sequences.

Example 4

Isolation of cDNA Clones Encoding Human PRO Polypeptides

Using the techniques described in Examples 1 to 3 above, numerous full-length cDNA clones were identified as encoding PRO polypeptides as disclosed herein. These cDNAs were then deposited under the terms of the Budapest Treaty with the American Type Culture Collection, 10801 University Blvd., Manassas, Va. 20110-2209, USA (ATCC) as shown in Table 7 below.

TABLE 7

| Material | ATCC Dep. No. | Deposit Date |
|---|---|---|
| DNA26843-1389 | 203099 | Aug. 4, 1998 |
| DNA30867-1335 | 209807 | Apr. 28, 1998 |
| DNA34431-1177 | 209399 | Oct. 17, 1997 |
| DNA38268-1188 | 209421 | Oct. 28, 1997 |
| DNA40621-1440 | 209922 | Jun. 2, 1998 |
| DNA40625-1189 | 209788 | Apr. 21, 1998 |
| DNA45409-2511 | 203579 | Jan. 12, 1999 |
| DNA45495-1550 | 203156 | Aug. 25, 1998 |
| DNA49820-1427 | 209932 | Jun. 2, 1998 |
| DNA56406-1704 | 203478 | Nov. 17, 1998 |
| DNA56410-1414 | 209923 | Jun. 2, 1998 |
| DNA56436-1448 | 209902 | May 27, 1998 |
| DNA56855-1447 | 203004 | Jun. 23, 1998 |
| DNA56860-1510 | 209952 | Jun. 9, 1998 |
| DNA56862-1343 | 203174 | Sep. 1, 1998 |
| DNA56868-1478 | 203024 | Jun. 23, 1998 |
| DNA56869-1545 | 203161 | Aug. 25, 1998 |
| DNA57704-1452 | 209953 | Jun. 9, 1998 |
| DNA58723-1588 | 203133 | Aug. 18, 1998 |
| DNA57827-1493 | 203045 | Jul. 1, 1998 |
| DNA58737-1473 | 203136 | Aug. 18, 1998 |
| DNA58846-1409 | 209957 | Jun. 9, 1998 |
| DNA58850-1495 | 209956 | Jun. 9, 1998 |
| DNA58855-1422 | 203018 | Jun. 23, 1998 |
| DNA59211-1450 | 209960 | Jun. 9, 1998 |
| DNA59212-1627 | 203245 | Sep. 9, 1998 |
| DNA59213-1487 | 209959 | Jun. 9, 1998 |
| DNA59605-1418 | 203005 | Jun. 23, 1998 |
| DNA59609-1470 | 209963 | Jun. 9, 1998 |
| DNA59610-1556 | 209990 | Jun. 16, 1998 |
| DNA59837-2545 | 203658 | Feb. 9, 1999 |
| DNA59844-2542 | 203650 | Feb. 9, 1999 |
| DNA59854-1459 | 209974 | Jun. 16, 1998 |
| DNA60625-1507 | 209975 | Jun. 16, 1998 |
| DNA60629-1481 | 209979 | Jun. 16, 1998 |
| DNA61755-1554 | 203112 | Aug. 11, 1998 |
| DNA62812-1594 | 203248 | Sep. 9, 1998 |
| DNA62815-1576 | 203247 | Sep. 9, 1998 |
| DNA64881-1602 | 203240 | Sep. 9, 1998 |
| DNA64886-1601 | 203241 | Sep. 9, 1998 |
| DNA64902-1667 | 203317 | Oct. 6, 1998 |
| DNA64950-1590 | 203224 | Sep. 15, 1998 |
| DNA65403-1565 | 203230 | Sep. 15, 1998 |
| DNA66308-1537 | 203159 | Aug. 25, 1998 |
| DNA66519-1535 | 203236 | Sep. 15, 1998 |
| DNA66521-1583 | 203225 | Sep. 15, 1998 |
| DNA66658-1584 | 203229 | Sep. 15, 1998 |
| DNA66660-1585 | 203279 | Sep. 22, 1998 |
| DNA66663-1598 | 203268 | Sep. 22, 1998 |
| DNA66674-1599 | 203281 | Sep. 22, 1998 |
| DNA68862-2546 | 203652 | Feb. 9, 1999 |
| DNA68866-1644 | 203283 | Sep. 22, 1998 |
| DNA68871-1638 | 203280 | Sep. 22, 1998 |
| DNA68880-1676 | 203319 | Oct. 6, 1998 |
| DNA68883-1691 | 203535 | Dec. 15, 1998 |
| DNA68885-1678 | 203311 | Oct. 6, 1998 |
| DNA71277-1636 | 203285 | Sep. 22, 1998 |
| DNA73727-1673 | 203459 | Nov. 3, 1998 |
| DNA73734-1680 | 203363 | Oct. 20, 1998 |
| DNA73735-1681 | 203356 | Oct. 20, 1998 |
| DNA76393-1664 | 203323 | Oct. 6, 1998 |
| DNA77301-1708 | 203407 | Oct. 27, 1998 |
| DNA77568-1626 | 203134 | Aug. 18, 1998 |
| DNA77626-1705 | 203536 | Dec. 15, 1998 |
| DNA81754-2532 | 203542 | Dec. 15, 1998 |
| DNA81757-2512 | 203543 | Dec. 15, 1998 |
| DNA82302-2529 | 203534 | Dec. 15, 1998 |
| DNA82340-2530 | 203547 | Dec. 22, 1998 |
| DNA83500-2506 | 203391 | Oct. 29, 1998 |
| DNA84920-2614 | 203966 | Apr. 27, 1999 |
| DNA85066-2534 | 203588 | Jan. 12, 1999 |
| DNA86571-2551 | 203660 | Feb. 9, 1999 |
| DNA87991-2540 | 203656 | Feb. 9, 1999 |
| DNA92238-2539 | 203602 | Jan. 20, 1999 |
| DNA96042-2682 | PTA-382 | Jul. 20, 1999 |
| DNA96787-2534 | 203589 | Jan. 12, 1999 |
| DNA125185-2806 | PTA-1031 | Dec. 7, 1999 |
| DNA147531-2821 | PTA-1185 | Jan. 11, 2000 |
| DNA115291-2681 | PTA-202 | Jun. 8, 1999 |
| DNA164625-28890 | PTA-1535 | Mar. 21, 2000 |
| DNA131639-2874 | PTA-1784 | Apr. 25, 2000 |
| DNA79230-2525 | 203549 | Dec. 22, 1998 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposits will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

Example 5

Use of PRO as a Hybridization Probe

The following method describes use of a nucleotide sequence encoding PRO as a hybridization probe.

DNA comprising the coding sequence of full-length or mature PRO as disclosed herein is employed as a probe to screen for homologous DNAs (such as those encoding naturally-occurring variants of PRO) in human tissue cDNA libraries or human tissue genomic libraries.

Hybridization and washing of filters containing either library DNAs is performed under the following high stringency conditions. Hybridization of radiolabeled PRO-derived probe to the filters is performed in a solution of 50% formamide, 5×SSC, 0.1% SDS, 0.1% sodium pyrophosphate, 50 mM sodium phosphate, pH 6.8, 2× Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence PRO can then be identified using standard techniques known in the art.

Example 6

Expression of PRO in E. coli

This example illustrates preparation of an unglycosylated form of PRO by recombinant expression in E. coli.

The DNA sequence encoding PRO is initially amplified using selected PCR primers. The primers should contain restriction enzyme sites which correspond to the restriction enzyme sites on the selected expression vector. A variety of expression vectors may be employed. An example of a suitable vector is pBR322 (derived from E. coli; see Bolivar et al., Gene, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the PRO coding region, lambda transcriptional terminator, and an argU gene.

The ligation mixture is then used to transform a selected E. coli strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized PRO protein can then be purified using a metal chelating column under conditions that allow tight binding of the protein.

PRO may be expressed in E. coli in a poly-His tagged form, using the following procedure. The DNA encoding PRO is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an E. coli host based on strain 52 (W3110 fuhA(tonA) lon galE rpoHts(htpRts) clpP(lacIq). Transformants are first grown in LB containing 50 mg/ml carbenicillin at 30° C. with shaking until an O.D.600 of 3–5 is reached. Cultures are then diluted 50–100 fold into CRAP media (prepared by mixing 3.57 g $(NH_4)_2SO_4$, 0.71 g sodium citrate.2H2O, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20–30 hours at 30° C. with shaking. Samples are removed to verify expression by SDS-PAGE analysis, and the bulk culture is centrifuged to pellet the cells. Cell pellets are frozen until purification and refolding.

E. coli paste from 0.5 to 1 L fermentations (6–10 g pellets) is resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution is stirred overnight at 4° C. This step results in a denatured protein with all cysteine residues blocked by sulfitolization. The solution is centrifuged at 40,000 rpm in a Beckman Ultracentifuge for 30 min. The supernatant is diluted with 3–5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12–36 hours. The refolding reaction is quenched by the addition of TFA to a final concentration of 0.4% (pH of approximately 3). Before further purification of the protein, the solution is filtered through a 0.22 micron filter and acetonitrile is added to 2–10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded PRO polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Many of the PRO polypeptides disclosed herein were successfully expressed as described above.

Example 7

Expression of PRO in Mammalian Cells

This example illustrates preparation of a potentially glycosylated form of PRO by recombinant expression in mammalian cells.

The vector, pRK5 (see EP 307,247, published Mar. 15, 1989), is employed as the expression vector. Optionally, the PRO DNA is ligated into pRK5 with selected restriction enzymes to allow insertion of the PRO DNA using ligation methods such as described in Sambrook et al., supra. The resulting vector is called pRK5-PRO.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 µg pRK5-PRO DNA is mixed with about 1 µg DNA encoding the VA RNA gene [Thimmappaya et al., Cell, 31:543 (1982)] and dissolved in. 500 µl of 1 mM Tris-HCl, 0.1 mM EDTA, 0.227 M $CaCl_2$. To this mixture is added, dropwise, 500 µl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 µCi/ml $^{35}$S-cysteine and 200 µCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of PRO polypeptide. The cultures containing transfected cells may undergo further incubation (in serum free medium) and the medium is tested in selected bioassays.

In an alternative technique, PRO may be introduced into 293 cells transiently using the dextran sulfate method described by Somparyrac et al., *Proc. Natl. Acad. Sci.*, 12:7575 (1981). 293 cells are grown to maximal density in a spinner flask and 700 µg pRK5-PRO DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 µg/ml bovine insulin and 0.1 µg/ml bovine transferrin. After about four days, the conditioned media is centrifuged and filtered to remove cells and debris. The sample containing expressed PRO can then be concentrated and purified by any selected method, such as dialysis and/or column chromatography.

In another embodiment, PRO can be expressed in CHO cells. The pRK5-PRO can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of PRO polypeptide, the culture medium may be replaced with serum free medium. Preferably, the cultures are incubated for about 6 days, and then the conditioned medium is harvested. The medium containing the expressed PRO can then be concentrated and purified by any selected method.

Epitope-tagged PRO may also be expressed in host CHO cells. The PRO may be subcloned out of the pRK5 vector. The subclone insert can undergo PCR to fuse in frame with a selected epitope tag such as a poly-his tag into a Baculovirus expression vector. The poly-his tagged PRO insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged PRO can then be concentrated and purified by any selected method, such as by $Ni^{2+}$-chelate affinity chromatography.

PRO may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., *Nucl. Acids Res.* 24:9 (1774–1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents SUPERFECT™ (Quiagen), DOSPER™ or FUGENE™ (Boehringer Mannheim). The cells are grown as described in Lucas et al., supra. Approximately $3 \times 10^{-7}$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 µm filtered PS20 with 5% 0.2 µm diafiltered fetal bovine serum). The cells are then aliquoted into a 100 mL spinner containing 90 mL of selective media. After 1–2 days, the cells are transferred into a 250 mL spinner filled with 150 mL selective growth medium and incubated at 37° C. After another 2–3 days, 250 mL, 500 mL and 2000 mL spinners are seeded with $3 \times 10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3L production spinner is seeded at $1.2 \times 10^6$ cells/mL. On day 0, the cell number pH ie determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 µm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4–5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 μL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Many of the PRO polypeptides disclosed herein were successfully expressed as described above.

Example 8

Expression of PRO in Yeast

The following method describes recombinant expression of PRO in yeast.

First, yeast expression vectors are constructed for intracellular production or secretion of PRO from the ADH2/GAPDH promoter. DNA encoding PRO and the promoter is inserted into suitable restriction enzyme sites in the selected plasmid to direct intracellular expression of PRO. For secretion, DNA encoding PRO can be cloned into the selected plasmid, together with DNA encoding the ADH2/GAPDH promoter, a native PRO signal peptide or other mammalian signal peptide, or, for example, a yeast alpha-factor or invertase secretory signal/leader sequence, and linker sequences (if needed) for expression of PRO.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant PRO can subsequently be isolated and purified by removing the yeast cells from the fermentation medium by centrifugation and then concentrating the medium using selected cartridge filters. The concentrate containing PRO may further be purified using selected column chromatography resins.

Many of the PRO polypeptides disclosed herein were successfully expressed as described above.

Example 9

Expression of PRO in Baculovirus-Infected Insect Cells

The following method describes recombinant expression of PRO in Baculovirus-infected insect cells.

The sequence coding for PRO is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding PRO or the desired portion of the coding sequence of PRO such as the sequence encoding the extracellular domain of a transmembrane protein or the sequence encoding the mature protein if the protein is extracellular is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BACULOGOLD™ virus DNA (Pharmingen) into *Spodoptera frugiperda* ("Sf9") cells (ATCC CRL 1711) using LIPOFECTIN cationic lipid (commercially available from GIBCO-BRL). After 4–5 days of incubation at 28° C., the released viruses are harvested and used for further amplifications. Viral infection and protein expression are performed as described by O'Reilley et al., *Baculovirus expression vectors: A Laboratory Manual*, Oxford: Oxford University Press (1994).

Expressed poly-his tagged PRO can then be purified, for example, by $Ni^{2+}$-chelate affinity chromatography as follows. Extracts are prepared from recombinant virus-infected Sf9 cells as described by Rupert et al., *Nature,* 362:175–179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 μm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged PRO are pooled and dialyzed against loading buffer.

Alternatively, purification of the IgG tagged (or Fc tagged) PRO can be performed using known chromatography techniques, including for instance, Protein A or protein G column chromatography.

Many of the PRO polypeptides disclosed herein were successfully expressed as described above.

Example 10

Preparation of Antibodies that Bind PRO

This example illustrates preparation of monoclonal antibodies which can specifically bind PRO.

Techniques for producing the monoclonal antibodies are known in the art and are described, for instance, in Goding, supra. Immunogens that may be employed include purified PRO, fusion proteins containing PRO, and cells expressing recombinant PRO on the cell surface. Selection of the immunogen can be made by the skilled artisan without undue experimentation.

Mice, such as Balb/c, are immunized with the PRO immunogen emulsified in complete Freund's adjuvant and injected subcutaneously or intraperitoneally in an amount from 1–100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-PRO antibodies.

After a suitable antibody titer has been detected, the animals "positive" for antibodies can be injected with a final intravenous injection of PRO. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against PRO. Determination of "positive" hybridoma cells secreting the desired monoclonal antibodies against PRO is within the skill in the art.

The positive hybridoma cells can be injected intraperitoneally into syngeneic Balb/c mice to produce ascites containing the anti-PRO monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 11

Purification of PRO Polypeptides Using Specific Antibodies

Native or recombinant PRO polypeptides may be purified by a variety of standard techniques in the art of protein purification. For example, pro-PRO polypeptide, mature PRO polypeptide, or pre-PRO polypeptide is purified by immunoaffinity chromatography using antibodies specific for the PRO polypeptide of interest. In general, an immunoaffinity column is constructed by covalently coupling the anti-PRO polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of PRO polypeptide by preparing a fraction from cells containing PRO polypeptide in a soluble form. This preparation is derived by solubilization of the whole cell or of a subcellular fraction obtained via differential centrifugation by the addition of detergent or by other methods well known in the art. Alternatively, soluble PRO polypeptide containing a signal sequence may be secreted in useful quantity into the medium in which the cells are grown.

A soluble PRO polypeptide-containing preparation is passed over the immunoaffinity column, and the column is washed under conditions that allow the preferential absorbance of PRO polypeptide (e.g., high ionic strength buffers in the presence of detergent). Then, the column is eluted under conditions that disrupt antibody/PRO polypeptide binding (e.g., a low pH buffer such as approximately pH 2–3, or a high concentration of a chaotrope such as urea or thiocyanate ion), and PRO polypeptide is collected.

Example 12

Drug Screening

This invention is particularly useful for screening compounds by using PRO polypeptides or binding fragment thereof in any of a variety of drug screening techniques. The PRO polypeptide or fragment employed in such a test may either be free in solution, affixed to a solid support, borne on a cell surface, or located intracellularly. One method of drug screening utilizes eukaryotic or prokaryotic host cells which are stably transformed with recombinant nucleic acids expressing the PRO polypeptide or fragment. Drugs are screened against such transformed cells in competitive binding assays. Such cells, either in viable or fixed form, can be used for standard binding assays. One may measure, for example, the formation of complexes between PRO polypeptide or a fragment and the agent being tested. Alternatively, one can examine the diminution in complex formation between the PRO polypeptide and its target cell or target receptors caused by the agent being tested.

Thus, the present invention provides methods of screening for drugs or any other agents which can affect a PRO polypeptide-associated disease or disorder. These methods comprise contacting such an agent with an PRO polypeptide or fragment thereof and assaying (I) for the presence of a complex between the agent and the PRO polypeptide or fragment, or (ii) for the presence of a complex between the PRO polypeptide or fragment and the cell, by methods well known in the art. In such competitive binding assays, the PRO polypeptide or fragment is typically labeled. After suitable incubation, free PRO polypeptide or fragment is separated from that present in bound form, and the amount of free or uncomplexed label is a measure of the ability of the particular agent to bind to PRO polypeptide or to interfere with the PRO polypeptide/cell complex.

Another technique for drug screening provides high throughput screening for compounds having suitable binding affinity to a polypeptide and is described in detail in WO 84/03564, published on Sep. 13, 1984. Briefly stated, large numbers of different small peptide test compounds are synthesized on a solid substrate, such as plastic pins or some other surface. As applied to a PRO polypeptide, the peptide test compounds are reacted with PRO polypeptide and washed. Bound PRO polypeptide is detected by methods well known in the art. Purified PRO polypeptide can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding PRO polypeptide specifically compete with a test compound for binding to PRO polypeptide or fragments thereof. In this manner, the antibodies can be used to detect the presence of any peptide which shares one or more antigenic determinants with PRO polypeptide.

Example 13

Rational Drug Design

The goal of rational drug design is to produce structural analogs of biologically active polypeptide of interest (i.e., a PRO polypeptide) or of small molecules with which they interact, e.g., agonists, antagonists, or inhibitors. Any of these examples can be used to fashion drugs which are more active or stable forms of the PRO polypeptide or which enhance or interfere with the function of the PRO polypeptide in vivo (c.f., Hodgson, *Bio/Technology*, 9: 19–21 (1991)).

In one approach, the three-dimensional structure of the PRO polypeptide, or of an PRO polypeptide-inhibitor complex, is determined by x-ray crystallography, by computer modeling or, most typically, by a combination of the two approaches. Both the shape and charges of the PRO polypeptide must be ascertained to elucidate the structure and to determine active site(s) of the molecule. Less often, useful information regarding the structure of the PRO polypeptide may be gained by modeling based on the structure of homologous proteins. In both cases, relevant structural information is used to design analogous PRO polypeptide-like molecules or to identify efficient inhibitors. Useful examples of rational drug design may include molecules which have improved activity or stability as shown by Braxton and Wells, *Biochemistry*, 31:7796–7801 (1992) or which act as inhibitors, agonists, or antagonists of native peptides as shown by Athauda et al., *J. Biochem.*, 113: 742–746 (1993).

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amounts of the PRO polypeptide may be made available to perform such analytical studies as X-ray crystallography. In addition, knowledge of the PRO polypeptide amino acid sequence provided herein will provide guidance to those employing computer modeling techniques in place of or in addition to x-ray crystallography.

Example 14

Pericyte c-Fos Induction (Assay 93)

This assay shows that certain polypeptides of the invention act to induce the expression of c-fos in pericyte cells and, therefore, are useful not only as diagnostic markers for particular types of pericyte-associated tumors but also for giving rise to antagonists which would be expected to be useful for the therapeutic treatment of pericyte-associated tumors. Induction of c-fos expression in pericytes is also indicative of the induction of angiogenesis and, as such, PRO polypeptides capable of inducing the expression of c-fos would be expected to be useful for the treatment of conditions where induced angiogenesis would be beneficial including, for example, wound healing, and the like. Specifically, on day 1, pericytes are received from VEC Technologies and all but 5 ml of media is removed from flask. On day 2, the pericytes are trypsinized, washed, spun and then plated onto 96 well plates. On day 7, the media is removed and the pericytes are treated with 100 μl of PRO polypeptide test samples and controls (positive control=DME+5% serum +/−PDGF at 500 ng/ml; negative control=protein 32). Replicates are averaged and SD/CV are determined. Fold increase over Protein 32 (buffer control) value indicated by chemiluminescence units (RLU) luminometer reading verses frequency is plotted on a histogram. Two-fold above Protein 32 value is considered positive for the assay. ASY Matrix: Growth media=low glucose DMEM=20% FBS+1× pen strep+1×fungizone. Assay Media=low glucose DMEM+ 5% FBS.

The following polypeptides tested positive in this assay: PRO1347 and PRO1340.

Example 15

Ability of PRO Polypeptides to Stimulate the Release of Proteoglycans from Cartilage (Assay 97)

The ability of various PRO polypeptides to stimulate the release of proteoglycans from cartilage tissue was tested as follows.

The metacarphophalangeal joint of 4–6 month old pigs was aseptically dissected, and articular cartilage was removed by free hand slicing being careful to avoid the underlying bone. The cartilage was minced and cultured in bulk for 24 hours in a humidified atmosphere of 95% air, 5% $CO_2$ in serum free (SF) media (DME/F12 1:1) woth 0.1% BSA and 100 U/ml penicillin and 100 μg/ml streptomycin. After washing three times, approximately 100 mg of articular cartilage was aliquoted into micronics tubes and incubated for an additional 24 hours in the above SF media. PRO polypeptides were then added at 1% either alone or in combination with 18 ng/ml interleukin-la, a known stimulator of proteoglycan release from cartilage tissue. The supernatant was then harvested and assayed for the amount of proteoglycans using the 1,9-dimethyl-methylene blue (DMB) colorimetric assay (Farndale and Buttle, *Biochem. Biophys. Acta* 883:173–177 (1985)). A positive result in this assay indicates that the test polypeptide will find use, for example, in the treatment of sports-related joint problems, articular cartilage defects, osteoarthritis or rheumatoid arthritis.

When various PRO polypeptides were tested in the above assay, the polypeptides demonstrated a marked ability to stimulate release of proteoglycans from cartilage tissue both basally and after stimulation with interleukin-la and at 24 and 72 hours after treatment, thereby indicating that these PRO polypeptides are useful for stimulating proteoglycan release from cartilage tissue. As such, these PRO polypeptides are useful for the treatment of sports-related joint problems, articular cartilage defects, osteoarthritis or rheumatoid arthritis. The polypeptides testing positive in this assay are: PRO1565, PRO1693, PRO1801 and PRO10096.

Example 16

Detection of Polypeptides that Affect Glucose or FFA Uptake in Skeletal Muscle (Assay 106)

This assay is designed to determine whether PRO polypeptides show the ability to affect glucose or FFA uptake by skeletal muscle cells. PRO polypeptides testing positive in this assay would be expected to be useful for the therapeutic treatment of disorders where either the stimulation or inhibition of glucose uptake by skeletal muscle would be beneficial including, for example, diabetes or hyper- or hypo-insulinemia.

In a 96 well format, PRO polypeptides to be assayed are added to primary rat differentiated skeletal muscle, and allowed to incubate overnight. Then fresh media with the PRO polypeptide and +/−insulin are added to the wells. The sample media is then monitored to determine glucose and FFA uptake by the skeletal muscle cells. The insulin will stimulate glucose and FFA uptake by the skeletal muscle, and insulin in media without the PRO polypeptide is used as a positive control, and a limit for scoring. As the PRO polypeptide being tested may either stimulate or inhibit glucose and FFA uptake, results are scored as positive in the assay if greater than 1.5 times or less than 0.5 times the insulin control.

The following PRO polypeptides tested positive as either stimulators or inhibitors of glucose and/or FFA uptake in this assay: PRO4405.

Example 17

Identification of PRO Polypeptides That Stimulate TNF-α Release In Human Blood (Assay 128)

This assay shows that certain PRO polypeptides of the present invention act to stimulate the release of TNF-α in human blood. PRO polypeptides testing positive in this assay are useful for, among other things, research purposes where stimulation of the release of TNF-α would be desired and for the therapeutic treatment of conditions wherein enhanced TNF-α release would be beneficial. Specifically, 200 μl of human blood supplemented with 50 mM Hepes buffer (pH 7.2) is aliquotted per well in a 96 well test plate. To each well is then added 300 μl of either the test PRO polypeptide in 50 mM Hepes buffer (at various concentrations) or 50 mM Hepes buffer alone (negative control) and the plates are incubated at 37° C. for 6 hours. The samples are then centrifuged and 50 μl of plasma is collected from each well and tested for the presence of TNF-α by ELISA assay. A positive in the assay is a higher amount of TNF-α in the PRO polypeptide treated samples as compared to the negative control samples.

The following PRO polypeptides tested positive in this assay: PRO263. PRO295, PRO1282, PRO1063, PRO1356, PRO3543, and PRO5990.

Example 18

Tumor Versus Normal Differential Tissue Expression Distribution

Oligonucleotide probes were constructed from some of the PRO polypeptide-encoding nucleotide sequences shown in the accompanying figures for use in quantitative PCR amplification reactions. The oligonucleotide probes were chosen so as to give an approximately 200–600 base pair amplified fragment from the 3′ end of its associated template in a standard PCR reaction. The oligonucleotide probes were employed in standard quantitative PCR amplification reactions with cDNA libraries isolated from different human tumor and normal human tissue samples and analyzed by agarose gel electrophoresis so as to obtain a quantitative determination of the level of expression of the PRO polypeptide-encoding nucleic acid in the various tumor and normal tissues tested. β-actin was used as a control to assure that equivalent amounts of nucleic acid was used in each reaction. Identification of the differential expression of the PRO polypeptide-encoding nucleic acid in one or more tumor tissues as compared to one or more normal tissues of the same tissue type renders the molecule useful diagnostically for the determination of the presence or absence of tumor in a subject suspected of possessing a tumor as well as therapeutically as a target for the treatment of a tumor in a subject possessing such a tumor. These assays provided the following results.

| Molecule | is more highly expressed in: | as compared to: |
|---|---|---|
| DNA26843-1389 | normal lung | lung tumor |
|  | rectum tumor | normal rectum |
| DNA30867-1335 | normal kidney | kidney tumor |
| DNA40621-1440 | normal lung | lung tumor |
| DNA40625-1189 | normal lung | lung tumor |
| DNA45409-2511 | melanoma tumor | normal skin |
| DNA56406-1704 | kidney tumor | normal kidney |
|  | normal skin | melanoma tumor |
| DNA56410-1414 | normal stomach | stomach tumor |
| DNA56436-1448 | normal skin | melanoma tumor |
| DNA56855-1447 | normal esophagus | esophageal tumor |
|  | rectum tumor | normal rectum |
| DNA56860-1510 | normal kidney | kidney tumor |
|  | rectum tumor | normal rectum |
| DNA56862-1343 | kidney tumor | normal kidney |
|  | normal lung | lung tumor |
| DNA56868-1478 | normal stomach | stomach tumor |
|  | normal lung | lung tumor |
| DNA56869-1545 | normal esophagus | esophageal tumor |
|  | normal skin | melanoma tumor |
| DNA57704-1452 | normal stomach | stomach tumor |
|  | rectum tumor | normal rectum |
| DNA58723-1588 | normal stomach | stomach tumor |
|  | kidney tumor | normal kidney |
|  | normal skin | melanoma tumor |
| DNA57827-1493 | normal stomach | stomach tumor |
|  | normal skin | melanoma tumor |
| DNA58737-1473 | esophageal tumor | normal esophagus |
|  | normal stomach | stomach tumor |
| DNA58846-1409 | lung tumor | normal lung |
| DNA58850-1495 | esophageal tumor | normal esophagus |
|  | kidney tumor | normal kidney |
| DNA58855-1422 | normal stomach | stomach tumor |
|  | rectum tumor | normal rectum |
| DNA59211-1450 | normal kidney | kidney tumor |
| DNA59212-1627 | normal skin | melanoma tumor |
| DNA59213-1487 | normal stomach | stomach tumor |
|  | normal skin | melanoma tumor |
| DNA59605-1418 | melanoma tumor | normal skin |
| DNA59609-1470 | esophageal tumor | normal esophagus |
| DNA59610-1556 | esophageal tumor | normal esophagus |
|  | lung tumor | normal lung |
|  | normal skin | melanoma tumor |
| DNA59837-2545 | normal skin | melanoma tumor |
| DNA59844-2542 | normal skin | melanoma tumor |
|  | esophageal tumor | normal esophagus |
| DNA59854-1459 | normal esophagus | esophageal tumor |
|  | stomach tumor | normal stomach |
|  | normal lung | lung tumor |
| DNA60625-1507 | normal lung | lung tumor |
| DNA60629-1481 | normal esophagus | esophageal tumor |
|  | normal rectum | rectum tumor |
| DNA61755-1554 | normal stomach | stomach tumor |
|  | kidney tumor | normal kidney |
| DNA62812-1594 | normal stomach | stomach tumor |
|  | normal lung | lung tumor |
|  | normal rectum | rectum tumor |
|  | normal skin | melanoma tumor |
| DNA62815-1576 | esophageal tumor | normal esophagus |
| DNA64881-1602 | normal stomach | stomach tumor |
|  | normal lung | lung tumor |

-continued

| Molecule | is more highly expressed in: | as compared to: |
|---|---|---|
| DNA64902-1667 | esophageal tumor | normal esophagus |
|  | kidney tumor | normal kidney |
| DNA65403-1565 | normal esophagus | esophageal tumor |
| DNA66308-1537 | normal lung | lung tumor |
| DNA66519-1535 | kidney tumor | normal kidney |
| DNA66521-1583 | normal esophagus | esophageal tumor |
|  | normal stomach | stomach tumor |
|  | normal lung | lung tumor |
|  | normal rectum | rectum tumor |
|  | normal skin | melanoma tumor |
| DNA66658-1584 | normal lung | lung tumor |
|  | melanoma tumor | normal skin |
| DNA66660-1585 | lung tumor | normal lung |
| DNA66674-1599 | kidney tumor | normal kidney |
|  | normal lung | lung tumor |
| DNA68862-2546 | melanoma tumor | normal skin |
| DNA68866-1644 | normal stomach | stomach tumor |
| DNA68871-1638 | lung tumor | normal lung |
|  | normal skin | melanoma tumor |
| DNA68880-1676 | normal lung | lung tumor |
|  | normal skin | melanoma tumor |
| DNA68883-1691 | esophageal tumor | normal esophagus |
| DNA68885-1678 | lung tumor | normal lung |
| DNA71277-1636 | normal stomach | stomach tumor |
| DNA73734-1680 | normal lung | lung tumor |
| DNA73735-1681 | esophageal tumor | normal esophagus |
|  | normal kidney | kidney tumor |
|  | lung tumor | normal lung |
|  | normal skin | melanoma tumor |
| DNA76393-1664 | esophageal tumor | normal esophagus |
|  | stomach tumor | normal stomach |
|  | lung tumor | normal lung |
|  | rectum tumor | normal rectum |
| DNA77568-1626 | normal stomach | stomach tumor |
|  | lung tumor | normal lung |
| DNA77626-1705 | normal rectum | rectum tumor |
| DNA81754-2532 | normal skin | melanoma tumor |
| DNA81757-2512 | esophageal tumor | normal esophagus |
|  | normal stomach | stomach tumor |
|  | melanoma tumor | normal skin |
| DNA82302-2529 | normal stomach | stomach tumor |
|  | normal lung | lung tumor |
| DNA82340-2530 | normal esophagus | esophageal tumor |
| DNA85066-2534 | lung tumor | normal lung |
|  | normal skin | melanoma tumor |
| DNA87991-2540 | esophageal tumor | normal esophagus |
| DNA92238-2539 | normal skin | melanoma tumor |
| DNA96787-2534 | normal kidney | kidney tumor |

Example 19

Identification of Receptor/Ligand Interactions

In this assay, various PRO polypeptides are tested for ability to bind to a panel of potential receptor or ligand molecules for the purpose of identifying receptor/ligand interactions. The identification of a ligand for a known receptor, a receptor for a known ligand or a novel receptor/ligand pair is useful for a variety of indications including, for example, targeting bioactive molecules (linked to the ligand or receptor) to a cell known to express the receptor or ligand, use of the receptor or ligand as a reagent to detect the presence of the ligand or receptor in a composition suspected of containing the same, wherein the composition may comprise cells suspected of expressing the ligand or receptor, modulating the growth of or another biological or immunological activity of a cell known to express or respond to the receptor or ligand, modulating the immune response of cells or toward cells that express the receptor or ligand, allowing the preparaion of agonists, antagonists and/or antibodies directed against the receptor or ligand which will modulate the growth of or a biological or immunological activity of a cell expressing the receptor or ligand, and various other indications which will be readily apparent to the ordinarily skilled artisan.

The assay is performed as follows. A PRO polypeptide of the present invention suspected of being a ligand for a receptor is expressed as a fusion protein containing the Fc domain of human IgG (an immunoadhesin). Receptor-ligand binding is detected by allowing interaction of the immunoadhesin polypeptide with cells (e.g. Cos cells) expressing candidate PRO polypeptide receptors and visualization of bound immunoadhesin with fluorescent reagents directed toward the Fc fusion domain and examination by microscope. Cells expressing candidate receptors are produced by transient transfection, in parallel, of defined subsets of a library of cDNA expression vectors encoding PRO polypeptides that may function as receptor molecules. Cells are then incubated for 1 hour in the presence of the PRO polypeptide immunoadhesin being tested for possible receptor binding. The cells are then washed and fixed with paraformaldehyde. The cells are then incubated with fluorescent conjugated antibody directed against the Fc portion of the PRO polypeptide immunoadhesin (e.g. FITC conjugated goat anti-human-Fc antibody). The cells are then washed again and examined by microscope. A positive interaction is judged by the presence of fluorescent labeling of cells transfected with cDNA encoding a particular PRO polypeptide receptor or pool of receptors and an absence of similar fluorescent labeling of similarly prepared cells that have been transfected with other cDNA or pools of cDNA. If a defined pool of cDNA expression vectors is judged to be positive for interaction with a PRO polypeptide immunoadhesin, the individual cDNA species that comprise the pool are tested individually (the pool is "broken down") to determine the specific cDNA that encodes a receptor able to interact with the PRO polypeptide immunoadhesin.

In another embodiment of this assay, an epitope-tagged potential ligand PRO polypeptide (e.g. 8 histidine "His" tag) is allowed to interact with a panel of potential receptor PRO polypeptide molecules that have been expressed as fusions with the Fc domain of human IgG (immunoadhesins). Following a 1 hour co-incubation with the epitope tagged PRO polypeptide, the candidate receptors are each immunoprecipitated with protein A beads and the beads are washed. Potential ligand interaction is determined by western blot analysis of the immunoprecipitated complexes with antibody directed towards the epitope tag. An interaction is judged to occur if a band of the anticipated molecular weight of the epitope tagged protein is observed in the western blot analysis with a candidate receptor, but is not observed to occur with the other members of the panel of potential receptors.

Using these assays, the following receptor/ligand interactions have been herein identified:

(1) PRO10272 binds to PRO5801.
(2) PRO20110 binds to the human IL-17 receptor (Yao et al., *Cytokine* 9(11):794–800 (1997); also herein designated as PRO1) and to PRO20040.
(3) PRO10096 binds to PRO20233.
(4) PRO19670 binds to PRO1890.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

The invention claimed is:

1. An isolated polypeptide comprising:
   (a) the amino acid sequence of the polypeptide of SEQ ID NO: 12;
   (b) the amino acid sequence of the polypeptide of SEQ ID NO: 12, lacking its associated signal peptide;
   (c) amino acids 59–100, or 151–161, or 224–239, or 284–323, or 407–427 of SEQ ID NO: 12;
   (d) amino acids 59–100, or 151–161, or 224–239, or 284–323, or 407–427 of SEQ ID NO: 12, and the associated signal peptide; or
   (e) the amino acid sequence of the polypeptide encoded by the full-length coding sequence of the cDNA deposited under ATCC accession number 209788.

2. The isolated polypeptide of claim 1 comprising the amino acid sequence of the polypeptide of SEQ ID NO: 12.

3. The isolated polypeptide of claim 1 comprising the amino acid sequence of the polypeptide of SEQ ID NO: 12, lacking its associated signal peptide.

4. The isolated polypeptide of claim 1 comprising the amino acid sequence of the polypeptide encoded by the full-length coding sequence of the cDNA deposited under ATCC accession number 209788.

5. A chimeric polypeptide comprising a polypeptide according to claim 1 fused to a heterologous polypeptide.

6. The chimeric polypeptide of claim 5, wherein said heterologous polypeptide is a tag polypeptide or an Fc region of an immunoglobulin.

7. The isolated polypeptide of claim 1 comprising amino acids 59–100, or 151–161, or 224–239, or 284–323, or 407–427 of SEQ ID NO:12.

8. The isolated polypeptide of claim 1 comprising amino acids 59–100, or 151–161, or 224–239, or 284–323, or 407–427 of SEQ ID NO:12, and the associated signal peptide.

* * * * *